(12) United States Patent
Rickard et al.

(10) Patent No.: US 11,806,343 B2
(45) Date of Patent: Nov. 7, 2023

(54) INHIBITORS OF DUX4 INDUCTION FOR REGULATION OF MUSCLE FUNCTION

(71) Applicant: Sonic Master Limited, Tortola (VG)

(72) Inventors: Amanda Rickard, San Diego, CA (US); Uli Schmidt, San Diego, CA (US); Alexander Kiselyov, San Diego, CA (US)

(73) Assignee: Sonic Master Limited, Tortola (VG)

( * ) Notice: Subject to any disclaimer, the term of this patent is extended or adjusted under 35 U.S.C. 154(b) by 175 days.

(21) Appl. No.: 17/375,577

(22) Filed: Jul. 14, 2021

(65) Prior Publication Data

US 2021/0361641 A1   Nov. 25, 2021

Related U.S. Application Data

(62) Division of application No. 16/753,247, filed as application No. PCT/US2018/057856 on Oct. 26, 2018, now Pat. No. 11,065,243.

(60) Provisional application No. 62/676,177, filed on May 24, 2018, provisional application No. 62/578,362, filed on Oct. 27, 2017.

(51) Int. Cl.
| | |
|---|---|
| *A61K 31/513* | (2006.01) |
| *A61K 9/00* | (2006.01) |
| *A61K 9/06* | (2006.01) |
| *A61K 31/427* | (2006.01) |
| *A61K 35/00* | (2006.01) |
| *A61K 31/4709* | (2006.01) |
| *A61P 21/00* | (2006.01) |
| *A61K 31/519* | (2006.01) |

(52) U.S. Cl.
CPC ........ *A61K 31/4709* (2013.01); *A61K 9/0053* (2013.01); *A61K 31/519* (2013.01); *A61P 21/00* (2018.01)

(58) Field of Classification Search
CPC ..... A61P 35/00; A61K 31/513; A61K 9/0014; A61K 9/06
See application file for complete search history.

(56) References Cited

U.S. PATENT DOCUMENTS

2015/0246033 A1   9/2015   Flynn et al.

FOREIGN PATENT DOCUMENTS

WO   WO 2012/115885   *   8/2012   ............... C12Q 1/68

OTHER PUBLICATIONS

Block et al, "Wnt/B-catenin signaling supresses DUX4 expression and prevents apoptosis of FSHD muscle cells", "Human Molecular Genetics", Jul. 2, 2013, pp. 4661-4672, vol. 22, No. 33, Publisher: Oxford University Press.

Cortes et al, "Phase 1 dose-findling study of rebastinib (DCC-2036) in patients with relapsed chronic myeloid leukemia and acute myeloid leukemia", Dec. 7, 2016, pp. 519-528, vol. 102, No. 3, Publisher: Haematologica, Mar. 2017.

* cited by examiner

*Primary Examiner* — Erich A Leeser

(57) ABSTRACT

Disclosed are methods and compositions for the treatment of facioscapulohumeral muscular dystrophy. In some cases, the methods and compositions involve the use of kinase inhibitors include Src, Syk, Abl, Tie, Flt, ErbB, Trk, PRKDC, and Yes families to repress DUX4 expression in muscle cells. Further disclosed are methods and cell based assays for screening compounds for the treatment of facioscapulohumeral muscular dystrophy.

5 Claims, 42 Drawing Sheets

AZM475271

TG100801

Erlotinib (OSI-744)

Saracatinib

SKLB4771

AZD2932

Tandutinib

AT9283

Crenolanib

MRX-2843

Dovitinib

Belizatinib

CHIR-124

RAF265 (CHIR-265)

TAK-632

INHIBITORS OF DUX4 INDUCTION FOR REGULATION OF MUSCLE FUNCTION

CROSS REFERENCE

This application is a divisional application of U.S. Ser. No. 16/753,247 filed Apr. 2, 2020 which claims priority to PCT Application No. US2018/057856 filed 26 Oct. 2018, which claims priority to U.S. Provisional Application No. 62/578,362, filed 27 Oct. 2017, and to U.S. Provisional Application No. 62/676,177, filed 24 May 2018, each of which are incorporated by reference herein in their entirety.

BACKGROUND OF THE INVENTION

Facioscapulohumeral dystrophy (FSHD) is a neuromuscular disease with a prevalence that could reach 1 in 8,000. It is typically characterized by progressive asymmetric muscle weakness. Manifestation of the disease includes both typical and asymmetric patterns of muscle involvement and disease progression. Two forms of FSHD have been identified: FSHD1 and FSHD2. Although both forms may display identical clinical phenotypes, it is unclear whether their genetic and epigenetic origins overlap or are distinct. To date, the exact nature of pathophysiology of FSHD has not been established. As a result, target or pathway-biased treatment for this disease is not available.

Chromatin is a complex of macromolecules (including DNA, protein, and RNA) with functions that include the packaging of DNA into smaller volumes to fit into a cell nucleus, and the control of gene expression. Histones are a major protein component of chromatin and bind DNA into protein-DNA complexes called nucleosomes. Epigenetic modifications (e.g., methylation, acetylation, ubiquitination, neddylation, phosphorylation) of histones, DNA and other macromolecules as well as multiple effector molecules may regulate chromatin compaction by causing the loosening or condensing chromatin, thereby affecting the ability of regulatory factors to access DNA.

SUMMARY OF THE INVENTION

The present disclosure provides methods and compositions for the treatment of facioscapulohumeral muscular dystrophy (FSHD) and other muscle disorders or diseases, particularly any disease or disorder associated with upregulated DUX4 expression or activity. In some cases, the methods and compositions involve the use of modulators of specific signaling pathways including Src, PRKDC (also known as DNA-PK), Tie, Abl, Fit, Trk, Yes. FAK kinase families to modulate DUX4 activity in muscle cells (e.g., by inhibiting or repressing its transcriptional activity, inhibiting or repressing its expression, increasing the degradation of DUX4, mRNA or protein, or any other mechanism that results in reduced DUX4 activity). Further disclosed herein are methods and cell based assays for screening compounds for the treatment of FSHD and other disorders or diseases, particularly a disorder associated with dysregulated or upregulated DUX4 activity or expression. Also disclosed herein are methods and compositions for the treatment of FSHD and other disorders or diseases, particularly a disorder associated with dysregulated or upregulated DUX4 activity or expression.

In some embodiments, this disclosure provides a method for modulating DUX4 activity in a subject in need thereof comprising administering to the subject in need thereof a composition comprising a compound, or a pharmaceutically acceptable salt thereof, having the structure of Formula (I):

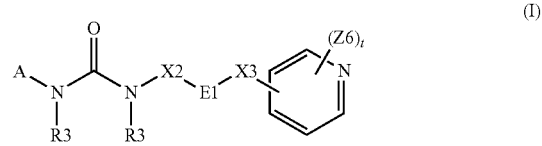

wherein E1 is phenyl, and wherein the E1 ring is substituted with one to three $R^{16}$ moieties;

wherein A is selected from the group consisting of imidazolyl, and pyrazolyl;

G1 is a heteroaryl taken from the group consisting of pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyrazinyl, and pyrimidinyl;

G4 is a heterocyclyl taken from the group consisting of oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl;

A ring is substituted at any substitutable position with one A1 moiety, wherein A1 is selected from the group consisting of;

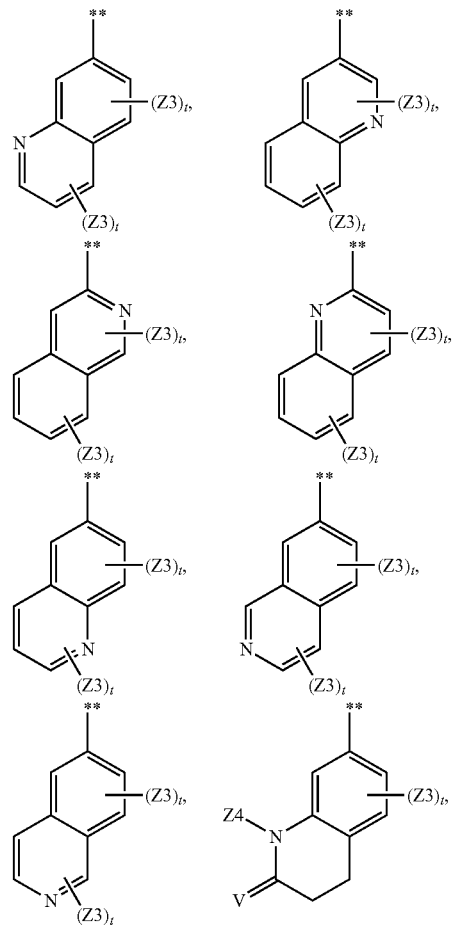

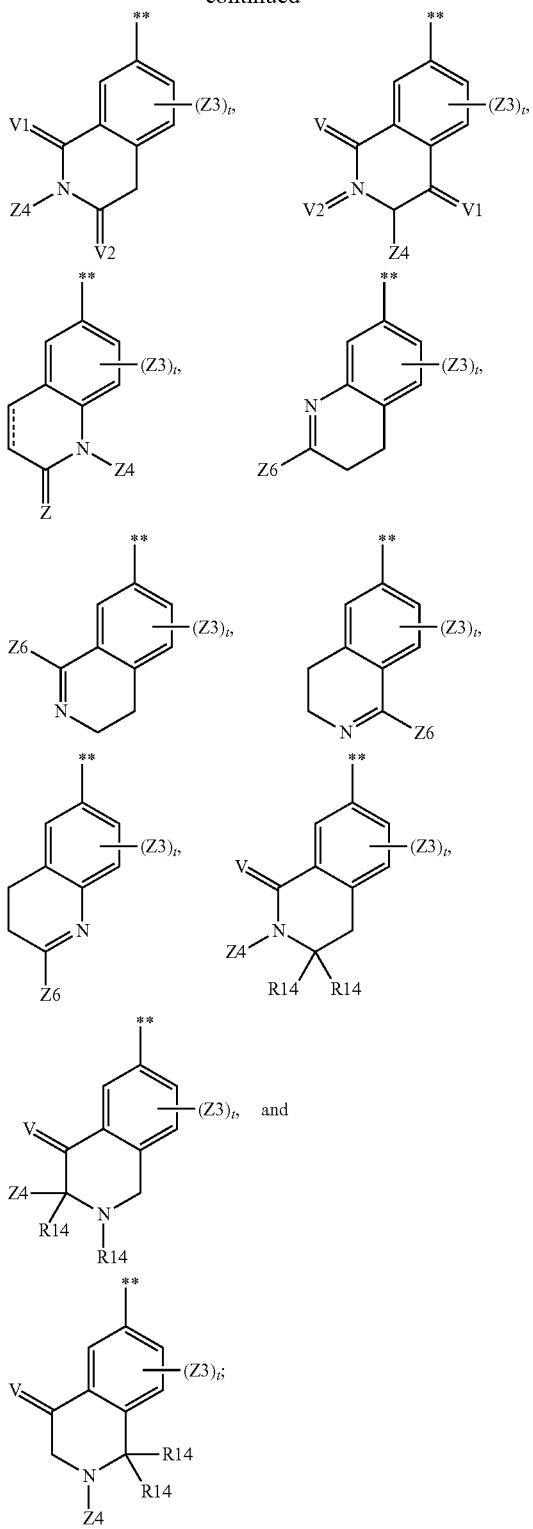

and wherein the symbol (**) is the point of attachment to the A ring of formula I;

and wherein ---- indicates either a saturated or unsaturated bond;

the A ring is optionally substituted with one or more R2 moieties;

X2 is a direct bond wherein E1 is directly linked to the NR3 group of formula I;

X3 is —O—;

V, V1, and V2 are each independently O or represent two hydrogens attached to the methylene carbon to which the V, V1, or V2 is attached;

each Z3 is independently and individually selected from the group consisting of H, C1-C6alkyl, branched C3-C7alkyl, C3-C8carbocyclyl, halogen, fluoroC1-C6alkyl wherein the alkyl moiety can be partially or fully fluorinated, cyano, hydroxyl, methoxy, oxo, $(R3)_2NC(O)$—, $(R4)_2NC(O)$—, —$N(R4)C(O)R8$, $(R3)_2NSO_2$—, $(R4)_2NSO_2$—, —$N(R4)SO_2R_5$, —$N(R4)SO_2R8$, —$(CH_2)N(R3)_2$, —$(CH_2)_qN(R4)_2$, —$O(CH_2)_qN(R4)_2$, —$O(CH_2)_qO$—C1-C6alkyl, —$N(R3)(CH2)_qO$—C1-C6alkyl, —$N(R3)(CH_2)_qN(R4)_2$, —$O(CH2)_qR5$, —$N(R3)(CH_2)_qR5$, —$C(O)R5$, —$C(O)R8$, and nitro;

in the event that Z3 contains an alkyl or alkylene moiety, such moieties may be further substituted with one or more C1-C6alkyls;

each Z4 is independently and individually selected from the group consisting of H, C1-C6alkyl, hydroxyC$_2$-C$_6$alkyl, C1-C6alkoxyC$_2$-C$_6$alkyl, $(R4)_2N$—C$_2$-C$_6$alkyl, $(R4)_2N$—C$_2$-C6alkylN(R4)-C$_2$-C$_6$alkyl, $(R4)_2N$—C$_2$-C$_6$alkyl-O—C$_2$-C$_6$alkyl, $(R4)_2NC(O)$—C1-C6alkyl, carboxyC1-C6alkyl-, C1-C6alkoxycarbonylC1-C6alkyl-, —C$_2$-C$_6$alkylN(R4)C(O)R8, R8-C(=NR3)-, —$SO_2R8$, —$C(O)R8$, —$(CH_2)_nG1$, —$(CH_2)_nG4$, —$(CH_2)_qO(CH_2)_nG1$, —$(CH_2)_qO(CH_2)_nG4$, —$(CH_2)_qN(R3)(CH_2)_nG1$, —$(CH_2)_qN(R3)(CH_2)_nG4$, —$(CH_2)_qNHC(O)(CH_2)_nR5$, —$(CH_2)_qC(O)NH(CH_2)_qR_5$, —$(CH_2)_qC(O)R5$, —$(CH_2)_qOC(O)R5$, —$(CH_2)_qR5$, —$(CH_2)_qNR4(CH_2)_qR5$, and —$(CH_2)_qO(CH_2)_qR5$;

in the event that Z4 contains an alkyl or alkylene moiety, such moieties may be further substituted with one or more C1-C6alkyls;

each Z6 is independently and individually selected from the group consisting of H, C1-C6alkyl, branched C3-C7alkyl, hydroxyl, hydroxyC1-C6alkyl, hydroxyC$_2$-C$_6$ branched alkyl, C1-C6alkoxy, C1-C6alkoxyC1-C6alkyl-, C1-C6alkoxyC$_2$-C$_6$ branched alkyl-, C$_2$-C$_6$ branched alkoxy-, C1-C6alkylthio-, $(R3)_2N$—, —$N(R3)C(O)R8$, $(R4)_2N$—, —R5, —$N(R4)C(O)R8$, —$N(R3)SO_2R6$, —$C(O)N(R3)_2$, —$C(O)N(R4)_2$, —$C(O)R5$, —$SO_2NH(R4)$, halogen, fluoroC1-C6alkyl wherein the alkyl is fully or partially fluorinated, cyano, fluoroC1-C6alkoxy wherein the alkyl is fully or partially fluorinated, —$O(CH_2)_qN(R4)_2$, —$N(R3)(CH_2)_qN(R4)_2$, —$O(CH_2)_qO$—C1-C6alkyl, —$O(CH_2)_qN(R4)_2$, —$N(R3)(CH_2)_qO$—C1-C6alkyl, —$N(R_3)(CH_2)_qN(R4)_2$, —$O(CH_2)_qR5$, $N(R3)(CH_2)_qR_5$, —$(NR3)_rR17$, —$(O)_rR17$, —$(S)_rR17$, —$(CH_2)_nR17$, —R17, —$(CH_2)_nG1$, —$(CH_2)_nG4$, —$(CH_2)_nO(CH_2)_nG1$, —$(CH_2)_nO(CH_2)_nG4$, —$(CH_2)_nN(R3)(CH_2)_nG1$, and —$(CH_2)_nN(R3)(CH2)_nG4$;

each R2 is selected from the group consisting of Z3-substituted aryl, Z3-substituted G1-, Z3-substituted G4-, C1-C6alkyl, branched C3-C8alkyl, R19 substituted C3-C8cycloalkyl fluoroC1-C6alkyl wherein the alkyl is fully or partially fluorinated, cyano, C1-C6alkoxy, and fluoroC1-C6alkoxy wherein the alkyl group is fully or partially fluorinated;

wherein each R3 is independently and individually selected from the group consisting of H, C1-C6alkyl, branched C3-C7alkyl, C3-C7-carbocyclyl, and Z3-substituted phenyl;

each R4 is independently and individually selected from the group consisting of H, C1-C6alkyl, hydroxyC1-C6alkyl-, dihydroxyC1-C6alkyl-, C1-C6alkoxyC1-C6alkyl-, branched C3-C7alkyl-, branched hydroxyC1-C6alkyl-, branched C1-C6alkoxyC1-C6alkyl-, branched dihydroxyC$_2$-C$_6$alkyl-, —(CH$_2$)$_p$N(R7)$_2$, —(CH$_2$)$_p$R5, —(CH$_2$)$_p$C(O)N(R7)$_2$, —(CH$_2$)$_n$C(O)R5, —(CH$_2$)$_n$C(O)OR3, C3-C7-carbocyclyl, hydroxyl substituted C3-C7-carbocyclyl-, alkoxy substituted C3-C7-carbocyclyl-, dihydroxyl substituted C3-C7-carbocyclyl-, and —(CH$_2$)$_n$R17;

each R5 is independently and individually selected from the group consisting of

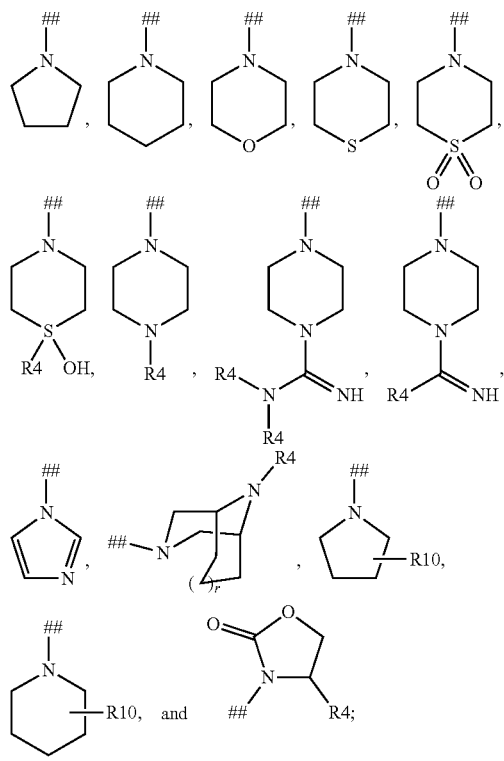

and wherein the symbol (##) is the point of attachment of the R5 moiety;

each R6 is independently and individually selected from the group consisting of C1-C6alkyl, branched C3-C7alkyl, C3-C7-carbocyclyl, phenyl, G1, and G4;

each R7 is independently and individually selected from the group consisting of H, C1-C6alkyl, hydroxyC$_2$-C$_6$alkyl-, dihydroxyC$_2$-C$_6$alkyl-, C$_2$-C$_6$alkoxyC$_2$-C$_6$alkyl-, branched C3-C7alkyl-, branched hydroxyC$_2$-C$_6$alkyl-, branched C$_2$-C$_6$alkoxyC$_2$-C$_6$alkyl-, branched dihydroxyC$_2$-C$_6$alkyl-, —(CH$_2$)$_q$R5, —)CH$_2$)$_n$C(O)R5, —(CH$_2$)$_n$C(O)OR3, C3-C7-carbocyclyl, hydroxyl substituted C3-C7-carbocyclyl-, alkoxy substituted C3-C7-carbocyclyl-, dihydroxy substituted C3-C7-carbocyclyl, and —(CH$_2$)$_n$R17;

each R8 is independently and individually selected from the group consisting of C1-C6alkyl, branched C3-C7alkyl, fluoroC1-C6alkyl wherein the alkyl moiety is partially or fully fluorinated, C3-C7-carbocyclyl, phenyl-, phenylC1-C6alkyl-, G1, G1-C1-C6alkyl-, G4, G4-C1-C6alkyl-, OH, C1-C6alkoxy, N(R3)$_2$, N(R4)$_2$, and R5;

each R9 is independently and individually selected from the group consisting of H, F, C1-C6alkyl, branched C3-C7alkyl, C3-C7-carbocyclyl, phenyl, phenyl-C1-C6alkyl-, —(CH$_2$)$_n$G1, and —(CH$_2$)$_n$G4;

each R10 is independently and individually selected from the group consisting of CO$_2$H, CO$_2$C1-C6alkyl, —C(O)N(R4)$_2$, OH, C1-C6alkoxy, and —N(R4)$_2$;

each R14 is independently and respectively selected from the group consisting of H, C1-C6alkyl, branched C3-C6alkyl, and C3-C7-carbocyclyl;

R16 is independently and individually selected from the group consisting of fluorine and methyl;

each R17 is taken from the group comprising phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, oxetanyl, azetidinyl, tetrahydrofuranyl, oxazolinyl, oxazolidinyl, pyranyl, thiopyranyl, tetrahydropyranyl, dioxalinyl, azepinyl, oxepinyl, and diazepinyl;

wherein R17 can be optionally substituted with an R3 substituent,

R19 is H or C1-C6 alkyl;

n is 0-6, p is 1-4, q is 2-6; r is 0 or 1; t is 1-3, and v is 1 or 2.

Another embodiment provides a method for modulating DUX4 activity in a subject in need thereof comprising administering to the subject in need thereof a composition comprising a compound, or a pharmaceutically acceptable salt thereof, having the structure of Formula (I), and further described by the structure of Formula (II):

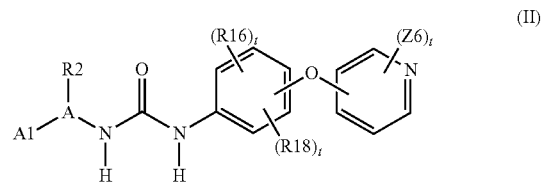

(II)

wherein A is pyrazolyl.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from the group consisting of:

1-(3-tert-butyl-1-(1,2,3,4-tetrahydroisoquinolin-6-yl)-1H-pyrazol-5-yl)-3-(3-fluoro-4-(2-(methylcarbamoyl)pyridin-4-yloxy)phenyl)urea;

1-(3-tert-butyl-1-(quinolin-6-yl)-1H-pyrazol-5-yl)-3-(2-fluoro-4-(2-(methylcarbamoyl)pyridin-4-yloxy)phenyl)urea;

1-(3-tert-butyl-1-(1,2,3,4-tetrahydroisoquinolin-6-yl)-1H-pyrazol-5-yl)-3-(2-fluoro-4-(2-(methylcarbamoyl)pyridin-4-yloxy)phenyl)urea;

1-(3-tert-butyl-1-(quinolin-6-yl)-1H-pyrazol-5-yl)-3-(3-fluoro-4-(2-(methylcarbamoyl)pyridin-4-yloxy)phenyl)urea;

1-(3-tert-butyl-1-(quinolin-6-yl)-1H-pyrazol-5-yl)-3-(2-fluoro-5-(pyridin-3-yloxy)phenyl)urea;

1-(3)-tert-butyl-1-(quinolin-6-yl)-1H-pyrazol-5-yl)-3-(3-methyl-4-(2-(methylcarbamoyl)pyridin-4-yloxy)phenyl)urea;
1-(3-tert-butyl-1-(quinolin-6-yl)-1H-pyrazol-5-yl)-3-(4-(2-carbamoylpyridin-4-yloxy)-2-fluorophenyl)urea;
1-(3-tert-butyl-1-(quinolin-6-yl)-1H-pyrazol-5-yl)-3-(3-fluoro-4-(2-(methylamino)pyridin-4-yloxy)phenyl)urea;
1-(2-fluoro-4-(2-(methylcarbamoyl)pyridin-4-yloxy)phenyl)-3-(3-isopropyl-1-(quinolin-6-yl)-1H-pyrazol-5-yl)urea;
1-(3-ethyl-1-(quinolin-6-yl)-1H-pyrazol-5-yl)-3-(2-fluoro-4-(2-(methylcarbamoyl)pyridin-4-yloxy)phenyl)urea;
1-(3-cyclopentyl-1-(quinolin-6-yl)-1H-pyrazol-5-yl)-3-(2-fluoro-4-(2-(methylcarbamoyl)pyridin-4-yloxy)phenyl)urea;
1-(3-tert-butyl-1-(quinolin-6-yl)-1H-pyrazol-5-yl)-3-(2-fluoro-5-(6-(hydroxymethyl)pyridin-3-yloxy)phenyl)urea;
1-(3-tert-butyl-1-(1,2,3,4-tetrahydroisoquinolin-6-yl)-1H-pyrazol-5-yl)-3-(4-methyl-3-(pyridin-3-yloxy)phenyl)urea;
1-(4-(2-carbamoylpyridin-4-yloxy)-2-fluorophenyl)-3-(3-isopropyl-1-(quinolin-6-yl)-1H-pyrazol-5-yl)urea;
1-(3-isopropyl-1-(quinolin-6-yl)-1H-pyrazol-5-yl)-3-(3-methyl-4-(2-(methylcarbamoyl)pyridin-4-yloxy)phenyl)urea; 1-(4-(2-carbamoylpyridin-4-yloxy)-2-fluorophenyl)-3-(3-ethyl-1-(quinolin-6-yl)-1H-pyrazol-5-yl)urea;
1-(3-tert-butyl-1-(quinolin-6-yl)-1H-pyrazol-5-yl)-3-(2-fluoro-5-(6-(methylcarbamoyl)pyridin-3-yloxy)phenyl)urea;
1-(4-(2-carbamoylpyridin-4-yloxy)-3-methylphenyl)-3-(3-isopropyl-1-(quinolin-6-yl)-1H-pyrazol-5-yl)urea;
1-(2-fluoro-4-(2-(1-methyl-1H-pyrazol-4-yl)pyridin-4-yloxy)phenyl)-3-(3-isopropyl-1-(quinolin-6-yl)-1H-pyrazol-5-yl)urea;
1-(3-ethyl-1-(quinolin-6-yl)-1H-pyrazol-5-yl)-3-(2-fluoro-4-(2-(1-methyl-1H-pyrazol-4-yl)pyridin-4-yloxy)phenyl)urea;
1-(4-(2-(1H-pyrazol-4-yl)pyridin-4-yloxy)-3-methylphenyl)-3-(3-isopropyl-1-(quinolin-6-yl)-1H-pyrazol-5-yl)urea;
1-(3-tert-butyl-1-(1,2,3,4-tetrahydroisoquinolin-6-yl)-1H-pyrazol-5-yl)-3-(2-fluoro-4-(2-(1-methyl-1H-pyrazol-4-yl)pyridin-4-yloxy)phenyl)urea;
1-(4-(2-(1H-pyrazol-4-yl)pyridin-4-yloxy)-2-fluorophenyl)-3-(3-tert-butyl-1-(1,2,3,4-tetrahydroisoquinolin-6-yl)-1H-pyrazol-5-yl)urea;
1-(4-(2-(1H-pyrazol-4-yl)pyridin-4-yloxy)-2-fluorophenyl)-3-(3-tert-butyl-1-(1,2,3,4-tetrahydroisoquinolin-7-yl)-1H-pyrazol-5-yl)urea;
1-(3-fluoro-4-(2-(isopropylamino)pyridin-4-yloxy)phenyl)-3-(3-isopropyl-1-(quinolin-6-yl)-1H-pyrazol-5-yl)urea;
1-(3-isopropyl-1-(quinolin-6-yl)-1H-pyrazol-5-yl)-3-(4-(2-(isopropylamino)pyridin-4-yloxy)-3-methylphenyl)urea;
1-(3-ethyl-1-(quinolin-6-yl)-1H-pyrazol-5-yl)-3-(2-fluoro-3-methyl-4-(2-(1-methyl-1H-pyrazol-4-yl)pyridin-4-yloxy)phenyl)urea, and
1-(2,3-difluoro-4-(2-(1-methyl-1H-pyrazol-4-yl)pyridin-4-yloxy)phenyl)-3-(3-ethyl-1-(quinolin-6-yl)-1H-pyrazol-5-yl)urea.

In some embodiments, this disclosure provides a method for modulating DUX4 activity (e.g., directly or vicariously) in a subject in need thereof comprising administering to the subject in need thereof a composition comprising 1-(3-tert-butyl-1-(quinolin-6-yl)-1H-pyrazol-5-yl)-3-(2-fluoro-4-(2-(methylcarbamoyl)pyridin-4-yloxy)phenyl)urea, or a pharmaceutically acceptable salt thereof.

In some embodiments, this disclosure provides a method for modulating DUX4 activity in a subject (e.g., directly or vicariously) in need thereof comprising administering to the subject in need thereof a composition comprising a compound, or a pharmaceutically acceptable salt thereof, selected from a compound provided in FIG. 1.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 2.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 3.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 4.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 5. Another embodiment provides the method for modulating DUX4 activity wherein the modulation of DUX4 activity is inhibition of DUX4 activity.

In some embodiments, this disclosure provides a method for treating a muscular degenerative disorder in a subject in need thereof comprising administering to the subject in need thereof a composition comprising a compound, or a pharmaceutically acceptable salt thereof, having the structure of Formula (I):

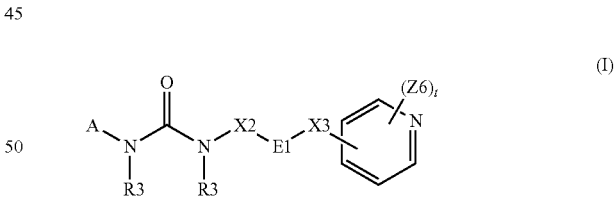

wherein E1 is phenyl, and wherein the E1 ring is substituted with one to three $R^{16}$ moieties;
wherein A is selected from the group consisting of imidazolyl, and pyrazolyl;
G1 is a heteroaryl taken from the group consisting of pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl,
G4 is a heterocyclyl taken from the group consisting of oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl;

A ring is substituted at any substitutable position with one A1 moiety, wherein A1 is selected from the group consisting of:

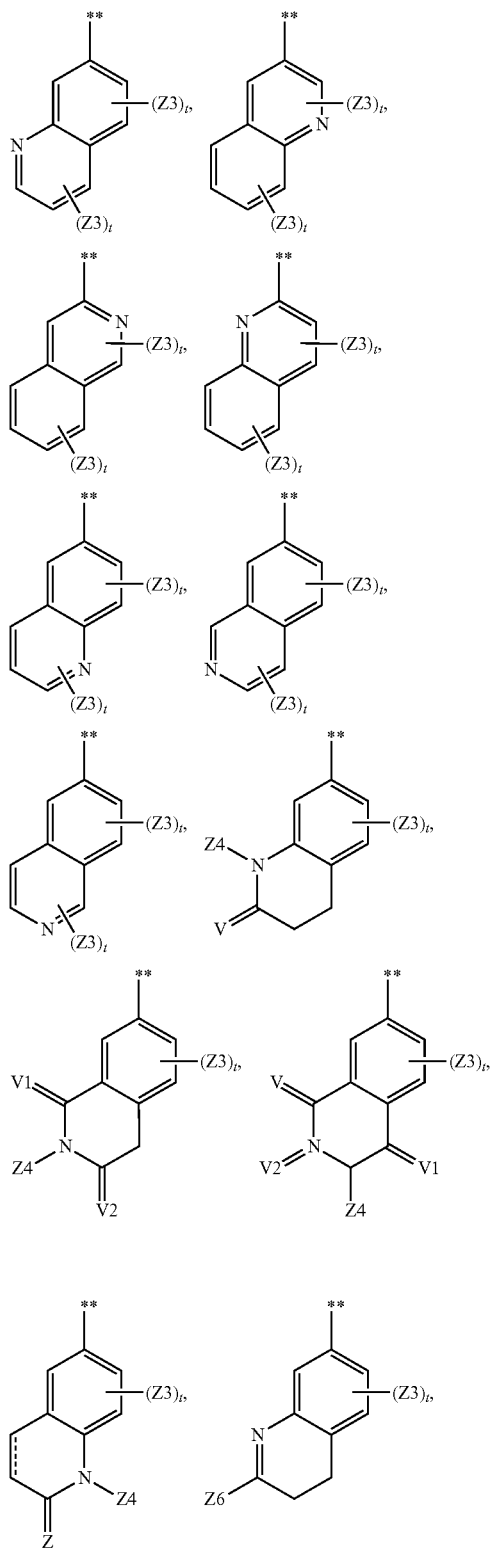
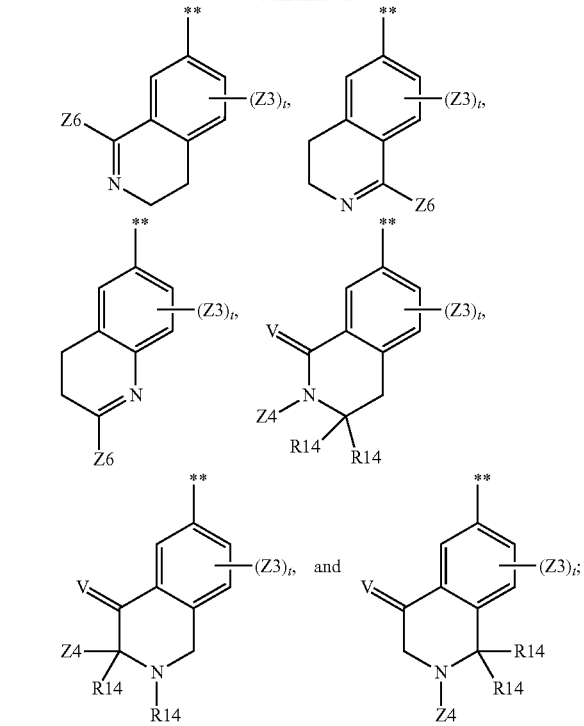

and wherein the symbol (**) is the point of attachment to the A ring of formula I,
and wherein ---- indicates either a saturated or unsaturated bond;
the A ring is optionally substituted with one or more R2 moieties;
X2 is a direct bond wherein E1 is directly linked to the NR3 group of formula I;
X3 is —O—;
V, V1, and V2 are each independently O or represent two hydrogens attached to the methylene carbon to which the V, V1, or V2 is attached,
each Z3 is independently and individually selected from the group consisting of H, C1-C6alkyl, branched C3-C7alkyl, C3-C8carbocyclyl, halogen, fluoroC1-C6alkyl wherein the alkyl moiety can be partially or fully fluorinated, cyano, hydroxyl, methoxy, oxo, (R3)$_2$NC(O)—, (R4)$_2$NC(O)—, —N(R4)C(O)R8, (R3)$_2$NSO$_2$—, (R4)$_2$NSO$_2$—, —N(R4)SO$_2$R$_5$, —N(R4)SO$_2$R8, —(CH$_2$)N(R3)$_2$, —(CH$_2$)$_q$N(R4)$_2$, —O(CH$_2$)$_q$N(R4)$_2$, —O(CH$_2$)$_q$O—C1-C6alkyl, —N(R3)(CH2)$_q$O—C1-C6alkyl, —N(R3)(CH$_2$)$_q$N(R4)$_2$, —O(CH2)$_q$R5, —N(R3)(CH$_2$)$_q$R5, —C(O)R5, —C(O)R8, and nitro;
in the event that Z3 contains an alkyl or alkylene moiety, such moieties may be further substituted with one or more C1-C6alkyls;
each Z4 is independently and individually selected from the group consisting of H, C1-C6alkyl, hydroxyC$_2$-C$_6$alkyl, C1-C6alkoxyC$_2$-C$_6$alkyl, (R4)$_2$N—C$_2$-C$_6$alkyl, (R4)$_2$N—C$_2$-C6alkylN(R4)-C$_2$-C$_6$alkyl, (R4)$_2$N—C$_2$-C$_6$alkyl-O—C$_2$-C$_6$alkyl, (R4)$_2$NC(O)—C1-C6alkyl, carboxyC1-C6alkyl-, C1-C6alkoxycarbonylC1-C6alkyl-, —C$_2$-C$_6$alkylN(R4)C(O)R8, R8-C(=NR3)-, —SO$_2$R8, —C(O)R8, —(CH$_2$)$_n$G1, —(CH$_2$)$_n$G4, —(CH$_2$)$_q$O(CH$_2$)$_n$G1, —(CH$_2$)$_q$O(CH$_2$)$_n$G4, —(CH$_2$)$_q$N(R3)(CH$_2$)$_n$G1, —(CH$_2$)$_q$N(R3)(CH$_2$)$_n$G4, —(CH$_2$)$_q$NHC(O)(CH$_2$)$_n$R5, —(CH$_2$)$_q$C(O)NH(CH$_2$)$_q$R5, —(CH$_2$)$_q$C(O)R5, —(CH$_2$)$_q$OC(O)R5, —(CH$_2$)$_q$R5, —(CH$_2$)$_q$NR4(CH$_2$)$_q$R5, and —(CH$_2$)$_q$O(CH$_2$)$_q$R5;

in the event that Z4 contains an alkyl or alkylene moiety, such moieties may be further substituted with one or more C1-C6alkyls;

each Z6 is independently and individually selected from the group consisting of H, C1-C6alkyl, branched C3-C7alkyl, hydroxyl, hydroxyC1-C6alkyl, hydroxyC$_2$-C$_6$ branched alkyl, C1-C6alkoxy, C1-C6alkoxyC1-C6alkyl-, C1-C6alkoxyC$_2$-C$_6$ branched alkyl-, C$_2$-C$_6$ branched alkoxy-, C1-C6alkylthio-, (R3)$_2$N—, —N(R3)C(O)R8, (R4)$_2$N—, —R5, —N(R4)C(O)R8, —N(R3)SO$_2$R6, —C(O)N(R3)$_2$, —C(O)N(R4)$_2$, —C(O)R5, —SO$_2$NH(R4), halogen, fluoroC1-C6alkyl wherein the alkyl is fully or partially fluorinated, cyano, fluoroC1-C6alkoxy wherein the alkyl is fully or partially fluorinated, —O(CH$_2$)$_q$N(R4)$_2$, —N(R3)(CH$_2$)$_q$N(R4)$_2$, —O(CH$_2$)$_q$O—C1-C6alkyl, —O(CH$_2$)$_q$N(R4)$_2$, —N(R3)(CH$_2$)$_q$O—C1-C6alkyl, —N(R$_3$)(CH$_2$)$_q$N(R4)$_2$, —O(CH$_2$)$_q$R5, N(R3)(CH$_2$)$_q$R$_5$, —(NR3)$_r$R17, —(O)$_r$R17, —(S)$_r$R17, —(CH$_2$)$_n$R17, —R17, —(CH$_2$)$_n$G1, —(CH$_2$)$_n$G4, —(CH$_2$)$_n$O(CH$_2$)$_n$G1, —(CH$_2$)$_n$O(CH$_2$)$_n$G4, —(CH$_2$)$_n$N(R3)(CH$_2$)$_n$G1, and —(CH$_2$)$_n$N(R3)(CH2)$_n$G4;

each R2 is selected from the group consisting of Z3-substituted aryl, Z3-substituted G1-, Z3-substituted G4-, C1-C6alkyl, branched C3-C8alkyl, R19 substituted C3-C8cycloalkyl fluoroC1-C6alkyl wherein the alkyl is fully or partially fluorinated, cyano, C1-C6alkoxy, and fluoroC1-C6alkoxy wherein the alkyl group is fully or partially fluorinated;

wherein each R3 is independently and individually selected from the group consisting of H, C1-C6alkyl, branched C3-C7alkyl, C3-C7-carbocyclyl, and Z3-substituted phenyl;

each R4 is independently and individually selected from the group consisting of H, C1-C6alkyl, hydroxyC1-C6alkyl-, dihydroxyC1-C6alkyl-, C1-C6alkoxyC1-C6alkyl-, branched C3-C7alkyl-, branched hydroxyC1-C6alkyl-, branched C1-C6alkoxyC1-C6alkyl-, branched dihydroxyC$_2$-C$_6$alkyl-, —(CH$_2$)$_p$N(R7)$_2$, —(CH$_2$)$_p$R5, —(CH$_2$)$_p$C(O)N(R7)$_2$, —(CH$_2$)$_n$C(O)R5, —(CH$_2$)$_n$C(O)OR3, C3-C7-carbocyclyl, hydroxyl substituted C3-C7, alkoxy substituted C3-C7-carbocyclyl-, dihydroxyl substituted C3-C7-carbocyclyl-, and —(CH$_2$)$_n$R17;

each R5 is independently and individually selected from the group consisting of

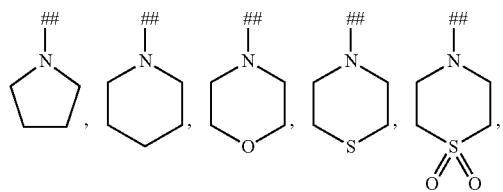

and wherein the symbol (##) is the point of attachment of the R5 moiety;

each R6 is independently and individually selected from the group consisting of C1-C6alkyl, branched C3-C7alkyl, C3-C7-carbocyclyl, phenyl, G1, and G4;

each R7 is independently and individually selected from the group consisting of H, C1-C6alkyl, hydroxyC$_2$-C$_6$alkyl-, dihydroxyC$_2$-C$_6$alkyl-, C$_2$-C$_6$alkoxyC$_2$-C$_6$alkyl-, branched C3-C7alkyl-, branched hydroxyC$_2$-C$_6$ alkyl-, branched C$_2$-C$_6$alkoxyC$_2$-C$_6$alkyl-, branched dihydroxyC$_2$-C$_6$alkyl-, —(CH$_2$)$_q$R5, —(CH$_2$)$_n$C(O)R5, —(CH$_2$)$_n$C(O)OR3, C3-C7-carbocyclyl, hydroxyl substituted C3-C7-carbocyclyl-, alkoxy substituted C3-C7-carbocyclyl-, dihydroxy substituted C3-C7-carbocyclyl, and —(CH$_2$)$_n$R17;

each R8 is independently and individually selected from the group consisting of C1-C6alkyl, branched C3-C7alkyl, fluoroC1-C6alkyl wherein the alkyl moiety is partially or fully fluorinated, C3-C7-carbocyclyl, phenyl-, phenylC1-C6alkyl-, G1, G1-C1-C6alkyl-, G4, G4-C1-C6alkyl-, OH, C1-C6alkoxy, N(R3)$_2$, N(R4)$_2$, and R5;

each R9 is independently and individually selected from the group consisting of H, F, C1-C6alkyl, branched C3-C7alkyl, C3-C7-carbocyclyl, phenyl, phenyl-C1-C6alkyl-, —(CH$_2$)$_n$G1, and —(CH$_2$)$_n$G4;

each R10 is independently and individually selected from the group consisting of CO$_2$H, CO$_2$C1-C6alkyl, —C(O)N(R4)$_2$, OH, C1-C6alkoxy, and —N(R4)$_2$;

each R14 is independently and respectively selected from the group consisting of H, C1-C6alkyl, branched C3-C6alkyl, and C3-C7-carbocyclyl;

R16 is independently and individually selected from the group consisting of fluorine and methyl;

each R17 is taken from the group comprising phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, oxetanyl, azetidinyl, tetrahydrofuranyl, oxazolinyl, oxazolidinyl, pyranyl, thiopyranyl, tetrahydropyranyl, dioxalinyl, azepinyl, oxepinyl, and diazepinyl;

wherein R17 can be optionally substituted with an R3 substituent,
R19 is H or C1-C6 alkyl;
n is 0-6, p is 1-4, q is 2-6; r is 0 or 1; t is 1-3, and v is 1 or 2.

Another embodiment provides a method for treating a muscular degenerative disorder in a subject in need thereof comprising administering to the subject in need thereof a composition comprising a compound, or a pharmaceutically acceptable salt thereof, having the structure of Formula (I), and further described by the structure of Formula (II):

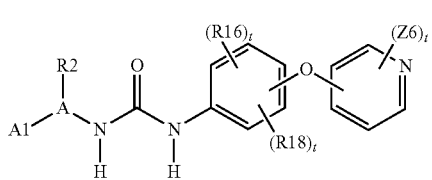

wherein A is pyrazolyl.

In some embodiments, this disclosure provides a method for treating a muscular degenerative disorder in a subject in need thereof comprising administering to the subject in need thereof a composition comprising a compound, or a pharmaceutically acceptable salt thereof, selected from the group consisting of:
  1-(3-tert-butyl-1-(1,2,3,4-tetrahydroisoquinolin-6-yl)-1H-pyrazol-5-yl)-3-(3-fluoro-4-(2-(methylcarbamoyl)pyridin-4-yloxy)phenyl)urea;
  1-(3-tert-butyl-1-(quinolin-6-yl)-1H-pyrazol-5-yl)-3-(2-fluoro-4-(2-(methylcarbamoyl)pyridin-4-yloxy)phenyl)urea;
  1-(3-tert-butyl-1-(1,2,3,4-tetrahydroisoquinolin-6-yl)-1H-pyrazol-5-yl)-3-(2-fluoro-4-(2-(methylcarbamoyl)pyridin-4-yloxy)phenyl)urea;
  1-(3-tert-butyl-1-(quinolin-6-yl)-1H-pyrazol-5-yl)-3-(3-fluoro-4-(2-(methylcarbamoyl)pyridin-4-yloxy)phenyl)urea;
  1-(3-tert-butyl-1-(quinolin-6-yl)-1H-pyrazol-5-yl)-3-(2-fluoro-5-(pyridin-3-yloxy)phenyl)urea;
  1-(3)-tert-butyl-1-(quinolin-6-yl)-1H-pyrazol-5-yl)-3-(3-methyl-4-(2-(methylcarbamoyl)pyridin-4-yloxy)phenyl)urea;
  1-(3-tert-butyl-1-(quinolin-6-yl)-1H-pyrazol-5-yl)-3-(4-(2-carbamoylpyridin-4-yloxy)-2-fluorophenyl)urea;
  1-(3-tert-butyl-1-(quinolin-6-yl)-1H-pyrazol-5-yl)-3-(2-fluoro-4-(2-(methylamino)pyridin-4-yloxy)phenyl)urea;
  1-(2-fluoro-4-(2-(methylcarbamoyl)pyridin-4-yloxy)phenyl)-3-(3-isopropyl-1-(quinolin-6-yl)-1H-pyrazol-5-yl)urea;
  1-(3-ethyl-1-(quinolin-6-yl)-1H-pyrazol-5-yl)-3-(2-fluoro-4-(2-(methylcarbamoyl)pyridin-4-yloxy)phenyl)urea;
  1-(3-cyclopentyl-1-(quinolin-6-yl)-1H-pyrazol-5-yl)-3-(2-fluoro-4-(2-(methylcarbamoyl)pyridin-4-yloxy)phenyl)urea;
  1-(3-tert-butyl-1-(quinolin-6-yl)-1H-pyrazol-5-yl)-3-(2-fluoro-5-(6-(hydroxymethyl)pyridin-3-yloxy)phenyl)urea;
  1-(3-tert-butyl-1-(1,2,3,4-tetrahydroisoquinolin-6-yl)-1H-pyrazol-5-yl)-3-(4-methyl-3-(pyridin-3-yloxy)phenyl)urea;
  1-(4-(2-carbamoylpyridin-4-yloxy)-2-fluorophenyl)-3-(3-isopropyl-1-(quinolin-6-yl)-1H-pyrazol-5-yl)urea;
  1-(3-isopropyl-1-(quinolin-6-yl)-1H-pyrazol-5-yl)-3-(3-methyl-4-(2-(methylcarbamoyl)pyridin-4-yloxy)phenyl)urea; 1-(4-(2-carbamoylpyridin-4-yloxy)-2-fluorophenyl)-3-(3-ethyl-1-(quinolin-6-yl)-1H-pyrazol-5-yl)urea;
  1-(3-tert-butyl-1-(quinolin-6-yl)-1H-pyrazol-5-yl)-3-(2-fluoro-5-(6-(methylcarbamoyl)pyridin-3-yloxy)phenyl)urea;
  1-(4-(2-carbamoylpyridin-4-yloxy)-3-methylphenyl)-3-(3-isopropyl-1-(quinolin-6-yl)-1H-pyrazol-5-yl)urea;
  1-(2-fluoro-4-(2-(1-methyl-1H-pyrazol-4-yl)pyridin-4-yloxy)phenyl)-3-(3-isopropyl-1-(quinolin-6-yl)-1H-pyrazol-5-yl)urea;
  1-(3-ethyl-1-(quinolin-6-yl)-1H-pyrazol-5-yl)-3-(2-fluoro-4-(2-(1-methyl-1H-pyrazol-4-yl)pyridin-4-yloxy)phenyl)urea;
  1-(4-(2-(1H-pyrazol-4-yl)pyridin-4-yloxy)-3-methylphenyl)-3-(3-isopropyl-1-(quinolin-6-yl)-1H-pyrazol-5-yl)urea;
  1-(3-tert-butyl-1-(1,2,3,4-tetrahydroisoquinolin-6-yl)-1H-pyrazol-5-yl)-3-(2-fluoro-4-(2-(1-methyl-1H-pyrazol-4-yl)pyridin-4-yloxy)phenyl)urea;
  1-(4-(2-(1H-pyrazol-4-yl)pyridin-4-yloxy)-2-fluorophenyl)-3-(3-tert-butyl-1-(1,2,3,4-tetrahydroisoquinolin-6-yl)-1H-pyrazol-5-yl)urea;
  1-(4-(2-(1H-pyrazol-4-yl)pyridin-4-yloxy)-2-fluorophenyl)-3-(3-tert-butyl-1-(1,2,3,4-tetrahydroisoquinolin-7-yl)-1H-pyrazol-5-yl)urea;
  1-(3-fluoro-4-(2-(isopropylamino)pyridin-4-yloxy)phenyl)-3-(3-isopropyl-1-(quinolin-6-yl)-1H-pyrazol-5-yl)urea;
  1-(3-isopropyl-1-(quinolin-6-yl)-1H-pyrazol-5-yl)-3-(4-(2-(isopropylamino)pyridin-4-yloxy)-3-methylphenyl)urea;
  1-(3-ethyl-1-(quinolin-6-yl)-1H-pyrazol-5-yl)-3-(2-fluoro-3-methyl-4-(2-(1-methyl-1H-pyrazol-4-yl)pyridin-4-yloxy)phenyl)urea, and
  1-(2,3-difluoro-4-(2-(1-methyl-1H-pyrazol-4-yl)pyridin-4-yloxy)phenyl)-3-(3-ethyl-1-(quinolin-6-yl)-1H-pyrazol-5-yl)urea.

In some embodiments, this disclosure provides a method for treating a muscular degenerative disorder in a subject in need thereof comprising administering to the subject in need thereof a composition comprising 1-(3-tert-butyl-1-(quinolin-6-yl)-1H-pyrazol-5-yl)-3-(2-fluoro-4-(2-(methylcarbamoyl)pyridin-4-yloxy)phenyl)urea, or a pharmaceutically acceptable salt thereof.

In some embodiments, this disclosure provides a method of treating a muscular degenerative disorder in a subject in need thereof, comprising administering to the subject in need thereof a therapeutically effective amount of a compound selected from the compounds provided in FIG. 1.

In some embodiments, this disclosure provides a method of treating a muscular degenerative disorder in a subject in need thereof, comprising administering to the subject in need thereof a therapeutically effective amount of a compound selected from the compounds provided in FIG. 2.

In some embodiments, this disclosure provides a method of treating a muscular degenerative disorder in a subject in need thereof, comprising administering to the subject in need thereof a therapeutically effective amount of a compound selected from the compounds provided in FIG. 3.

In some embodiments, this disclosure provides a method of treating a muscular degenerative disorder in a subject in need thereof, comprising administering to the subject in need thereof a therapeutically effective amount of a compound selected from the compounds provided in FIG. 4.

In some embodiments, this disclosure provides a method of treating a muscular degenerative disorder in a subject in need thereof, comprising administering to the subject in need thereof a therapeutically effective amount of a compound selected from the compounds provided in FIG. 5.

Another embodiment proves the method of treating a muscular degenerative disorder wherein the muscular degenerative disorder is selected from facioscapulohumeral muscular dystrophy (FSHD), facioscapulohumeral muscular dystrophy-1 (FSHD1), facioscapulohumeral muscular dystrophy-2 (FSHD2), Becker muscular dystrophy, Duchenne muscular dystrophy, myotonic dystrophies type 1, myotonic dystrophies types 2, nemaline myopathy or spinal muscular atrophy. Another embodiment proves the method wherein the subject is a human.

In some embodiments, this disclosure provides a method for modulating DUX4 activity in a subject in need thereof comprising administering to the subject in need thereof a composition comprising a compound, or a pharmaceutically acceptable salt thereof, having the structure of Formula (III):

Formula (III)

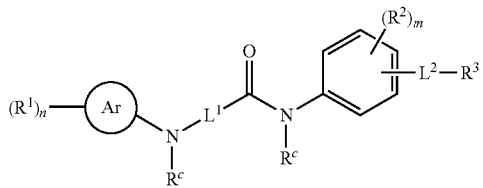

wherein
Ar is phenyl or 5- or 6-membered heteroaryl;
each $R^1$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;
n is 0-5;
$L^1$ is absent or *—(CR$^a$R$^b$)—C(=O)—, wherein * denotes attachment point to the carbonyl carbon;
$R^a$ and $R^b$ are independently selected from hydrogen, $C_1$-$C_6$alkyl, or $C_1$-$C_6$ haloalkyl;
or $R^a$ and $R^b$ are taken together with the carbon to which they are attached to form a 3-, 4-, 5-, or 6-membered cycloalkyl or a 3-, 4-, 5-, or 6-membered heterocycloalkyl;
each $R^2$ is independently hydrogen, halogen, —CN, —OH, —OR$^{20}$, —NR$^{21}$R$^{21}$, —C(=O)R$^{20}$, —OC(=O)R$^{20}$, —C(=O)OR$^{21}$, —C(=O)NR$^{21}$R$^{21}$, —NR$^{21}$C(=O)R$^{20}$, $C_1$-$C_6$ alkyl, or $C_1$-$C_6$ haloalkyl;
or two $R^2$ on adjacent atoms are taken together with the atoms to which they are attached to form an unsubstituted or substituted cycloalkyl, unsubstituted or substituted heterocycloalkyl, unsubstituted or substituted aryl, or unsubstituted or substituted heteroaryl;
m is 0-4;
$L^2$ is absent, —O—, —O—($C_1$-$C_4$ alkylene)-, or —NR$^c$—C(=O)—;
each $R^c$ is independently selected from hydrogen, $C_1$-$C_6$ alkyl, or $C_1$-$C_6$ haloalkyl;
$R^3$ is unsubstituted or substituted cycloalkyl, unsubstituted or substituted heterocycloalkyl, unsubstituted or substituted aryl, or unsubstituted or substituted heteroaryl; wherein when $R^3$ is substituted, it is substituted by 1-3 $R^4$;
each $R^4$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;
each $R^{20}$ is independently selected from unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;
each $R^{21}$ is independently selected from hydrogen, unsubstituted or substituted $C_1$-$C_6$alkyl, unsubstituted or substituted $C_1$-$C_6$alkenyl, unsubstituted or substituted $C_1$-$C_6$alkynyl, unsubstituted or substituted cycloalkyl, unsubstituted or substituted heterocycloalkyl, unsubstituted or substituted aryl, or unsubstituted or substituted heteroaryl;
or two $R^{21}$ on the same N atom are taken together with the N atom to which they are attached to form an unsubstituted or substituted N-containing heterocycle;
wherein when any $R^1$, $R^2$, $R^4$, $R^{20}$, or $R^{21}$ is substituted, substituents on the $R^1$, $R^2$, $R^4$, $R^{20}$, or $R^{21}$ are independently selected at each occurrence from halogen, —CN, —NO$_2$, —OR$^{22}$, —CO$_2$R$^{22}$, —C(=O)R$^{23}$, —C(=O)NR$^{22}$R$^{22}$, —NR$^{22}$R$^{22}$, —NR$^{22}$C(=O)R$^{23}$, —NR$^{22}$C(=O)OR$^{22}$, —SR$^{22}$, —S(=O)R$^{23}$, —SO$_2$R$^{23}$, —SO$_2$NR$^{22}$NR$^{22}$, $C_1$-$C_6$ alkyl, $C_1$-$C_6$ haloalkyl, monocyclic cycloalkyl, monocyclic heterocycloalkyl, phenyl, benzyl, 5-membered heteroaryl, and 6-membered heteroaryl; or two substituents on the same carbon atom are taken together to form a C=O or C=S;
each $R^{22}$ is independently selected from hydrogen, $C_1$-$C_6$ alkyl, $C_3$-$C_6$ cycloalkyl, phenyl, benzyl, 5-membered heteroaryl, and 6-membered heteroaryl;
or two $R^{22}$ groups are taken together with the N atom to which they are attached to form a N-containing heterocycle; and
each $R^{23}$ is independently selected from $C_1$-$C_6$alkyl, $C_3$-$C_6$ cycloalkyl, phenyl, benzyl, 5-membered heteroaryl, and 6-membered heteroaryl.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, having the structure of Formula (IV):

Formula (IV)

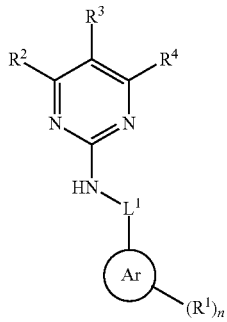

wherein
- L is absent or —$C_1$-$C_4$ alkylene;
- Ar is phenyl or 5- or 6-membered heteroaryl;
- each $R^1$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;
- or two $R^1$ on adjacent atoms are taken together with the atoms to which they are attached to form a unsubstituted or substituted carbocycle, or unsubstituted or substituted heterocycle; wherein if the carbocycle or heterocycle is substituted, it is substituted with 1-3 $R^7$;
- each $R^7$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{10}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;
- n is 0-5;
- $R^2$ and $R^4$ are each independently hydrogen, or —NR$^5$R$^6$, or unsubstituted or substituted heterocycle;
  - each $R^5$ and $R^6$ is independently hydrogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;
  - or $R^5$ and $R^6$ are taken together with the N atom to which they are attached to form an unsubstituted or substituted N-containing heterocycle;
- $R^3$ is hydrogen, halogen, $C_1$-$C_6$ alkyl or $C_1$-$C_6$ haloalkyl;
- or $R^2$ and $R^3$ are taken together with the atoms to which they are attached to form a unsubstituted or substituted carbocycle, or unsubstituted or substituted heterocycle; wherein if the carbocycle or heterocycle is substituted, it is substituted with 1-3 $R^8$;
  - each $R^8$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;
- or two $R^7$ on the same carbon atom are taken together to form a C=O, or C=S;
- each $R^{20}$ is independently selected from unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;
- each $R^{21}$ is independently selected from hydrogen, unsubstituted or substituted $C_1$-$C_6$alkyl, unsubstituted or substituted $C_1$-$C_6$alkenyl, unsubstituted or substituted $C_1$-$C_6$ alkynyl, unsubstituted or substituted cycloalkyl, unsubstituted or substituted heterocycloalkyl, unsubstituted or substituted aryl, or unsubstituted or substituted heteroaryl;
- or two $R^{21}$ on the same N atom are taken together with the N atom to which they are attached to form an unsubstituted or substituted N-containing heterocycle;
- wherein when any $R^1$, $R^2$, $R^4$, $R^5$, $R^6$, $R^7$, $R^{20}$, or $R^{21}$ is substituted, substituents on the $R^1$, $R^2$, $R^4$, $R^5$, $R^6$, $R^7$, $R^{20}$, or $R^{21}$are independently selected at each occurrence from halogen, —CN, —NO$_2$, —OR$^{22}$, —CO$_2$R$^{22}$, —C(=O)R$^{23}$, —C(=O)NR$^{22}$R$^{22}$, —NR$^{22}$R$^{22}$, —NR$^{22}$C(=O)R$^{23}$, —NR$^{22}$C(=O)OR$^{22}$, —SR$^{22}$, —S(=O)R$^{23}$, —SO$_2$R$^{23}$, —SO$_2$NR$^{22}$R$^{22}$, —NR$^{22}$SO$_2$R$^{23}$, $C_1$-$C_6$ alkyl, $C_1$-$C_6$ haloalkyl, monocyclic cycloalkyl, monocyclic heterocycloalkyl, phenyl, benzyl, 5-membered heteroaryl, and 6-membered heteroaryl; or two substituents on the same carbon atom are taken together to form a C=O or C=S;
  - each $R^{22}$ is independently selected from hydrogen, $C_1$-$C_6$alkyl, $C_1$-$C_6$ hydroxyalkyl, $C_3$-$C_6$ cycloalkyl, phenyl, benzyl, 5-membered heteroaryl, and 6-membered heteroaryl;
  - or two $R^{22}$groups are taken together with the N atom to which they are attached to form a N-containing heterocycle; and each $R^{23}$ is independently selected from $C_1$-$C_6$ alkyl, $C_1$-$C_6$ hydroxyalkyl, $C_1$-$C_6$ alkyl $C_3$-$C_6$ cycloalkyl, phenyl, benzyl, 5-membered heteroaryl, and 6-membered heteroaryl.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, having the structure of Formula (V):

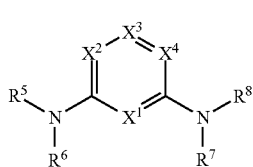

Formula (V)

wherein $X^1$ is N or $CR^1$;

$R^1$ is hydrogen, halogen, $C_1$-$C_6$ alkyl, or $C_1$-$C_6$ haloalkyl;

$X^2$ is N or $CR^2$;

$R^2$ is hydrogen, halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

$X^3$ is N or $CR^3$;

$R^3$ is hydrogen, halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

$X^4$ is N or $CR^4$;

$R^4$ is hydrogen, halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl;

wherein 0, 1, or 2 of $X^1$, $X^2$, $X^3$, and $X^4$ are N;

$R^5$ is hydrogen, unsubstituted or substituted aryl, or unsubstituted or substituted heteroaryl;

wherein if $R^5$ is substituted, it is substituted with 1-3 $R^9$;

each $R^9$ is independently halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl;

$R^6$ is hydrogen, $C_1$-$C_6$ alkyl or $C_1$-$C_6$ haloalkyl;

or $R^5$ and $R^6$ are taken together with the N atom to which they are attached to form an unsubstituted or substituted N-containing heterocycle; wherein if the heterocycle is substituted, it is substituted by 1-3 $R^{13}$;

each $R^{13}$ is independently halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

$R^7$ is hydrogen, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, or —$C(=O)R^{11}$;

$R^{11}$ unsubstituted phenyl, or phenyl substituted by 1-3 $R^{12}$, each $R^{12}$ is independently halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —C$_1$-C$_6$-alkylene-aryl, or unsubstituted or substituted —C$_1$-C$_6$-alkylene-heteroaryl;

R$^8$ is hydrogen, C$_1$-C$_6$alkyl or C$_1$-C$_6$ haloalkyl;

or R$^7$ and R$^8$ are taken together with the N atom to which they are attached to form an unsubstituted or substituted N-containing heterocycle; wherein if the heterocycle is substituted, it is substituted by 1-3 R$^{10}$;

each R$^{10}$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

each R$^{20}$ is independently selected from unsubstituted or substituted C$_1$-C$_6$alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, unsubstituted or substituted heteroaryl;

each R$^{21}$ is independently selected from hydrogen, unsubstituted or substituted C$_1$-C$_6$alkyl, unsubstituted or substituted C$_1$-C$_6$alkenyl, unsubstituted or substituted C$_1$-C$_6$alkynyl, unsubstituted or substituted cycloalkyl, unsubstituted or substituted heterocycloalkyl, unsubstituted or substituted aryl, unsubstituted or substituted heteroaryl;

or two R$^{21}$ on the same N atom are taken together with the N atom to which they are attached to form an unsubstituted or substituted N-containing heterocycle;

wherein when any R$^2$, R$^3$, R$^4$, R$^7$, R$^9$, R$^{10}$, R$^{12}$, R$^{13}$, R$^{20}$, or R$^{21}$ is substituted, substituents on the R$^2$, R$^3$, R$^4$, R$^7$, R$^9$, R$^{10}$, R$^{12}$, R$^{13}$, R$^{20}$, or R$^{21}$ are independently selected at each occurrence from halogen, —CN, —NO$_2$, —OR$^{22}$, —CO$_2$R$^{22}$, —C(=O)R$^{23}$, —C(=O)NR$^{22}$R$^{22}$, —C(=O)NR$^{22}$—OR$^{22}$, —NR$^{22}$R$^{22}$, —NR$^{22}$C(=O)R$^{23}$, —NR$^{22}$C(=O)OR$^{22}$, —SR$^{22}$, —S(=O)R$^{23}$, —SO$_2$R$^{23}$, —SO$_2$NR$^{22}$R$^{22}$, C$_1$-C$_6$ alkyl, C$_1$-C$_6$ haloalkyl, monocyclic cycloalkyl, monocyclic heterocycloalkyl, monocyclic heterocycloalkyl substituted with a R$^{23}$, phenyl, benzyl, 5-membered heteroaryl, and 6-membered heteroaryl; or two substituents on the same carbon atom are taken together to form a C=O or C=S;

each R$^{22}$ is independently selected from hydrogen, C$_1$-C$_6$ alkyl, C$_3$-C$_6$ cycloalkyl, phenyl, benzyl, 5-membered heteroaryl, and 6-membered heteroaryl;

or two R$^{22}$ groups are taken together with the N atom to which they are attached to form a N-containing heterocycle; and each R$^{23}$ is independently selected from C$_1$-C$_6$ alkyl, C$_3$-C$_6$ cycloalkyl, phenyl, benzyl, 5-membered heteroaryl, and 6-membered heteroaryl.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, having the structure of Formula (VI):

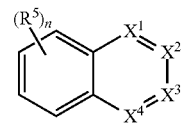

Formula (VI)

wherein:

X$^1$ and X$^2$ are independently N or CH;

X$^3$ is N or CR$^3$;

R$^3$ is hydrogen, —CN, or -L-Ar,

X$^4$ is N or CR$^4$;

R$^4$ is hydrogen, or -L-Ar;

wherein one of X$^3$ and X$^4$ is C-L-Ar;

L is —NH—, —O—, —S—, —C$_1$-C$_2$ alkylene-, or -heterocycloalkylene-C(=O)—;

Ar is substituted or unsubstituted phenyl or substituted or unsubstituted 5- or 6-membered heteroaryl; wherein when Ar is substituted, it is substituted with 1-3 R$^6$;

each R$^6$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$^2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —(C$_1$-C$_4$ alkylene)-C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

or two R$^6$ on adjacent atoms are taken together with the atoms to which they are attached to form an unsubstituted or substituted cycloalkyl, unsubstituted or substituted heterocycloalkyl, unsubstituted or substituted aryl, or unsubstituted or substituted heteroaryl;

each R$^5$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

n is 0-4, each R$^{20}$ is independently selected from unsubstituted or substituted C$_1$-C$_6$alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —C$_1$-C$_6$-alkylene-cycloalkyl, unsubstituted or substituted —C$_1$-C$_6$-alkylene-heterocycloalkyl, unsubstituted or substituted —C$_1$-C$_6$-alkylene-aryl, or unsubstituted or substituted —C$_1$-C$_6$-alkylene-heteroaryl;

each $R^{21}$ is independently selected from hydrogen, unsubstituted or substituted $C_1$-$C_6$ alkyl, unsubstituted or substituted $C_1$-$C_6$ alkenyl, unsubstituted or substituted $C_1$-$C_6$ alkynyl, unsubstituted or substituted cycloalkyl, unsubstituted or substituted heterocycloalkyl, unsubstituted or substituted aryl, or unsubstituted or substituted heteroaryl;

or two $R^{21}$ on the same N atom are taken together with the N atom to which they are attached to form an unsubstituted or substituted N-containing heterocycle;

wherein when any $R^5$, $R^6$, $R^{20}$, or $R^{21}$ is substituted, substituents on the $R^5$, $R^6$, $R^{20}$, or $R^{21}$ are independently selected at each occurrence from halogen, —CN, —NO$_2$, —OR$^{22}$, —CO$_2$R$^{22}$, —C(=O)R$^{23}$, —OC(=O)R$^{23}$, —C(=O)NR$^{22}$R$^{22}$, —NR$^{22}$R$^{22}$, —NR$^{22}$C(=O)R$^{23}$, —NR$^{22}$C(=O)OR$^{22}$, —SR$^{22}$, —S(=O)R$^{23}$, —SO$_2$R$^{23}$, —SO$_2$NR$^{22}$R$^{22}$, $C_1$-$C_6$ alkyl, $C_1$-$C_6$ haloalkyl, monocyclic cycloalkyl, monocyclic heterocycloalkyl, phenyl, benzyl, 5-membered heteroaryl, and 6-membered heteroaryl; or two substituents on the same carbon atom are taken together to form a C=O or C=S;

each $R^{22}$ is independently selected from hydrogen, $C_1$-$C_6$ alkyl, $C_3$-$C_6$ cycloalkyl, phenyl, benzyl, 5-membered heteroaryl, and 6-membered heteroaryl;

or two $R^{22}$ groups are taken together with the N atom to which they are attached to form a N-containing heterocycle; and each $R^{23}$ is independently selected from $C_1$-$C_6$ alkyl, $C_3$-$C_6$ cycloalkyl, phenyl, benzyl, 5-membered heteroaryl, and 6-membered heteroaryl.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, having the structure of Formula (VII):

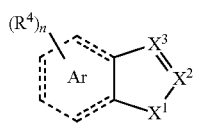

Formula (VII)

wherein:
$X^1$ is —S—, —O—, or —NR$^1$—;
$R^1$ is hydrogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl; wherein when $R^1$ is substituted, it is substituted by 1-3 $R^7$;

each $R^7$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{21}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$alkyl, unsubstituted or substituted cycloalkyl, unsubstituted or substituted heterocycloalkyl, unsubstituted or substituted aryl, or unsubstituted or substituted heteroaryl;

$X^2$ is N or CR$^2$;
$R^2$ is hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl; wherein when $R^2$ is substituted, it is substituted by 1-3 $R^8$;

each $R^8$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$alkyl, unsubstituted or substituted cycloalkyl, unsubstituted or substituted heterocycloalkyl, unsubstituted or substituted aryl, or unsubstituted or substituted heteroaryl;

$X^3$ is N or CR$^3$; wherein $X^2$ and $X^3$ are not both N;
$R^3$ is hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl; wherein when $R^3$ is substituted, it is substituted by 1-3 $R^9$;

each $R^{10}$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)$_2$R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;

Ar is a 6-membered aromatic ring comprising 0-2 nitrogen atoms;
each $R^4$ is independently hydrogen, halogen, —CN, —OH, —OR$^5$, —SH, —SR$^5$, —NO$_2$, —NR$^6$R$^6$, —S(=O)$_2$R$^5$, —NR$^6$S(=O)$_2$R$^5$, —S(=O)R$^5$, —S(=O)$_2$NR$^6$R$^6$, —C(=O)R$^5$, —OC(=O)R$^5$, —C(=O)OR$^6$, —OC(=O)OR$^6$, —C(=O)NR$^6$R$^6$, —OC(=O)NR$^6$R$^6$, —NR$^6$C(=O)NR$^6$R$^6$, —NR$^6$C(=O)R$^5$, —NR$^6$C(=O)OR$^6$, unsubstituted or substituted C$_1$-C$_6$alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —C$_1$-C$_6$-alkylene-cycloalkyl, unsubstituted or substituted —C$_1$-C$_6$-alkylene-heterocycloalkyl, unsubstituted or substituted —C$_1$-C$_6$-alkylene-aryl, or unsubstituted or substituted —C$_1$-C$_6$-alkylene-heteroaryl;

each R$^5$ is independently selected from unsubstituted or substituted C$_1$-C$_6$ alkyl, unsubstituted or substituted C$_2$-C$_6$ alkenyl, unsubstituted or substituted C$_1$-C$_6$ alkynyl, unsubstituted or substituted cycloalkyl, unsubstituted or substituted heterocycloalkyl, unsubstituted or substituted aryl, or unsubstituted or substituted heteroaryl; wherein if R$^5$ is substituted, it is substituted by 1-3 R$^{10}$;

each R$^{10}$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

each R$^6$ is independently selected from hydrogen, unsubstituted or substituted C$_1$-C$_6$ alkyl, unsubstituted or substituted C$_1$-C$_6$ alkenyl, unsubstituted or substituted C$_1$-C$_6$ alkynyl, unsubstituted or substituted cycloalkyl, unsubstituted or substituted heterocycloalkyl, unsubstituted or substituted aryl, or unsubstituted or substituted heteroaryl; wherein if R$^6$ is substituted, it is substituted by 1-3 R$^{11}$;

each R$^{11}$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

n is 0-4, each R$^{20}$ is independently selected from unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —C$_1$-C$_6$-alkylene-cycloalkyl, unsubstituted or substituted —C$_1$-C$_6$-alkylene-heterocycloalkyl, unsubstituted or substituted —C$_1$-C$_6$-alkylene-aryl, or unsubstituted or substituted —C$_1$-C$_6$-alkylene-heteroaryl;

each R$^{21}$ is independently selected from hydrogen, unsubstituted or substituted C$_1$-C$_6$ alkyl, unsubstituted or substituted C$_1$-C$_6$ alkenyl, unsubstituted or substituted C$_1$-C$_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —C$_1$-C$_6$-alkylene-cycloalkyl, unsubstituted or substituted —C$_1$-C$_6$-alkylene-heterocycloalkyl, unsubstituted or substituted —C$_1$-C$_6$-alkylene-aryl, or unsubstituted or substituted —C$_1$-C$_6$-alkylene-heteroaryl;

or two R$^{21}$ on the same N atom are taken together with the N atom to which they are attached to form an unsubstituted or substituted N-containing heterocycle;

wherein when any R$^4$, R$^7$, R$^8$, R$^9$, R$^{10}$, R$^{11}$, R$^{20}$, or R$^{21}$ is substituted, substituents on the R$^4$, R$^7$, R$^8$, R$^9$, R$^{10}$, R$^{11}$, R$^{20}$, or R$^{21}$ are independently selected at each occurrence from halogen, —CN, —NO$_2$, —OR$^{22}$, —CO$_2$R$^{22}$, —C(=O)R$^{23}$, —C(=O)NR$^{22}$R$^{22}$, —NR$^{22}$R$^{22}$, —NR$^{22}$C(=O)R$^{23}$, —NR$^{22}$C(=O)OR$^{22}$, —SR$^{22}$, —S(=O)R$^{23}$, —SO$_2$R$^{23}$, —SO$_2$NR$^{22}$R$^{22}$, C$_1$-C$_6$ alkyl, C$_1$-C$_6$ haloalkyl, C$_1$-C$_6$ hydroxyalkyl, monocyclic cycloalkyl, monocyclic heterocycloalkyl, phenyl, benzyl, benzyl substituted with phenyl, 5-membered heteroaryl, and 6-membered heteroaryl; or two substituents on the same carbon atom are taken together to form a C=O or C=S;

each R$^{22}$ is independently selected from hydrogen, C$_1$-C$_6$ alkyl, C$_3$-C$_6$ cycloalkyl, phenyl. benzyl, 5-membered heteroaryl, and 6-membered heteroaryl;

or two R$^{22}$ groups are taken together with the N atom to which they are attached to form a N-containing heterocycle; and each R$^{23}$ is independently selected from C$_1$-C$_6$ alkyl, C$_1$-C$_6$ cycloalkyl, phenyl, benzyl, 5-membered heteroaryl, and 6-membered heteroaryl.

In some embodiments, this disclosure provides a method for treating a muscular degenerative disorder in a subject in need thereof comprising administering to the subject in need thereof a composition comprising a compound, or a pharmaceutically acceptable salt thereof, having the structure of Formula (III):

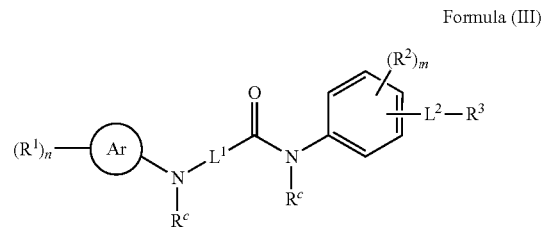

Formula (III)

wherein

Ar is phenyl or 5- or 6-membered heteroaryl;

each R$^1$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;

n is 0-5;

$L^1$ is absent or *—($CR^aR^b$)—C(=O)—, wherein * denotes attachment point to the carbonyl carbon;

$R^a$ and $R^b$ are independently selected from hydrogen, $C_1$-$C_6$alkyl, or $C_1$-$C_6$ haloalkyl;

or $R^a$ and $R^b$ are taken together with the carbon to which they are attached to form a 3-, 4-, 5-, or 6-membered cycloalkyl or a 3-, 4-, 5-, or 6-membered heterocycloalkyl;

each $R^2$ is independently hydrogen, halogen, —CN, —OH, —$OR^{20}$, —$NR^{21}R^{21}$, —$C(=O)R^{20}$, —$OC(=O)R^{20}$, —$C(=O)OR^{21}$, —$C(=O)NR^{21}R^{21}$, —$NR^{21}C(=O)R^{20}$, $C_1$-$C_6$ alkyl, or $C_1$-$C_6$ haloalkyl;

or two $R^2$ on adjacent atoms are taken together with the atoms to which they are attached to form an unsubstituted or substituted cycloalkyl, unsubstituted or substituted heterocycloalkyl, unsubstituted or substituted aryl, or unsubstituted or substituted heteroaryl;

m is 0-4;

$L^2$ is absent, —O—, —O—($C_1$-$C_4$ alkylene)-, or —$NR^c$—C(=O)—;

each $R^c$ is independently selected from hydrogen, $C_1$-$C_6$ alkyl, or $C_1$-$C_6$ haloalkyl;

$R^3$ is unsubstituted or substituted cycloalkyl, unsubstituted or substituted heterocycloalkyl, unsubstituted or substituted aryl, or unsubstituted or substituted heteroaryl; wherein when $R^3$ is substituted, it is substituted by 1-3 $R^4$;

each $R^4$ is independently hydrogen, halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

each $R^{20}$ is independently selected from unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

each $R^{21}$ is independently selected from hydrogen, unsubstituted or substituted $C_1$-$C_6$alkyl, unsubstituted or substituted $C_1$-$C_6$alkenyl, unsubstituted or substituted $C_1$-$C_6$alkynyl, unsubstituted or substituted cycloalkyl, unsubstituted or substituted heterocycloalkyl, unsubstituted or substituted aryl, or unsubstituted or substituted heteroaryl;

or two $R^{21}$ on the same N atom are taken together with the N atom to which they are attached to form an unsubstituted or substituted N-containing heterocycle;

wherein when any $R^1$, $R^2$, $R^4$, $R^{20}$, or $R^{21}$ is substituted, substituents on the $R^1$, $R^2$, $R^4$, $R^{20}$, or $R^{21}$ are independently selected at each occurrence from halogen, —CN, —$NO_2$, —$OR^{22}$, —$CO_2R^{22}$, —$C(=O)R^{23}$, —$C(=O)NR^{22}R^{22}$, —$NR^{22}R^{22}$, —$NR^{22}C(=O)R^{23}$, —$NR^{22}C(=O)OR^{22}$, —$SR^{22}$, —$S(=O)R^{23}$, —$SO_2R^{23}$, —$SO_2NR^{22}NR^{23}$, $C_1$-$C_6$ alkyl, $C_1$-$C_6$ haloalkyl, monocyclic cycloalkyl, monocyclic heterocycloalkyl, phenyl, benzyl, 5-membered heteroaryl, and 6-membered heteroaryl; or two substituents on the same carbon atom are taken together to form a C=O or C=S;

each $R^{22}$ is independently selected from hydrogen, $C_1$-$C_6$ alkyl, $C_3$-$C_6$ cycloalkyl, phenyl, benzyl, 5-membered heteroaryl, and 6-membered heteroaryl;

or two $R^{22}$ groups are taken together with the N atom to which they are attached to form a N-containing heterocycle; and each $R^{23}$ is independently selected from $C_1$-$C_6$alkyl, $C_3$-$C_6$ cycloalkyl, phenyl, benzyl, 5-membered heteroaryl, and 6-membered heteroaryl.

In some embodiments, this disclosure provides a method for treating a muscular degenerative disorder in a subject in need thereof comprising administering to the subject in need thereof a composition comprising a compound, or a pharmaceutically acceptable salt thereof, having the structure of Formula (IV):

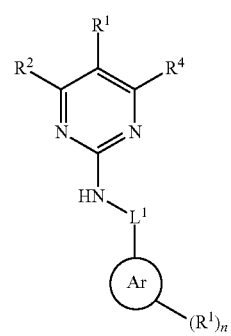

Formula (IV)

wherein

L is absent or —$C_1$-$C_4$ alkylene;

Ar is phenyl or 5- or 6-membered heteroaryl;

each $R^1$ is independently hydrogen, halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

or two $R^1$ on adjacent atoms are taken together with the atoms to which they are attached to form a unsubstituted or substituted carbocycle, or unsubstituted or substituted heterocycle; wherein if the carbocycle or heterocycle is substituted, it is substituted with 1-3 $R^7$;

each $R^7$ is independently hydrogen, halogen, —CN, —OH, —$OR^{20}$, —SH, —$SR^{20}$, —$NO_2$, —$NR^{21}R^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{10}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

n is 0-5;

R$^2$ and R$^4$ are each independently hydrogen, or —NR$^5$R$^6$, or unsubstituted or substituted heterocycle;

each R$^5$ and R$^6$ is independently hydrogen, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —C$_1$-C$_6$-alkylene-cycloalkyl, unsubstituted or substituted —C$_1$-C$_6$-alkylene-heterocycloalkyl, unsubstituted or substituted —C$_1$-C$_6$-alkylene-aryl, or unsubstituted or substituted —C$_1$-C$_6$-alkylene-heteroaryl;

or R$^5$ and R$^6$ are taken together with the N atom to which they are attached to form an unsubstituted or substituted N-containing heterocycle;

R$^3$ is hydrogen, halogen, C$_1$-C$_6$ alkyl or C$_1$-C$_6$ haloalkyl;

or R$^2$ and R$^3$ are taken together with the atoms to which they are attached to form a unsubstituted or substituted carbocycle, or unsubstituted or substituted heterocycle; wherein if the carbocycle or heterocycle is substituted, it is substituted with 1-3 R$^8$;

each R$^8$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

or two R$^7$ on the same carbon atom are taken together to form a C=O, or C=S;

each R$^{20}$ is independently selected from unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

each R$^{21}$ is independently selected from hydrogen, unsubstituted or substituted C$_1$-C$_6$alkyl, unsubstituted or substituted C$_1$-C$_6$alkenyl, unsubstituted or substituted C$_1$-C$_6$ alkynyl, unsubstituted or substituted cycloalkyl, unsubstituted or substituted heterocycloalkyl, unsubstituted or substituted aryl, or unsubstituted or substituted heteroaryl;

or two R$^{21}$ on the same N atom are taken together with the N atom to which they are attached to form an unsubstituted or substituted N-containing heterocycle;

wherein when any R$^1$, R$^2$, R$^4$, R$^5$, R$^6$, R$^7$, R$^{20}$, or R$^{21}$ is substituted, substituents on the R$^1$, R$^2$, R$^4$, R$^5$, R$^6$, R$^7$, R$^{20}$, or R$^{21}$are independently selected at each occurrence from halogen, —CN, —NO$_2$, —OR$^{22}$, —CO$_2$R$^{22}$, —C(=O)R$^{23}$, —C(=O)NR$^{22}$R$^{22}$, —NR$^{22}$R$^{22}$, —NR$^{22}$C(=O)R$^{23}$, —NR$^{22}$C(=O)OR$^{22}$, —SR$^{22}$, —S(=O)R$^{23}$, —SO$_2$R$^{23}$, —SO$_2$NR$^{22}$R$^{22}$, —NR$^{22}$SO$_2$R$^{23}$, C$_1$-C$_6$ alkyl, C$_1$-C$_6$ haloalkyl, monocyclic cycloalkyl, monocyclic heterocycloalkyl, phenyl, benzyl, 5-membered heteroaryl, and 6-membered heteroaryl; or two substituents on the same carbon atom are taken together to form a C=O or C=S;

each R$^{22}$ is independently selected from hydrogen, C$_1$-C$_6$alkyl, C$_1$-C$_6$ hydroxyalkyl, C$_3$-C$_6$ cycloalkyl, phenyl, benzyl, 5-membered heteroaryl, and 6-membered heteroaryl;

or two R$^{22}$groups are taken together with the N atom to which they are attached to form a N-containing heterocycle; and each R$^{23}$ is independently selected from C$_1$-C$_6$alkyl, C$_1$-C$_6$ hydroxyalkyl, C$_1$-C$_6$alkyl C$_3$-C$_6$ cycloalkyl, phenyl, benzyl, 5-membered heteroaryl, and 6-membered heteroaryl.

In some embodiments, this disclosure provides a method for treating a muscular degenerative disorder in a subject in need thereof comprising administering to the subject in need thereof a composition comprising a compound, or a pharmaceutically acceptable salt thereof, having the structure of Formula (V)

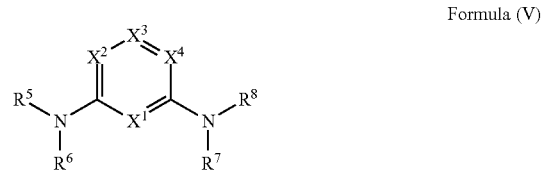

Formula (V)

wherein

X$^1$ is N or CR$^1$;

R$^1$ is hydrogen, halogen, C$_1$-C$_6$alkyl, or C$_1$-C$_6$ haloalkyl;

X$^2$ is N or CR$^2$;

R$^2$ is hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=OX)R$^{21}$, —OC(=O)OR$^{21}$, —C(=O)NR$^{21}$R$^{21}$, —OC(O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

X$^3$ is N or CR$^3$;

R$^3$ is hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

$X^4$ is N or $CR^4$;

$R^4$ is hydrogen, halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl;

wherein 0, 1, or 2 of $X^1$, $X^2$, $X^3$, and $X^4$ are N;

$R^5$ is hydrogen, unsubstituted or substituted aryl, or unsubstituted or substituted heteroaryl;

wherein if $R^5$ is substituted, it is substituted with 1-3 $R^9$;

each $R^9$ is independently halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl;

$R^6$ is hydrogen, $C_1$-$C_6$alkyl or $C_1$-$C_6$ haloalkyl;

or $R^5$ and $R^6$ are taken together with the N atom to which they are attached to form an unsubstituted or substituted N-containing heterocycle; wherein if the heterocycle is substituted, it is substituted by 1-3 $R^{13}$;

each $R^{13}$ is independently halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

$R^7$ is hydrogen, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, or —$C(=O)R^{11}$;

$R^{11}$ unsubstituted phenyl, or phenyl substituted by 1-3 $R^{12}$;

each $R^{12}$ is independently halogen, —CN, —H, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;

$R^8$ is hydrogen, $C_1$-$C_6$ alkyl or $C_1$-$C_6$ haloalkyl;

or $R^7$ and $R^8$ are taken together with the N atom to which they are attached to form an unsubstituted or substituted N-containing heterocycle; wherein if the heterocycle is substituted, it is substituted by 1-3 $R^{10}$;

each $R^{10}$ is independently halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

each $R^{20}$ is independently selected from unsubstituted or substituted C1-C6alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl;

each $R^{21}$ is independently selected from hydrogen, unsubstituted or substituted $C_1$-$C_6$ alkyl, unsubstituted or substituted $C_1$-$C_6$alkenyl, unsubstituted or substituted $C_1$-$C_6$ alkynyl, unsubstituted or substituted cycloalkyl, unsubstituted or substituted heterocycloalkyl, unsubstituted or substituted aryl, unsubstituted or substituted heteroaryl;

or two $R^{21}$ on the same N atom are taken together with the N atom to which they are attached to form an unsubstituted or substituted N-containing heterocycle;

wherein when any $R^2$, $R^3$, $R^4$, $R^7$, $R^9$, $R^{10}$, $R^{12}$, $R^{13}$, $R^{20}$, or $R^{21}$ is substituted, substituents on the $R^2$, $R^3$, $R^4$, $R^7$, $R^9$, $R^{10}$, $R^{12}$, $R^{13}$, $R^{20}$, or $R^{21}$ are independently selected at each occurrence from halogen, —CN, —$NO_2$, —$OR^{22}$, —$CO_2R^{22}$, —$C(=O)R^{23}$, —$C(=O)NR^{22}R^{22}$, —$C(=O)NR^{22}$—$OR^{22}$, —$NR^{22}R^{22}$, —$NR^{22}C(=O)R^{23}$, —$NR^{22}C(=O)OR^{22}$, —$SR^{22}$, —$S(=O)R^{23}$, —$SO_2R^{23}$, —$SO_2NR^{22}R^{22}$, $C_1$-$C_6$alkyl, $C_1$-$C_6$ haloalkyl, monocyclic cycloalkyl, monocyclic heterocycloalkyl, monocyclic heterocycloalkyl substituted with a $R^{23}$, phenyl, benzyl, 5-membered heteroaryl, and 6-membered heteroaryl; or two substituents on the same carbon atom are taken together to form a C=O or C=S;

each $R^{22}$ is independently selected from hydrogen, $C_1$-$C_6$ alkyl, $C_3$-$C_6$ cycloalkyl, phenyl, benzyl, 5-membered heteroaryl, and 6-membered heteroaryl;

or two $R^{22}$ groups are taken together with the N atom to which they are attached to form a N-containing heterocycle; and each $R^{23}$ is independently selected from $C_1$-$C_6$ alkyl, $C_3$-$C_6$ cycloalkyl, phenyl, benzyl, 5-membered heteroaryl, and 6-membered heteroaryl.

In some embodiments, this disclosure provides a method for treating a muscular degenerative disorder in a subject in need thereof comprising administering to the subject in need thereof a composition comprising a compound, or a pharmaceutically acceptable salt thereof, having the structure of Formula (VI):

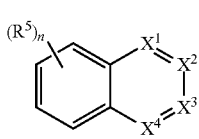

Formula (VI)

wherein:

$X^1$ and $X^2$ are independently N or CH;

$X^3$ is N or $CR^3$;

$R^3$ is hydrogen, —CN, or -L-Ar, $X^4$ is N or $CR^4$;

$R^4$ is hydrogen, or -L-Ar;

wherein one of $X^3$ and $X^4$ is C-L-Ar;

L is —NH—, —O—, —S—, —$C_1$-$C_2$ alkylene-, or -heterocycloalkylene-C(=O)—;

Ar is substituted or unsubstituted phenyl or substituted or unsubstituted 5- or 6-membered heteroaryl; wherein when Ar is substituted, it is substituted with 1-3 $R^6$;

each $R^6$ is independently halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)^2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —($C_1$-$C_4$ alkylene)-$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

or two $R^6$ on adjacent atoms are taken together with the atoms to which they are attached to form an unsubstituted or substituted cycloalkyl, unsubstituted or substituted heterocycloalkyl, unsubstituted or substituted aryl, or unsubstituted or substituted heteroaryl;

each $R^5$ is independently hydrogen, halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

n is 0-4, each $R^{20}$ is independently selected from unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;

each $R^{21}$ is independently selected from hydrogen, unsubstituted or substituted $C_1$-$C_6$alkyl, unsubstituted or substituted $C_1$-$C_6$ alkenyl, unsubstituted or substituted $C_1$-$C_6$ alkynyl, unsubstituted or substituted cycloalkyl, unsubstituted or substituted heterocycloalkyl, unsubstituted or substituted aryl, or unsubstituted or substituted heteroaryl;

or two $R^{21}$ on the same N atom are taken together with the N atom to which they are attached to form an unsubstituted or substituted N-containing heterocycle;

wherein when any $R^5$, $R^6$, $R^{20}$, or $R^{21}$ is substituted, substituents on the $R^5$, $R^6$, $R^{20}$, or $R^{21}$ are independently selected at each occurrence from halogen, —CN, —$NO_2$, —$OR^{22}$, —$CO_2R^{22}$, —$C(=O)R^{23}$, —$OC(=O)R^{23}$, —$C(=O)NR^{22}R^{22}$, —$NR^{22}R^{22}$, —$NR^{22}C(=O)R^{23}$, —$NR^{22}C(=O)OR^{22}$, —$SR^{22}$, —$S(=O)R^{23}$, —$SO_2R^{23}$, —$SO_2NR^{22}R^{22}$, $C_1$-$C_6$ alkyl, $C_1$-$C_6$ haloalkyl, monocyclic cycloalkyl, monocyclic heterocycloalkyl, phenyl, benzyl, 5-membered heteroaryl, and 6-membered heteroaryl; or two substituents on the same carbon atom are taken together to form a C=O or C=S;

each $R^{22}$ is independently selected from hydrogen, $C_1$-$C_6$ alkyl, $C_3$-$C_6$ cycloalkyl, phenyl, benzyl, 5-membered heteroaryl, and 6-membered heteroaryl;

or two $R^{22}$ groups are taken together with the N atom to which they are attached to form a N-containing heterocycle; and each $R^{23}$ is independently selected from $C_1$-$C_6$alkyl, $C_3$-$C_6$ cycloalkyl, phenyl, benzyl, 5-membered heteroaryl, and 6-membered heteroaryl.

In some embodiments, this disclosure provides a method for treating a muscular degenerative disorder in a subject in need thereof comprising administering to the subject in need thereof a composition comprising a compound, or a pharmaceutically acceptable salt thereof, having the structure of Formula (VII):

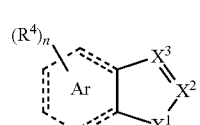

Formula (VII)

wherein:

$X^1$ is —S—, —O—, or —$NR^1$—;

$R^1$ is hydrogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl, wherein when $R^1$ is substituted, it is substituted by 1-3 $R^7$;

each $R^7$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted cycloalkyl, unsubstituted or substituted heterocycloalkyl, unsubstituted or substituted aryl, or unsubstituted or substituted heteroaryl;

$X^2$ is N or $CR^2$;

$R^2$ is hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl; wherein when $R^2$ is substituted, it is substituted by 1-3 $R^8$;

each $R^8$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$alkyl, unsubstituted or substituted cycloalkyl, unsubstituted or substituted heterocycloalkyl, unsubstituted or substituted aryl, or unsubstituted or substituted heteroaryl;

$X^3$ is N or $CR^3$; wherein $X^2$ and $X^3$ are not both N;

$R^3$ is hydrogen, halogen, —CN, —OH, —OR$^{20}$, —SH, —SR$^{20}$, —NO$_2$, —NR$^{21}$R$^{21}$, —S(O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl; wherein when $R^3$ is substituted, it is substituted by 1-3 $R^9$;

each $R^9$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl, Ar is a 6-membered aromatic ring comprising 0-2 nitrogen atoms;

each $R^4$ is independently hydrogen, halogen, —CN, —OH, —OR$^5$, —SH, —SR$^5$, —NO$_2$, —NR$^6$R$^6$, —S(=O)$_2$R$^5$, —NR$^6$S(=O)$_2$R$^5$, —S(=O)R$^5$, —S(=O)$_2$NR$^6$R$^6$, —C(=O)R$^5$, —OC(=O)R$^5$, —C(=O)OR$^6$, —OC(=O)OR$^6$, —C(=O)NR$^6$R$^6$, —OC(=O)NR$^6$R$^6$, —NR$^6$C(=O)NR$^6$R$^6$, —NR$^6$C(=O)R$^5$, —NR$^6$C(=O)OR$^6$, unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;

each $R^5$ is independently selected from unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl; wherein if $R^5$ is substituted, it is substituted by 1-3 $R^{10}$;

each $R^{10}$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

each $R^6$ is independently selected from hydrogen, unsubstituted or substituted $C_1$-$C_6$ alkyl, unsubstituted or substituted $C_1$-$C_6$ alkenyl, unsubstituted or substituted $C_1$-$C_6$ alkynyl, unsubstituted or substituted cycloalkyl, unsubstituted or substituted heterocycloalkyl, unsubstituted or substituted aryl, or unsubstituted or substituted heteroaryl; wherein if $R^6$ is substituted, it is substituted by 1-3 $R^{11}$;

each $R^{11}$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

n is 0-4;

each $R^{20}$ is independently selected from unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$ alkylene-heteroaryl;

each $R^{21}$ is independently selected from hydrogen, unsubstituted or substituted $C_1$-$C_6$ alkyl, unsubstituted or substituted $C_1$-$C_6$ alkenyl, unsubstituted or substituted $C_1$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;

or two $R^{21}$ on the same N atom are taken together with the N atom to which they are attached to form an unsubstituted or substituted N-containing heterocycle;

wherein when any $R^4$, $R^7$, $R^8$, $R^9$, $R^{10}$, $R^{11}$, $R^{20}$, or $R^{21}$ is substituted, substituents on the $R^4$, $R^7$, $R^8$, $R^9$, $R^{10}$, $R^{11}$, $R^{20}$, or $R^{21}$ are independently selected at each occurrence from halogen, —CN, —$NO_2$, —$OR^{22}$, —$CO_2R^{22}$, —C(=O)$R^{23}$, —C(=O)$NR^{22}R^{22}$, —$NR^{22}R^{22}$, —$NR^{22}$C(=O)$R^{23}$, —$NR^{22}$C(=O)$OR^{22}$, —$SR^{22}$, —S(=O)$R^{23}$, —$SO_2R^{23}$, —$SO_2NR^{22}R^{22}$, $C_1$-$C_6$ alkyl, $C_1$-$C_6$ haloalkyl, $C_1$-$C_6$ hydroxyalkyl, monocyclic cycloalkyl, monocyclic heterocycloalkyl, phenyl, benzyl, benzyl substituted with phenyl, 5-membered heteroaryl, and 6-membered heteroaryl, or two substituents on the same carbon atom are taken together to form a C=O or C=S;

each $R^{22}$ is independently selected from hydrogen, $C_1$-$C_6$ alkyl, $C_3$-$C_6$ cycloalkyl, phenyl, benzyl, 5-membered heteroaryl, and 6-membered heteroaryl;

or two $R^{22}$ groups are taken together with the N atom to which they are attached to form a N-containing heterocycle; and each $R^{23}$ is independently selected from $C_1$-$C_6$ alkyl, $C_3$-$C_6$ cycloalkyl, phenyl, benzyl, 5-membered heteroaryl, and 6-membered heteroaryl.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 18 or 19.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 20 or 21.

In some embodiments, this disclosure provides a method for modulating DUX4 activity in a subject in need thereof comprising administering to the subject in need thereof a composition comprising a compound, or a pharmaceutically acceptable salt thereof, selected from a compound provided in FIG. 22 or 23.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 24 or 25.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 26 or 27.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 28 or 29. Another embodiment provides a method for modulating DUX4 activity wherein the modulation of DUX4 activity is inhibition of DUX4 activity.

In some embodiments, this disclosure provides a method of treating a muscular degenerative disorder in a subject in need thereof, comprising administering to the subject in need thereof a therapeutically effective amount of a compound selected from the compounds provided in FIG. 18 or 19.

In some embodiments, this disclosure provides a method of treating a muscular degenerative disorder in a subject in need thereof, comprising administering to the subject in need thereof a therapeutically effective amount of a compound selected from the compounds provided in FIG. 20 or 21.

In some embodiments, this disclosure provides a method of treating a muscular degenerative disorder in a subject in need thereof, comprising administering to the subject in need thereof a therapeutically effective amount of a compound selected from the compounds provided in FIG. 22 or 23.

In some embodiments, this disclosure provides a method of treating a muscular degenerative disorder in a subject in need thereof, comprising administering to the subject in need thereof a therapeutically effective amount of a compound selected from the compounds provided in FIG. 24 or 25.

In some embodiments, this disclosure provides a method of treating a muscular degenerative disorder in a subject in need thereof, comprising administering to the subject in need thereof a therapeutically effective amount of a compound selected from the compounds provided in FIG. 26 or 27.

In some embodiments, this disclosure provides a method of treating a muscular degenerative disorder in a subject in need thereof, comprising administering to the subject in need thereof a therapeutically effective amount of a compound selected from the compounds provided in FIG. 28 or 29.

In some embodiments, this disclosure provides a method of treating a muscular degenerative disorder wherein the muscular degenerative disorder is selected from facioscapulohumeral muscular dystrophy (FSHD), facioscapulohumeral muscular dystrophy-1 (FSHD1), facioscapulohumeral muscular dystrophy-2 (FSHD2). Becker muscular dystrophy, Duchenne muscular dystrophy, myotonic dystrophies type 1, myotonic dystrophies types 2, nemaline myopathy, spinal muscular atrophy, congenital myotonic dystrophy, congenital muscular dystrophies, LAMA2, SEPN1, GNE myopathies, and SMARD1.

In some embodiments, this disclosure provides a method of treating a muscular degenerative disorder in a subject in need thereof, wherein the subject is a human.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or compound according to any one of formulas I-VII, or a salt thereof), wherein the modulating DUX4 activity comprises reducing expression of DUX4.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or compound according to any one of formulas I-VII, or a salt thereof), wherein the reduction of DUX4 expression occurs at the mRNA level.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or compound according to any one of formulas I-VII, or a salt thereof), wherein the reduction of DUX4 expression occurs at the protein level.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or compound according to any one of formulas I-VII, or a salt thereof), wherein the subject has upregulated DUX4 expression or activity prior to administration of the compound.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or compound according to any one of formulas I-VII, or a salt thereof), wherein the method further comprises detecting activity or expression of DUX4 in the subject prior to, following, or both prior to and following administration of the compound.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or compound according to any one of formulas I-VII, or a salt thereof), wherein the method further comprises monitoring DUX4 expression or activity in a tissue of the subject following administration of the compound. In some embodiments, DUX4 expression is monitored by monitoring DUX4 mRNA expression, DUX4 protein expression, or both DUX4 mRNA expression and DUX4 protein expression. In some embodiments, the method comprises taking a blood, plasma, serum or urine sample from the subject and detecting the level of a marker of muscle injury. In some embodiments, the method comprises taking a blood, plasma, serum or urine sample from the subject and detecting the level of creatinine kinase, aldolase, and/or muscle enzymes in the sample. In some embodiments, the method comprises monitoring the level of DUX4, creatinine kinase, aldolase, or muscle enzymes or any combination thereof over time, such as over two time points, over three time points. In cases where a marker of muscle injury increases or stays the same, the level of compound administered to the subject may, in some embodiments, be adjusted upwards. In uses where the marker decreases over time, the level of the compound administered to the subject may, in some embodiments, be maintained or adjusted downward. In some embodiments, provided herein is a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein, following administration of the compound, the subject in need thereof experiences a least a 10%, at least a 25%, at least a 50%, at least a 75%, or at least a 100% decrease in a marker of muscle injury, a muscle enzyme, creatinine kinase, and/or aldolase, or any combination thereof.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein the method further comprises detecting activity or expression of a DUX4 target gene prior to, following, or both prior to and following administration of the compound. In some embodiments, wherein the DUX4 target gene is one or more genes selected from the group consisting of CCNA1, KHDC1L, LEUTX, M8D3L2, PRAMEF2, PRAMEF6, SPRYD5, TRIM43, TRIM49, ZNF296, and ZSCAN4.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein, following administration of the compound, the subject in need thereof experiences a least a 10%, at least a 25%, at least a 50%, at least a 75%, or at least 100% decrease in DUX4 expression or activity. In some embodiments, the decrease in DUX4 expression or activity occurs in muscle tissue, or observed in a muscle biopsy. In some cases, the decrease occurs in a blood, serum, plasma, or urine sample and may detected by sampling blood, scrum, plasma or urine.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein the method further comprises conducting a muscle or tissue biopsy on the subject in need thereof.

In some embodiments, this disclosure provides a method of treating a muscular degenerative disorder in a subject in need thereof or modulating DUX4 activity in a subject in need there of using any of the compounds described herein (e.g. rebastinib, or a salt or analog thereof, or a compound according to any one formulas I-VII, or a salt thereof), wherein the muscle or tissue biopsy is assessed for DUX4 expression or activity. In some embodiments, the method comprises monitoring the level or activity of DUX4 in the subject over time, following administration of the compound. In some embodiments, the level or activity of DUX4 is monitored in one or more tissues such as blood, serum, plasma, muscle tissue, or other tissue. In some embodiments, the level or activity of DUX4 is monitored in a particular cell type such as multi-nucleated cell, myoblast, or myotube.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein the method further comprises monitoring a level of the compound in the subject over time.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein the method further comprises monitoring a level of the compound in blood, serum, plasma, tissue, or muscle tissue of the subject in need thereof.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein the compound is administered orally, intramuscularly, or transdermally to the subject in need thereof. In some embodiments, the compound is administered orally.

In some embodiments, this disclosure provides a method of treating a muscular degenerative disorder in a subject in need thereof or modulating DUX4 activity in a subject in need there of using any of the compounds described herein (e.g., rebastinib, or a salt thereof, or a compound according to any one of formulas I-VII, or a salt thereof), wherein the compound is administered orally to the subject in need thereof and wherein a concentration of the compound is measured in muscle tissue of the subject.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein the compound is administered orally to the subject in need thereof and wherein DUX4 expression or activity is measured in muscle tissue of the subject.

In some embodiments, this disclosure provides a method of treating a muscular degenerative disorder in a subject in need thereof or modulating DUX4 activity in a subject in need there of using any of the compounds described herein (e.g. rebastinib, or a salt thereof or a compound according to any one of formulas I-VII, or a salt thereof), wherein the compound is administered at a daily dose of less than 100 mg, a daily dose of less than 90 mg, or a daily dose of less than 80 mg. In some embodiments, the daily dose is less than 100 mg.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein the compound is administered at a daily dose of between 50-60 mg/m$^2$. In some embodiments, the daily dose is between 10-80 mg/m$^2$.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein the compound is administered for over 28 contiguous days.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein the compound is administered to the subject in need thereof at least once every other day over a period of at least 28 days.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein the compound is administered to the subject in need thereof at least once every other day over a period of at least 1 month, 2 months, 6 months, 1 year, 2 years, or 5 years.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein the compound comprises rebastinib, 4-(4-(3-(3-(tert-butyl)-1-(quinolin-6-yl)-1H-pyrazol-5-yl)ureido)-2-methylphenoxy)-N-methylpicolinamide, or 4-(4-(3-(3-(tert-butyl)-1-(1H-indazol-5-yl)-1H-pyrazol-5-yl)ureido)-3-fluorophenoxy)-N-methylpicolinamide. In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein the compound comprises rebastinib.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein the compound comprises 4-(4-(3-(3-(tert-butyl)-1-(quinolin-6-yl)-1H-pyrazol-5-yl)ureido)-2-methylphenoxy)-N-methylpicolinamide.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according to any one of formulas I-VII, or a salt thereof), wherein the compound comprises 4-(4-(3-(3-(tert-butyl)-1-(1H-indazol-5-yl)-1H-pyrazol-5-yl)ureido)-3-fluorophenoxy)-N-methylpicolinamide.

In some embodiments, this disclosure provides a method of treating facioscapulohumeral muscular dystrophy (FSHD) in a subject in need thereof, comprising administering a SRC kinase inhibitor to a subject having FSHD. In some embodiments, this disclosure provides a method of treating facioscapulohumeral muscular dystrophy (FSHD) comprising administering a PRKDC kinase inhibitor and/or a Src kinase inhibitor to a subject having a muscle deficiency or disorder or a disorder associated with upregulated DUX4 expression or activity.

In some embodiments, this disclosure provides a method of treating facioscapulohumeral muscular dystrophy (FSHD) comprising administering a PRKDC kinase inhibitor to a subject having FSHD or to as subject with a disease or disorder associated with upregulated DUX4 expression. In some embodiments, the method further comprises administering a SRC kinase inhibitor to the subject having FSHD. In some embodiments, the method further comprises (a) administering a compound that functions as both a PRKDC inhibitor and as a SRC inhibitor to the subject having FSHD or (b) administering two separate compounds to the subject having FSHD wherein one of the separate compounds is a PRKDC inhibitor and the other separate compound is a SRC inhibitor.

INCORPORATION BY REFERENCE

All publications, patents, and patent applications mentioned in this specification are herein incorporated by reference in their entireties and to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
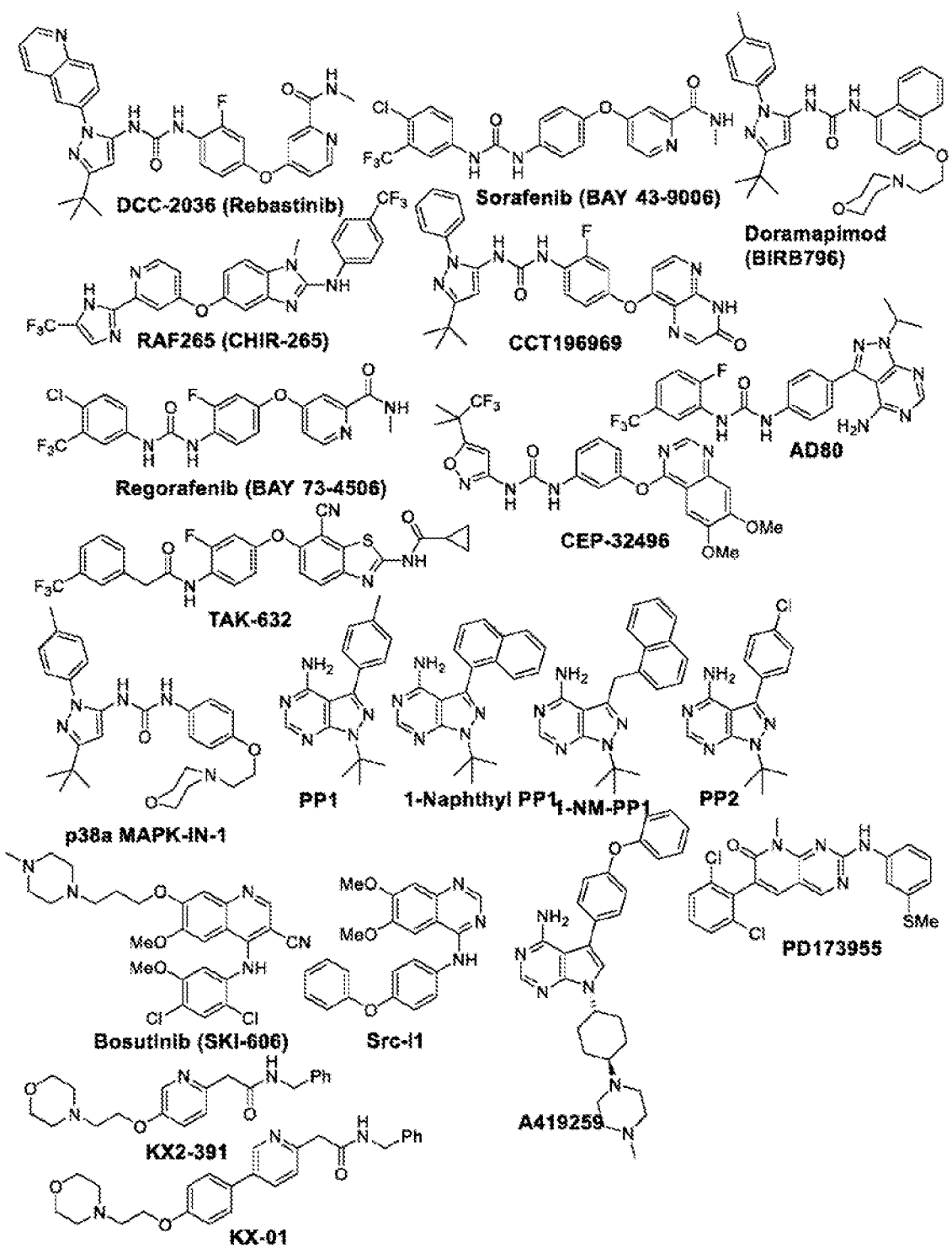
FIG. 1 provides the structures of compounds for modulating DUX4 activity.

The present disclosure describes the use of Src, Tie, Abl, Flt, Trk, Yes, FAK, PRKDC kinase family inhibitors to treat subjects with muscular anomalies such as facioscapulohumeral muscular dystrophy (FSHD). The kinase inhibitors may be administered singly, in combination, or in combination with other compounds or therapies such as a cell therapy. In some embodiments, the kinase inhibitor is rebastinib, or a salt of analog thereof, or one or more compounds according to any of formulas I-VI. This disclosure also provides cell-based assays to identify candidate compounds flat reduce or eliminate DUX4 expression.

Examples of Src, Tie, Abl, Trk, Fit, Yes, FAK, PRKDC kinase family inhibitors that are used in the present methods and compositions include primarily rebastinib and analogues or salts of thereof, sorafenib and analogues or salts thereof, doramapimod and analogues or salts thereof, imatinib and analogs of thereof, PP2 and analogues or salts thereof, a compound of FIGS. 1-5 (or analogues or salts thereof), or a compound of any one of Formulas (I)-(VII) (or analogues or salts thereof). In some embodiments, the Src, Tie, Abl, Trk, Flt, Yes, FAK, PRKDC kinase family inhibitors modulate DUX4 activity. In other embodiments, the Src, Tie, Abl, Trk, Flt, Yes, FAK, PRKDC kinase family inhibitors downregulate DUX4 activity

TABLE 1

Representative Src, Tie, Abl, Trk, Flt, Yes, FAK kinase families inhibitors that downregulate the expression of DUX4.

| Compound | Target | DUX4 Effect, Y/N | Quantitation % of DUX4 reduction @the lowest significant [C] | EC50 (nM) |
|---|---|---|---|---|
| A419259 | Src | N | | |
| Asciminib | Src | N | | |
| AZM475271 | Src | N/A | | |
| Bosutinib | Src | Y | 70.58% (3 µM) | N/A |
| Crenolanib | Src | N/A | | |
| Dasatinib | Src | N/A | | |
| DCC2036 | Src | Y | 66.39% (0.3 µM) | 117.5 |
| | | Y | 51.75% (0.05 µM) | 37.87 |
| | | Y | 79.76% (0.88 µM) | 178.5 |
| | | Y | 82.94% (0.88 µM) | 75.97 |
| Erlotinib | Src | N/A | | |
| KB SRC4 | Src | N | | |
| LCB 03-0110 | Src | N | | |

TABLE 1-continued

Representative Src, Tie, Abl, Trk, Flt, Yes, FAK kinase families inhibitors that downregulate the expression of DUX4.

| Compound | Target | DUX4 Effect, Y/N | Quantitation % of DUX4 reduction @the lowest significant [C] | EC50 (nM) |
|---|---|---|---|---|
| PP1 | Src | N/A | | |
| PP2 | Src | Y | 41.77% (0.03 µM) | 153.3 |
| | | Y | 66.61% (0.88 µM) | 287.2 |
| Saracatinib | Src | N/A | | |
| Src I1 | Src | N | | |
| XL228 | Src | Y | | |
| Foretinib | Tie2 | N/A | | |
| Pexmetinib | Tie2 | N/A | | |
| LDC1267 | Axl | N/A | | |
| PD173074 | PDGFR | N/A | | |
| NVP-BHG712 | EphB4 | N/A | | |
| Ponatinib | Abl | N/A | | |
| Flumatinib | Abl | Y | 76.09% (2.08 µM) | 82.05 |
| Imatinib | Abl | Y | 61.13% (2.08 µM) | 380.3 |
| Asciminib | Abl | N | | |
| AT9283 | Abl | N/A | | |
| AZD3463 | Abl | N/A | | |
| Bafetinib | Abl | Y | 67.90% (2.08 µM) | 132.3 |
| GNF-5 | Abl | N | | |
| G2D824 | Abl | Y | | |
| Lyn-IN-1 | Abl | Y | 70.73% (0.88 µM) | 174.6 |
| Nilotinib | Abl | Y | 76.71% (5 µM) | N/A |

The compounds, methods and compositions disclosed herein may be used to treat subjects with muscular degenerative diseases or muscular disorders stemming from a variety of causes, including, but not limited, to, genetic disorders, sporadic diseases, cachexia, muscle strain, muscle injury, muscle atrophy, as well as sarcopenia and the general aging process. The disclosed compounds may be administered to a subject by a variety of routes, including but not limited to, orally, intravenously, intramuscularly, subcutaneously, and transdermally. Without wishing to be bound by theory, the compounds may block de-repression or activation of DUX4 and/or interfere with the activity of DUX4 subsequent to de-repression. As a result of administration of compounds provided herein (e.g., a compound of FIGS. 1-5, or a compound of any one of Formulas (I)-(VII), subjects may experience improvements in muscle strength, performance, stamina and reduced symptoms of muscle weakness.

In some embodiments, compounds as described herein administered parenterally may be formulated in an aqueous solution. For parenteral administration of compounds described herein (e.g., rebastinib or salts or analogues thereof or one or more compounds according to any of formulas I-VI) in an aqueous solution, the solution may be buffered and the liquid formulation first rendered isotonic with sufficient saline or glucose. Such aqueous solutions are especially suitable for intravenous, intramuscular, subcutaneous and/or intraperitoneal administration. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580).

In some embodiments, compounds as described herein administered parenterally may be formulated in an oil-based solution. For parenteral administration of compounds described herein (e.g. rebastinib or analogues or salts thereof or compounds according to any of formulas I-VI) in an oil-based solution, the solution may comprise one or more of an excipient such as PhytoSolve, Myglyol 810 N (e.g. 45% in solution). Phosal (e.g. 50% in solution), medium-chain triglyceride (MCT) oil (e.g. 20% MCT in aqueous solution), soybean phospholipids (e.g., 5% in aqueous solution), or Polysorbate 80 (Tween-20, e.g. 5% in solution). The present disclosure describes the use of Src, Abl, Tie2, Flt, Yes, FAK, Trk, or PRKDC kinases inhibitors (e.g., a compound of FIGS. 1-5, rebastinib (or salt or analog thereof) or one or more compounds of any one of Formulas (I)-(VII) (or any combination thereof, e g, Src inhibitor and a PRKDC inhibitor) to treat subjects with muscular deficiencies such as FSHD The Src, Abl, Tie2, Flt, Yes, FAK, PRKDC and/or Trk inhibitors may be administered alone or in combination with other compounds or therapies such as a cell therapy. The Abl inhibitors may be administered alone or in combination with ether compounds or therapies such as a cell therapy. The Tie2 inhibitors may be administered alone or in combination with other compounds or therapies such as a cell therapy. The Flt inhibitors may be administered alone or in combination with other compounds or therapies such as a cell therapy. The Yes inhibitors may be administered alone or in combination with ether compounds or therapies such as a cell therapy. The FAK inhibitors may be administered alone or in combination with other compounds or therapies such as a cell therapy. The TRK inhibitors may be administered alone or in combination with other compounds or therapies such as a cell therapy.

Examples of Src, Tie2, Abl, FAK, Flt, Yes, Trk, and/or PRKDC inhibitors that are used in the present methods and compositions include but are not limited to one or more of the compounds described in any one of FIGS. 1-5. In some embodiments, the compound used to treat subjects with muscular deficiencies such is FSHD is rebastinib or analogs or salts thereof. In some cases, the compound used to treat subjects with muscular deficiencies such as FSHD is one or more compounds according to any of formulas I-VI. In some embodiments, the compound used to treat subjects with muscular deficiencies such as FSHD is rebastinib or analogs or salts thereof. In some embodiments, the compound used to treat subjects with muscular deficiencies such as FSHD is PP1 or analogs or salts thereof. In some embodiments, the compound used to treat subjects with muscular deficiencies such as FSHD is PP2 or analogs or salts thereof. In some embodiments, the compound used to treat subjects with muscular deficiencies such as FSHD is sorafenib or analogs or salts thereof. In some embodiments, the compound used to treat subjects with muscular deficiencies such as FSHD is doramapimod or analogs or salts thereof. In some embodiments, the compound used to treat subjects with muscular deficiencies such as FSHD is imatinib or analogs or salts thereof. In some embodiments, the compound used to treat subjects with muscular deficiencies such as FSHD is rebastinib or analogs or salts thereof. In some embodiments, the compound used to treat subjects with muscular deficiencies such as FSHD is pamapimod or analogs or salts thereof. In some embodiments, the compound used to treat subjects with muscular deficiencies such as FSHD is bosutinib, or analogs or salts thereof. In some embodiments, the compound used to treat subjects with muscular deficiencies such as FSHD is ponatinib, or analogs or salts thereof. In some embodiments, the compound used to treat subjects with muscular deficiencies such as FSHD is a SRC inhibitor. In some embodiments, the compound used to treat subjects with muscular deficiencies such as FSHD is a PRKDC inhibitor In some embodiments, the compound used to treat subjects with muscular deficiencies such is FSHD is a single compound that functions as both a PRKDC inhibitor and a SRC inhibitor. In some embodiments, the compound used to treat subjects with muscular deficiencies such as FSHD is a mixture of compounds that includes a PRKDC inhibitor and a SRC inhibitor. In some embodiments, the compound used to treat subjects with muscular deficiencies such as FSHD is a mixture of compounds that includes a PRKDC inhibitor and a SRC kinase family inhibitor.

Subjects to be Treated

The subjects treated by the methods and compositions provided herein may have or may be suspected of having any of a number of muscular degenerative diseases and muscular disorders. In some cases, the subject treated by the methods and compositions provided herein has, or is suspected of having, dysregulated DUX4 expression or activity (e.g., upregulated DUX4 expression or activity). In some cases, the subject treated by the methods and compositions provided herein has, or is suspected of having, dysregulated DUX4 expression or activity (e.g., upregulated DUX4 expression) at compared to a control, such as the level (or absence) of DUX4 expression in healthy tissue. In some cases, the DUX4 expression is assayed in comparison to a different gene, such as a housekeeping gene. In some cases, the subject treated by the methods and compositions provided herein has detectable DUX4 expression or activity, or DUX4 expression or activity that is above a negligible amount. The methods and compositions herein may include methods or compositions for treating a subject suffering or suspected to be suffering from FSHD or other muscular or neuromuscular dystrophy. In some cases, the muscular dystrophy is facioscapulohumeral muscular dystrophy-1 (FSHD1). In some cases, the muscular dystrophy is facioscapulohumeral muscular dystrophy-2 (FSHD2). In some cases the muscular or neuromuscular dystrophy is one of the following disorders: Becker muscular dystrophy, Duchenne muscular dystrophy, myotonic dystrophies types 1 and 2, nemaline myopathy or spinal muscular atrophy.

In some cases, a subject treated by the methods or compositions provided herein may be treated for a disease or disorder associated with upregulated DUX4 expression or activity. In some cases, the disease or disorder associated with upregulated DUX4 expression or activity is a chronic disease or disorder. In some cases, the disease or disorder associated with upregulated DUX4 expression or activity is a non-acute disease or disorder. In some cases, the disease or disorder associated with upregulated DUX4 expression or activity is a muscular disease or disorder, or deficiency. In some cases, the disease or disorder associated with upregulated DUX4 expression or activity is not cancer.

In some embodiments, this disclosure provides a method for treating a muscular degenerative disorder in a subject in need thereof comprising administering to the subject in need thereof a composition comprising a compound, or a pharmaceutically acceptable salt thereof, having the structure of Formula (I):

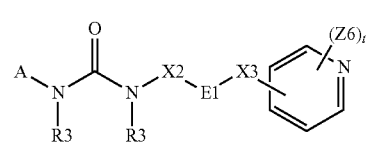

wherein E1 is phenyl, and wherein the E1 ring is substituted with one to three R16 moieties;

wherein A is selected from the group consisting of imidazolyl, and pyrazolyl;

G1 is a heteroaryl taken from the group consisting of pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl, G4 is a heterocyclyl taken from the group consisting of oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl;

A ring is substituted at any substitutable position with one A1 moiety, wherein A1 is selected from the group consisting of:

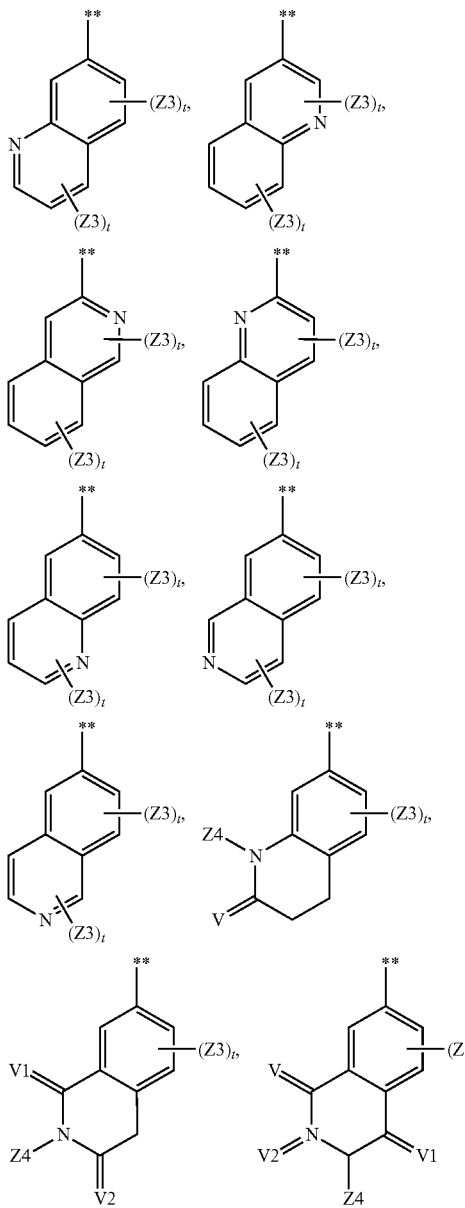

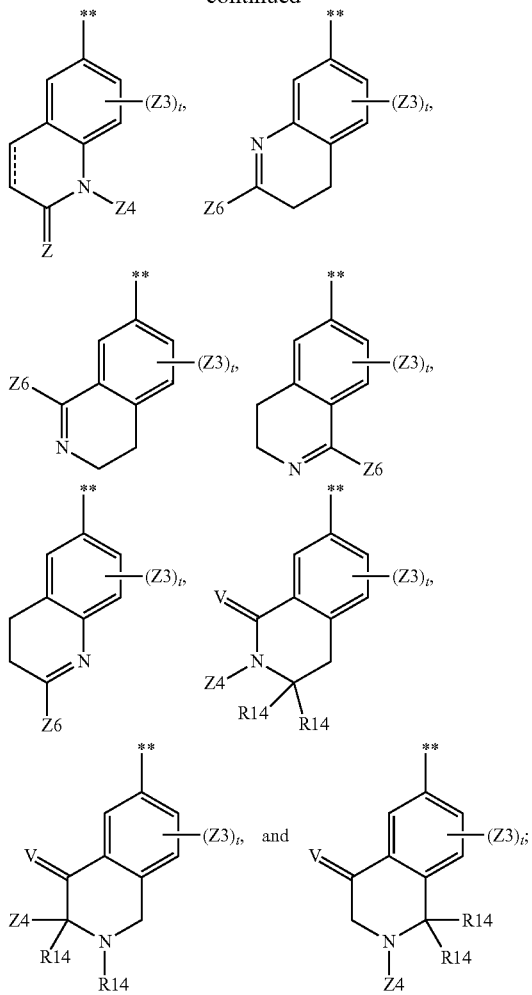

and wherein the symbol (**) is the point of attachment to the A ring of formula I;

and wherein ---- indicates either a saturated or unsaturated bond;

the A ring is optionally substituted with one or more R2 moieties;

X2 is a direct bond wherein E1 is directly linked to the NR3 group of formula I;

X3 is —O—;

V, V1, and V2 are each independently O or represent two hydrogens attached to the methylene carbon to which the V, V1, or V2 is attached;

each Z3 is independently and individually selected from the group consisting of H, C1-C6alkyl, branched C3-C7alkyl, C3-C8carbocyclyl, halogen, fluoroC1-C6alkyl wherein the alkyl moiety can be partially or fully fluorinated, cyano, hydroxyl, methoxy, oxo, (R3)$_2$NC(O)—, (R4)$_2$NC(O)—, —N(R4)C(O)R8, (R3)$_2$NSO$_2$—, (R4)$_2$NSO$_2$—, —N(R4)SO$_2$R$_5$, —N(R4)SO$_2$R8, —(CH$_2$)N(R3)$_2$, —(CH$_2$)$_q$N(R4)$_2$, —O(CH$_2$)$_q$N(R4)$_2$, —O(CH$_2$)$_q$O—C1-C6alkyl, —N(R3)(CH$_2$)$_q$O—C1-C6alkyl, —N(R3)(CH$_2$)$_q$N(R4)$_2$, —O(CH2)$_q$R5, —N(R3)(CH$_2$)$_q$R5, —C(O)R5, —C(O)R8, and nitro;

in the event that Z3 contains an alkyl or alkylene moiety, such moieties may be further substituted with one or more C1-C6alkyls;

each Z4 is independently and individually selected from the group consisting of H, C1-C6alkyl, hydroxyC$_2$-C$_6$alkyl, C1-C6alkoxyC$_2$-C$_6$alkyl, (R4)$_2$N—C$_2$-C$_6$alkyl, (R4)$_2$N—C$_2$-C6alkylN(R4)-C$_2$-C$_6$alkyl, (R4)$_2$N—C$_2$-C$_6$alkyl-O—C$_2$-C$_6$alkyl, (R4)$_2$NC(O)—C1-C6alkyl, carboxyC1-C6alkyl-, C1-C6alkoxycarbonylC1-C6alkyl-, —C2-C6alkylN(R4)C(O)R8, R8-C(=NR3)-, —SO$_2$R8, —C(O)R8, —(CH$_2$)$_n$G1, —(CH$_2$)$_n$G4, —(CH$_2$)$_q$O(CH$_2$)$_n$G1, —(CH$_2$)$_q$O(CH$_2$)$_n$G4, —(CH$_2$)$_q$N(R3)(CH$_2$)$_n$G1, —(CH$_2$)$_q$N(R3)(CH$_2$)$_n$G4, —(CH$_2$)$_q$NHC(O)(CH$_2$)$_n$R5, —(CH$_2$)$_q$C(O)NH(CH$_2$)$_n$R$_5$, —(CH$_2$)$_q$C(O)R5, —(CH$_2$)$_q$OC(O)R5, —(CH$_2$)$_q$R5, —(CH$_2$)$_q$NR4(CH$_2$)$_q$R5, and —(CH$_2$)$_q$O(CH$_2$)$_q$R5;

in the event that Z4 contains an alkyl or alkylene moiety, such moieties may be further substituted with one or more C1-C6alkyls;

each Z6 is independently and individually selected from the group consisting of H, C1-C6alkyl, branched C3-C7alkyl, hydroxyl, hydroxyC1-C6alkyl, hydroxyC$_2$-C$_6$ branched alkyl, C1-C6alkoxy, C1-C6alkoxyC1-C6alkyl-, C1-C6alkoxyC$_2$-C$_6$ branched alkyl-, C2-C6 branched alkoxy-, C1-C6alkylthio-, (R3)$_2$N—, —N(R3)C(O)R8, (R4)$_2$N—, —R5, —N(R4)C(O)R8, —N(R3)SO$_2$R6, —C(O)N(R3)$_2$, —C(O)N(R4)$_2$, —C(O)R5, —SO$_2$NH(R4), halogen, fluoroC1-C6alkyl wherein the alkyl is fully or partially fluorinated, cyano, fluoroC1-C6alkoxy wherein the alkyl is fully or partially fluorinated, —O(CH$_2$)$_q$N(R4)$_2$, —N(R3)(CH$_2$)$_q$N(R4)$_2$, —O(CH$_2$)$_q$O—C1-C6alkyl, —O(CH$_2$)$_q$N(R4)$_2$, —N(R3)(CH$_2$)$_q$O—C1-C6alkyl, —N(R$_3$)(CH$_2$)$_q$N(R4)$_2$, —O(CH$_2$)$_q$R5, N(R3)(CH$_2$)$_q$R$_5$, —(NR3)$_r$R17, —(O)$_r$R17, —(S)$_r$R17, —(CH$_2$)$_n$R17, —R17, —(CH$_2$)$_n$G1, —(CH$_2$)$_n$G4, —(CH$_2$)$_n$O(CH$_2$)$_n$G1, —(CH$_2$)$_n$O(CH$_2$)$_n$G4, —(CH$_2$)$_n$N(R3)(CH$_2$)$_n$G1, and —(CH$_2$)$_n$N(R3)(CH2)$_n$G4;

each R2 is selected from the group consisting of Z3-substituted aryl, Z3-substituted G1-, Z3-substituted G4-, C1-C6alkyl, branched C3-C8alkyl, R19 substituted C3-C8cycloalkyl fluoroC1-C6alkyl wherein the alkyl is fully or partially fluorinated, cyano, C1-C6alkoxy, and fluoroC1-C6alkoxy wherein the alkyl group is fully or partially fluorinated;

wherein each R3 is independently and individually selected from the group consisting of H, C1-C6alkyl, branched C3-C7alkyl, C3-C7-carbocyclyl, and Z3-substituted phenyl;

each R4 is independently and individually selected from the group consisting of H, C1-C6alkyl, hydroxyC1-C6alkyl-, dihydroxyC1-C6alkyl-, C1-C6alkoxyC1-C6alkyl-, branched C3-C7alkyl-, branched hydroxyC1-C6alkyl-, branched C1-C6alkoxyC1-C6alkyl-, branched dihydroxyC$_2$-C$_6$alkyl-, —(CH$_2$)$_n$N(R7)$_2$, —(CH$_2$)$_p$R5, —(CH$_2$)$_p$C(O)N(R7)$_2$, —(CH$_2$)$_n$C(O)R5, —(CH$_2$)$_n$C(O)OR3, C3-C7-carbocyclyl, hydroxyl substituted C3-C7-carbocyclyl-, alkoxy substituted C3-C7-carbocyclyl-, dihydroxyl substituted C3-C7-carbocyclyl-, and —(CH$_2$)$_n$R17;

each R5 is independently and individually selected from the group consisting of

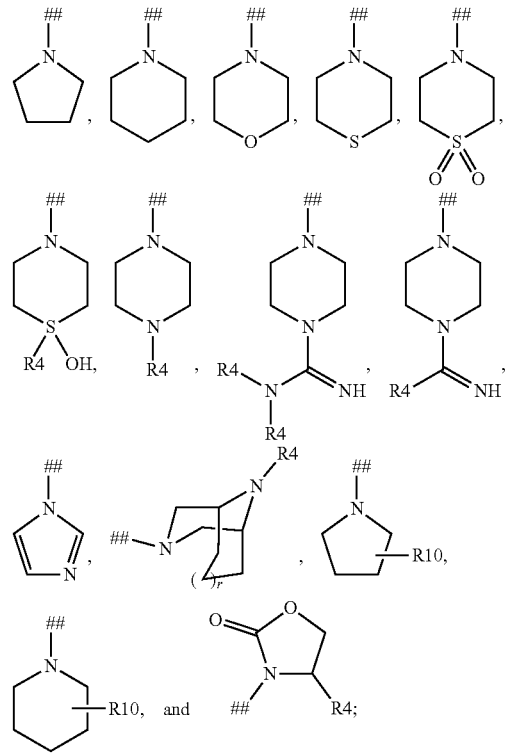

and wherein the symbol (##) is the point of attachment of the R5 moiety;

each R6 is independently and individually selected from the group consisting of C1-C6alkyl, branched C3-C7alkyl, C3-C7-carbocyclyl, phenyl, G1, and G4;

each R7 is independently and individually selected from the group consisting of H, C1-C6alkyl, hydroxyC$_2$-C$_6$alkyl-, dihydroxyC$_2$-C$_6$alkyl-, C$_2$-C$_6$alkoxyC$_2$-C$_6$alkyl-, branched C3-C7alkyl-, branched hydroxyC$_2$-C$_6$ alkyl-, branched C$_2$-C$_6$alkoxyC$_2$-C$_6$alkyl-, branched dihydroxyC$_2$-C$_6$alkyl-, —(CH$_2$)$_q$R5, —)CH$_2$)$_n$C(O)R5, —(CH$_2$)$_n$C(O)OR3, C3-C7-carbocyclyl, hydroxyl substituted C3-C7-carbocyclyl-, alkoxy substituted C3-C7-carbocyclyl-, dihydroxy substituted C3-C7-carbocyclyl, and —(CH$_2$)$_n$R17;

each R8 is independently and individually selected from the group consisting of C1-C6alkyl, branched C3-C7alkyl, fluoroC1-C6alkyl wherein the alkyl moiety is partially or fully fluorinated, C3-C7-carbocyclyl, phenyl-, phenylC1-C6alkyl-, G1, G1-C1-C6alkyl-, G4, G4-C1-C6alkyl-, OH, C1-C6alkoxy, N(R3)$_2$, N(R4)$_2$, and R5;

each R9 is independently and individually selected from the group consisting of H, F, C1-C6alkyl, branched C3-C7alkyl, C3-C7-carbocyclyl, phenyl, phenyl-C1-C6alkyl-, —(CH$_2$)$_n$G1, and —(CH$_2$)$_n$G4;

each R10 is independently and individually selected from the group consisting of CO$_2$H, CO$_2$C1-C6alkyl, —C(O)N(R4)$_2$, OH, C1-C6alkoxy, and —N(R4)$_2$;

each R14 is independently and respectively selected from the group consisting of H, C1-C6alkyl, branched C3-C6alkyl, and C3-C7-carbocyclyl;

R16 is independently and individually selected from the group consisting of fluorine and methyl;

each R17 is taken from the group comprising phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, oxetanyl, azetidinyl, tetrahydrofuranyl, oxazolinyl, oxazolidinyl, pyranyl, thiopyranyl, tetrahydropyranyl, dioxalinyl, azepinyl, oxepinyl, and diazepinyl;

wherein R17 can be optionally substituted with an R3 substituent,

R19 is H or C1-C6 alkyl;

n is 0-6, p is 1-4, q is 2-6; r is 0 or 1; t is 1-3, and v is 1 or 2.

Another embodiment provides a method for treating a muscular degenerative disorder in a subject in need thereof comprising administering to the subject in need thereof a composition comprising a compound, or a pharmaceutically acceptable salt thereof, having the structure of Formula (I), and further described by the structure of Formula (II):

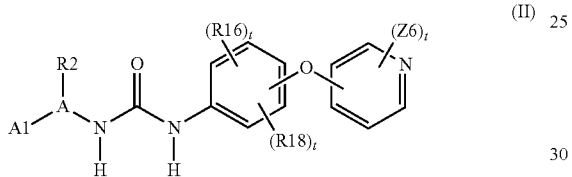

wherein A is pyrazolyl.

In some embodiments, this disclosure provides a method for treating a muscular degenerative disorder in a subject in need thereof comprising administering to the subject in need thereof a composition comprising a compound, or a pharmaceutically acceptable salt thereof, selected from the group consisting of:

1-(3-tert-butyl-1-(1,2,3,4-tetrahydroisoquinolin-6-yl)-1H-pyrazol-5-yl)-3-(3-fluoro-4-(2-(methylcarbamoyl)pyridin-4-yloxy)phenyl)urea;
1-(3-tert-butyl-1-(quinolin-6-yl)-1H-pyrazol-5-yl)-3-(2-fluoro-4-(2-(methylcarbamoyl)pyridin-4-yloxy)phenyl)urea;
1-(3-tert-butyl-1-(1,2,3,4-tetrahydroisoquinolin-6-yl)-1H-pyrazol-5-yl)-3-(2-fluoro-4-(2-(methylcarbamoyl)pyridin-4-yloxy)phenyl)urea;
1-(3-tert-butyl-1-(quinolin-6-yl)-1H-pyrazol-5-yl)-3-(3-fluoro-4-(2-(methylcarbamoyl)pyridin-4-yloxy)phenyl)urea;
1-(3-tert-butyl-1-(quinolin-6-yl)-1H-pyrazol-5-yl)-3-(2-fluoro-5-(pyridin-3-yloxy)phenyl)urea;
1-(3)-tert-butyl-1-(quinolin-6-yl)-1H-pyrazol-5-yl)-3-(3-methyl-4-(2-(methylcarbamoyl)pyridin-4-yloxy)phenyl)urea;
1-(3-tert-butyl-1-(quinolin-6-yl)-1H-pyrazol-5-yl)-3-(4-(2-carbamoylpyridin-4-yloxy)-2-fluorophenyl)urea;
1-(3-tert-butyl-1-(quinolin-6-yl)-1H-pyrazol-5-yl)-3-(2-fluoro-4-(2-(methylamino)pyridin-4-yloxy)phenyl)urea;
1-(2-fluoro-4-(2-(methylcarbamoyl)pyridin-4-yloxy)phenyl)-3-(3-isopropyl-1-(quinolin-6-yl)-1H-pyrazol-5-yl)urea;
1-(3-ethyl-1-(quinolin-6-yl)-1H-pyrazol-5-yl)-3-(2-fluoro-4-(2-(methylcarbamoyl)pyridin-4-yloxy)phenyl)urea;
1-(3-cyclopentyl-1-(quinolin-6-yl)-1H-pyrazol-5-yl)-3-(2-fluoro-4-(2-(methylcarbamoyl)pyridin-4-yloxy)phenyl)urea;
1-(3-tert-butyl-1-(quinolin-6-yl)-1H-pyrazol-5-yl)-3-(2-fluoro-5-(6-(hydroxymethyl)pyridin-3-yloxy)phenyl)urea;
1-(3-tert-butyl-1-(1,2,3,4-tetrahydroisoquinolin-6-yl)-1H-pyrazol-5-yl)-3-(4-methyl-3-(pyridin-3-yloxy)phenyl)urea;
1-(4-(2-carbamoylpyridin-4-yloxy)-2-fluorophenyl)-3-(3-isopropyl-1-(quinolin-6-yl)-1H-pyrazol-5-yl)urea;
1-(3-isopropyl-1-(quinolin-6-yl)-1H-pyrazol-5-yl)-3-(3-methyl-4-(2-(methylcarbamoyl)pyridin-4-yloxy)phenyl)urea; 1-(4-(2-carbamoylpyridin-4-yloxy)-2-fluorophenyl)-3-(3-ethyl-1-(quinolin-6-yl)-1H-pyrazol-5-yl)urea;
1-(3-tert-butyl-1-(quinolin-6-yl)-1H-pyrazol-5-yl)-3-(2-fluoro-5-(6-(methylcarbamoyl)pyridin-3-yloxy)phenyl)urea;
1-(4-(2-carbamoylpyridin-4-yloxy)-3-methylphenyl)-3-(3-isopropyl-1-(quinolin-6-yl)-1H-pyrazol-5-yl)urea;
1-(2-fluoro-4-(2-(1-methyl-1H-pyrazol-4-yl)pyridin-4-yloxy)phenyl)-3-(3-isopropyl-1-(quinolin-6-yl)-1H-pyrazol-5-yl)urea;
1-(3-ethyl-1-(quinolin-6-yl)-1H-pyrazol-5-yl)-3-(2-fluoro-4-(2-(1-methyl-1H-pyrazol-4-yl)pyridin-4-yloxy)phenyl)urea;
1-(4-(2-(1H-pyrazol-4-yl)pyridin-4-yloxy)-3-methylphenyl)-3-(3-isopropyl-1-(quinolin-6-yl)-1H-pyrazol-5-yl)urea;
1-(3-tert-butyl-1-(1,2,3,4-tetrahydroisoquinolin-6-yl)-1H-pyrazol-5-yl)-3-(2-fluoro-4-(2-(1-methyl-1H-pyrazol-4-yl)pyridin-4-yloxy)phenyl)urea;
1-(4-(2-(1H-pyrazol-4-yl)pyridin-4-yloxy)-2-fluorophenyl)-3-(3-tert-butyl-1-(1,2,3,4-tetrahydroisoquinolin-6-yl)-1H-pyrazol-5-yl)urea;
1-(4-(2-(1H-pyrazol-4-yl)pyridin-4-yloxy)-2-fluorophenyl)-3-(3-tert-butyl-1-(1,2,3,4-tetrahydroisoquinolin-7-yl)-1H-pyrazol-5-yl)urea;
1-(3-fluoro-4-(2-(isopropylamino)pyridin-4-yloxy)phenyl)-3-(3-isopropyl-1-(quinolin-6-yl)-1H-pyrazol-5-yl)urea;
1-(3-isopropyl-1-(quinolin-6-yl)-1H-pyrazol-5-yl)-3-(4-(2-(isopropylamino)pyridin-4-yloxy)-3-methylphenyl)urea;
1-(3-ethyl-1-(quinolin-6-yl)-1H-pyrazol-5-yl)-3-(2-fluoro-3-methyl-4-(2-(1-methyl-1H-pyrazol-4-yl)pyridin-4-yloxy)phenyl)urea, and
1-(2,3-difluoro-4-(2-(1-methyl-1H-pyrazol-4-yl)pyridin-4-yloxy)phenyl)-3-(3-ethyl-1-(quinolin-6-yl)-1H-pyrazol-5-yl)urea.

In some embodiments, this disclosure provides a method for treating a muscular degenerative disorder in a subject in need thereof comprising administering to the subject in need thereof a composition comprising 1-(3-tert-butyl-1-(quinolin-6-yl)-1H-pyrazol-5-yl)-3-(2-fluoro-4-(2-(methylcarbamoyl)pyridin-4-yloxy)phenyl)urea, or a pharmaceutically acceptable salt thereof.

In some embodiments, this disclosure provides a method of treating a muscular degenerative disorder in a subject in need thereof, comprising administering to the subject in need thereof a therapeutically effective amount of a compound selected from the compounds provided in FIG. 1.

Figure 2:
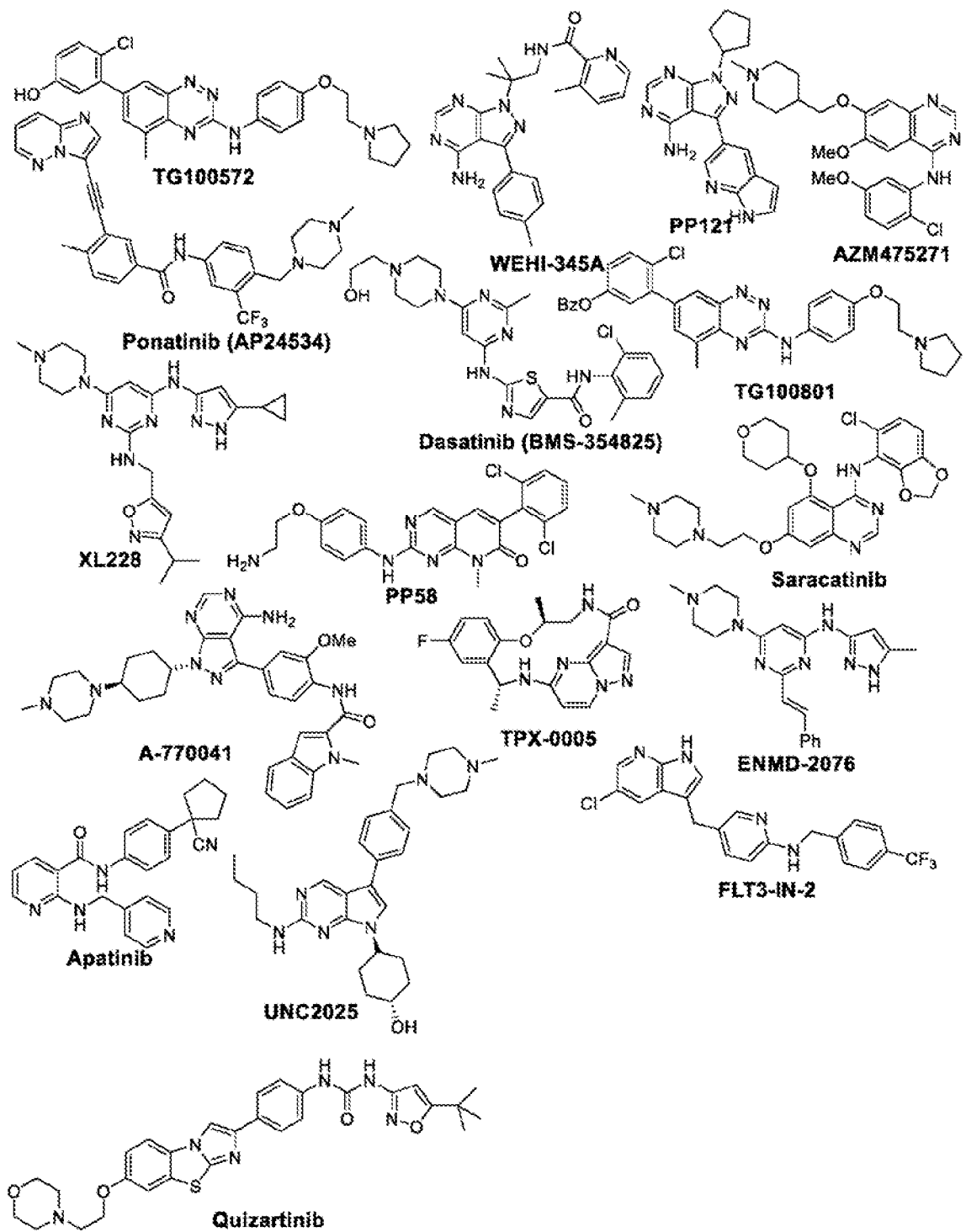
FIG. 2 provides the structures of compounds for modulating DUX4 activity.

In some embodiments, this disclosure provides a method of treating a muscular degenerative disorder in a subject in need thereof, comprising administering to the subject in need thereof a therapeutically effective amount of a compound selected from the compounds provided in FIG. 2.

Figure 3:
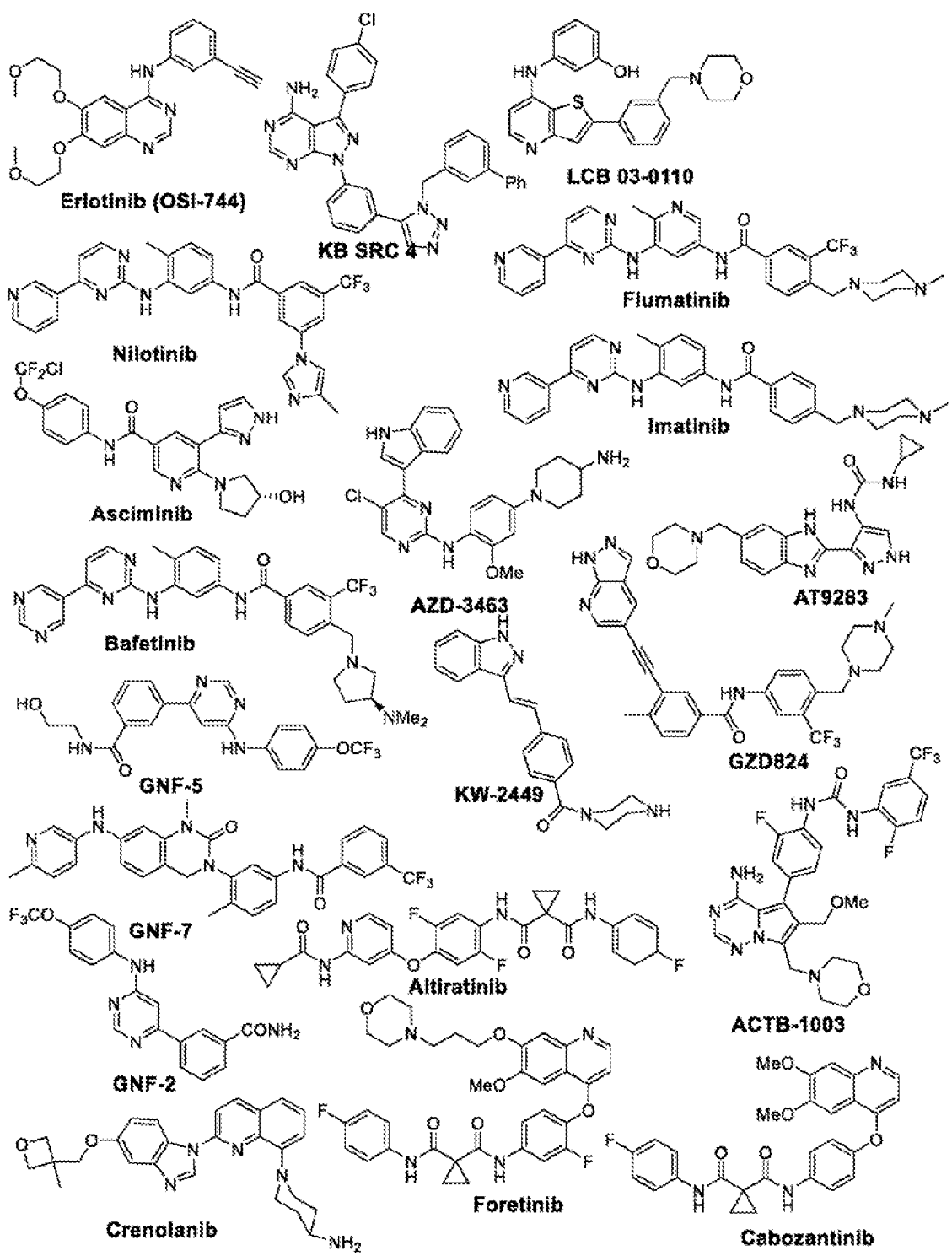
FIG. 3 provides the structures of compounds for modulating DUX4 activity.

In some embodiments, this disclosure provides a method of treating a muscular degenerative disorder in a subject in need thereof, comprising administering to the subject in need thereof a therapeutically effective amount of a compound selected from the compounds provided in FIG. 3.

Figure 4:
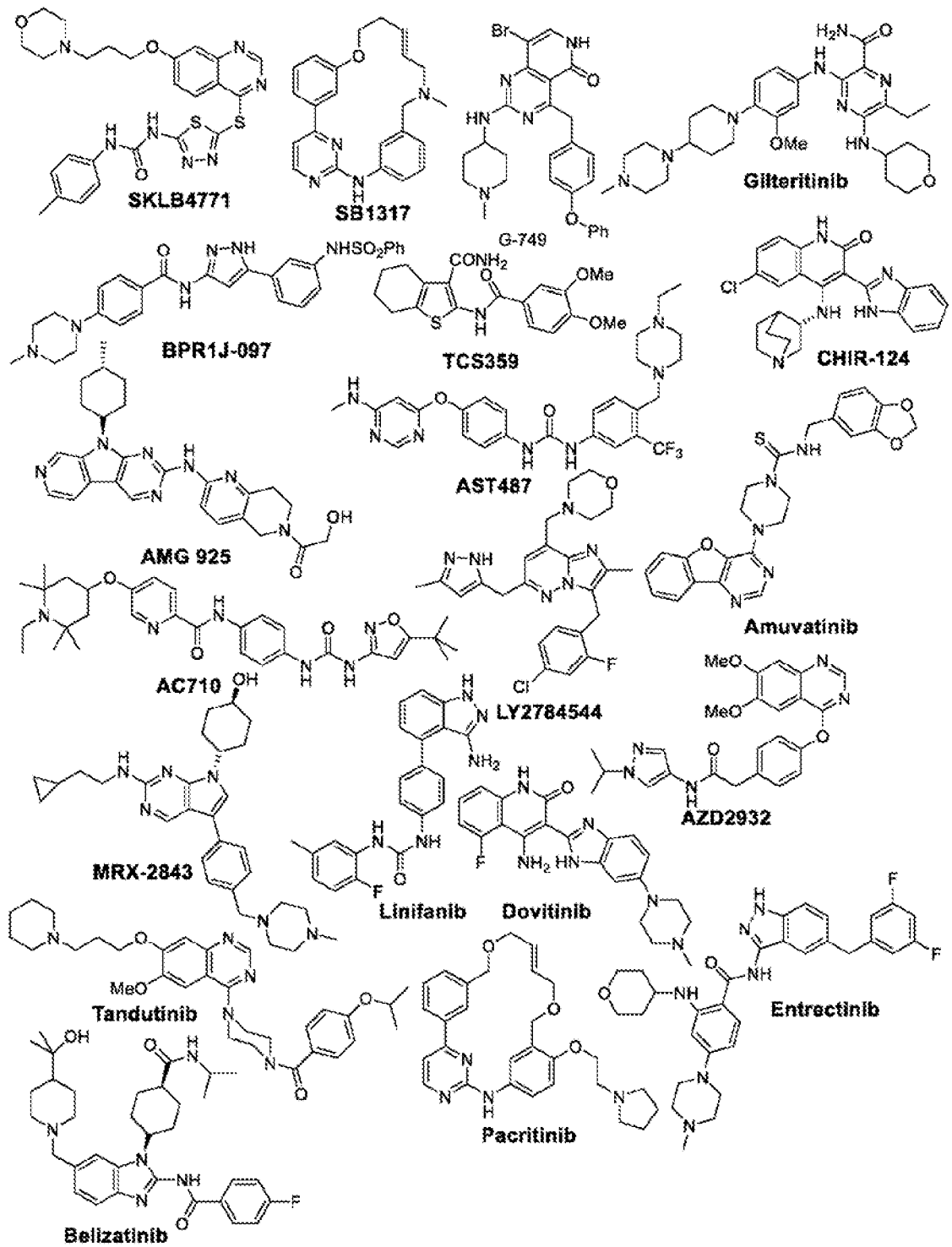
FIG. 4 provides the structures of compounds for modulating DUX4 activity.

In some embodiments, this disclosure provides a method of treating a muscular degenerative disorder in a subject in need thereof, comprising administering to the subject in need thereof a therapeutically effective amount of a compound selected from the compounds provided in FIG. 4.

Figure 5:
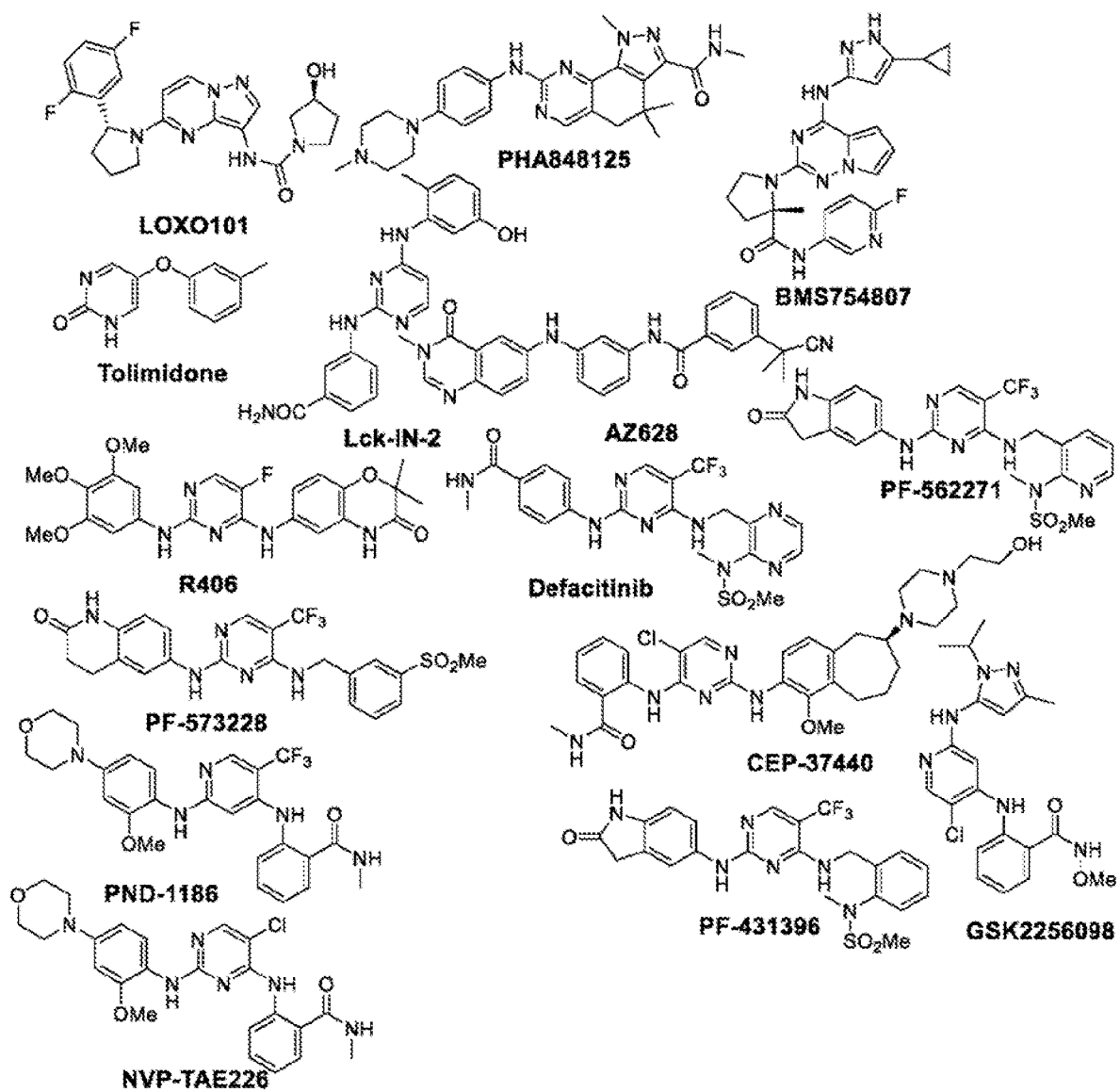
FIG. 5 provides the structures of compounds for modulating DUX4 activity.

In some embodiments, this disclosure provides a method of treating a muscular degenerative disorder in a subject in need thereof, comprising administering to the subject in need thereof a therapeutically effective amount of a compound selected from the compounds provided in FIG. 5.

Another embodiment proves the method of treating a muscular degenerative disorder wherein the muscular degenerative disorder is selected from facioscapulohumeral muscular dystrophy (FSHD), facioscapulohumeral muscular dystrophy-1 (FSHD1), facioscapulohumeral muscular dystrophy-2 (FSHD2), Becker muscular dystrophy, Duchenne muscular dystrophy, myotonic dystrophies type 1, myotonic dystrophies types 2, nemaline myopathy or spinal muscular atrophy. Another embodiment proves the method wherein the subject is a human.

In some embodiments, this disclosure provides a method for treating a muscular degenerative disorder in a subject in need thereof comprising administering to the subject in need thereof a composition comprising a compound, or a pharmaceutically acceptable salt thereof, having the structure of Formula (III):

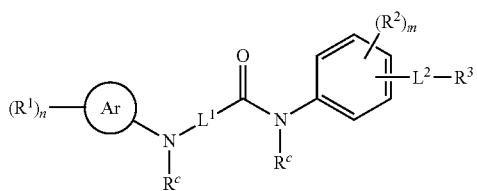

Formula (III)

wherein
Ar is phenyl or 5- or 6-membered heteroaryl;
each $R^1$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;
n is 0-5;
$L^1$ is absent or *—(CR$^a$R$^b$)—C(=O)—, wherein * denotes attachment point to the carbonyl carbon;
$R^a$ and $R^b$ are independently selected from hydrogen, $C_1$-$C_6$alkyl, or $C_1$-$C_6$ haloalkyl;
or $R^a$ and $R^b$ are taken together with the carbon to which they are attached to form a 3-, 4-, 5-, or 6-membered cycloalkyl or a 3-, 4-, 5-, or 6-membered heterocycloalkyl;
each $R^2$ is independently hydrogen, halogen, —CN, —OH, —OR$^{20}$, —NR$^{21}$R$^{21}$, —C(=O)R$^{20}$, —OC(=O)R$^{20}$, —C(=O)OR$^{21}$, —C(=O)NR$^{21}$R$^{21}$, —NR$^{21}$C(=O)R$^{20}$, $C_1$-$C_6$ alkyl, or $C_1$-$C_6$ haloalkyl;
or two $R^2$ on adjacent atoms are taken together with the atoms to which they are attached to form an unsubstituted or substituted cycloalkyl, unsubstituted or substituted heterocycloalkyl, unsubstituted or substituted aryl, or unsubstituted or substituted heteroaryl;
m is 0-4;
$L^2$ is absent, —O—, —O—($C_1$-$C_4$ alkylene)-, or —NR$^c$—C(=O)—;
each $R^c$ is independently selected from hydrogen, $C_1$-$C_6$ alkyl, or $C_1$-$C_6$ haloalkyl;
$R^3$ is unsubstituted or substituted cycloalkyl, unsubstituted or substituted heterocycloalkyl, unsubstituted or substituted aryl, or unsubstituted or substituted heteroaryl; wherein when $R^3$ is substituted, it is substituted by 1-3 $R^4$;
each $R^4$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;
each $R^{20}$ is independently selected from unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;
each $R^{21}$ is independently selected from hydrogen, unsubstituted or substituted $C_1$-$C_6$alkyl, unsubstituted or substituted $C_1$-$C_6$alkenyl, unsubstituted or substituted $C_1$-$C_6$alkynyl, unsubstituted or substituted cycloalkyl, unsubstituted or substituted heterocycloalkyl, unsubstituted or substituted aryl, or unsubstituted or substituted heteroaryl;
or two $R^{21}$ on the same N atom are taken together with the N atom to which they are attached to form an unsubstituted or substituted N-containing heterocycle;
wherein when any $R^1$, $R^2$, $R^4$, $R^{20}$, or $R^{21}$ is substituted, substituents on the $R^1$, $R^2$, $R^4$, $R^{20}$, or $R^{21}$ are independently selected at each occurrence from halogen, —CN, —NO$_2$, —OR$^{22}$, —CO$_2$R$^{22}$, —C(=O)R$^{23}$, —C(=O)NR$^{22}$R$^{22}$, —NR$^{22}$R$^{22}$, —NR$^{22}$C(=O)R$^{23}$, —NR$^{22}$C(=O)OR$^{22}$, —SR$^{22}$, —S(=O)R$^{23}$, —SO$_2$R$^{23}$, —SO$_2$NR$^{22}$NR$^{22}$, $C_1$-$C_6$ alkyl, $C_1$-$C_6$ haloalkyl, monocyclic cycloalkyl, monocyclic heterocycloalkyl, phenyl, benzyl, 5-membered heteroaryl, and 6-membered heteroaryl; or two substituents on the same carbon atom are taken together to form a C=O or C=S;

each $R^{22}$ is independently selected from hydrogen, $C_1$-$C_6$ alkyl, $C_3$-$C_6$ cycloalkyl, phenyl, benzyl, 5-membered heteroaryl, and 6-membered heteroaryl;

or two $R^{22}$ groups are taken together with the N atom to which they are attached to form a N-containing heterocycle; and each $R^{23}$ is independently selected from $C_1$-$C_6$alkyl, $C_3$-$C_6$ cycloalkyl, phenyl, benzyl, 5-membered heteroaryl, and 6-membered heteroaryl.

In some embodiments, this disclosure provides a method for treating a muscular degenerative disorder in a subject in need thereof comprising administering to the subject in need thereof a composition comprising a compound, or a pharmaceutically acceptable salt thereof, having the structure of Formula (IV):

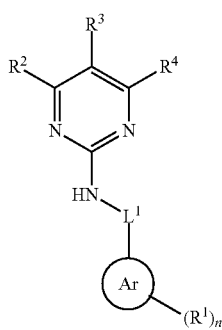

Formula (IV)

wherein

L is absent or —$C_1$-$C_4$ alkylene;

Ar is phenyl or 5- or 6-membered heteroaryl;

each $R^1$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

or two $R^1$ on adjacent atoms are taken together with the atoms to which they are attached to form a unsubstituted or substituted carbocycle, or unsubstituted or substituted heterocycle; wherein if the carbocycle or heterocycle is substituted, it is substituted with 1-3 $R^7$;

each $R^7$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

n is 0-5;

$R^2$ and $R^4$ are each independently hydrogen, or —NR$^5$R$^6$, or unsubstituted or substituted heterocycle;

each $R^5$ and $R^6$ is independently hydrogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;

or $R^5$ and $R^6$ are taken together with the N atom to which they are attached to form an unsubstituted or substituted N-containing heterocycle;

$R^3$ is hydrogen, halogen, $C_1$-$C_6$ alkyl or $C_1$-$C_6$ haloalkyl;

or $R^2$ and $R^3$ are taken together with the atoms to which they are attached to form a unsubstituted or substituted carbocycle, or unsubstituted or substituted heterocycle; wherein if the carbocycle or heterocycle is substituted, it is substituted with 1-3 $R^8$;

each $R^8$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

or two $R^7$ on the same carbon atom are taken together to form a C=O, or C=S;

each $R^{20}$ is independently selected from unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

each $R^{21}$ is independently selected from hydrogen, unsubstituted or substituted $C_1$-$C_6$alkyl, unsubstituted or substituted $C_1$-$C_6$alkenyl, unsubstituted or substituted $C_1$-$C_6$ alkynyl, unsubstituted or substituted cycloalkyl, unsubstituted or substituted heterocycloalkyl, unsubstituted or substituted aryl, or unsubstituted or substituted heteroaryl;

or two $R^{21}$ on the same N atom are taken together with the N atom to which they are attached to form an unsubstituted or substituted N-containing heterocycle;

wherein when any $R^1$, $R^2$, $R^4$, $R^5$, $R^6$, $R^7$, $R^{20}$, or $R^{21}$ is substituted, substituents on the $R^1$, $R^2$, $R^4$, $R^5$, $R^6$, $R^7$, $R^{20}$, or $R^{21}$ are independently selected at each occurrence from halogen, —CN, —NO$_2$, —OR$^{22}$, —CO$_2$R$^{22}$, —C(=O)R$^{23}$, —C(=O)NR$^{22}$R$^{22}$, —NR$^{22}$R$^{22}$, —NR$^{22}$C(=O)R$^{23}$, —NR$^{22}$C(=O)OR$^{22}$, —SR$^{22}$, —S(=O)R$^{23}$, —SO$_2$R$^{23}$, —SO$_2$NR$^{22}$R$^{22}$, —NR$^{22}$SO$_2$R$^{23}$, $C_1$-$C_6$ alkyl, $C_1$-$C_6$ haloalkyl, monocyclic cycloalkyl, monocyclic heterocycloalkyl, phenyl, benzyl, 5-membered heteroaryl, and 6-membered heteroaryl; or two substituents on the same carbon atom are taken together to form a C=O or C=S;

each $R^{22}$ is independently selected from hydrogen, $C_1$-$C_6$alkyl, $C_1$-$C_6$ hydroxyalkyl, $C_3$-$C_6$ cycloalkyl, phenyl, benzyl, 5-membered heteroaryl, and 6-membered heteroaryl;

or two $R^{22}$ groups are taken together with the N atom to which they are attached to form a N-containing heterocycle; and each $R^{23}$ is independently selected from $C_1$-$C_6$alkyl, $C_1$-$C_6$ hydroxyalkyl, $C_1$-$C_6$alkyl $C_3$-$C_6$ cycloalkyl, phenyl, benzyl, 5-membered heteroaryl, and 6-membered heteroaryl;

In some embodiments, this disclosure provides a method for treating a muscular degenerative disorder in a subject in need thereof comprising administering to the subject in need thereof a composition comprising a compound, or a pharmaceutically acceptable salt thereof, having the structure of Formula (V):

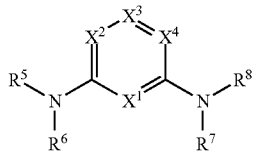

Formula (V)

wherein
$X^1$ is N or $CR^1$;
$R^1$ is hydrogen, halogen, $C_1$-$C_6$ alkyl, or $C_1$-$C_6$ haloalkyl;
$X^2$ is N or $CR^2$;
$R^2$ is hydrogen, halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;
$X^3$ is N or $CR^3$;
$R^3$ is hydrogen, halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;
$X^4$ is N or $CR^4$;
$R^4$ is hydrogen, halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$C(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl;

wherein 0, 1, or 2 of $X^1$, $X^2$, $X^3$, and $X^4$ are N;
$R^5$ is hydrogen, unsubstituted or substituted aryl, or unsubstituted or substituted heteroaryl; wherein if $R^5$ is substituted, it is substituted with 1-3 $R^9$;
each $R^9$ is independently halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl;
$R^6$ is hydrogen, $C_1$-$C_6$ alkyl or $C_1$-$C_6$ haloalkyl;
or $R^5$ and $R^6$ are taken together with the N atom to which they are attached to form an unsubstituted or substituted N-containing heterocycle; wherein if the heterocycle is substituted, it is substituted by 1-3 $R^{13}$;
each $R^{13}$ is independently halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;
$R^7$ is hydrogen, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, or —$C(=O)R^{11}$;
$R^{11}$ unsubstituted phenyl, or phenyl substituted by 1-3 $R^{12}$,
each $R^{12}$ is independently halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;
$R^8$ is hydrogen, $C_1$-$C_6$alkyl or $C_1$-$C_6$ haloalkyl;
or $R^7$ and $R^8$ are taken together with the N atom to which they are attached to form an unsubstituted or substituted N-containing heterocycle; wherein if the heterocycle is substituted, it is substituted by 1-3 $R^{10}$;

each $R^{10}$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

each $R_{20}$ is independently selected from unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl;

each $R^{21}$ is independently selected from hydrogen, unsubstituted or substituted $C_1$-$C_6$ alkyl, unsubstituted or substituted $C_1$-$C_6$alkenyl, unsubstituted or substituted $C_1$-$C_6$ alkynyl, unsubstituted or substituted cycloalkyl, unsubstituted or substituted heterocycloalkyl, unsubstituted or substituted aryl, unsubstituted or substituted heteroaryl;

or two $R^{21}$ on the same N atom are taken together with the N atom to which they are attached to form an unsubstituted or substituted N-containing heterocycle;

wherein when any $R^2$, $R^3$, $R^4$, $R^7$, $R^9$, $R^{10}$, $R^{12}$, $R^{13}$, $R^{20}$, or $R^{21}$ is substituted, substituents on the $R^2$, $R^3$, $R^4$, $R^7$, $R^9$, $R^{10}$, $R^{12}$, $R^{13}$, $R^{20}$, or $R^{21}$ are independently selected at each occurrence from halogen, —CN, —NO$_2$, —OR$^{22}$, —CO$_2$R$^{22}$, —C(=O)R$^{23}$, —C(=O)NR$^{22}$R$^{22}$, —C(=O)NR$^{22}$—OR$^{22}$, —NR$^{22}$R$^{22}$, —NR$^{22}$C(=O)R$^{23}$, —NR$^{22}$C(=O)OR$^{22}$, —SR$^{22}$, —S(=O)R$^{23}$, —SO$_2$R$^{23}$, —SO$_2$NR$^{22}$R$^{22}$, $C_1$-$C_6$ alkyl, $C_1$-$C_6$ haloalkyl, monocyclic cycloalkyl, monocyclic heterocycloalkyl, monocyclic heterocycloalkyl substituted with a $R^{23}$, phenyl, benzyl, 5-membered heteroaryl, and 6-membered heteroaryl; or two substituents on the same carbon atom are taken together to form a C=O or C=S;

each $R^{22}$ is independently selected from hydrogen, $C_1$-$C_6$ alkyl, $C_3$-$C_6$ cycloalkyl, phenyl, benzyl, 5-membered heteroaryl, and 6-membered heteroaryl;

or two $R^{22}$ groups are taken together with the N atom to which they are attached to form a N-containing heterocycle; and each $R^{23}$ is independently selected from $C_1$-$C_6$ alkyl, $C_3$-$C_6$ cycloalkyl, phenyl, benzyl, 5-membered heteroaryl, and 6-membered heteroaryl.

In some embodiments, this disclosure provides a method for treating a muscular degenerative disorder in a subject in need thereof comprising administering to the subject in need thereof a composition comprising a compound, or a pharmaceutically acceptable salt thereof, having the structure of Formula (VI):

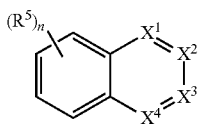

Formula (VI)

wherein:

$X^1$ and $X^2$ are independently N or CH;

$X^3$ is N or CR$^3$;

$R^3$ is hydrogen, —CN, or -L-Ar, $X^4$ is N or CR$^4$;

$R^4$ is hydrogen, or -L-Ar;

wherein one of $X^3$ and $X^4$ is C-L-Ar;

L is —NH—, —O—, —S—, —$C_1$-$C_2$ alkylene-, or -heterocycloalkylene-C(=O)—;

Ar is substituted or unsubstituted phenyl or substituted or unsubstituted 5- or 6-membered heteroaryl; wherein when Ar is substituted, it is substituted with 1-3 $R^6$;

each $R^6$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —($C_1$-$C_4$ alkylene)-C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

or two $R^6$ on adjacent atoms are taken together with the atoms to which they are attached to form an unsubstituted or substituted cycloalkyl, unsubstituted or substituted heterocycloalkyl, unsubstituted or substituted aryl, or unsubstituted or substituted heteroaryl;

each $R^5$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

n is 0-4, each $R^{20}$ is independently selected from unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;

each $R^{21}$ is independently selected from hydrogen, unsubstituted or substituted $C_1$-$C_6$alkyl, unsubstituted or substituted $C_1$-$C_6$ alkenyl, unsubstituted or substituted $C_1$-$C_6$ alkynyl, unsubstituted or substituted cycloalkyl, unsubstituted or substituted heterocycloalkyl, unsubstituted or substituted aryl, or unsubstituted or substituted heteroaryl;

or two $R^{21}$ on the same N atom are taken together with the N atom to which they are attached to form an unsubstituted or substituted N-containing heterocycle;

wherein when any $R^5$, $R^6$, $R^{20}$, or $R^{21}$ is substituted, substituents on the $R^5$, $R^6$, $R^{20}$, or $R^{21}$ are independently selected at each occurrence from halogen, —CN, —NO$_2$, —OR$^{22}$, —CO$_2$R$^{22}$, —C(=O)R$^{23}$, —OC(=O)R$^{23}$, —C(=O)NR$^{22}$R$^{22}$, —NR$^{22}$R$^{22}$, —NR$^{22}$C(=O)R$^{23}$, —NR$^{22}$C(=O)OR$^{22}$, —SR$^{22}$, —S(=O)R$^{23}$, —SO$_2$R$^{23}$, —SO$_2$NR$^{22}$R$^{22}$, C$_1$-C$_6$ alkyl, C$_1$-C$_6$ haloalkyl, monocyclic cycloalkyl, monocyclic heterocycloalkyl, phenyl, benzyl, 5-membered heteroaryl, and 6-membered heteroaryl; or two substituents on the same carbon atom are taken together to form a C=O or C=S;

each R$^{22}$ is independently selected from hydrogen, C$_1$-C$_6$ alkyl, C$_3$-C$_6$ cycloalkyl, phenyl, benzyl, 5-membered heteroaryl, and 6-membered heteroaryl;

or two R$^{22}$ groups are taken together with the N atom to which they are attached to form a N-containing heterocycle; and each R$^{23}$ is independently selected from C$_1$-C$_6$ alkyl, C$_3$-C$_6$ cycloalkyl, phenyl, benzyl, 5-membered heteroaryl, and 6-membered heteroaryl.

In some embodiments, this disclosure provides a method for treating a muscular degenerative disorder in a subject in need thereof comprising administering to the subject in need thereof a composition comprising a compound, or a pharmaceutically acceptable salt thereof, having the structure of Formula (VII):

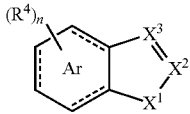

Formula (VII)

wherein:

X$^1$ is —S—, —O—, or —NR$^1$—;

R$^1$ is hydrogen, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl; wherein when R$^1$ is substituted, it is substituted by 1-3 R$^7$;

each R$^7$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted cycloalkyl, unsubstituted or substituted heterocycloalkyl, unsubstituted or substituted aryl, or unsubstituted or substituted heteroaryl;

X$^2$ is N or CR$^2$;

R$^2$ is hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl; wherein when R$^2$ is substituted, it is substituted by 1-3 R$^8$;

each R$^8$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted cycloalkyl, unsubstituted or substituted heterocycloalkyl, unsubstituted or substituted aryl, or unsubstituted or substituted heteroaryl;

X$^3$ is N or CR$^3$; wherein X$^2$ and X$^3$ are not both N;

R$^3$ is hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —C$_1$-C$_6$-alkylene-cycloalkyl, unsubstituted or substituted —C$_1$-C$_6$-alkylene-heterocycloalkyl, unsubstituted or substituted —C$_1$-C$_6$-alkylene-aryl, or unsubstituted or substituted —C$_1$-C$_6$-alkylene-heteroaryl; wherein when R$^3$ is substituted, it is substituted by 1-3 R$^9$;

each R$^9$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)$_2$R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted cycloalkyl, unsubstituted or substituted heterocycloalkyl, unsubstituted or substituted aryl, unsubstituted or substituted heteroaryl, unsubstituted or substituted —C$_1$-C$_6$-alkylene-cycloalkyl, unsubstituted or substituted —C$_1$-C$_6$-alkylene-heterocycloalkyl, unsubstituted or substituted —C$_1$-C$_6$-alkylene-aryl, or unsubstituted or substituted —C$_1$-C$_6$-alkylene-heteroaryl;

Ar is a 6-membered aromatic ring comprising 0-2 nitrogen atoms;

each R$^4$ is independently hydrogen, halogen, —CN, —OH, —OR$^5$, —SH, —SR$^5$, —NO$_2$, —NR$^6$R$^6$, —S(=O)$_2$R$^5$, —NR$^6$S(=O)$_2$R$^5$, —S(=O)R$^5$, —S(=O)$_2$NR$^6$R$^6$, —C(=O)R$^5$, —OC(=O)R$^5$, —C(=O)OR$^6$, —OC(=O)OR$^6$, —C(=O)NR$^6$R$^6$, —OC(=O)NR$^6$R$^6$, —NR$^6$C(=O)NR$^6$R$^6$, —NR$^6$C(=O)R$^5$, —NR$^6$C(=O)OR$^6$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —C$_1$-C$_6$-alkylene-cycloalkyl, unsubstituted or substituted —C$_1$-C$_6$-alkylene-heterocycloalkyl, unsubstituted or substituted —C$_1$-C$_6$-alkylene-aryl, or unsubstituted or substituted —C$_1$-C$_6$-alkylene-heteroaryl;

each $R^5$ is independently selected from unsubstituted or substituted $C_1$-$C_6$ alkyl, unsubstituted or substituted $C_2$-$C_6$ alkenyl, unsubstituted or substituted $C_1$-$C_6$ alkynyl, unsubstituted or substituted cycloalkyl, unsubstituted or substituted heterocycloalkyl, unsubstituted or substituted aryl, or unsubstituted or substituted heteroaryl; wherein if $R^5$ is substituted, it is substituted by 1-3 $R^{10}$;

each $R^{10}$ is independently halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

each $R^6$ is independently selected from hydrogen, unsubstituted or substituted $C_1$-$C_6$ alkyl, unsubstituted or substituted $C_1$-$C_6$ alkenyl, unsubstituted or substituted $C_1$-$C_6$ alkynyl, unsubstituted or substituted cycloalkyl, unsubstituted or substituted heterocycloalkyl, unsubstituted or substituted aryl, or unsubstituted or substituted heteroaryl; wherein if $R^6$ is substituted, it is substituted by 1-3 $R^{11}$;

each $R^{11}$ is independently halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

n is 0-4, each $R^{20}$ is independently selected from unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;

each $R^{21}$ is independently selected from hydrogen, unsubstituted or substituted $C_1$-$C_6$ alkyl, unsubstituted or substituted $C_1$-$C_6$ alkenyl, unsubstituted or substituted $C_1$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;

or two $R^{21}$ on the same N atom are taken together with the N atom to which they are attached to form an unsubstituted or substituted N-containing heterocycle;

wherein when any $R^4$, $R^7$, $R^8$, $R^9$, $R^{10}$, $R^{11}$, $R^{20}$, or $R^{21}$ is substituted, substituents on the $R^4$, $R^7$, $R^8$, $R^9$, $R^{10}$, $R^{11}$, $R^{20}$, or $R^{21}$ are independently selected at each occurrence from halogen, —CN, —$NO_2$, —$OR^{22}$, —$CO_2R^{22}$, —$C(=O)R^{23}$, —$C(=O)NR^{22}R^{22}$, —$NR^{22}R^{22}$, —$NR^{22}C(=O)R^{23}$, —$NR^{22}C(=O)OR^{22}$, —$SR^{22}$, —$S(=O)R^{23}$, —$SO_2R^{23}$, —$SO_2NR^{22}R^{22}$, $C_1$-$C_6$ alkyl, $C_1$-$C_6$ haloalkyl, $C_1$-$C_6$ hydroxyalkyl, monocyclic cycloalkyl, monocyclic heterocycloalkyl, phenyl, benzyl, benzyl substituted with phenyl, 5-membered heteroaryl, and 6-membered heteroaryl; or two substituents on the same carbon atom are taken together to form a C=O or C=S;

each $R^{22}$ is independently selected from hydrogen, $C_1$-$C_6$ alkyl, $C_3$-$C_6$ cycloalkyl, phenyl, benzyl, 5-membered heteroaryl, and 6-membered heteroaryl;

or two $R^{22}$ groups are taken together with the N atom to which they are attached to form a N-containing heterocycle; and each $R^{23}$ is independently selected from $C_1$-$C_6$ alkyl, $C_1$-$C_6$ cycloalkyl, phenyl, benzyl, 5-membered heteroaryl, and 6-membered heteroaryl.

Figure 18:
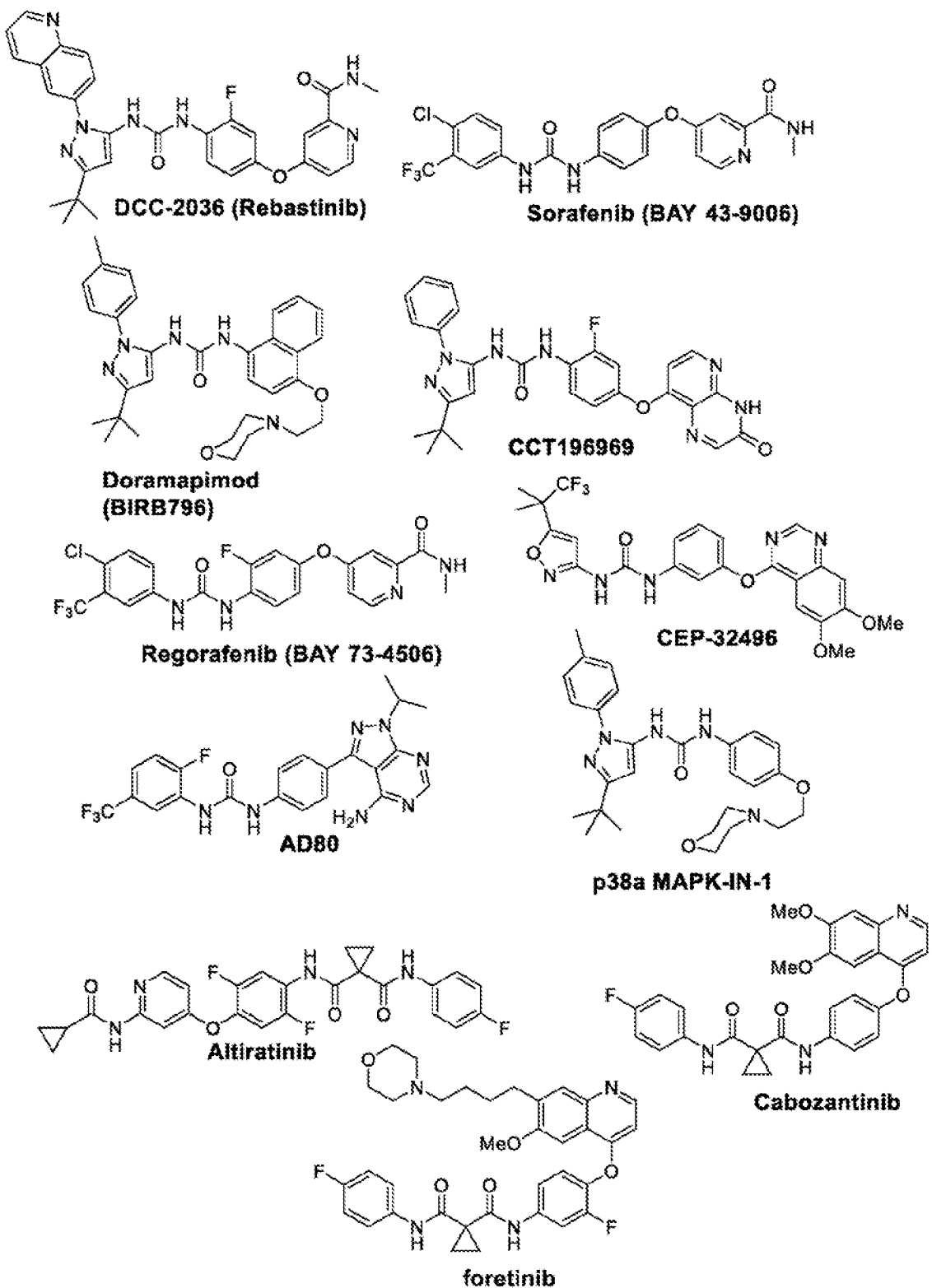
FIG. 18 provides the structures of compounds for modulating DUX4 activity.
Figure 19:
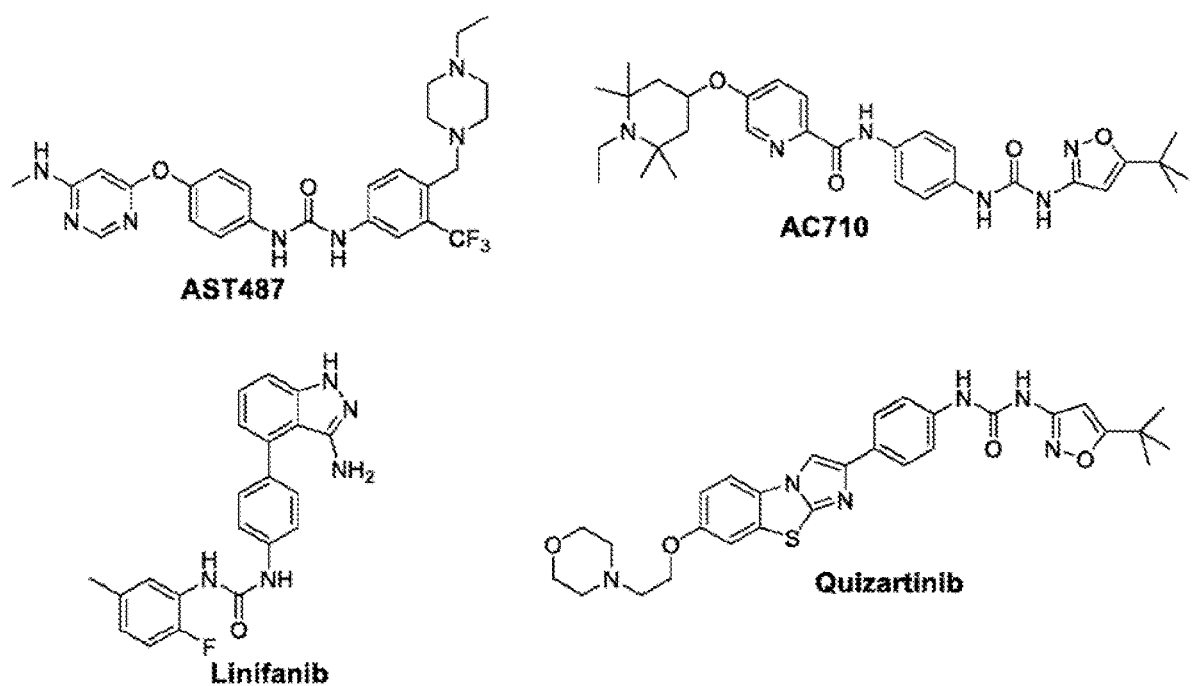
FIG. 19 provides the structures of compounds for modulating DUX4 activity.

In some embodiments, this disclosure provides a method of treating a muscular degenerative disorder in a subject in need thereof, comprising administering to the subject in need thereof a therapeutically effective amount of a compound selected from the compounds provided in FIG. 18 or 19.

Figure 20:
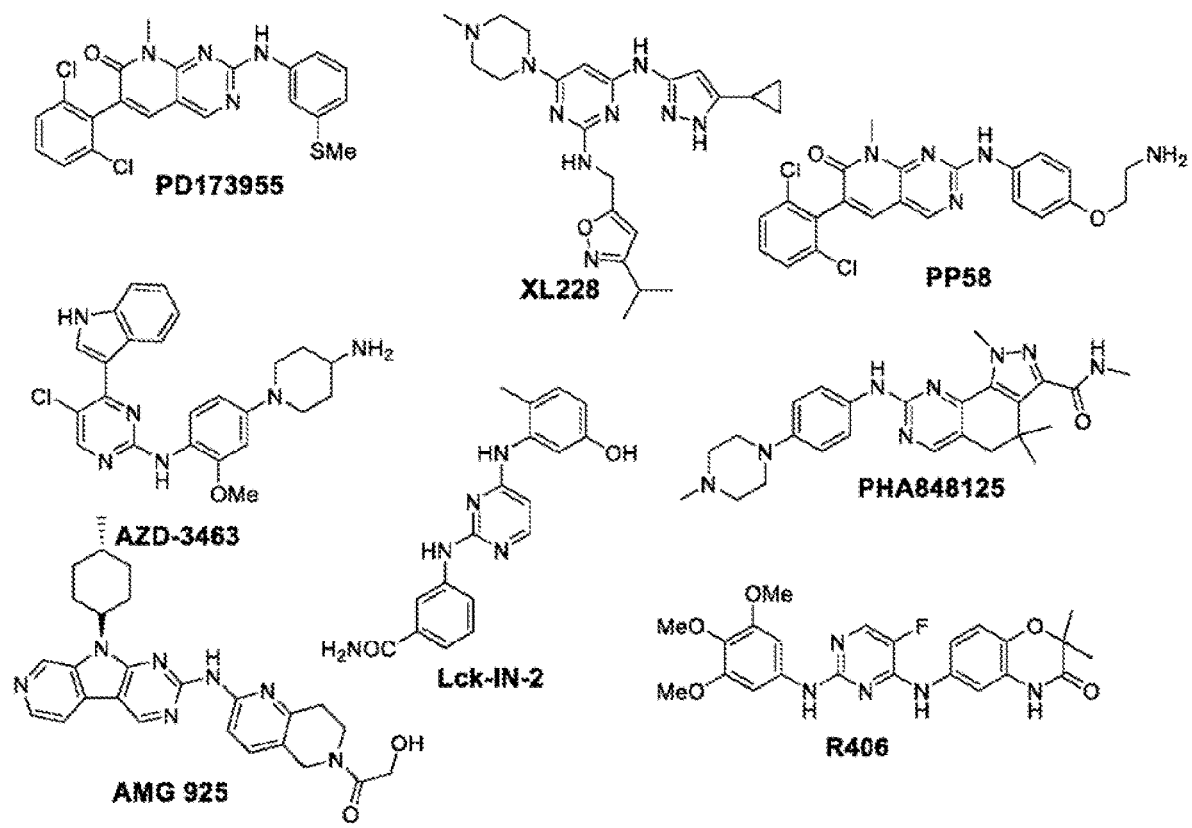
FIG. 20 provides the structures of compounds for modulating DUX4 activity.
Figure 21:
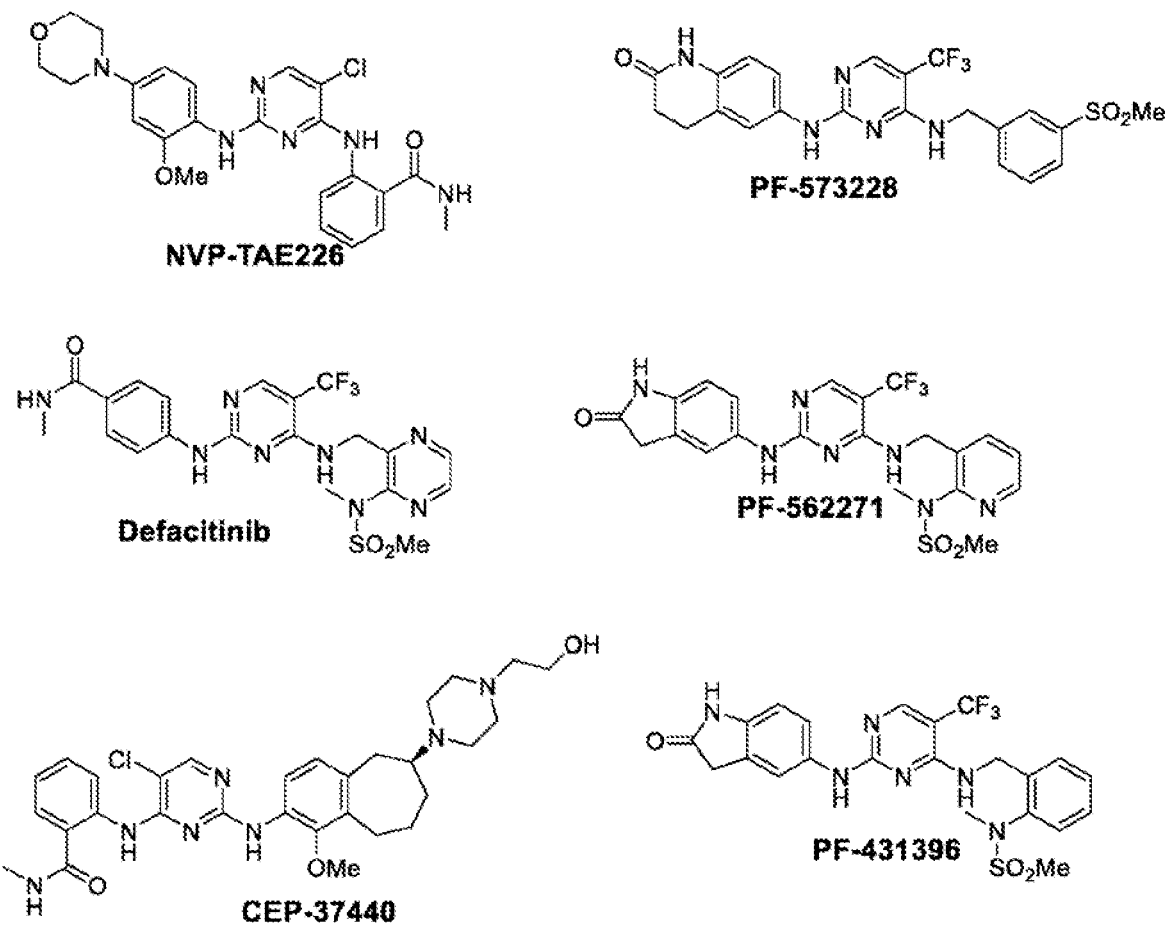
FIG. 21 provides the structures of compounds for modulating DUX4 activity.

In some embodiments, this disclosure provides a method of treating a muscular degenerative disorder in a subject in need thereof, comprising administering to the subject in need thereof a therapeutically effective amount of a compound selected from the compounds provided in FIG. 20 or 21.

Figure 22:
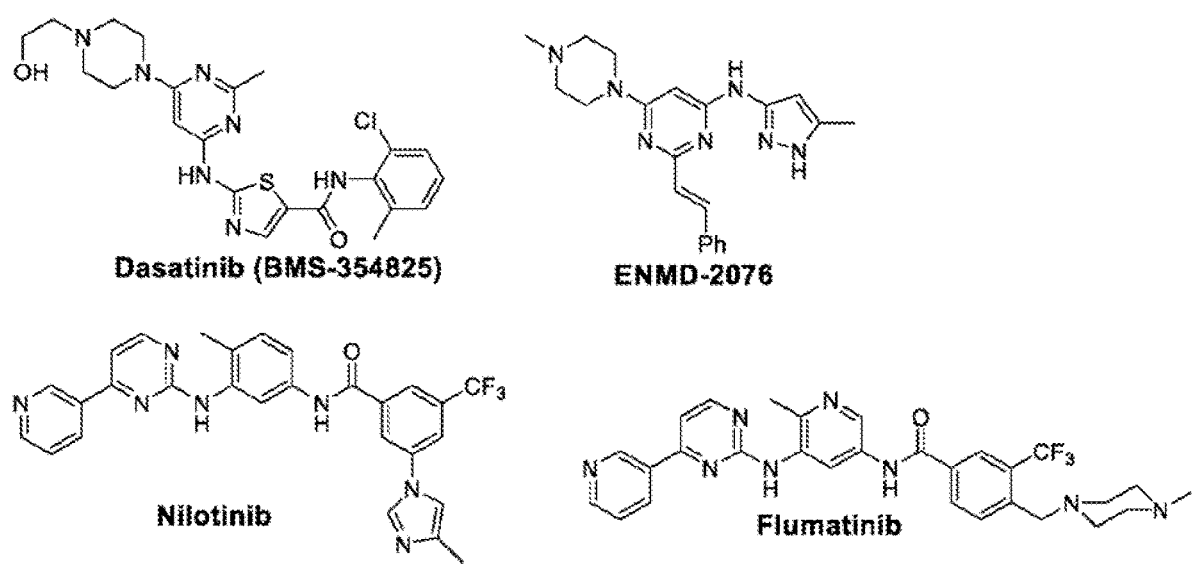
FIG. 22 provides the structures of compounds for modulating DUX4 activity.
Figure 23:
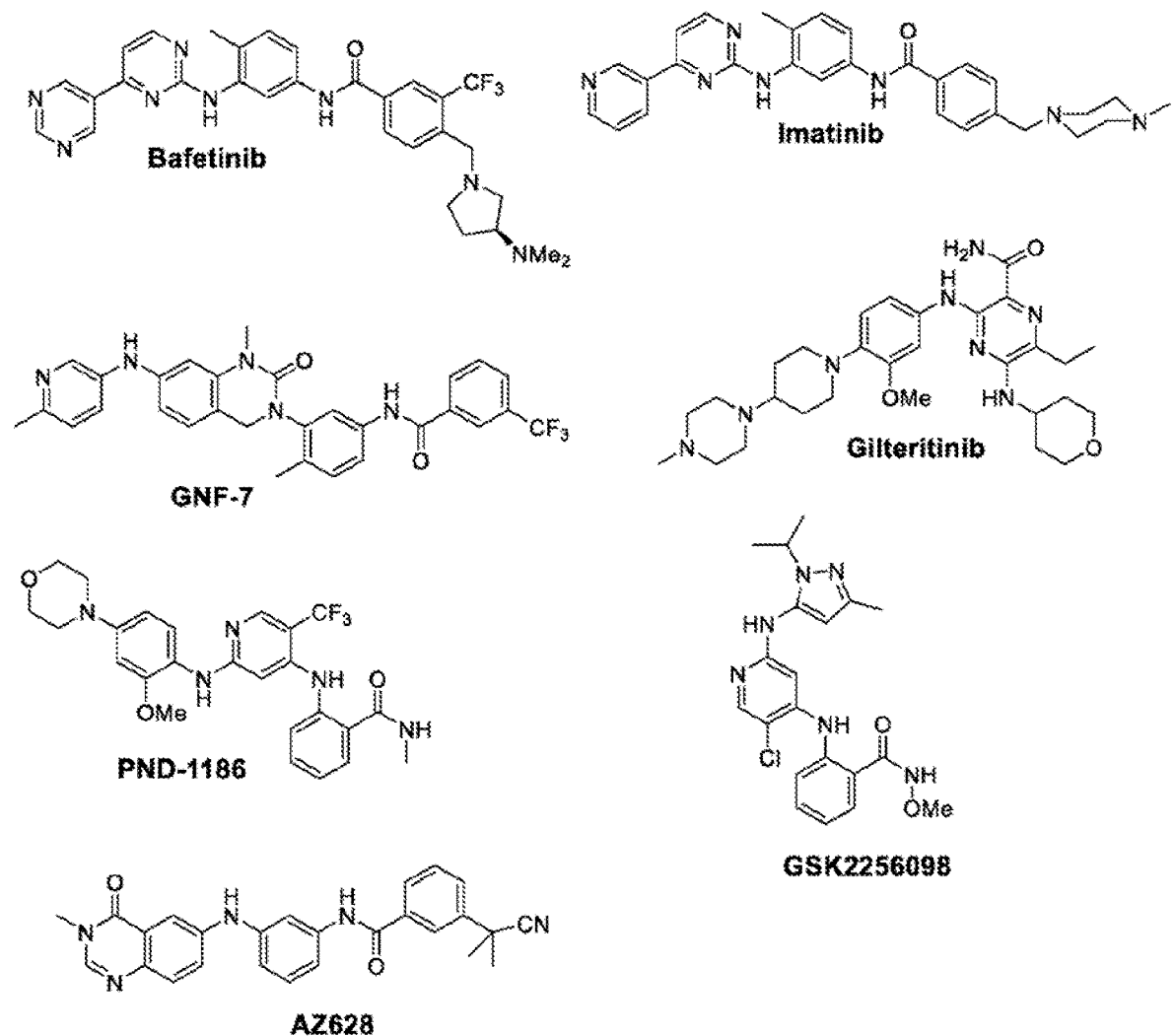
FIG. 23 provides the structures of compounds for modulating DUX4 activity.

In some embodiments, this disclosure provides a method of treating a muscular degenerative disorder in a subject in need thereof, comprising administering to the subject in need thereof a therapeutically effective amount of a compound selected from the compounds provided in FIG. 22 or 23.

Figure 24:
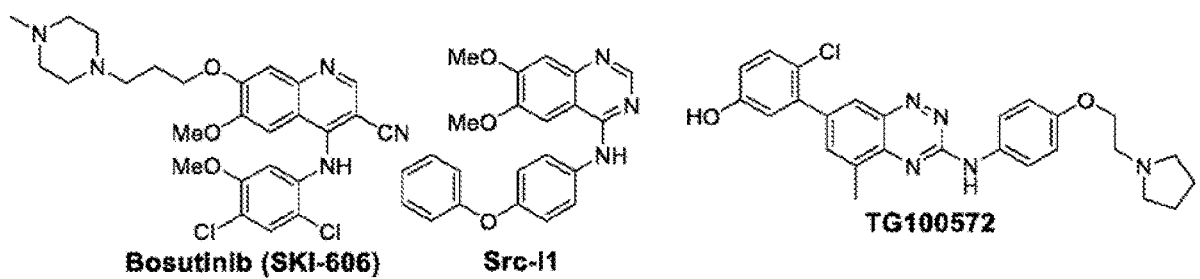
FIG. 24 provides the structures of compounds for modulating DUX4 activity.
Figure 25:
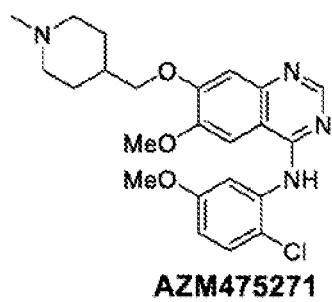
FIG. 25 provides the structures of compounds for modulating DUX4 activity.
Figure 25:
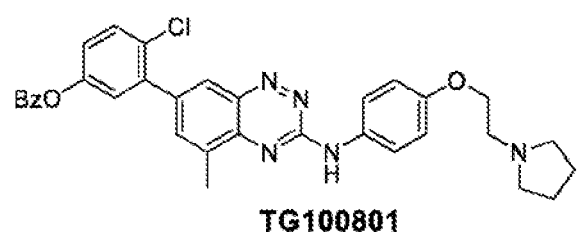
Figure 25:
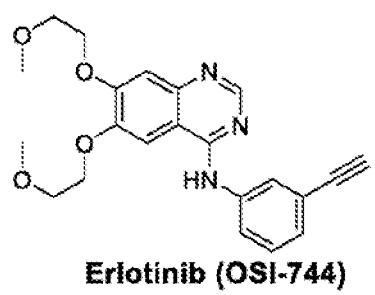
Figure 25:
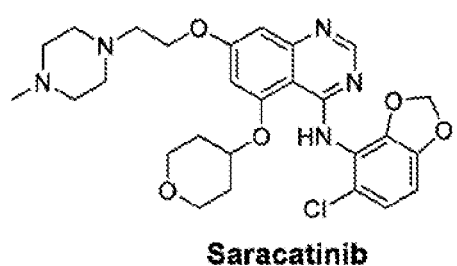
Figure 25:
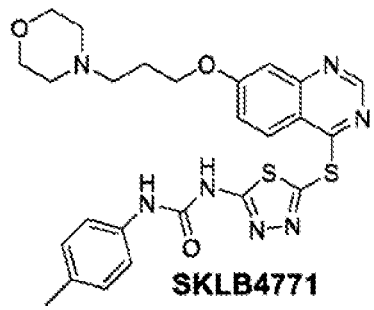
Figure 25:
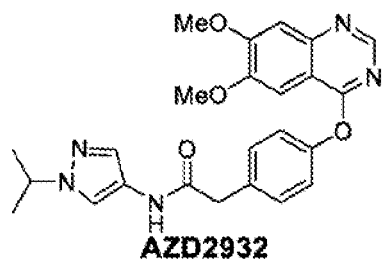
Figure 25:
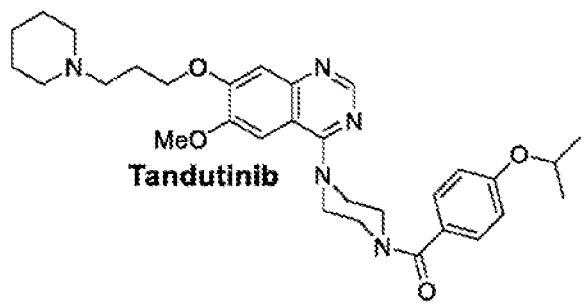

In some embodiments, this disclosure provides a method of treating a muscular degenerative disorder in a subject in need thereof, comprising administering to the subject in need thereof a therapeutically effective amount of a compound selected from the compounds provided in FIG. 24 or 25.

Figure 26:
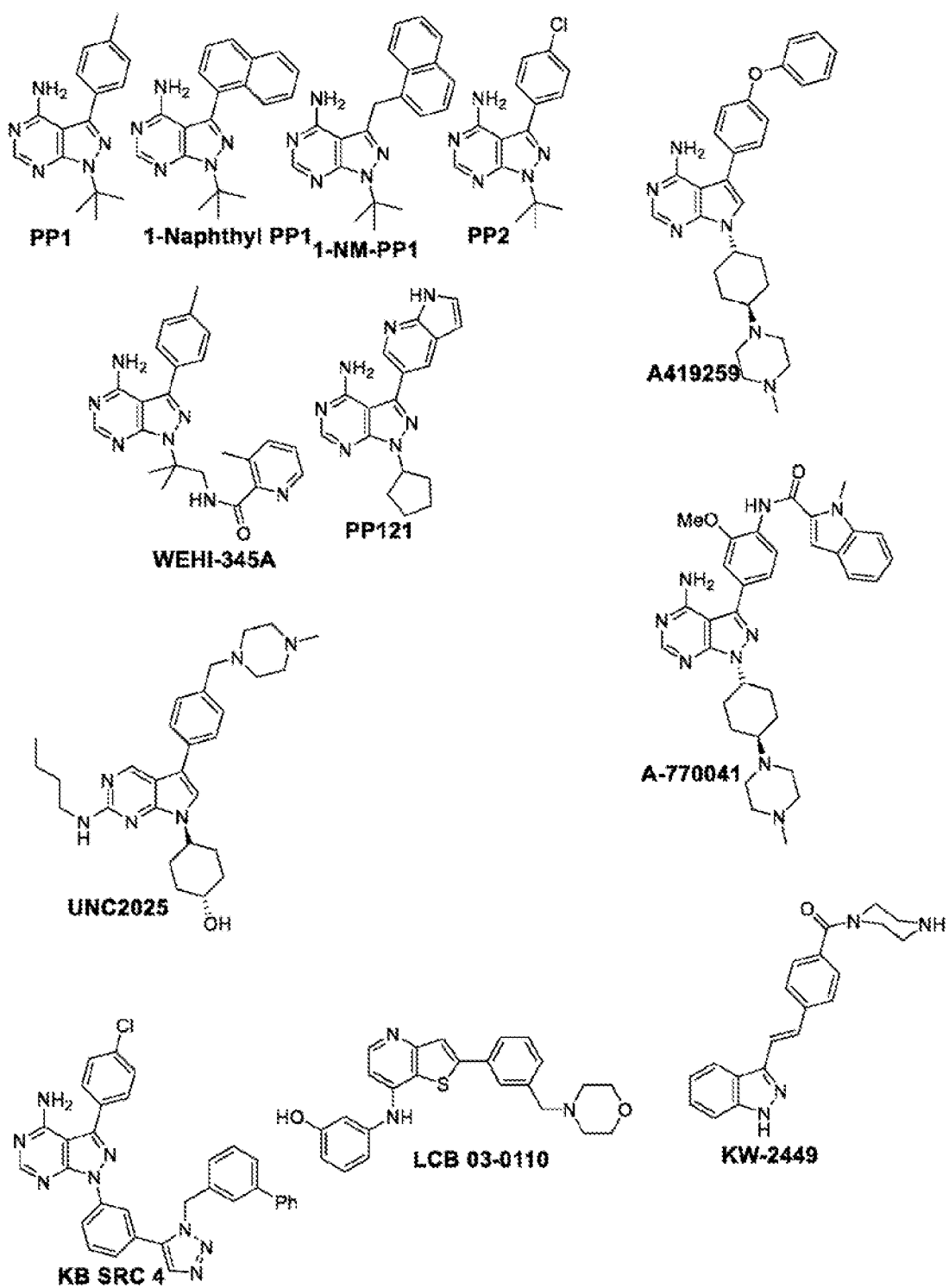
FIG. 26 provides the structures of compounds for modulating DUX4 activity.
Figure 27:
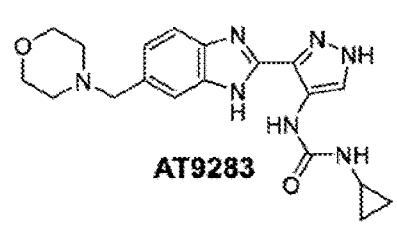
FIG. 27 provides the structures of compounds for modulating DUX4 activity.
Figure 27:
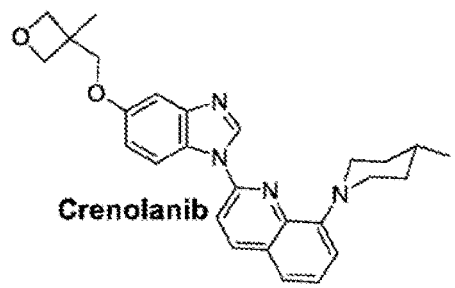
Figure 27:
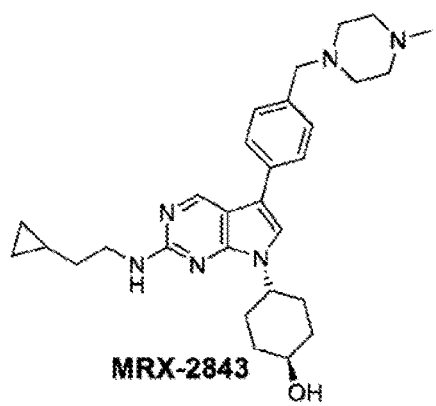
Figure 27:
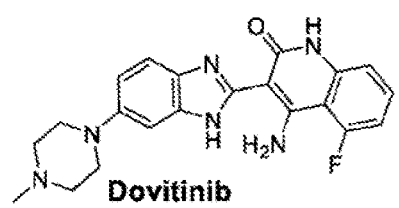
Figure 27:
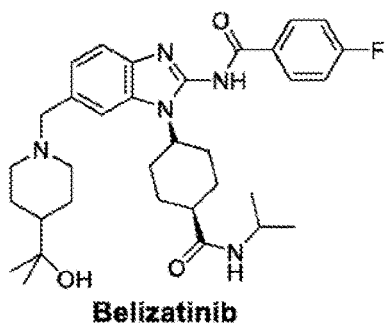
Figure 27:
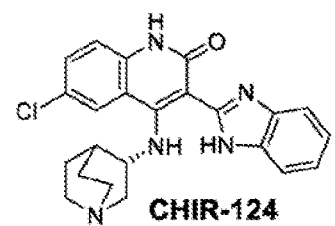
Figure 27:
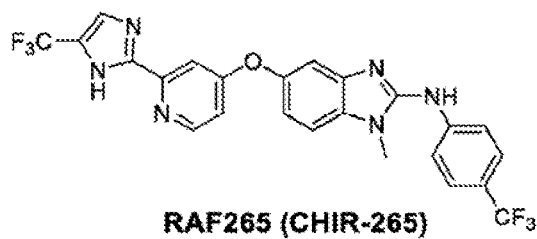
Figure 27:
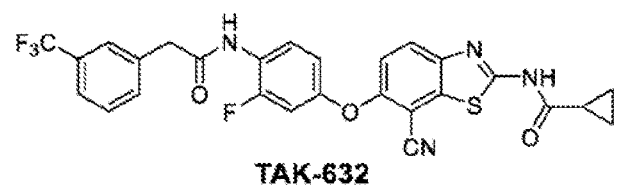

In some embodiments, this disclosure provides a method of treating a muscular degenerative disorder in a subject in need thereof, comprising administering to the subject in need thereof a therapeutically effective amount of a compound selected from the compounds provided in FIG. 26 or 27.

Figure 28:
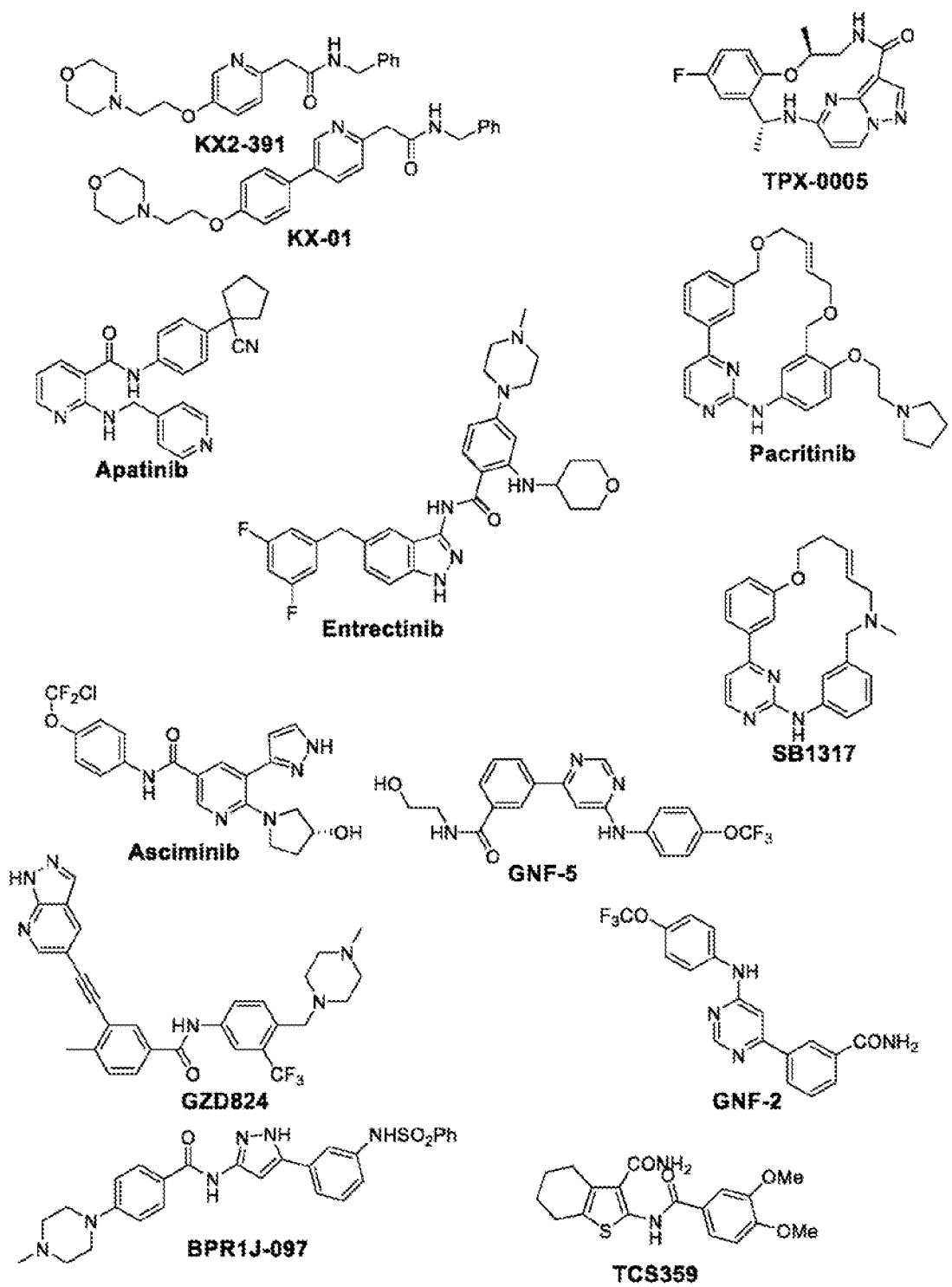
FIG. 28 provides the structures of compounds for modulating DUX4 activity.
Figure 29:
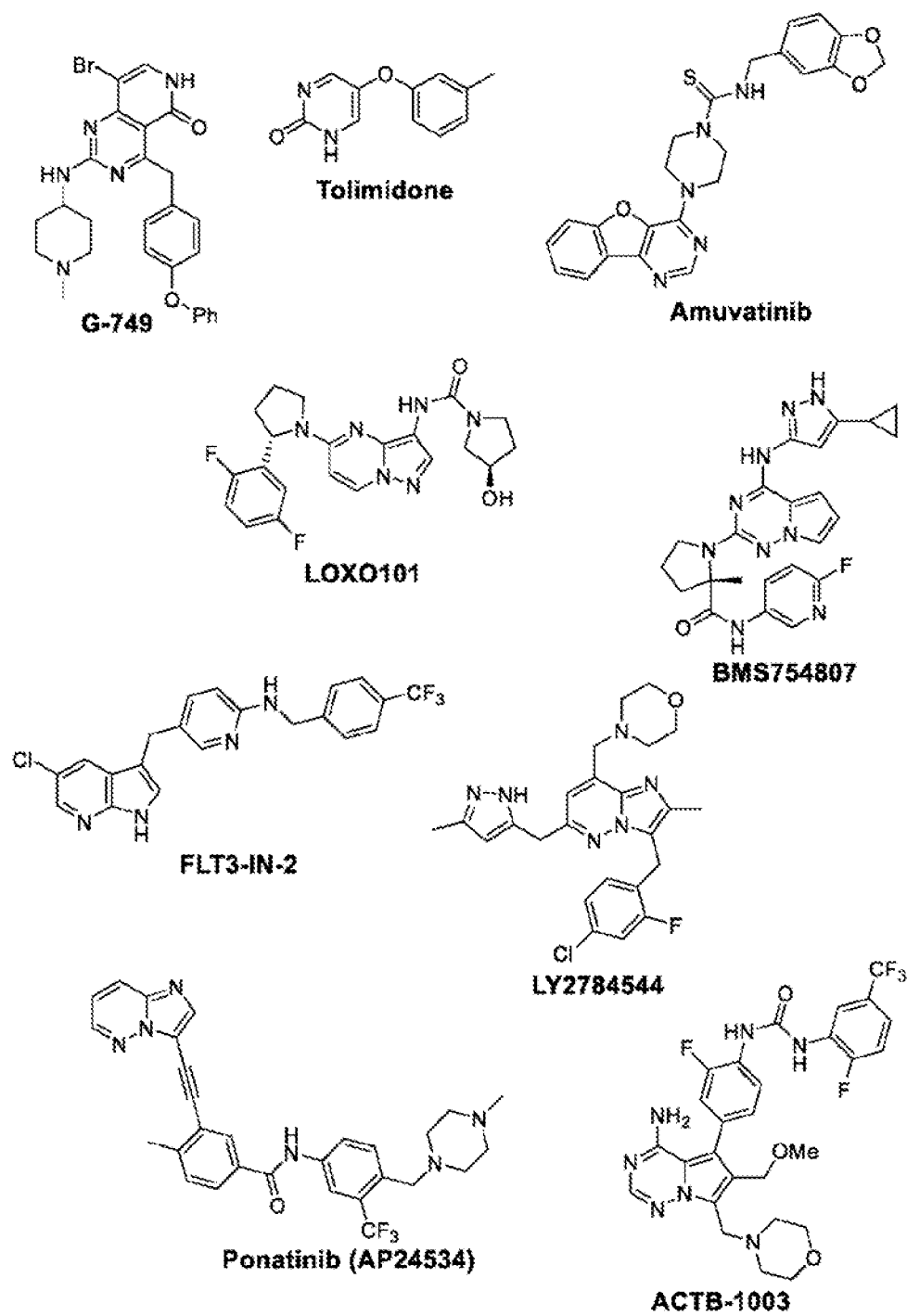
FIG. 29 provides the structures of compounds for modulating DUX4 activity.

In some embodiments, this disclosure provides a method of treating a muscular degenerative disorder in a subject in need thereof, comprising administering to the subject a therapeutically effective amount of a compound selected from the compounds provided in FIG. 28 or 29. In some embodiments, this disclosure provides a method of treating a muscular degenerative disorder wherein the muscular degenerative disorder is selected from facioscapulohumeral muscular dystrophy (FSHD), facioscapulohumeral muscular dystrophy-1 (FSHD1), facioscapulohumeral muscular dystrophy-2 (FSHD2), Becker muscular dystrophy, Duchenne muscular dystrophy, myotonic dystrophies type 1, myotonic dystrophies types 2, nemaline myopathy, spinal muscular atrophy, congenital myotonic dystrophy, congenital muscular dystrophies, LAMA2, SEPN1, GNE myopathies, and SMARD1. In some embodiments, this disclosure provides a method of treating a muscular degenerative disorder in a subject in need thereof, wherein the subject is a human.

The subjects are preferably human subjects or patients, but in some cases may be non-human subjects, (e.g., non-human mammals). Examples of non-human mammals include, but are not limited to, non-human primates (e.g., apes, monkeys, gorillas), rodents (e.g., mice, rats), cows, pigs, sheep, horses, dogs, cats, and rabbits.

Subjects who may benefit from the methods and compositions provided herein may be suffering or suspected to be suffering from FSHD or other muscular or neuromuscular dystrophy at any stage of disease. For example, such subjects may be suffering from FSHD at an early stage of pathogenesis and may even be unaware of disease symptoms. In some cases, a subject may have other symptoms that may appear early in the pathogenesis of FSHD, such as weakness around the eyes and/or the mouth, an inability to purse or pucker the lips, a difficulty with turning up the corners of the mouth when smiling, and an inability to close the eyes. Subjects who may benefit from treatment according to the methods and compositions provided herein may be suffering from FSHD at an intermediate stage of pathogenesis. Such subjects may experience muscle pain and aching, including, but not limited to aching in the area around the shoulders; a loss of stability around the shoulders, including, but not limited to a loss of stability that impedes the subject's ability to throw objects or lift the arms above the head; and/or unequal muscle weakening, including, but not limited to the biceps, triceps, deltoids, and lower arm muscles. In some cases, subjects who may benefit from treatment according to the methods and compositions provided herein may be suffering from FSHD at a late stage of pathogenesis Such subjects may experience weakening of abdominal muscles and hip muscles, which may lead to an exaggerated curvature of the lower spine, and/or weakening of muscles throughout the body, including, but not limited to muscles of the foot, ankle, hips, and abdomen.

Subjects in need of treatment according to the methods and compositions provided herein may be male or female. Subjects may include adults, teenagers, adolescents, children, toddlers, infants, and neonates. Such subjects may be of a range of ages, which may include >10 minutes old, >1 hour old, >1 day old, >1 month old, >2 months old, >6 months old, >1 year old, >2 years old, >5 years old, >10 years old, >15 years old, >18 years old, >25 years old, >35 years old, >45 years old, >55 years old, >65 years old, >80 years old, <80 years old, <70 years old, <60 years old, <50 years old, <40 years old, <30 years old, <20 years old or <10 years old. The subject may be a neonatal infant. In some cases, the subject is a child or an adult. In some examples, the tissue is from a human of age 2, 5, 10 or 20 hours. In other examples, the tissue is from a human of age 1 month, 2 months, 3 months, 4 months, 5 months, 6 months, 9 months or 12 months. In some cases, the tissue is from a human of age 1 year, 2 years, 3 years, 4 years, 5 years, 18 years, 20 years, 21 years, 23 years, 24 years, 25 years, 28 years, 29 years, 31 years, 33 years, 34 years, 35 years, 37 years, 38 years, 40 years, 41 years, 42 years, 43 years, 44 years, 47 years, 51 years, 55 years, 61 years, 62 years, 65 years, 70 years, 77 years, or 85 years. Subjects may have differing genetic backgrounds, including different racial groups or genetically admixed populations.

Effects or Activity of Compounds Provided Herein

In some embodiments, treatment of a subject in need thereof (e.g. an FSHD patient) with compounds described herein (e.g. rebastinib, or an analog or salt thereof, or a compound according to any one of formulas I-VII) results in a decrease in DUX4 activity in a cell or tissue of the subject of at least 10%, at least 20%, at least 30%, at least 40%, at least 50%, at least 60%, at least 70%, at least 80%, at least 90%, at least 95%, at least 98%, or 100% compared to an untreated cell or tissue from the subject. In some embodiments, treatment of a subject in need thereof (e.g. an FSHD patient) with compounds described herein (e.g. rebastinib, or an analog or salt thereof, or a compound according to any one of formulas I-VII) results in a decrease in DUX4 effector activity (e.g., expression or function) in a cell or tissue of the subject of at least 20%, at least 30%, at least 40%, at least 50%, at least 60%, at least 70%, at least 80%, at least 90%, at least 95%, at least 98%, or 100% compared to an untreated cell or tissue from the subject. The cell in which DUX4 activity is assessed is preferably a muscle cell. The tissue in which DUX4 activity is assessed is preferably muscle tissue. Exemplary DUX4 effectors (e.g. target genes) include CCNA1, KHDC1L, LEUTX, M8D3L2, PRAMEF2, PRAMEF6, SPRYD5, TRIM43, TRIM49, ZNF296, and ZSCAN4. As such, in some embodiments, expression or activity of these target genes may be assessed in order to measure or detect DUX4 expression or activity. For example, western blot or other assay may be used to detected expression of target gene protein. In some cases, quantitative PCR, RNAseq, gene array, and/or Northern blot or other assay may be used to detect expression of target gene RNA.

In some cases, following administration of a compound provided herein to a subject, the resulting DUX4 activity or function of the subject may closely resemble that of a normal, healthy cell or tissue that is unaffected with a muscle deficiency disorder such as FSHD. In some cases, the resulting DUX4 activity or function may be the same as that of a normal healthy cell or tissue (e.g. non-FSHD affected cell or tissue), may be within about 2% of DUX4 activity or function in that of a normal healthy cell or tissue (e.g., non-FSHD affected cell or tissue), may be within about 5% of DUX4 activity or Junction in that of a normal healthy cell or tissue (e.g., non-FSHD affected cell or tissue), or may be within about 10% of DUX4 activity or function in that of a normal healthy cell or tissue (e.g., non-FSHD affected cell or tissue).

The compounds or agents provided herein may cause cells or tissue with irregular DUX4 expression (e.g., an FSHD-affected skeletal muscle cell or tissue) to express DUX4 (mRNA and/or protein) at levels similar to that of normal, healthy muscle cells (e.g., non-FSHD affected cell or tissue), in some cases, the level of DUX4 expression may be reduced by at least 20%, at least 30%, at least 40%, at least 50%, at least 60%, at least 70%, at least 75%, at least 80%, at least 85%, at least 90%, at least 95%, at least 98%, or 100% following administration of a compound provided herein. In some cases, following administration of a compound provided herein to a subject, the resulting DUX4 expression of the subject may closely resemble that of a normal, healthy cell or tissue that is unaffected with a muscle deficiency disorder such as FSHD. In some cases, the resulting DUX4 expression may be the same as that of a normal healthy cell or tissue (e.g., non-FSHD affected cell or tissue), may be within about 2% of the level of DUX4 expression in that of a normal healthy cell or tissue (e.g., non-FSHD affected cell or tissue), may be within about 5% of the level of DUX4 expression in that of a normal healthy cell or tissue (e.g., non-FSHD affected cell or tissue), or may be within about 10% of the level of DUX4 expression in that of a normal healthy cell or tissue (e.g., non-FSHD affected cell or tissue) DUX4 expression may be measured or detected using any known technique in the art. For example, western blot or other assay may be used to detected expression of DUX4 protein, quantitative PCR, RNAseq, gene array, and/or Northern blot or other assay may be used to detect expression of DUX4 RNA. In some cases, specific cell types may be analyzed, such as muscle cells, myoblast cells, multi-nucleated cells and/or myotubes.

In some cases, a subject or patient with elevated DUX4 expression or activity may have increased cell death or apoptosis in muscle cells or tissues (or other tissues) associated with the DUX4 expression or activity. As such, administration of a compound provided herein (e.g., rebastinib or a salt of analog thereof, or one or more compounds according to any of formulas I-VI) may treat such patient or subject by causing a reduction or eradication of cell death or apoptosis that was caused by the elevated DUX4 expression or activity. Such reduction in cell death or apoptosis may be assessed by any assay known in the art, including a Caspase 3/7 cleavage or activity assay.

According to the methods provided herein, the compounds or agents, for example rebastinib may have a half maximal effective concentration ($EC_{50}$) of less than 5 µM. In some examples, the compound or compounds may have an $EC_{50}$ less than about 5 µM, less than about 4 µM, less than about 3 µM, less than about 2 µM, less than about 1 µM, less than about 500 nM, or less than about 100 nM. In a preferred embodiment, the compound or compounds have an $EC_{50}$ of less than about 5 µM.

The compounds or agents provided herein may not be toxic to FSHD-affected skeletal muscle cells There may not be any increase in cell death in FSHD-affected skeletal muscle cells contacted with a compound or agent provided herein compared to FSHD-affected skeletal muscle cells not contacted by a compound or agent provided herein.

In some cases, the compounds or agents provided herein are administered to a subject in order to reduce or eliminate the symptoms of FSHD. Such symptoms include, but are not limited to abdominal muscle weakness, poor cardiac or respiratory function, facial weakness, hip weakness, lower leg weakness, depression, decreased energy, and skeletal muscle weakness. In some cases, the compounds or agents provided herein are administered to a subject to treat FSHD or ataxia.

In some cases, the compounds or agents provided herein are administered to a subject in order to improve one or more functional measures negatively affected by FSHD. Such measures negatively affected include grip strength (e.g. measured by a grip meter test), skeletal muscle strength, the sit-to-stand test, the stance-to-sit test, the step-up test, the step-down test, antigravity tests, 6-minute walk test, and neuromuscular quality of life score (e.g. as measured by INQoL scores as in Sadjadi et al. Health Qualm Life Outcomes 2011; 9:114.

In some embodiments, this disclosure provides a method for modulating DUX4 activity in a subject in need thereof comprising administering to the subject in need thereof a composition comprising a compound, or a pharmaceutically acceptable salt thereof, having the structure of Formula (I):

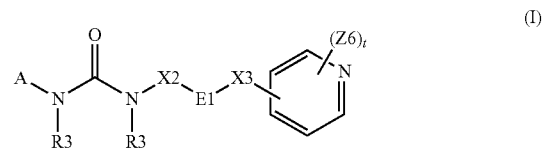

wherein E1 is phenyl, and wherein the E1 mg is substituted with one to three R16 moieties;

wherein A is selected from the group consisting of imidazolyl, and pyrazolyl,

G1 is a heteroaryl taken from the group consisting of pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl;

G4 is a heterocyclyl taken from the group consisting of oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl;

A ring is substituted at any substitutable position with one A1 moiety, wherein A1 is selected from the group consisting of

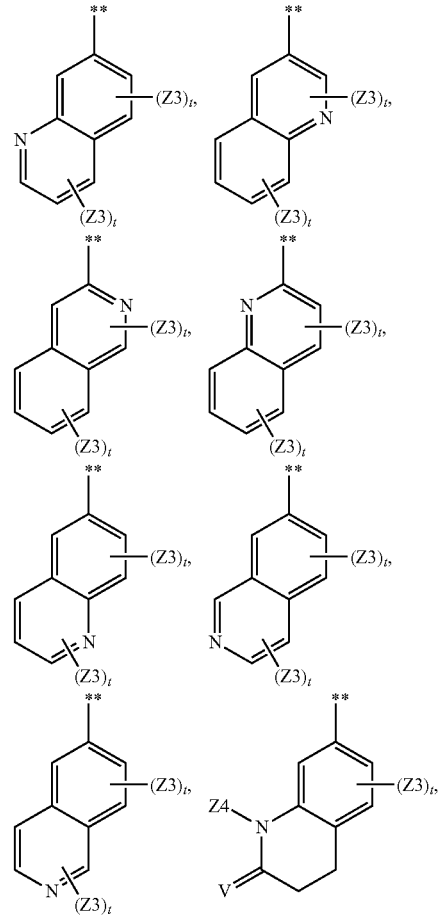

-continued

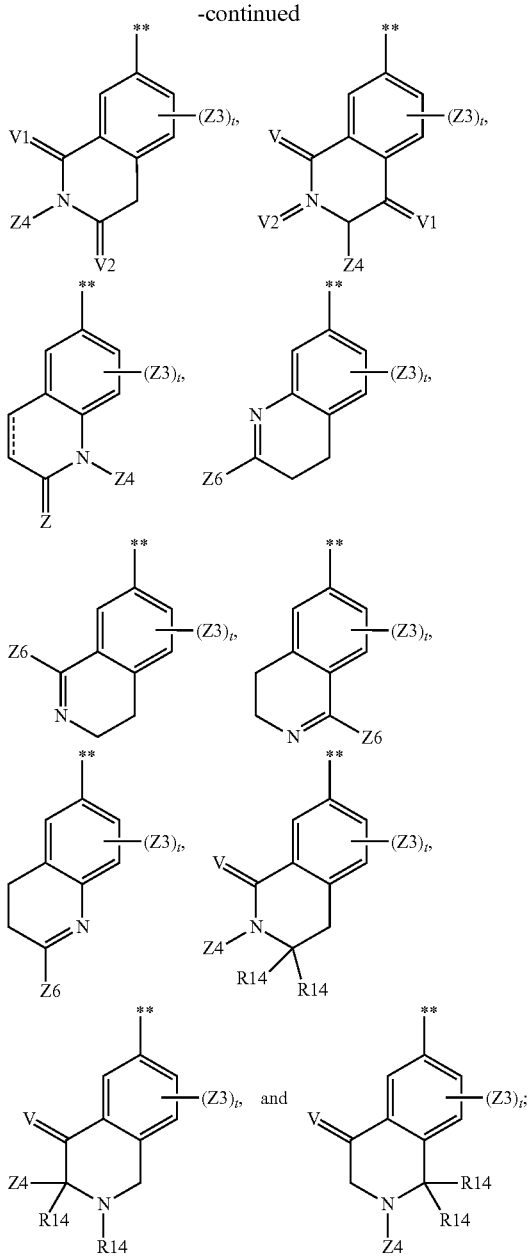

and wherein the symbol (**) is the point of attachment to the A ring of formula I;
and wherein ---- indicates either a saturated or unsaturated bond;
the A ring is optionally substituted with one or more R2 moieties;
X2 is a direct bond wherein E1 is directly linked to the NR3 group of formula I;
X3 is —O—;
V, V1, and V2 are each independently O or represent two hydrogens attached to the methylene carbon to which the V, V1, or V2 is attached;
each Z3 is independently and individually selected from the group consisting of H, C1-C6alkyl, branched C3-C7alkyl, C3-C8carbocyclyl, halogen, fluoroC1-C6alkyl wherein the alkyl moiety can be partially or fully fluorinated, cyano, hydroxyl, methoxy, oxo, (R3)$_2$NC(O)—, (R4)$_2$NC(O)—, —N(R4)C(O)R8, (R3)$_2$NSO$_2$—, (R4)$_2$NSO$_2$—, —N(R4)SO$_2$R5, —N(R4)SO$_2$R8, —(CH$_2$)N(R3)$_2$, —(CH$_2$)$_q$N(R4)$_2$, —O(CH$_2$)$_q$N(R4)$_2$, —O(CH$_2$)$_q$O—C1-C6alkyl, —N(R3)(CH2)$_q$O—C1-C6alkyl, —N(R3)(CH$_2$)$_q$N (R4)$_2$, —O(CH2)$_q$R5, —N(R3)(CH$_2$)$_q$R5, —C(O)R5, —C(O)R8, and nitro;
in the event that Z3 contains an alkyl or alkylene moiety, such moieties may be further substituted with one or more C1-C6alkyls;
each Z4 is independently and individually selected from the group consisting of H, C1-C6alkyl, hydroxyC$_2$-C$_6$alkyl, C1-C6alkoxyC$_2$-C$_6$alkyl, (R4)$_2$N—C$_2$-C$_6$alkyl, (R4)$_2$N—C$_2$-C6alkylN(R4)-C$_2$-C$_6$alkyl, (R4)$_2$N—C$_2$-C$_6$alkyl-O—C$_2$-C$_6$alkyl, (R4)$_2$NC(O)—C1-C6alkyl, carboxyC1-C6alkyl-, C1-C6alkoxycarbonylC1-C6alkyl-, —C$_2$-C$_6$alkylN (R4)C(O)R8, R8-C(=NR3)-, —SO$_2$R8, —C(O)R8, —(CH$_2$)$_n$G1, —(CH$_2$)$_n$G4, —(CH$_2$)$_q$O(CH$_2$)$_n$G1, —(CH$_2$)$_q$O(CH$_2$)$_n$G4, —(CH$_2$)$_q$N(R3)(CH$_2$)$_n$G1, —(CH$_2$)$_q$N(R3)(CH$_2$)$_n$G4, —(CH$_2$)$_q$NHC(O) (CH$_2$)$_n$R5, —(CH$_2$)$_q$C(O)NH(CH$_2$)$_q$R$_5$, —(CH$_2$)$_q$C (O)R5, —(CH$_2$)$_q$OC(O)R5, —(CH$_2$)$_q$R5, —(CH$_2$)$_q$NR4(CH$_2$)$_q$R5, and —(CH$_2$)$_q$O(CH$_2$)$_q$R5;
in the event that Z4 contains an alkyl or alkylene moiety, such moieties may be further substituted with one or more C1-C6alkyls;
each Z6 is independently and individually selected from the group consisting of H, C1-C6alkyl, branched C3-C7alkyl, hydroxyl, hydroxyC1-C6alkyl, hydroxyC$_2$-C$_6$ branched alkyl, C1-C6alkoxy, C1-C6alkoxyC1-C6alkyl-, C1-C6alkoxyC$_2$-C$_6$ branched alkyl-, C$_2$-C$_6$ branched alkoxy-, C1-C6alkylthio-, (R3)$_2$N—, —N(R3)C(O)R8, (R4)$_2$N—, —R5, —N(R4)C(O)R8, —N(R3)SO$_2$R6, —C(O)N(R3)$_2$, —C(O)N(R4)$_2$, —C(O)R5, —SO$_2$NH (R4), halogen, fluoroC1-C6alkyl wherein the alkyl is fully or partially fluorinated, cyano, fluoroC1-C6alkoxy wherein the alkyl is fully or partially fluorinated, —O(CH$_2$)$_q$N(R4)$_2$, —N(R3)(CH$_2$)$_q$N(R4)$_2$, —O(CH$_2$)$_q$O—C1-C6alkyl, —O(CH$_2$)$_q$N(R4)$_2$, —N(R3)(CH$_2$)$_q$O—C1-C6alkyl, —N(R$_3$)(CH$_2$)$_q$N (R4)$_2$, —O(CH$_2$)$_q$R5, N(R3)(CH$_2$)$_q$R5, —(NR3),R17, —(O)$_r$R17, —(S)$_r$R17, —(CH$_2$)$_n$R17, —R17, —(CH$_2$)$_n$G1, —(CH$_2$)$_n$G4, —(CH$_2$)$_n$O(CH$_2$)$_n$G1, —(CH$_2$)$_n$O(CH$_2$)$_n$G4, —(CH$_2$)$_n$N(R3)(CH$_2$)$_n$G1, and —(CH$_2$)$_n$N(R3)(CH2)$_n$G4;
each R2 is selected from the group consisting of Z3-substituted aryl, Z3-substituted G1-, Z3-substituted G4-, C1-C6alkyl, branched C3-C8alkyl, R19 substituted C3-C8cycloalkyl fluoroC1-C6alkyl wherein the alkyl is fully or partially fluorinated, cyano, C1-C6alkoxy, and fluoroC1-C6alkoxy wherein the alkyl group is fully or partially fluorinated;
wherein each R3 is independently and individually selected from the group consisting of H, C1-C6alkyl, branched C3-C7alkyl, C3-C7-carbocyclyl, and Z3-substituted phenyl;
each R4 is independently and individually selected from the group consisting of H, C1-C6alkyl, hydroxyC1-C6alkyl-, dihydroxyC1-C6alkyl-, C1-C6alkoxyC1-C6alkyl-, branched C3-C7alkyl-, branched hydroxyC1-C6alkyl-, branched C1-C6alkoxyC1-C6alkyl-, branched dihydroxyC$_2$-C$_6$alkyl-, —(CH$_2$)$_p$N(R7)$_2$, —(CH$_2$)$_p$R5, —(CH$_2$)$_p$C(O)N(R7)$_2$, —(CH$_2$)$_n$C(O) R5, —(CH$_2$)$_n$C(O)OR3, C3-C7-carbocyclyl, hydroxyl substituted C3-C7-carbocyclyl-, alkoxy substituted C3-C7-carbocyclyl-, dihydroxyl substituted C3-C7-carbocyclyl-, and —(CH$_2$)$_n$R17;

each R5 is independently and individually selected from the group consisting of

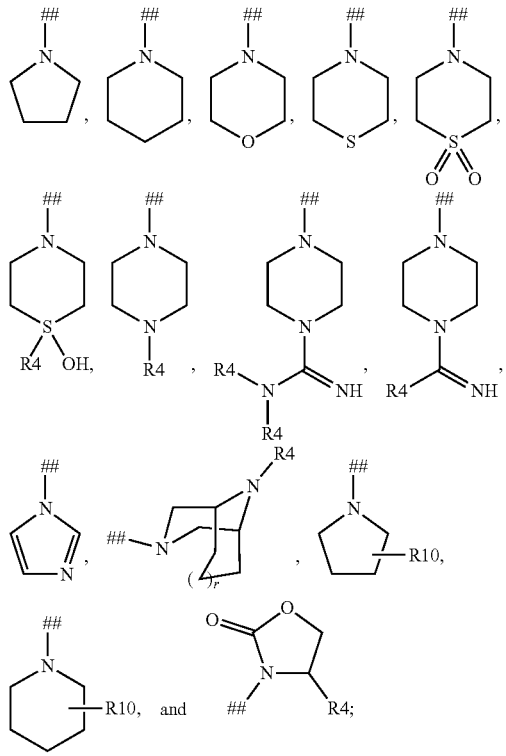

and wherein the symbol (##) is the point of attachment of the R5 moiety;

each R6 is independently and individually selected from the group consisting of C1-C6alkyl, branched C3-C7alkyl, C3-C7-carbocyclyl, phenyl, G1, and G4;

each R7 is independently and individually selected from the group consisting of H, C1-C6alkyl, hydroxyC$_2$-C$_6$alkyl-, dihydroxyC$_2$-C$_6$alkyl-, C$_2$-C$_6$alkoxyC$_2$-C$_6$alkyl-, branched C3-C7alkyl-, branched hydroxyC$_2$-C$_6$alkyl-, branched C$_2$-C$_6$alkoxyC$_2$-C$_6$alkyl-, branched dihydroxyC$_2$-C$_6$alkyl-, —(CH$_2$)$_q$R5, —(CH$_2$)$_n$C(O)R5, —(CH$_2$)$_n$C(O)OR3, C3-C7-carbocyclyl, hydroxyl substituted C3-C7-carbocyclyl-, alkoxy substituted C3-C7-carbocyclyl-, dihydroxy substituted C3-C7-carbocyclyl-, and —(CH$_2$)$_n$R17;

each R8 is independently and individually selected from the group consisting of C1-C6alkyl, branched C3-C7alkyl, fluoroC1-C6alkyl wherein the alkyl moiety is partially or fully fluorinated, C3-C7-carbocyclyl, phenyl-, phenylC1-C6alkyl-, G1, G1-C1-C6alkyl-, G4, G4-C1-C6alkyl-, OH, C1-C6alkoxy, N(R3)$_2$, N(R4)$_2$, and R5;

each R9 is independently and individually selected from the group consisting of H, F, C1-C6alkyl, branched C3-C7alkyl, C3-C7-carbocyclyl, phenyl, phenyl-C1-C6alkyl-, —(CH$_2$)$_n$G1, and —(CH$_2$)$_n$G4;

each R10 is independently and individually selected from the group consisting of CO$_2$H, CO$_2$C1-C6alkyl, —C(O)N(R4)$_2$, OH, C1-C6alkoxy, and —N(R4)$_2$;

each R14 is independently and respectively selected from the group consisting of H, C1-C6alkyl, branched C3-C6alkyl, and C3-C7-carbocyclyl;

R16 is independently and individually selected from the group consisting of fluorine and methyl;

each R17 is taken from the group comprising phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, oxetanyl, azetidinyl, tetrahydrofuranyl, oxazolinyl, oxazolidinyl, pyranyl, thiopyranyl, tetrahydropyranyl, dioxalinyl, azepinyl, oxepinyl, and diazepinyl;

wherein R17 can be optionally substituted with an R3 substituent,

R19 is H or C1-C6 alkyl;

n is 0-6, p is 1-4, q is 2-6; r is 0 or 1; t is 1-3, and v is 1 or 2.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, having the structure of Formula (IX and further described by the structure of Formula (II):

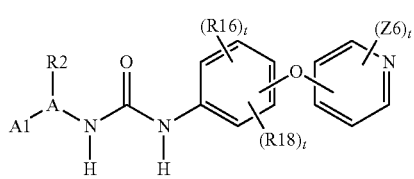

wherein A is pyrazolyl.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from the group consisting of:

1-(3-tert-butyl-1-(1,2,3,4-tetrahydroisoquinolin-6-yl)-1H-pyrazol-5-yl)-3-(3-fluoro-4-(2-(methylcarbamoyl)pyridin-4-yloxy)phenyl)urea;

1-(3-tert-butyl-1-(quinolin-6-yl)-1H-pyrazol-5-yl)-3-(2-fluoro-4-(2-(methylcarbamoyl)pyridin-4-yloxy)phenyl)urea;

1-(3-tert-butyl-1-(1,2,3,4-tetrahydroisoquinolin-6-yl)-1H-pyrazol-5-yl)-3-(2-fluoro-4-(2-(methylcarbamoyl)pyridin-4-yloxy)phenyl)urea;

1-(3-tert-butyl-1-(quinolin-6-yl)-1H-pyrazol-5-yl)-3-(3-fluoro-4-(2-(methylcarbamoyl)pyridin-4-yloxy)phenyl)urea;

1-(3-tert-butyl-1-(quinolin-6-yl)-1H-pyrazol-5-yl)-3-(2-fluoro-5-(pyridin-3-yloxy)phenyl)urea;

1-(3)-tert-butyl-1-(quinolin-6-yl)-1H-pyrazol-5-yl)-3-(3-methyl-4-(2-(methylcarbamoyl)pyridin-4-yloxy)phenyl)urea;

1-(3-tert-butyl-1-(quinolin-6-yl)-1H-pyrazol-5-yl)-3-(4-(2-carbamoylpyridin-4-yloxy)-2-fluorophenyl)urea;

1-(3-tert-butyl-1-(quinolin-6-yl)-1H-pyrazol-5-yl)-3-(2-fluoro-4-(2-(methylamino)pyridin-4-yloxy)phenyl)urea;

1-(2-fluoro-4-(2-(methylcarbamoyl)pyridin-4-yloxy)phenyl)-3-(3-isopropyl-1-(quinolin-6-yl)-1H-pyrazol-5-yl)urea;

1-(3-ethyl-1-(quinolin-6-yl)-1H-pyrazol-5-yl)-3-(2-fluoro-4-(2-(methylcarbamoyl)pyridin-4-yloxy)phenyl)urea;

1-(3-cyclopentyl-1-(quinolin-6-yl)-1H-pyrazol-5-yl)-3-(2-fluoro-4-(2-(methylcarbamoyl)pyridin-4-yloxy)phenyl)urea;

1-(3-tert-butyl-1-(quinolin-6-yl)-1H-pyrazol-5-yl)-3-(2-fluoro-5-(6-(hydroxymethyl)pyridin-3-yloxy)phenyl)urea;

1-(3-tert-butyl-1-(1,2,3,4-tetrahydroisoquinolin-6-yl)-1H-pyrazol-5-yl)-3-(4-methyl-3-(pyridin-3-yloxy)phenyl)urea;

1-(4-(2-carbamoylpyridin-4-yloxy)-2-fluorophenyl)-3-(3-isopropyl-1-(quinolin-6-yl)-1H-pyrazol-5-yl)urea;

1-(3-isopropyl-1-(quinolin-6-yl)-1H-pyrazol-5-yl)-3-(3-methyl-4-(2-(methylcarbamoyl)pyridin-4-yloxy)phenyl)urea; 1-(4-(2-carbamoylpyridin-4-yloxy)-2-fluorophenyl)-3-(3-ethyl-1-(quinolin-6-yl)-1H-pyrazol-5-yl)urea;

1-(3-tert-butyl-1-(quinolin-6-yl)-1H-pyrazol-5-yl)-3-(2-fluoro-5-(6-(methylcarbamoyl)pyridin-3-yloxy)phenyl)urea;

1-(4-(2-carbamoylpyridin-4-yloxy)-3-methylphenyl)-3-(3-isopropyl-1-(quinolin-6-yl)-1H-pyrazol-5-yl)urea;

1-(2-fluoro-4-(2-(1-methyl-1H-pyrazol-4-yl)pyridin-4-yloxy)phenyl)-3-(3-isopropyl-1-(quinolin-6-yl)-1H-pyrazol-5-yl)urea;

1-(3-ethyl-1-(quinolin-6-yl)-1H-pyrazol-5-yl)-3-(2-fluoro-4-(2-(1-methyl-1H-pyrazol-4-yl)pyridin-4-yloxy)phenyl)urea;

1-(4-(2-(1H-pyrazol-4-yl)pyridin-4-yloxy)-3-methylphenyl)-3-(3-isopropyl-1-(quinolin-6-yl)-1H-pyrazol-5-yl)urea;

1-(3-tert-butyl-1-(1,2,3,4-tetrahydroisoquinolin-6-yl)-1H-pyrazol-5-yl)-3-(2-fluoro-4-(2-(1-methyl-1H-pyrazol-4-yl)pyridin-4-yloxy)phenyl)urea;

1-(4-(2-(1H-pyrazol-4-yl)pyridin-4-yloxy)-2-fluorophenyl)-3-(3-tert-butyl-1-(1,2,3,4-tetrahydroisoquinolin-6-yl)-1H-pyrazol-5-yl)urea;

1-(4-(2-(1H-pyrazol-4-yl)pyridin-4-yloxy)-2-fluorophenyl)-3-(3-tert-butyl-1-(1,2,3,4-tetrahydroisoquinolin-7-yl)-1H-pyrazol-5-yl)urea;

1-(3-fluoro-4-(2-(isopropylamino)pyridin-4-yloxy)phenyl)-3-(3-isopropyl-1-(quinolin-6-yl)-1H-pyrazol-5-yl)urea;

1-(3-isopropyl-1-(quinolin-6-yl)-1H-pyrazol-5-yl)-3-(4-(2-(isopropylamino)pyridin-4-yloxy)-3-methylphenyl)urea;

1-(3-ethyl-1-(quinolin-6-yl)-1H-pyrazol-5-yl)-3-(2-fluoro-3-methyl-4-(2-(1-methyl-1H-pyrazol-4-yl)pyridin-4-yloxy)phenyl)urea, and 1-(2,3-difluoro-4-(2-(1-methyl-1H-pyrazol-4-yl)pyridin-4-yloxy)phenyl)-3-(3-ethyl-1-(quinolin-6-yl)-1H-pyrazol-5-yl)urea.

In some embodiments, this disclosure provides a method for modulating DUX4 activity (e.g., directly or vicariously) in a subject in need thereof comprising administering to the subject in need thereof a composition comprising 1-(3-tert-butyl-1-(quinolin-6-yl)-1H-pyrazol-5-yl)-3-(2-fluoro-4-(2-(methylcarbamoyl)pyridin-4-yloxy)phenyl)urea, or a pharmaceutically acceptable salt thereof.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 1.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 2.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 3.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 4.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 5. Another embodiment provides the method for modulating DUX4 activity wherein the modulation of DUX4 activity is inhibition of DUX4 activity.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, having the structure of Formula (III):

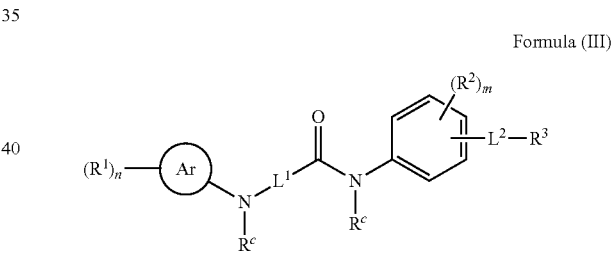

Formula (III)

wherein

Ar is phenyl or 5- or 6-membered heteroaryl;

each $R^1$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;

n is 0-5;

$L^1$ is absent or *—(CR$^a$R$^b$)—C(=O)—, wherein * denotes attachment point to the carbonyl carbon;

R$^a$ and R$^b$ are independently selected from hydrogen, C$_1$-C$_6$alkyl, or C$_1$-C$_6$ haloalkyl;

or R$^a$ and R$^b$ are taken together with the carbon to which they are attached to form a 3-, 4-, 5-, or 6-membered cycloalkyl or a 3-, 4-, 5-, or 6-membered heterocycloalkyl;

each R$^2$ is independently hydrogen, halogen, —CN, —OH, —OR$^{20}$, —NR$^{21}$R$^{21}$, —C(=O)R$^{20}$, —OC(=O)R$^{20}$, —C(=O)OR$^{21}$, —C(=O)NR$^{21}$R$^{21}$, —NR$^{21}$C(=O)R$^{20}$, C$_1$-C$_6$ alkyl, or C$_1$-C$_6$ haloalkyl;

or two R$^2$ on adjacent atoms are taken together with the atoms to which they are attached to form an unsubstituted or substituted cycloalkyl, unsubstituted or substituted heterocycloalkyl, unsubstituted or substituted aryl, or unsubstituted or substituted heteroaryl;

m is 0-4;

L$^2$ is absent, —O—, —O—(C$_1$-C$_4$ alkylene)-, or —NR$^c$—C(=O)—;

each R$^c$ is independently selected from hydrogen, C$_1$-C$_6$ alkyl, or C$_1$-C$_6$ haloalkyl;

R$^3$ is unsubstituted or substituted cycloalkyl, unsubstituted or substituted heterocycloalkyl, unsubstituted or substituted aryl, or unsubstituted or substituted heteroaryl; wherein when R$^3$ is substituted, it is substituted by 1-3 R$^4$;

each R$^4$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

each R$^{20}$ is independently selected from unsubstituted or substituted C$_1$-C$_6$alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

each R$^{21}$ is independently selected from hydrogen, unsubstituted or substituted C$_1$-C$_6$alkyl, unsubstituted or substituted C$_1$-C$_6$alkenyl, unsubstituted or substituted C$_1$-C$_6$alkynyl, unsubstituted or substituted cycloalkyl, unsubstituted or substituted heterocycloalkyl, unsubstituted or substituted aryl, or unsubstituted or substituted heteroaryl;

or two R$^{21}$ on the same N atom are taken together with the N atom to which they are attached to form an unsubstituted or substituted N-containing heterocycle;

wherein when any R$^1$, R$^2$, R$^4$, R$^{20}$, or R$^{21}$ is substituted, substituents on the R$^1$, R$^2$, R$^4$, R$^{20}$, or R$^{21}$ are independently selected at each occurrence from halogen, —CN, —NO$_2$, —OR$^{22}$, —CO$_2$R$^{22}$, —C(=O)R$^{23}$, —C(=O)NR$^{22}$R$^{22}$, —NR$^{22}$R$^{22}$, —NR$^{22}$C(=O)R$^{23}$, —NR$^{22}$C(=O)OR$^{22}$, —SR$^{22}$, —S(=O)R$^{23}$, —SO$_2$R$^{23}$, —SO$_2$NR$^{22}$NR$^{23}$, C$_1$-C$_6$ alkyl, C$_1$-C$_6$ haloalkyl, monocyclic cycloalkyl, monocyclic heterocycloalkyl, phenyl, benzyl, 5-membered heteroaryl, and 6-membered heteroaryl; or two substituents on the same carbon atom are taken together to form a C=O or C=S;

each R$^{22}$ is independently selected from hydrogen, C$_1$-C$_6$ alkyl, C$_3$-C$_6$ cycloalkyl, phenyl, benzyl, 5-membered heteroaryl, and 6-membered heteroaryl;

or two R$^{22}$ groups are taken together with the N atom to which they are attached to form a N-containing heterocycle; and each R$^{23}$ is independently selected from C$_1$-C$_6$alkyl, C$_3$-C$_6$ cycloalkyl, phenyl, benzyl, 5-membered heteroaryl, and 6-membered heteroaryl.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, having the structure of Formula (IV):

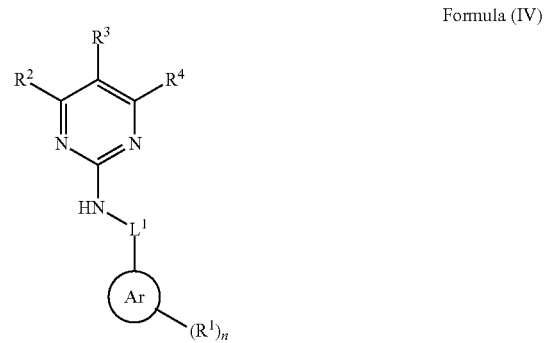

Formula (IV)

wherein

L is absent or —C$_1$-C$_4$ alkylene;

Ar is phenyl or 5- or 6-membered heteroaryl;

each R$^1$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

or two R$^1$ on adjacent atoms are taken together with the atoms to which they are attached to form a unsubstituted or substituted carbocycle, or unsubstituted or substituted heterocycle; wherein if the carbocycle or heterocycle is substituted, it is substituted with 1-3 R$^7$;

each R$^7$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

n is 0-5;

$R^2$ and $R^4$ are each independently hydrogen, or —$NR^5R^6$, or unsubstituted or substituted heterocycle;

each $R^5$ and $R^6$ is independently hydrogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;

or $R^5$ and $R^6$ are taken together with the N atom to which they are attached to form an unsubstituted or substituted N-containing heterocycle;

$R^3$ is hydrogen, halogen, $C_1$-$C_6$ alkyl or $C_1$-$C_6$ haloalkyl;

or $R^2$ and $R^3$ are taken together with the atoms to which they are attached to form a unsubstituted or substituted carbocycle, or unsubstituted or substituted heterocycle; wherein if the carbocycle or heterocycle is substituted, it is substituted with 1-3 $R^8$;

each $R^8$ is independently hydrogen, halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

or two $R^7$ on the same carbon atom are taken together to form a C=O, or C=S;

each $R^{20}$ is independently selected from unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

each $R^{21}$ is independently selected from hydrogen, unsubstituted or substituted $C_1$-$C_6$alkyl, unsubstituted or substituted $C_1$-$C_6$alkenyl, unsubstituted or substituted $C_1$-$C_6$ alkynyl, unsubstituted or substituted cycloalkyl, unsubstituted or substituted heterocycloalkyl, unsubstituted or substituted aryl, or unsubstituted or substituted heteroaryl;

or two $R^{21}$ on the same N atom are taken together with the N atom to which they are attached to form an unsubstituted or substituted N-containing heterocycle;

wherein when any $R^1$, $R^2$, $R^4$, $R^5$, $R^6$, $R^7$, $R^{20}$, or $R^{21}$ is substituted, substituents on the $R^1$, $R^2$, $R^4$, $R^5$, $R^6$, $R^7$, $R^{20}$, or $R^{21}$ are independently selected at each occurrence from halogen, —CN, —$NO_2$, —$OR^{22}$, —$CO_2R^{22}$, —$C(=O)R^{23}$, —$C(=O)NR^{22}R^{22}$, —$NR^{22}R^{22}$, —$NR^{22}C(=O)R^{23}$, —$NR^{22}C(=O)OR^{22}$, —$SR^{22}$, —$S(=O)R^{23}$, —$SO_2R^{23}$, —$SO_2NR^{22}R^{22}$, —$NR^{22}SO_2R^{23}$, $C_1$-$C_6$ alkyl, $C_1$-$C_6$ haloalkyl, monocyclic cycloalkyl, monocyclic heterocycloalkyl, phenyl, benzyl, 5-membered heteroaryl, and 6-membered heteroaryl; or two substituents on the same carbon atom are taken together to form a C=O or C=S;

each $R^{22}$ is independently selected from hydrogen, $C_1$-$C_6$alkyl, $C_1$-$C_6$ hydroxyalkyl, $C_3$-$C_6$ cycloalkyl, phenyl, benzyl, 5-membered heteroaryl, and 6-membered heteroaryl;

or two $R^{22}$ groups are taken together with the N atom to which they are attached to form a N-containing heterocycle; and each $R^{23}$ is independently selected from $C_1$-$C_6$alkyl, $C_1$-$C_6$ hydroxyalkyl, $C_1$-$C_6$alkyl $C_3$-$C_6$ cycloalkyl, phenyl, benzyl, 5-membered heteroaryl, and 6-membered heteroaryl.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, having the structure of Formula (V):

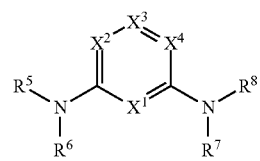

Formula (V)

wherein $X^1$ is N or $CR^1$;

$R^1$ is hydrogen, halogen, $C_1$-$C_6$ alkyl, or $C_1$-$C_6$ haloalkyl;

$X^2$ is N or $CR^2$;

$R^2$ is hydrogen, halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

$X^3$ is N or $CR^3$;

$R^3$ is hydrogen, halogen, —CN, —OH, —$OR^{20}$, —SH, —$SR^{20}$, —$NO_2$, —$NR^{21}R^{21}$, —$S(=O)_2R^{20}$, —$NR^{21}S(=O)_2R^{20}$, —$S(=O)R^{20}$, —$S(=O)_2NR^{21}R^{21}$, —$C(=O)R^{20}$, —$OC(=O)R^{20}$, —$C(=O)OR^{21}$, —$OC(=O)OR^{21}$, —$C(=O)NR^{21}R^{21}$, —$OC(=O)NR^{21}R^{21}$, —$NR^{21}C(=O)NR^{21}R^{21}$, —$NR^{21}C(=O)R^{20}$, —$NR^{21}C(=O)OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

$X^4$ is N or $CR^4$;

$R^4$ is hydrogen, halogen, —CN, —OH, —$OR^{20}$, —SH, —$SR^{20}$, —$NO_2$, —$NR^{21}R^{21}$, —$S(=O)_2R^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, unsubstituted or substituted heteroaryl;

wherein 0, 1, or 2 of X$^1$, X$^2$, X$^3$, and X$^4$ are N;

R$^5$ is hydrogen, unsubstituted or substituted aryl, or unsubstituted or substituted heteroaryl;

wherein if R$^5$ is substituted, it is substituted with 1-3 R$^9$;

each R$^9$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, unsubstituted or substituted heteroaryl;

R$^6$ is hydrogen, C$_1$-C$_6$ alkyl or C$_1$-C$_6$ haloalkyl;

or R$^5$ and R$^6$ are taken together with the N atom to which they are attached to form an unsubstituted or substituted N-containing heterocycle; wherein if the heterocycle is substituted, it is substituted by 1-3 R$^{13}$;

each R$^{13}$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

R$^7$ is hydrogen, unsubstituted or substituted cycloalkyl, unsubstituted or substituted heterocycloalkyl, unsubstituted or substituted aryl, unsubstituted or substituted heteroaryl, unsubstituted or substituted —C$_1$-C$_6$-alkylene-cycloalkyl, or —C(=O)R$^{11}$;

R$^{11}$ unsubstituted phenyl, or phenyl substituted by 1-3 R$^{12}$;

each R$^{12}$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —C$_1$-C$_6$-alkylene-cycloalkyl, unsubstituted or substituted —C$_1$-C$_6$-alkylene-heterocycloalkyl, unsubstituted or substituted —C$_1$-C$_6$-alkylene-aryl, or unsubstituted or substituted —C$_1$-C$_6$-alkylene-heteroaryl;

R$^8$ is hydrogen, C$_1$-C$_6$alkyl or C$_1$-C$_6$ haloalkyl;

or R$^7$ and R$^8$ are taken together with the N atom to which they are attached to form an unsubstituted or substituted N-containing heterocycle; wherein if the heterocycle is substituted, it is substituted by 1-3 R$^{10}$;

each R$^{10}$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

each R$_{20}$ is independently selected from unsubstituted or substituted C$_1$-C$_6$alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, unsubstituted or substituted heteroaryl;

each R$^{21}$ is independently selected from hydrogen, unsubstituted or substituted C$_1$-C$_6$alkyl, unsubstituted or substituted C$_1$-C$_6$alkenyl, unsubstituted or substituted C$_1$-C$_6$alkynyl, unsubstituted or substituted cycloalkyl, unsubstituted or substituted heterocycloalkyl, unsubstituted or substituted aryl, unsubstituted or substituted heteroaryl;

or two R$^{21}$ on the same N atom are taken together with the N atom to which they are attached to form an unsubstituted or substituted N-containing heterocycle;

wherein when any R$^2$, R$^3$, R$^4$, R$^7$, R$^9$, R$^{10}$, R$^{12}$, R$^{13}$, R$^{20}$, or R$^{21}$ is substituted, substituents on the R$^2$, R$^3$, R$^4$, R$^7$, R$^9$, R$^{10}$, R$^{12}$, R$^{13}$, R$^{20}$, or R$^{21}$are independently selected at each occurrence from halogen, —CN, —NO$_2$, —OR$^{22}$, —CO$_2$R$^{22}$, —C(=O)R$^{23}$, —C(=O)NR$^{22}$R$^{22}$, —C(=O)NR$^{22}$—OR$^{22}$, —NR$^{22}$R$^{22}$, —NR$^{22}$C(=O)R$^{23}$, —NR$^{22}$C(=O)OR$^{22}$, —SR$^{22}$, —S(=O)R$^{23}$, —SO$_2$R$^{23}$, —SO$_2$NR$^{22}$R$^{22}$, C$_1$-C$_6$ alkyl, C$_1$-C$_6$ haloalkyl, monocyclic cycloalkyl, monocyclic heterocycloalkyl, monocyclic heterocycloalkyl substituted with a R$^{23}$, phenyl, benzyl, 5-membered heteroaryl, and 6-membered heteroaryl; or two substituents on the same carbon atom are taken together to form a C=O or C=S;

each R$^{22}$ is independently selected from hydrogen, C$_1$-C$_6$ alkyl, C$_3$-C$_6$ cycloalkyl, phenyl, benzyl, 5-membered heteroaryl, and 6-membered heteroaryl;

or two R$^{22}$groups are taken together with the N atom to which they are attached to form a N-containing heterocycle; and each R$^{23}$ is independently selected from C$_1$-C$_6$ alkyl, C$_3$-C$_6$ cycloalkyl, phenyl, benzyl, 5-membered heteroaryl, and 6-membered heteroaryl.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, having the structure of Formula (VI);

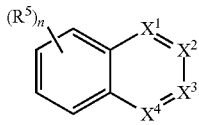

Formula (VI)

wherein:
$X^1$ and $X^2$ are independently N or CH;
$X^3$ is N or $CR^3$;
$R^3$ is hydrogen, —CN, or -L-Ar,
$X^4$ is N or $CR^4$;
$R^4$ is hydrogen, or -L-Ar;
wherein one of $X^3$ and $X^4$ is C-L-Ar;
L is —NH—, —O—, —S—, —$C_1$-$C_2$ alkylene-, or -heterocycloalkylene-C(=O)—;
Ar is substituted or unsubstituted phenyl or substituted or unsubstituted 5- or 6-membered heteroaryl; wherein when Ar is substituted, it is substituted with 1-3 $R^6$;
each $R^6$ is independently halogen, —CN, —OH, —$OR^{20}$, —SH, —$SR^{20}$, —$NO_2$, —$NR^{21}R^{21}$, —S(=O)$_2R^{20}$, —$NR^{21}$S(=O)$_2R^{20}$, —S(=O)$R^{20}$, —S(=O)$^2NR^{21}R^{21}$, —C(=O)$R^{20}$, —OC(=O)$R^{20}$, —C(=O)$OR^{21}$, —OC(=O)$OR^{21}$, —C(=O)$NR^{21}R^{21}$, —($C_1$-$C_4$ alkylene)-C(=O)$NR^{21}R^{21}$, —OC(=O)$NR^{21}R^{21}$, —$NR^{21}$C(=O)$NR^{21}R^{21}$, —$NR^{21}$C(=O)$R^{20}$, —$NR^{21}$C(=O)$OR^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;
or two $R^6$ on adjacent atoms are taken together with the atoms to which they are attached to form an unsubstituted or substituted cycloalkyl, unsubstituted or substituted heterocycloalkyl, unsubstituted or substituted aryl, or unsubstituted or substituted heteroaryl;
each $R^5$ is independently hydrogen, halogen, —CN, —OH, —$OR^{20}$, —SH, —$SR^{20}$, —$NO_2$, —$NR^{21}R^{21}$, —S(=O)$_2R^{20}$, —$NR^{21}$S(=O)$_2R^{20}$, —S(=O)$R^{20}$, —S(=O)$_2NR^{21}R^{21}$, —C(=O)$R^{20}$, —OC(=O)$R^{20}$, —C(=O)$OR^{21}$, —OC(=O)$OR^{21}$, —C(=O)$NR^{21}R^{21}$, —OC(=O)$NR^{21}R^{21}$, —$NR^{21}$C(=O)$NR^{21}R^{21}$, —$NR^{21}$C(=O)$R^{20}$, —$NR^{21}$C(=O)$OR^{21}$, unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;
n is 0-4,
each $R^{20}$ is independently selected from unsubstituted or substituted $C_1$-$C_6$alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;
each $R^{21}$ is independently selected from hydrogen, unsubstituted or substituted $C_1$-$C_6$alkyl, unsubstituted or substituted $C_1$-$C_6$ alkenyl, unsubstituted or substituted $C_1$-$C_6$ alkynyl, unsubstituted or substituted cycloalkyl, unsubstituted or substituted heterocycloalkyl, unsubstituted or substituted aryl, or unsubstituted or substituted heteroaryl;
or two $R^{21}$ on the same N atom are taken together with the N atom to which they are attached to form an unsubstituted or substituted N-containing heterocycle;
wherein when any $R^5$, $R^6$, $R^{20}$, or $R^{21}$ is substituted, substituents on the $R^5$, $R^6$, $R^{20}$, or $R^{21}$ are independently selected at each occurrence from halogen, —CN, —$NO_2$, —$OR^{22}$, —$CO_2R^{22}$, —C(=O)$R^{23}$, —OC(=O)$R^{23}$, —C(=O)$NR^{22}R^{22}$, —$NR^{22}R^{22}$, —$NR^{22}$C(=O)$R^{23}$, —$NR^{22}$C(=O)$OR^{22}$, —$SR^{22}$, —S(=O)$R^{23}$, —SO$_2R^{23}$, —SO$_2NR^{22}R^{22}$, $C_1$-$C_6$ alkyl, $C_1$-$C_6$ haloalkyl, monocyclic cycloalkyl, monocyclic heterocycloalkyl, phenyl, benzyl, 5-membered heteroaryl, and 6-membered heteroaryl; or two substituents on the same carbon atom are taken together to form a C=O or C=S;
each $R^{22}$ is independently selected from hydrogen, $C_1$-$C_6$ alkyl, $C_3$-$C_6$ cycloalkyl, phenyl, benzyl, 5-membered heteroaryl, and 6-membered heteroaryl;
or two $R^{22}$groups are taken together with the N atom to which they are attached to form a N-containing heterocycle; and
each $R^{23}$ is independently selected from $C_1$-$C_6$alkyl, $C_3$-$C_6$ cycloalkyl, phenyl, benzyl, 5-membered heteroaryl, and 6-membered heteroaryl.

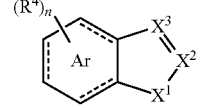

Formula (VII)

wherein:
$X^1$ is —S—, —O—, or —$NR^1$—;
$R^1$ is hydrogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl; wherein when $R^1$ is substituted, it is substituted by 1-3 $R^7$;
each $R^7$ is independently halogen, —CN, —OH, —$OR^{20}$, —SH, —$SR^{20}$, —$NO_2$, —$NR^{21}R^{21}$, —S(=O)$_2R^{20}$, —$NR^{21}$S(=O)$_2R^{20}$, —S(=O)$R^{20}$, —S(=O)$_2NR^{21}R^{21}$, —C(=O)$R^{21}$, —OC(=O)$R^{20}$, —C(=O)$OR^{21}$, —OC(=O)$OR^{21}$, —C(=O)$NR^{21}R^{21}$, —OC(=O)$NR^{21}R^{21}$, —$NR^{21}$C(=O)$NR^{21}R^{21}$, —$NR^{21}$C(=O)$R^{20}$, —$NR^{21}$C(=O)$OR^{21}$, unsubstituted or substituted $C_1$-$C_6$alkyl, unsubstituted or substituted cycloalkyl, unsubstituted or substituted heterocycloalkyl, unsubstituted or substituted aryl, or unsubstituted or substituted heteroaryl;
$X^2$ is N or $CR^2$;
$R^2$ is hydrogen, halogen, —CN, —OH, —$OR^{20}$, —SH, —$SR^{20}$, —$NO_2$, —$NR^{21}R^{21}$, —S(=O)$_2R^{20}$, —NR$^{21}$S(=O)$_2$R$^{20}$, —S(=O)R$^{20}$, —S(=O)NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl; wherein when R$^2$ is substituted, it is substituted by 1-3 R$^8$;

each R$^8$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$alkyl, unsubstituted or substituted cycloalkyl, unsubstituted or substituted heterocycloalkyl, unsubstituted or substituted aryl, or unsubstituted or substituted heteroaryl;

X$^3$ is N or CR$^3$; wherein X$^2$ and X$^3$ are not both N;

R$^3$ is hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —C$_1$-C$_6$-alkylene-cycloalkyl, unsubstituted or substituted —C$_1$-C$_6$-alkylene-heterocycloalkyl, unsubstituted or substituted —C$_1$-C$_6$-alkylene-aryl, or unsubstituted or substituted —C$_1$-C$_6$-alkylene-heteroaryl; wherein when R$^3$ is substituted, it is substituted by 1-3 R$^9$;

each R$^{10}$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)$_2$R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted cycloalkyl, unsubstituted or substituted heterocycloalkyl, unsubstituted or substituted aryl, unsubstituted or substituted heteroaryl, unsubstituted or substituted —C$_1$-C$_6$-alkylene-cycloalkyl, unsubstituted or substituted —C$_1$-C$_6$-alkylene-heterocycloalkyl, unsubstituted or substituted —C$_1$-C$_6$-alkylene-aryl, or unsubstituted or substituted —C$_1$-C$_6$-alkylene-heteroaryl;

Ar is a 6-membered aromatic ring comprising 0-2 nitrogen atoms;

each R$^4$ is independently hydrogen, halogen, —CN, —OH, —OR$^5$, —SH, —SR$^5$, —NO$_2$, —NR$^6$R$^6$, —S(=O)$_2$R$^5$, —NR$^6$S(=O)$_2$R$^5$, —S(=O)R$^5$, —S(=O)$_2$NR$^6$R$^6$, —C(=O)R$^5$, —OC(=O)R$^5$, —C(=O)OR$^6$, —OC(=O)OR$^6$, —C(=O)NR$^6$R$^6$, —OC(=O)NR$^6$R$^6$, —NR$^6$C(=O)NR$^6$R$^6$, —NR$^6$C(=O)R$^5$, —NR$^6$C(=O)OR$^6$, unsubstituted or substituted C$_1$-C$_6$alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —C$_1$-C$_6$-alkylene-cycloalkyl, unsubstituted or substituted —C$_1$-C$_6$-alkylene-heterocycloalkyl, unsubstituted or substituted —C$_1$-C$_6$-alkylene-aryl, or unsubstituted or substituted —C$_1$-C$_6$-alkylene-heteroaryl;

each R$^5$ is independently selected from unsubstituted or substituted C$_1$-C$_6$ alkyl, unsubstituted or substituted C$_2$-C$_6$ alkenyl, unsubstituted or substituted C$_1$-C$_6$ alkynyl, unsubstituted or substituted cycloalkyl, unsubstituted or substituted heterocycloalkyl, unsubstituted or substituted aryl, or unsubstituted or substituted heteroaryl; wherein if R$^5$ is substituted, it is substituted by 1-3 R$^{10}$;

each R$^{10}$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

each R$^6$ is independently selected from hydrogen, unsubstituted or substituted C$_1$-C$_6$ alkyl, unsubstituted or substituted C$_1$-C$_6$ alkenyl, unsubstituted or substituted C$_1$-C$_6$ alkynyl, unsubstituted or substituted cycloalkyl, unsubstituted or substituted heterocycloalkyl, unsubstituted or substituted aryl, or unsubstituted or substituted heteroaryl; wherein if R$^6$ is substituted, it is substituted by 1-3 R$^{11}$;

each R$^{11}$ is independently halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)R$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, or unsubstituted or substituted heteroaryl;

n is 0-4, each R$^{20}$ is independently selected from unsubstituted or substituted C$_1$-C$_6$ alkyl, unsubstituted or substituted C$_2$-C$_6$ alkenyl, unsubstituted or substituted C$_2$-C$_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —C$_1$-C$_6$-alkylene-cycloalkyl, unsubstituted or substituted C$_1$-C$_6$-alkylene-heterocycloalkyl, unsubstituted or substituted —$C_1$-$C_6$-alkylene-aryl, or unsubstituted or substituted —$C_1$-$C_6$-alkylene-heteroaryl;

each $R^{21}$ is independently selected from hydrogen, unsubstituted or substituted $C_1$-$C_6$ alkyl, unsubstituted or substituted $C_1$-$C_6$ alkenyl, unsubstituted or substituted $C_1$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;

or two $R^{21}$ on the same N atom are taken together with the N atom to which they are attached to form an unsubstituted or substituted N-containing heterocycle;

wherein when any $R^4$, $R^7$, $R^8$, $R^9$, $R^{10}$, $R^{11}$, $R^{20}$, or $R^{21}$ is substituted, substituents on the $R^4$, $R^7$, $R^8$, $R^9$, $R^{10}$, $R^{11}$, $R^{20}$, or $R^{21}$ are independently selected at each occurrence from halogen, —CN, —$NO_2$, —$OR^{22}$, —$CO_2R^{22}$, —C(=O)$R^{23}$, —C(=O)$NR^{22}R^{22}$, —$NR^{22}R^{22}$, —$NR^{22}$C(=O)$R^{23}$, —$NR^{22}$C(=O)$OR^{22}$, —$SR^{22}$, —S(=O)$R^{23}$, —$SO_2R^{23}$, —$SO_2NR^{22}R^{22}$, $C_1$-$C_6$ alkyl, $C_1$-$C_6$ haloalkyl, $C_1$-$C_6$ hydroxyalkyl, monocyclic cycloalkyl, monocyclic heterocycloalkyl, phenyl, benzyl, benzyl substituted with phenyl, 5-membered heteroaryl, and 6-membered heteroaryl; or two substituents on the same carbon atom are taken together to form a C=O or C=S;

each $R^{22}$ is independently selected from hydrogen, $C_1$-$C_6$ alkyl, $C_3$-$C_6$ cycloalkyl, phenyl, benzyl, 5-membered heteroaryl, and 6-membered heteroaryl;

or two $R^{22}$ groups are taken together with the N atom to which they are attached to form a N-containing heterocycle; and each $R^{23}$ is independently selected from $C_1$-$C_6$ alkyl, $C_1$-$C_6$ cycloalkyl, phenyl, benzyl, 5-membered heteroaryl, and 6-membered heteroaryl.

In some cases, the compound for modulating DUX4 activity is selected from a compound listed below.

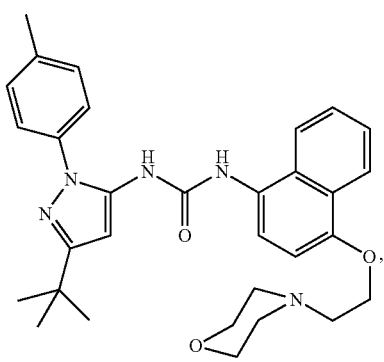

Doramapimod (BIRB796)

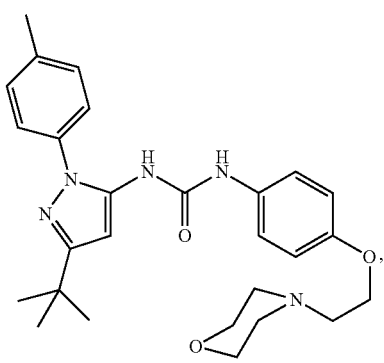

p38α MAPK-IN-1

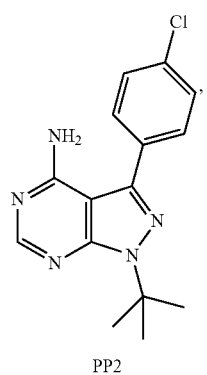

PP2

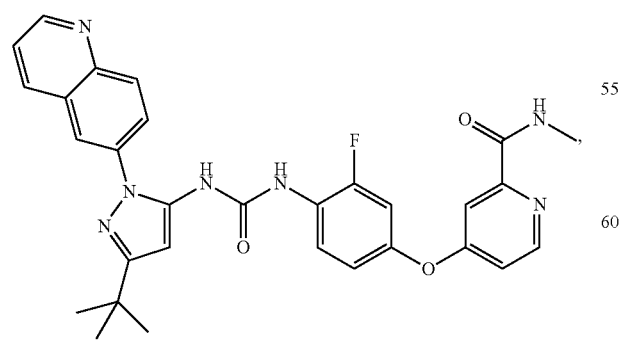

DCC-2036 (Rebastinib)

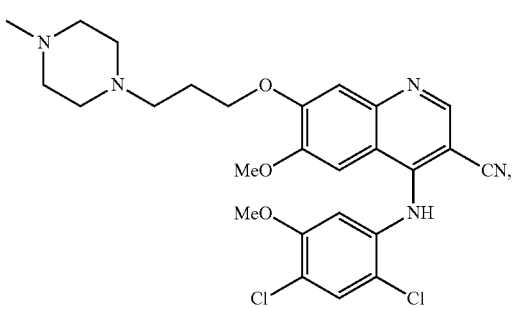

Bosutinib (SKI-606)

-continued

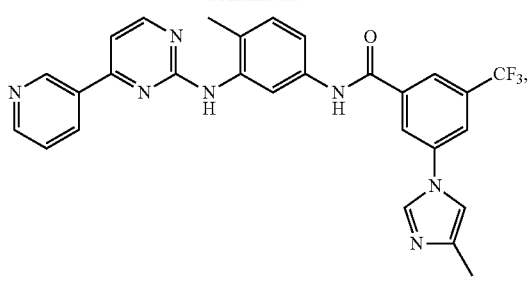

p38a MPK-IN-1

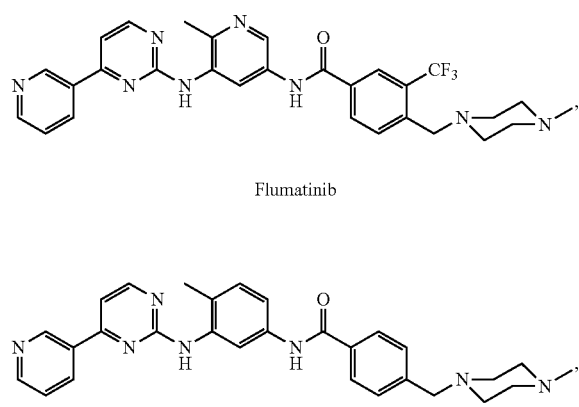

Flumatinib

Imatinib

Bafetinib

LYN-IN-1

-continued

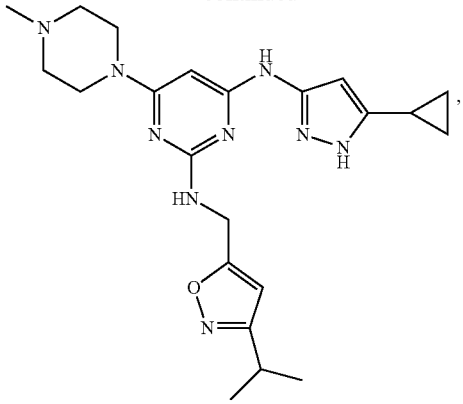

XL228

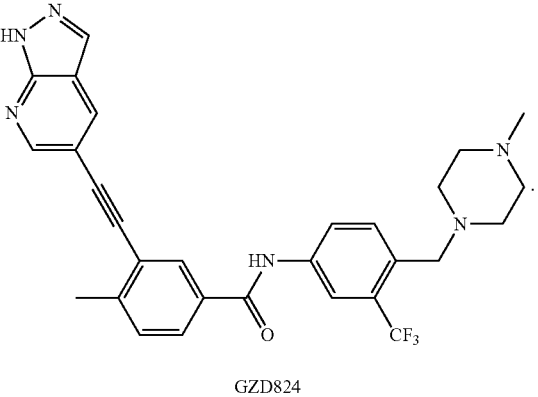

GZD824

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 18 or In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 20 or 21.

In some embodiments, this disclosure provides a method for modulating DUX4 activity (e.g., directly or vicariously) in a subject in need thereof comprising administering to the subject in need thereof a composition comprising a compound, or is pharmaceutically acceptable salt thereof, selected from a compound provided in FIG. 22 or 23.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 24 or 25.

In some embodiments, this disclosure provides a method for modulating DUX4 activity (e.g., directly or vicariously) in a subject in need thereof comprising administering to the subject in need thereof a composition comprising a compound, or a pharmaceutically acceptable salt thereof, selected from a compound provided in FIG. 26 or 27.

In some embodiments, this disclosure provides a method for modulating DUX4 activity (e.g., directly or vicariously)

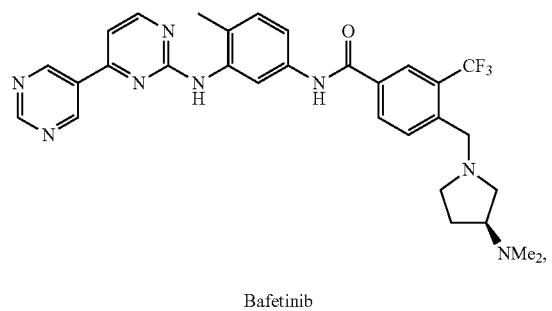

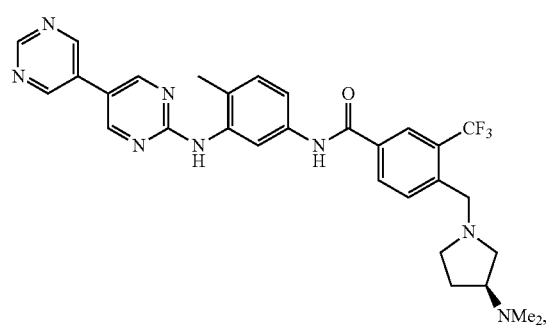

in a subject in need thereof comprising administering to the subject in need thereof a composition comprising a compound, or a pharmaceutically acceptable salt thereof, selected from a compound provided in FIG. 28 or 29. Another embodiment provides a method for modulating DUX4 activity wherein the modulation of DUX4 activity is inhibition of DUX4 activity.

Certain Definitions

As used herein, the term "or" is used to refer to a nonexclusive or, such as "A or B" includes "A but not B," "B but not A," and "A and B," unless otherwise indicated.

As used herein, the term "about" when referring to a number or a numerical range means that the number or numerical range referred to is an approximation within experimental variability (or within statistical experimental error), and thus the number or numerical range may vary from, for example, between 1% and 15% of the stated number or numerical range. In some embodiments, the term "about" refers to ±10%, of a stated number or value.

As used herein, the terms "treat," "ameliorate," "treatment," and "treating" are used interchangeably. These terms refer to an approach for obtaining beneficial or desired results including, but not limited to, therapeutic benefit and/or a prophylactic benefit. By therapeutic benefit is meant eradication or amelioration or improvement of the underlying disorder being treated. Also, a therapeutic benefit is achieved with the eradication or amelioration or improvement of one or more of the physiological symptoms associated with the underlying disorder such that an improvement is observed in the patient, notwithstanding that the patient can still be afflicted with the underlying disorder. For a prophylactic benefit, a compound provided herein may be administered to a patient at risk of developing a particular disease, or to a patient reporting one or more of the physiological symptoms of a disease, even though a diagnosis of this disease may not have been made.

As used herein, in general, "a", "an" or "the" includes both single and plural references, unless dictated otherwise by context. For example, "a compound may include a single compound or a plurality of" compounds, unless dictated otherwise by context.

The term "$C_{x-y}$" or "$C_x$-$C_y$" when used in conjunction with a chemical moiety, such as alkyl, alkenyl, or alkynyl is meant to include groups that contain from x toy carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain. The terms "$C_{x-y}$ alkenyl" and "$C_{x-y}$ alkynyl" refer to substituted or unsubstituted straight-chain or branched-chain unsaturated hydrocarbon groups that contain at least one double or triple bond respectively. Unless stated otherwise specifically in the specification, a $C_{x-y}$ alkyl, $C_{x-y}$ alkenyl, or $C_{x-y}$ alkynyl is optionally substituted by one or more substituents such as those substituents described herein.

"Carbocycle" refers to a saturated, unsaturated or aromatic ring in which each atom of the ring is a carbon atom. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents such as those substituents described herein.

"Aryl" refers to a hydrocarbon ring system moiety comprising 6 to 18 carbon atoms and at least one aromatic ring. For purposes of this invention, the aryl moiety is a monocyclic, bicyclic, tricyclic, or tetracyclic ring system, which may include fused or bridged ring systems Aryl moieties include, but are not limited to, aceanthrylene, acenaphthylene, acephenanthrylene, anthracene, azulene, benzene, chrysene, fluoranthene, fluorene, as-indacene, s-indacene indane, indene, naphthalene, phenalene, phenanthrene, pleiadene, pyrene, and triphenylene. Unless stated otherwise specifically in the specification, the term "aryl" is meant to include aryl groups that are optionally substituted.

"Heterocycle" refers to a saturated, unsaturated or aromatic ring comprising one or more heteroatoms Exemplary heteroatoms include N, O, Si, P, B, and S atoms. Heterocycles include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. The heterocycle may be attached to the rest of the molecule through any atom of the heterocycle, valence permitting, such as a carbon or nitrogen atom of the heterocycle. In some embodiments, the heterocycle is a heteroaryl. In some embodiments, the heterocycle is a heterocycloalkyl. In an exemplary embodiment, a heterocycle, e.g., pyridyl, may be fused to a saturated or unsaturated ring, e.g., cyclohexane, cyclopentane, or cyclohexene.

"Heteroaryl" refers to a 3- to 12-membered aromatic ring that comprises at least one heteroatom wherein each heteroatom may be independently selected from N, O, and S. As used herein, the heteroaryl ring may be selected from monocyclic or bicyclic and fused or bridged ring systems rings wherein at least one of the rings in the ring system is aromatic, it contains a cyclic, delocalized (4n+2) π-electron system in accordance with the Hückel theory. The heteroatom(s) in the heteroaryl may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b], [1,4]dioxepanyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5] thieno[2,3-d]pyrimidinyl, 5,6-dihydrobenzo[h]quinazolinyl, 5,6-dihydrobenzo[h]cinnolinyl, 6,7-dihydro-5H-benzo[6,7] cyclohepta[1,2-c]pyridazinyl, dibenzofuranyl, dibenzothiophenyl, furanyl, furanonyl, furo[3,2-c]pyridinyl, 5,6,7,8,9, 10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryls as defined above which are optionally substituted by one or more substituents such as those substituents described herein.

Compounds of the present disclosure also include crystalline and amorphous forms of those compounds, pharmaceutically acceptable salts, and active metabolites of these compounds having, the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly, found in nature. All isotopic variations of the compounds of the present disclosure, whether radioactive or not, are encompassed within the scope of the present disclosure. For example, hydrogen has three naturally occurring isotopes, denoted $^1$H (protium), $^2$H (deuterium), and $^3$H (tritium). Protium is the most abundant isotope of hydrogen in nature. Enriching for deuterium may of certain therapeutic advantages, such as increased in half-life and/or exposure, or may provide a compound useful for investigating in vivo routes of drug elimination and metabolism. Isotopically-enriched compounds may be prepared by conventional techniques well known to those skilled in the art.

Chemical entities having carbon-carbon double bonds or carbon-nitrogen double bonds may exist in Z- or E-form (or cis- or trans-form) Furthermore, some chemical entities may exist in various tautomeric forms. Unless otherwise specified, chemical entities described herein are intended to include all Z-, E- and tautomeric forms as well.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic, compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, to sulfamoyl, a sulfonamido, a sulfonyl, a heterocyclyl, an aralkyl, a carbocycle, a heterocycle, a cycloalkyl, a heterocycloalkyl, an aromatic and heteroaromatic moiety. In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, hydroxy, haloalkyl, haloalkenyl, haloalkynyl, oxo (=O), thioxo (—S), cyano (—CN), nitro (—NO$_2$), imino (=N—H), oximo (=N—H), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each R$^a$, valence permitting, may be optionally substituted with alkyl, alkenyl, alkynyl, halogen, haloalkyl, haloalkenyl, haloalkynyl, oxo (=O), thioxo (—S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkaline, alkenylene, or alkynylene chain, and each R$^c$ is a straight or branched alkylene, alkenylene or alkynylene chain.

It will be understood by those skilled in the art that substituents can themselves be substituted, if appropriate Unless specifically stated as "unsubstituted," references to chemical moieties herein are understood to include substituted variants. For example, reference to a "heteroaryl" group or moiety implicitly includes both substituted and unsubstituted variants.

Where substituent groups are specified by their conventional chemical formulae, written from left to right, they equally encompass the chemically identical substituents that would result from writing the structure from right to left, e.g., —CH$_2$O— is equivalent to —OCH$_2$—.

"Prodrug" is meant to indicate a compound that may be converted under physiological conditions or by solvolysis to a biologically active compound described herein (e.g., a compound of Table 1, FIGS. 1-5 or compound of Formula (I)-(VII)). Thus, the term "prodrug" refers to a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14, and Bioreversible Carriers in Drug Design, ed. Edward B. Roche, American Pharmaceutical Association and Pergamon Press) each of which is incorporated in full by reference herein. The term "prodrugs" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either: n routine manipulation or in vivo, to the parent active compound Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

"Optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

The compounds of the current disclosure, or their pharmaceutically acceptable salts may contain one or more asymmetric centers and may thus give rise to enantiomers, diastereomers, and other stereoisomeric forms that are defined, in terms of absolute stereochemistry, as (R)- or (S)- or, as (D)- or (L)- for amino acids. The present invention is meant to include all such possible isomers, as well as their racemic and optically pure forms. A "stereoisomer" refers to a compound made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are nonsuperimposable mirror images of one another. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

When desired, the (R)- and (S)-isomers of the compounds of the present disclosure, if present, may be resolved by methods known to those skilled in the an, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by convening one enantiomer to the other by asymmetric transformation.

Compounds may be dosed in their enantiomerically pure form. In some examples, the compound has an enantiomeric excess greater than about 50%, 60%, 70%, 80%, 90%, 95%, 96%, 97%, 98%, or 99%. Compounds may be dosed in their diasteriomerically pure form. In some examples, the compound has a diasteriomeric excess greater than about 50%, 60%, 70%, 80%, 90%, 95%, 96%, 97%, 98%, or 99%.

Stereocenters may be defined using the Cahn-Ingold-Prelog priority rules. Compounds may have stereocenters in the R-configuration, Compounds may have stereocenters in the S-configuration.

Therapeutic Agent Formulations

A pharmaceutical composition (e.g., for oral administration or for injection, infusion, buccal delivery, subcutaneous delivery, intramuscular delivery, intraperitoneal delivery, sublingual delivery, sub-dermao, or other method) may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants, chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. In another embodiment, for treatment of an ophthalmological condition or disease, a liquid pharmaceutical composition may be applied to the eye in the form of eye drops. A liquid pharmaceutical composition may be delivered orally.

For oral formulations, at least one of the compounds or agents described herein may be used alone or in combination with appropriate additives to make tablets, powders, granules or capsules, and if desired, with diluents, buffering agents, moistening agents, preservatives, coloring agents, and flavoring agents. The compounds or agents may be formulated with a buffering agent to provide for protection of the compound from low pH of the gastric environment and/or an enteric coating. A compound included in a pharmaceutical composition may be formulated for oral delivery with a flavoring agent, in a liquid, solid or semi-solid formulation and/or with an enteric coating). In some cases, the compounds of this disclosure may be solubilized and encapsulated (e.g., in a liposome or a biodegradable polymer), or used in the form of microcrystals coated with an appropriate nontoxic lipid.

A pharmaceutical composition comprising any one of the compounds or agents described herein may be formulated for sustained or slow release (also called timed release or controlled release). Such compositions may generally be prepared using suitable technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. Non-limiting examples of excipients include water, alcohol, glycerol, chitosan, alginate, chondroitin, Vitamin E, mineral oil, and dimethyl sulfoxide (DMSO). The amount of compound contained within a sustained release formulation depends upon the site of implantation, the rate and expected duration of release, and the nature of the condition, disease or disorder to be treated or prevented.

Some compounds may exhibit polymorphism. It is to be understood that the present disclosure encompasses any racemic, optically-active, polymorphic, or stereoisomeric form, or mixtures thereof, of a compound of the disclosure, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

The present disclosure further provides salts of any compound described herein. The term "salt" or "pharmaceutically acceptable salt" refers to salts derived from a variety of organic and inorganic counter ions well known in the art. Salts include, for example, acid-addition salts and base-addition salts. The acid that is added to a compound to form an acid-addition salt can be an organic acid or an inorganic acid. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid ethanesulfonic acid, p toluenesulfonic acid, salicylic acid, and the like. A base that is added to a compound to form a base-addition salt can be an organic base or an inorganic base. In some cases, a salt can be a metal salt. In some cases, a salt can be an ammonium salt. Inorganic bases from which salts can be derived include, for example, sodium, potassium, lithium, ammonium, calcium, magnesium, iron, zinc, copper, magnesium, aluminum, and the like. Organic bases from which salts can be derived include, for example, primary, secondary, and tertiary amines, substituted amines. Including naturally occurring substituted amines, cyclic amines, basic ion exchange resins, and the like.

Acid addition salts can arise from the addition of an add to a compound described herein. In some cases, the acid can be organic. In some cases, the acid can be inorganic. Non-limiting examples of suitable acids include hydrochloric acid, hydrobromic acid, hydroiodic acid, nitric acid, nitrous acid, sulfuric acid, sulfurous acid, a phosphoric acid, nicotinic acid, isonicotinic acid, lactic acid, salicylic acid, 4-aminosalicylic acid, tartaric acid, ascorbic acid, gentisinic acid, ginconic acid, glucaronic acid, saccharic acid, formic acid, benzoic acid, glutainic acid, pantothenic acid, acetic acid, propionic acid, butyric acid, fumaric acid, succinic acid, citric acid, oxalic acid, maleic acid, hydroxymaleic acid, methylinaleic acid, glycolic acid, malic acid, cinnamic acid, mandelic acid, 2-phenoxybenzoic acid, 2-acetoxybenzoic acid, embonic acid, phenylacetic acid, N-cyclohexylsulfamic acid, methanesulfonic acid, ethanesulfonic acid, benzenesulfonic acid p-toluenesulfonic acid, 2-hydroxyethanesulfonic acid, ethane-1,2-disulfonic acid, 4-methylbenzenesulfonic acid, naphthalene-2-sulfonic acid, naphthalene-1,5-disulfonic acid, 2-phosphoglyceric acid, 3-phosphoglyceric acid, glucose-6-phosphoric acid, and an amino acid.

Non-limiting examples of suitable acid addition salts include a hydrochloride salt, a hydrobromide salt, a hydroiodide salt, a nitrate salt, a nitrite salt, a sulfate salt, a sulfite salt, a phosphate salt, a hydrogen phosphate salt, a dihydrofuran phosphate salt, a carbonate salt, a bicarbonate salt, a nicotinate salt, an isonicotinate salt, a lactate salt, a salicylate salt, a 4-aminosalicylate salt, a tartrate salt, an ascorbate salt, a gentisinate salt, a gluconate salt, a glucuronate salt, a saccharate salt, a formate salt, a benzoate salt, a glutamate salt, a pantothenate salt, an acetate salt, a propionate salt, a butyrate salt, a fumarate salt, a succinate salt, a citrate salt, an oxalate salt, a maleate salt, a hydroxymaleate salt, a methylmaleate salt, a glycolate salt, a malate salt, a cinnamate salt, a mandelate salt, a 2-phenoxybenzoate salt, a 2-acetoxybenzoate salt, an embonate salt, a phenylacetate salt, an N-cyclohexylsulfamate salt, a methanesulfonate salt, an ethanesulfonate salt, a benzenesulfonate salt, a p-toluenesulfonate salt, a 2-hydroxyethanesulfonate salt, an ethane-1,2-disulfonate salt, a 4-methylbenzenesulfonate salt, a naphthalene-2-sulfonate salt, a naphthalene-1,5-disulfonate salt, a 2-phosphoglycerate salt, a 3-phosphoglycerate salt, a glucose-6-phosphate salt, and an amino acid salt.

Metal salts can arise from the addition of an inorganic base to a compound described herein. The inorganic base consists of a metal cation paired with a basic counterion, such as, for example, hydroxide, carbonate, bicarbonate, or phosphate. The metal can be an alkali metal, alkaline earth metal, transition metal, or main group metal. Non-limiting examples of suitable metals include lithium, sodium, potassium, caesium, cerium, magnesium, manganese, iron, calcium, strontium, cobalt, titanium, aluminum, copper, cadmium, and zinc.

Non-limiting examples of suitable metal salts include a lithium salt, a sodium salt, a potassium salt, a caesium salt, a cerium salt, a magnesium salt, a manganese salt, an iron salt, a calcium salt, a strontium salt, a cobalt salt, a titanium salt, an aluminum salt, a copper salt, a cadmium salt, and a zinc salt.

Ammonium salts can arise from the addition of ammonia or an organic amine to a compound described herein. Non-limiting examples of suitable organic amities include triethyl amine, diisopropyl amine, ethanol amine, diethanol amine, triethanol amine, morpholine, N-methylmorpholine, piperidine. N-methylpiperidine, N-ethylpiperidine, dibenzyl amine, piperazine, pyridine, pyrrazole, pipyrrazole, imidazole, pyrazine, piperazine, ethylenediamine, N,N'-dibenzylethylene diamine, procaine, chloroprocaine, choline, dicyclohexyl amine, and N-methylglucamine.

Non-limiting examples of suitable ammonium salts can be a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzyl amine salt, a piperazine salt, a pyridine salt, a pyrrazole salt, a pipyrrazole salt, an imidazole salt, a pyrazine salt, a piperazine salt, an ethylene diamine salt, an N,N'-dibenzylethylene diamine salt, a procaine salt, a chloroprocaine salt, a choline salt, a dicyclohexyl amine salt, and a N-methylglucamine salt.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the disclosure is contemplated Supplementary active ingredients can al also be incorporated into the compositions.

The term "pharmaceutically acceptable excipient" is intended to include vehicles and carriers capable of being co-administered with a compound to facilitate the performance of its intended function. The use of such media for pharmaceutically active substances is well known in the art Examples of such vehicles and carriers include solutions, solvents, dispersion media, delay agents, emulsions and the like. Any other conventional carrier suitable for use with the multi-binding compounds also falls within the scope of the present disclosure.

In making the compositions of this disclosure, the active ingredient can be diluted by an excipient. Some examples of suitable excipients include lactose, dextrose, sucrose, sorbitol, mannitol, starches, gum acacia, calcium phosphate, alginates, tragacanth, gelatin, calcium silicate microcrystalline cellulose, PEG, polyvinylpyrrolidone, cellulose, water, sterile saline, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

In a some cases, the pharmaceutical compositions described herein may comprise an excipient that can provide long term preservation, bulk up a formulation that contains potent active ingredients, facilitate drug absorption, reduce viscosity, add flavoring, or enhance the solubility of the pharmaceutical composition. Non-limiting examples of excipients can include anti-adherents, binders (e.g., sucrose, lactose, starches, cellulose, gelatin, or polyethylene glycol), coatings (e.g., hydroxypropyl methyl cellulose or gelatin), disintegrants, dyes, flavors (e.g., mint, peach, raspberry, or vanilla), glidants, lubricants, preservatives (e.g., acids, esters, phenols, mercurial compounds, or ammonium compounds), sachems, or vehicles (e.g., petroleum or mineral oil).

The pharmaceutical compositions disclosed herein may be any type of formulation including solid formulations. In some cases the solid formulation (or other type of formulation) comprises at least 0.01 mg, 0.1 mg, 1 mg, 2 mg, 1 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg of a compound provided in FIGS. 1-5, or a compound of any one of Formulas (I)-(VII).

In some cases, the liquid formulation may comprise a compound provided in FIGS. 1-5, or a compound of any one of Formulas (I)-(VII) of at least 0.1 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 150 mg/ml, 200 mg/ml, 250 mg/ml, 300 mg/ml, 350 mg/ml, 400 mg/ml, 450 mg/ml, 500 mg/ml, 550 mg/ml, 600 mg/ml, 650 mg/ml, 700 mg/ml, 750 mg/ml, 800 mg/ml, 850 mg/ml, 900 mg/ml, 950 mg/ml, or 1000 mg/ml.

In some cases, a pharmaceutical composition or formulation described herein may comprise a combination of different agents. In some cases, a pharmaceutical composition described herein may comprise at least 2 agents, at least 3 agents, at least 4 agents, at least 5 agents, or more agents.

Kits

In some cases, the pharmaceutical compositions disclosed herein may be assembled into kits. In some cases, the kit can comprise one or more compounds provide herein. In some cases, the kit may also comprise instructions for use. The kit may also comprise vials, tubes, needles, packaging, or other material.

Kits with unit doses of one or more of the compounds described herein, usually in oral or injectable doses, are provided. Such kits may include a container containing the unit dose, an informational package insert describing the use and attendant benefits of the drugs in treating the disease, and optionally an appliance or device for delivery of the composition.

The kit may further comprise any device suitable for administration of the composition. For example, a kit comprising an injectable formulation of pharmaceutical compositions may comprise a needle suitable for subcutaneous administration and an alcohol wipe for sterilization of the injection site.

In some cases, kits may be provided with instructions. The instructions may be provided in the kit or they may be accessed electronically (e.g., on the World Wide Web). The instructions may provide information on how to use the compositions of the present disclosure. The instructions may further provide information on how to use the devices of the present disclosure. The instructions may provide information on how to perform the methods of the disclosure. In some cases, the instructions may provide dosing information. The instructions may provide drug information such as the mechanism of action, the formulation of the drug, adverse risks, contraindications, and the like. In some cases, the kit is purchased by a physician or health care provider for administration at a clinic or hospital. In some cases, the kit is purchased by a laboratory and used for screening candidate compounds.

Therapeutic Agent Administration

The compounds of the current disclosure may be administered to a subject with a muscle disease or deficiency in order to treat the muscle disease or deficiency. In some cases the compounds may be Src, Tie, Abl, Trk, Flt, Yes, FAK, and/or PRKDC inhibitors. In some cases, the compound may be rebastinib or analog or salt thereof. In some cases, the compound may be a compound of FIGS. 1-5, or a compound of any one of Formulas (I)-(VII).

The compounds of the current disclosure may be administered by any of the accepted modes of administration of agents having similar utilities, for example, by cutaneous, oral, topical, intradermal, intrathecal, intravenous, subcutaneous, intramuscular, intra-articular, intraspinal or spinal, nasal, epidural, rectal, vaginal, or transdermal/transmucosal routes. The most suitable route will depend on the nature and severity of the condition being treated. Subcutaneous, intradermal and percutaneous injections can be routes for the compounds of this disclosure. Sublingual administration may be a route of administration for compounds of this disclosure, intravenous administration may be a route of administration for compounds of this disclosure. In a particular example, the pharmaceutical composition provided herein may be administered to a patient orally.

In some aspects, the methods provided herein involve administering a compound or agent for a period of time to a subject, followed by withdrawal of the compound or agent. For example, the compound or agent may be administered for 24 hours or less, followed by withdrawal of the compound or agent. In some cases, DUX4 expression remains inhibited after withdrawal of the compound or agent. For example, DUX4 expression may remain inhibited for at least 1 day, at least 2 days, at least 3 days, at least 4 days, at least 5 days, at least 6 days, at least 7 days, at least 8 days, at least 9 days, at least 10 days or greater than 10 days after withdrawal of the compound or agent in some cases, the compound or agent is administered one or more additional times after withdrawal.

In some cases, the compound or agent is administered as a stand-alone agent. In other cases, the compound or agent is co-administered with one or more additional therapies (e.g., drug). In some cases, the compound or agent is co-administered (or co-formulated) with a cell-based therapy for the treatment of a muscular or neuromuscular dystrophy (e.g., FSHD).

The compounds of the present disclosure, or their pharmaceutically acceptable salts, are generally administered in a therapeutically effective amount. The term "therapeutically effective amount" may generally refer to the amount (or dose) of a compound or other therapy that is minimally sufficient to prevent, reduce, treat or eliminate a condition, or risk thereof, when administered to a subject in need of such compound or other therapy. In some instances the term "therapeutically effective amount" may refer to that amount of compound or other therapy that is sufficient to have a prophylactic effect when administered to a subject. The therapeutically effective amount may vary; for example, it may vary depending upon the subject's condition, the weight and age of the subject, the severity of the disease condition, the manner of administration and the like, all of which ma be determined by one of ordinary skill in the art. The amount of the compound actually administered may be determined by a physician or caregiver, in the light of the relevant circumstances, including the condition to be treated, the chosen route of administration, the compound administered and its relative activity, the age, weight, the response of the individual patient, the severity of the patient's symptoms, and the like.

In some cases, administering a compound herein (e.g., rebastinib or a salt of analog thereof, or one or more compounds according to any of formulas I-VI)) to a subject or patient may comprise administering a daily dose of greater than 0 mg/m$^2$, greater than 1 mg/m$^2$, greater than 2 mg/m$^2$, greater than 3 mg/m$^2$, greater than 4 mg/m$^2$, greater than 5 mg/m$^2$, greater than 6 mg/m$^2$, greater than 7 mg/m$^2$, greater than 8 mg/m$^2$, greater than 9 mg/m$^2$, greater than 10 mg/m$^2$, greater than 12 mg/m$^2$, greater than 13 mg/m$^2$, greater than 14 mg/m$^2$, greater than 15 mg/m$^2$, greater than 16 mg/m$^2$, greater than 17 mg/m$^2$, greater than 18 mg/m$^2$, greater than 19 mg/m$^2$, greater than 20 mg/m$^2$, greater than 21 mg/m$^2$, greater than 22 mg/m$^2$, greater than 23 mg/m$^2$, greater than 24 mg/m$^2$, greater than 25 mg/m$^2$, greater than 26 mg/m$^2$, greater than 27 mg/m$^2$, greater than 28 mg/m$^2$, greater than 29 mg/m$^2$, greater than 30 mg/m$^2$, greater than 31 mg/m$^2$, greater than 32 mg/m$^2$, greater than 33 mg/m$^2$, greater than 34 mg/m$^2$, greater than 35 mg/m$^2$, greater than 36 mg/m$^2$, greater than 37 mg/m$^2$, greater than 38 mg/m$^2$, greater than 39 mg/m$^2$, greater than 40 mg/m$^2$, greater than 41 mg/m$^2$, greater than 42 mg/m$^2$, greater than 43 mg/m$^2$, greater than 44 mg/m$^2$, greater than 45 mg/m$^2$, greater than 46 mg/m$^2$, greater than 47 mg/m$^2$, greater than 48 mg/m$^2$, greater than 49 mg/m$^2$, greater than 50 mg/m$^2$, greater than 51 mg/m$^2$, greater than 52 mg/m$^2$, greater than 53 mg/m$^2$, greater than 54 mg/m$^2$, greater than 55 mg/m$^2$, greater than 56 mg/m$^2$, greater than 57 mg/m$^2$, greater than 58 mg/m$^2$, greater than 59 mg/m$^2$, greater than 60 mg/m$^2$, greater than 70 mg/m$^2$, greater than 80 mg/m$^2$, greater than 90 mg/m$^2$, greater than 100 mg/m$^2$, greater than 110 mg/m$^2$, greater than 120 mg/m$^2$, greater than 130 mg/m$^2$, greater than 140 mg/m$^2$, greater than 150 mg/m$^2$, greater than 200 mg/m$^2$, greater than 300 mg/m$^2$, greater than 350 mg/m$^2$, greater than 400 mg/m$^2$, greater than 450 mg/m$^2$, greater than 500 mg/m$^2$, greater than 750 mg/m$^2$, greater than 1000 mg/m$^2$, greater than 1250 mg/m$^2$, greater than 1500 mg/m$^2$, greater than 1750 mg/m$^2$, or greater than 2000 mg/m$^2$ of a compound (e.g. rebastinib or a salt of analog thereof, or one or more compounds according to any of formulas I-VI)) to a subject or patient.

In some cases, administering a compound herein (e.g., rebastinib or a salt of analog thereof, or one or more compounds according to any of formulas I-VI)) to a subject or patient may comprise administering a daily dose of less than 0.5 mg/m$^2$, less than 1 mg/m$^2$, less than 2 mg/m$^2$, less than 3 mg/m$^2$, less than 4 mg/m$^2$, less than 5 mg/m$^2$, less than 6 mg/m$^2$, less than 7 mg/m$^2$, less than 8 mg/m$^2$, less than 9 mg/m$^2$, less than 10 mg/m$^2$, 11 mg/m$^2$, less than 12 mg/m$^2$, less than 13 mg/m$^2$, less than 14 mg/m$^2$, less than 15 mg/m$^2$, less than 16 mg/m$^2$, less than 17 mg/m$^2$, less than 18 mg/m$^2$, less than 19 mg/m$^2$, less than 20 mg/m$^2$, less than 21 mg/m$^2$, less than 22 mg/m$^2$, less than 23 mg/m$^2$, less than 24 mg/m$^2$, less than 25 mg/m$^2$, less than 26 mg/m$^2$, less than 27 mg/m$^2$, less than 28 mg/m$^2$, less than 29 mg/m$^2$, less than 30 mg/m$^2$, less than 31 mg/m$^2$, less than 32 mg/m$^2$, less than 33 mg/m$^2$, less than 34 mg/m$^2$, less than 35 mg/m$^2$, less than 36 mg/m$^2$, less than 37 mg/m$^2$, less than 38 mg/m$^2$, less than 39 mg/m$^2$, less than 40 mg/m$^2$, less than 41 mg/m$^2$, less than 42 mg/m$^2$, less than 43 mg/m$^2$, less than 44 mg/m$^2$, less than 45 mg/m$^2$, less than 46 mg/m$^2$, less than 47 mg/m$^2$, less than 48 mg/m$^2$, less than 49 mg/m$^2$, less than 50 mg/m$^2$, less than 51 mg/m$^2$, less than 52 mg/m$^2$, less than 53 mg/m$^2$, less than 54 mg/m$^2$, less than 55 mg/m$^2$, less than 56 mg/m$^2$, less than 57 mg/m$^2$, less than 58 mg/m$^2$, less than 59 mg/m$^2$, less than 60 mg/m$^2$, less than 70 mg/m$^2$, less than 80 mg/m$^2$, less than 90 mg/m$^2$, less than 100 mg/m$^2$, less than 110 mg/m$^2$, less than 120 mg/m$^2$, less than 130 mg/m$^2$, less than 140 mg/m$^2$, less than 150 mg/m$^2$, less than 200 mg/m$^2$, less than 250 mg/m$^2$, less than 300 mg/m$^2$, less than 350 mg/m$^2$, less than 400 mg/m$^2$, less than 450 mg/m$^2$, less than 500 mg/m$^2$, less than 750 mg/m$^2$, less than 1000 mg/m$^2$, less than 1250 mg/m$^2$, less than 1500 mg/m$^2$, less than 1750 mg/m$^2$, or less than 2000 mg/m$^2$, of a compound (e.g., rebastinib or a salt of analog thereof, or one or more compounds according to any of formulas I-VI)) to a subject or patient.

In some cases, administering a compound herein (e.g., rehastinib or a salt of analog thereof, or one or more compounds according to any of formulas I-VI)) to a subject or patient may comprise administering a daily dose of the compound (or compounds) of between 1 mg/m² and 120 mg/m². In some instances, the administering a compound (e.g., rebastinib or a salt of analog thereof, or one or more compounds according to any of formulas I-VI)) to a subject or patient may comprise administering a daily dose of the compound or compounds of between 20 mg/m² and 100 mg/m². In some instances, the administering a compound (e.g., rebastinib or a salt of analog thereof, or one or more compounds according to any of formulas I-VI)) to a subject or patient may comprise administering a daily dose of between 30 mg/m² and 80 In some instances, the administering a compound (e.g., rebastinib or a salt of analog thereof, or one or more compounds according to any of formulas I-VI) to a subject or patient may comprise administering a daily dose of between 40 mg/m² and 80 mg/m². In some instances, when the administering a compound (e.g., rebastinib or a salt of analog thereof, or one or more compounds according to any of formulas I-VI)) to a subject or patient comprises administering a daily dose of between 40 mg/m² and 80 mg/m², the subject or patient is an adult. In some instances, when the administering a compound (e.g., rebastinib or a salt of analog thereof, or one or more compounds according to any of formulas I-VI)) to a subject or patient comprises administering a daily dose of between 40 mg/m² and 80 mg/m², the subject or patient is a child. In some instances, the administering a compound (e.g., rebastinib or a salt of analog thereof, or one or more compounds according to any of formulas I-VI)) to a subject or patient may comprise administering a daily dose of between 50 mg/m² and 80 mg/m². In some instances, the administering a compound (e.g., rebastinib or a salt of analog thereof, or one or more compounds according to any of formulas I-VI)) to a subject or patient may comprise administering a daily dose of between 40 mg/m² and 60 mg/m². In some instances, the administering a compound (e.g., rebastinib or a salt of analog thereof, or one or more compounds according to any of formulas I-VI)) to a subject or patient may comprise administering a daily dose of between 50 mg/m² and 60 mg/m². In some instances, the administering a compound (e.g., rebastinib or a salt of analog thereof, or one or more compounds according to any of formulas I-VI)) to a subject or patient may comprise administering a daily dose of between 45 mg/m² and 65 mg/m².

In some cases, administering a compound herein (e.g., rebastinib or a salt of analog thereof, or one or more compounds according to any of formulas I-VI)) to a subject or patient may comprise administering a daily dose of less than 150 mg, less than 140 mg, less than 130 mg, less than 120 mg, less than 110 mg, less than 100 mg, less than 98 mg, less than 96 mg, less than 95 mg, less than 90 mg, less than 85 mg, less than 80 mg, less than 75 mg, less than 70 mg, less than 65 mg, less than 60 mg, less than 55 mg, less than 50 mg, less than 45 mg, less than 40 mg, less than 35 mg, less than 30 mg, less than 25 mg, less than 20 mg, less than 15 mg, less than 10 mg, less than 9 mg, less than 8 mg, less than 7 mg, less than 6 mg, less than 5 mg, less than 4 mg, less than 3 mg, less than 2 mg, or less than 1 mg. In some instances, the subject or patient to which the compound herein is administered is an adult. In some instances, the subject or patient to which the compound herein is administered is a child.

In some cases, administering a compound herein (e.g., rebastinib or a salt of analog thereof, or one or more compounds according to any of formulas I-VI)) to a subject or patient may comprise administering a daily dose of less than about 150 mg, less than about 140 mg, less than about 130 mg, less than about 120 mg, less than about 110 mg, less than about 100 mg, less than about 98 mg, less than about 96 mg, less than about 95 mg, less than about 90 mg, less than about 85 mg, less than about 80 mg, less than about 75 mg, less than about 70 mg, less than about 65 mg, less than about 60 mg, less than about 55 mg, less than about 50 mg, less than about 45 mg, less than about 40 mg, less than about 35 mg, less than about 30 mg, less than about 25 mg, less than about 20 mg, less than about 15 mg, less than about 10 mg, less than about 9 mg, less than about 8 mg, less than about 7 mg, less than about 6 mg, less than about 5 mg, less than about 4 mg, less than about 3 mg, less than about 2 mg, or less than about 1 mg. In some instances, the subject or patient to which the compound herein is administered is an adult. In some instances, the subject or patient to which the compound herein is administered is a child.

In some cases, administering a compound herein (e.g., rebastinib or a salt of analog thereof, or one or more compounds according to any of formulas I-VI)) to a subject or patient may comprise administering a daily dose of greater than 150 mg, greater than 140 mg, greater than 130 mg, greater than 120 mg, greater than 110 mg, greater than 100 mg, greater than 95 mg, greater than 90 mg, greater than 95 mg, greater than 90 mg, greater than 85 mg, greater than 80 mg, greater than 75 mg, greater than 70 mg, greater than 65 mg, greater than 60 mg, greater than 55 mg, greater than 50 mg, greater than 45 mg, greater than 40 mg, greater than 35 mg, greater than 30 mg, greater than 25 mg, greater than 20 mg, greater than 15 mg, greater than 10 mg, greater than 9 mg, greater than 8 mg, greater than 7 mg, greater than 6 mg, greater than 5 mg, greater than 4 mg, greater than 3 mg, greater than 2 mg, greater than or greater than 1 mg. In some instances, the subject or patient to which the compound herein is administered is an adult. In some instances, the subject or patient to which the compound herein is administered is a child.

In some cases, administering a compound herein (e.g., rebastinib or a salt of analog thereof, or one or more compounds according to any of formulas I-VI)) involves administering a dose that is selected to avoid or minimize one or more adverse events including but not limited to hematologic toxicity (e.g., anemia, myelosuppression, leukopenia, thrombocytopenia), nausea, diarrhea, vomiting, constipation, paresthesia, hypoesthesia, decreased appetite, or fatigue. In some cases, administering a compound herein (e.g., rebastinib or a salt of analog thereof, or one or more compounds according to any of formulas I-VI)) involves administering a dose that is selected to avoid or minimize cytotoxicity (e.g. to neurons, muscle cells, or gastrointestinal cells).

In some cases, administering a compound herein (e.g., rebastinib or a salt of analog thereof, or one or more compounds according to any of formulas I-VI) to a patient may comprise administering a daily dose of 0.1 mg/m², 0.2 mg/m², 0.3 mg/m², 0.4 mg/m², 0.5 mg/m², 0.6 mg/m², 0.7 mg/m², 0.8 mg/m², 0.9 mg/m², 1 mg/m², 1.1 mg/m², 1.2 mg/m², 1.3 mg/m², 1.4 mg/m², 1.5 mg/m², 1.6 mg/m², 1.7 mg/m², 1.8 mg/m², 1.9 mg/m², 2 mg/m², 2.1 mg/m², 2.2 mg/m², 2.3 mg/m², 2.4 mg/m², 2.5 mg/m², 2.6 mg/m², 2.7 mg/m², 2.8 mg/m², 2.9 mg/m², 3 mg/m², 3.1 mg/m², 3.2 mg/m², 3.3 mg/m², 3.4 mg/m², 3.5 mg/m², 3.6 mg/m², 3.7 mg/m², 3.8 mg/m², 3.9 mg/m², 4 mg/m², 4.1 mg/m², 4.2 mg/m², 4.3 mg/m², 4.4 mg/m², 4.5 mg/m², 4.6 mg/m², 4.7 mg/m², 4.8 mg/m², 4.9 mg/m², 5 mg/m², 5.1 mg/m², 5.2 mg/m², 5.3 mg/m², 5.4 mg/m², 5.5 mg/m², 5.6 mg/m², 5.7 mg/m², 5.8 mg/m², 5.9 mg/m², 6 mg/m², 6.1 mg/m², 6.2 mg/m², 6.3 mg/m², 6.4 mg/m², 6.5 mg/m², 6.6 mg/m², 6.7 mg/m², 6.8 mg/m², 6.9 mg/m², 7 mg/m², 7.1 mg/m², 7.2 mg/m², 7.3 mg/m², 7.4 mg/m², 7.5 mg/m², 7.6 mg/m², 7.7 mg/m², 7.8 mg/m², 7.9 mg/m², 8 mg/m², 8.1 mg/m², 8.2 mg/m², 8.3 mg/m², 8.4 mg/m², 8.5 mg/m², 8.6 mg/m², 8.7 mg/m², 8.8 mg/m², 8.9 mg/m², 9 mg/m², 9.1 mg/m², 9.2 mg/m², 9.3 mg/m², 9.4 mg/m², 9.5 mg/m², 9.6 mg/m², 9.7 mg/m², 9.8 mg/m², 9.9 mg/m², 10 mg/m², 11 mg/m², 12 mg/m², 13 mg/m², 14 mg/m², 15 mg/m², 16 mg/m², 17 mg/m², 18 mg/m², 19 mg/m², 20 mg/m², 21 mg/m², 22 mg/m², 23 mg/m², 24 mg/m², 25 mg/m², 26 mg/m², 27 mg/m², 28 mg/m², 29 mg/m², 30 mg/m², 31 mg/m², 32 mg/m², 33 mg/m², 34 mg/m², 35 mg/m², 36 mg/m², 37 mg/m², 38 mg/m², 39 mg/m², 40 mg/m², 41 mg/m², 42 mg/m², 43 mg/m², 44 mg/m², 45 mg/m², 46 mg/m², 47 mg/m², 48 mg/m², 49 mg/m², 50 mg/m², 51 mg/m², 52 mg/m², 53 mg/m², 54 mg/m², 55 mg/m², 56 mg/m², 57 mg/m², 58 mg/m², 59 mg/m², 60 mg/m², 61 mg/m², 62 mg/m², 63 mg/m², 64 mg/m², 65 mg/m², 66 mg/m², 67 mg/m², 68 mg/m², 69 mg/m², 70 mg/m², 71 mg/m², 72 mg/m², 73 mg/m², 74 mg/m², 75 mg/m², 76 mg/m², 77 mg/m², 78 mg/m², 79 mg/m², 80 mg/m², 81 mg/m², 82 mg/m², 83 mg/m², 84 mg/m², 85 mg/m², 86 mg/m², 87 mg/m², 88 mg/m², 89 mg/m², 90 mg/m², 91 mg/m², 92 mg/m², 93 mg/m², 94 mg/m², 95 mg/m², 96 mg/m², 97 mg/m², 98 mg/m², 99 mg/m², or 100 mg/m² of the compound.

The daily dose of the compound may be greater than 0 mg, greater than 1 mg, greater than 2 mg, greater than 3 mg, greater than 4 mg, greater than 5 mg, greater than 6 mg, greater than 7 mg, greater than 8 mg, greater than 9 mg, greater than 10 mg, greater than 11 mg, greater than 12 mg, greater than 13 mg, greater than 14 mg, greater than 15 mg, greater than 16 mg, greater than 17 mg, greater than 18 mg, greater than 19 mg, greater than 20 mg, greater than 21 mg, greater than 22 mg, greater than 23 mg, greater than 24 mg, greater than 25 mg, greater than 26 mg, greater than 27 mg, greater than 28 mg, greater than 29 mg, greater than 30 mg, greater than 31 mg, greater than 32 mg, greater than 33 mg, greater than 34 mg, greater than 35 mg, greater than 36 mg, greater than 37 mg, greater than 38 mg, greater than 39 mg, greater than 40 mg, greater than 41 mg, greater than 42 mg, greater than 43 mg, greater than 44 mg, greater than 45 mg, greater than 46 mg, greater than 47 mg, greater than 48 mg, greater than 49 mg, greater than 50 mg, greater than 100 mg, greater than 150 mg, greater than 200 mg, greater than 300 mg, greater than 350 mg, greater than 400 mg, greater than 450 mg, greater than 500 mg, greater than 750 mg, greater than 1 g, greater than 5 g, greater than 10 g, or higher.

In some cases, the daily dose of the compound may be administered in a single dose. In some cases, the daily dose may be divided into 1, 2, 3, 4, 5, 6, 7, 8, 9, or 10 doses per day. For example, the daily dose can be divided into 3 doses per day. In some cases, the daily dose may be divided into at least 1, 2, 3, 4, 5, 6, 7, 8, 9, 10, 15, 20, 25, 30, 35, 40, 45, 50, 55, or 60 infusions per hour. In some cases, each infusion of a composition comprising a drug as described herein (e.g. rebastinib or on or more compounds according to any of formulas I-VII) may last for at least 5 minutes, 10 minutes, 15 minutes, 20 minutes, 25 minutes, 30 minutes, 35 minutes, 40 minutes, 45 minutes, 50 minutes, 55 minutes, 1 hour, 1.5 hours, 2 hours, 2.5 hours, 3 hours, 3.5 hours, 4 hours, 4.5 hours, 5 hours, 5.5 hours, or 6 hours.

In some cases, the daily dose of the compound may be administered in a single dose. In some cases, the daily dose may be divided into 1, 2, 3, 4, 5, 6, 7, 8, 9, or 10 doses per day. For example, the daily dose can be divided into 3 doses per day. In some cases, the daily dose may be divided into at least 1, 2, 3, 4, 5, 6, 7, 8, 9, 10, 15, 20, 25, 30, 35, 40, 45, 50, 55, or 60 infusions per hour. In some cases, each infusion of a composition comprising a drug as described, herein (e.g., 0, rebastinib or on or more compounds according to any of formulas I-VII) may last, for at least 5 minutes, 10 minutes, 15 minutes, 20 minutes, 25 minutes, 30 minutes, 35 minutes, 40 minutes, 45 minutes, 50 minutes, 55 minutes, 1 hour, 1.5 hours, 2 hours, 2.5 how's, 3 hours, 3.5 hours, 4 hours, 4.5 hours, 5 hours, 5.5 hours, or 6 hours.

The compounds described herein may be administered to a patient one or more times per day. In some cases, the compounds may be administered to a patient one time per day. In some cases, the compounds may be administered to a patient at least 2 times, 3 times, 4 times 5 times, 6 times, 7 times, 8 times, 9 times, 10 times, 11 times, 12 times, 13 times, 14 times, 15 times, 16 times, 17 times, 18 times, 19 times, 20 times, 21 times, 22 times. 23 times, or 24 times per day. For example, a compound may be administered to a patient 3 times per day.

The compounds described herein may be administered to a patient for one or more days. In some cases, the compound may be administered to a patient for one day. In some cases, the pharmaceutical composition may be administered to the patient for at least 2 days, at least 3 days, at least 4 days, at least 5 days, at least 6 days, at least. 1 week, at least 2 weeks, at least 3 weeks, at least 1 month, at least 2 months, at least 3 months, at least 4 months, at least 5 months, at least 6 months, at least 7 months, at least 8 months, at least 9 months, at least 10 months, at least 11 months, at least 1 year, at least 2 years, at least 3 years, at least 4 years, at least 5 years, at least 6 years, at least 7 years, at least 8 years, at least 9 years, at least 10 years, at least 20 years, at least 30 years, at least 40 years, or at least 50 years. In some cases, the pharmaceutical composition may be administered to the patient for at least 20 contiguous days, at least 28 contiguous days, at least 40 contiguous days, at least 60 contiguous days, at least 90 contiguous days, at least 100 contiguous days, or at least 200 contiguous days. In some cases, the contiguous administration is near-contiguous. For example, the administration may be for at least 28 contiguous days, except for one or two days during that period which may be skipped.

The compounds described herein may be effective over time. In some cases, the compounds may be effective for one or more days. In some cases, the duration of efficacy of the compounds is over a long period of time. In some cases, the efficacy of the compound may be greater than 2 days, 3 days, 4 days, 5 days, 6 days, 1 week, 2 weeks, 3 weeks, or 1 month. In some cases, the efficacy of the compound may be less than 2 days, 3 days, 4 days, 5 days, 6 days, 1 week, 2 weeks, 3 weeks, or 1 month. The compound as described herein (e.g., rebastinib or a salt of analog thereof, or one or more compounds according to any of formulas VI) may be administered to maintain a therapeutic serum concentration range within the subject or patient for an extended period of time, chronically, or indefinitely. In some embodiments, the compound is administered to maintain a therapeutic serum concentration range for greater than 10, greater than 15, greater than 20, greater than 25, greater than 30, greater than 45, or greater than 50 days. In some embodiments, the compound is administered to maintain a therapeutic serum concentration range for greater than 1 month, greater than 2 months, greater than 3 months, greater than 4 months, greater than 5 months, greater than 6 months, greater than 7 months, greater than 8 months, greater than 9 months, greater than 10 months, greater than 11 months, greater than 12 months, greater than 5 years, greater than 10 years, greater than 15 years, greater than 20 years, greater than 30 years, or longer. In some embodiments, the compound is administered to maintain a therapeutic muscular concentration range (e.g. therapeutic drug concentration in skeletal muscle range) for greater than 10, greater than 15, greater than 20, greater than 25, greater than 30, greater than 45, or greater than 50 days. In some embodiments, the compound is administered to maintain a therapeutic muscle concentration range for greater than 1 month, greater than 2 months, greater than 3 months, greater than 4 months, greater than 5 months, greater than 6 months, greater than 7 months, greater than 8 months, greater than 9 months, greater than 10 months, greater than 11 months, greater than 12 months, greater than 5 years, greater than 10 years, greater than 15 years, greater than 20 years, greater than 30 years, or longer.

In some embodiments, the compound is administered daily for greater than 10, greater than 15, greater than 20, greater than 25, greater than 30, greater than 45, or greater than 50 days. In some embodiments, the compound is administered daily for greater than 1 month, greater than 2 months, greater than 3 months, greater than 4 months, greater than 5 months, greater than 6 months, greater than 7 months, greater than 8 months, greater than 9 months, greater than 10 months, greater than 11 months, greater than 12 months, greater than 5 years, greater than 10 years, greater than 15 years, greater than 20 years, greater than 30 years, or longer. In some embodiments, the compound is administered weekly or bi-weekly for greater than 1 month, greater than 2 months, greater than 3 months, greater than 4 months, greater than 5 months, greater than 6 months, greater than 7 months, greater than 8 months, greater than 9 months, greater than 10 months, greater than 11 months, greater than 12 months, greater than 5 years, greater than 10 years, greater than 15 years, greater than 20 years, greater than 30 years, or longer.

In some cases, including situations when the compound (e.g., rebastinib or a salt of analog thereof, or one or more compounds according to any of formulas I-VI) is administered for an extended period of time or chronically, DUX4 inhibition may be monitored over time. Effective inhibition of DUX4 activity can be monitored, for example, by periodic (e.g. every 1, 2, 3, 4, 5, 6 months) biopsy of tissue (e.g., skeletal muscle) of the patient followed by measurement of DUX4 expression and/or by measurement of markers of DUX4 activity (e.g. activation or expression of target genes including but not limited to CCNA1, KHDC1L, LEUTX, M8D3L2, PRAMEF2, PRAMEF6, SPRYD5, TRIM43, TRIM49, ZNF296, ZSCAN4 by western blot, Q-PCR, RNA sequencing, or another suitable method) in the biopsied cells or tissue. The DUX4 may be detected at the mRNA level or the protein level, or by a functional assay. Suitable skeletal muscles for periodic biopsy include muscles of the upper torso, deltoid muscles, or trapezius muscles. In some cases, specific cell types may be analyzed, such as muscle cells, myoblast cells, or myotubes. In some embodiments, skeletal muscle is biopsied both before and after treatment to provide information on the degree of inhibition of DUX4 activity provided by the administered compound. In instances where the compound does not lead to complete inhibition of DUX4 activity as determined by biopsy, the dose of the compound may be adjusted upward. Alternatively, when side effects are observed due to administration of the compound or DUX4 inhibition determined by biopsy is sufficient, the dose of the compound may be adjusted downward. In some cases, where stable inhibition of DUX4 is detected, the dose of the compound administered to the patient may be maintained over time.

In some embodiments, this disclosure provides a method of treating a muscular degenerative disorder in a subject in need thereof or modulating DUX4 activity in a subject in need there of using any of the compounds described herein (e.g. rebastinib, or a salt thereof, or a compound according, to any one of formulas or a salt thereof), wherein the method further comprises monitoring DUX4 expression or activity in a tissue of the subject following administration of the compound. In some embodiments, DUX4 expression is monitored by monitoring DUX4 mRNA expression, DUX4 protein expression, or both DUX4 mRNA expression and DUX4 protein expression. In some cases, the method comprises taking a blood, plasma, serum or urine sample from the subject and detecting the level of a marker of muscle injury. In some cases, the method comprises taking a blood, plasma, serum or urine sample from the subject and detecting the level of creatinine kinase, aldolase, and/or muscle enzymes in the sample. In some embodiments, the method comprises monitoring the level of DUX4, creatinine kinase, aldolase, or muscle enzymes or any combination thereof over time, such as over two time points, over three time points. In cases where a marker of muscle injury increases or stays the same, the level of compound administered to the subject may, in some cases, be adjusted upwards. In cases where the marker decreases over time, the level of the compound administered to the subject may, in some cases, be maintained or adjusted downward. In some embodiments, provided herein is a method of treating a muscular degenerative disorder in a subject in need thereof or modulating DUX4 activity in a subject in need there of using any of the compounds described herein (e.g. rebastinib, or a salt: thereof, or a compound according to any one of formulas I-VII, or a salt thereof), wherein, following administration of the compound, the subject in need thereof experiences a least a 10%, at least a 25%, at least a 50%, at least a 75%, or at least a 100% decrease in a marker of muscle injury, creatinine kinase, and/or aldolase.

In some embodiments, DUX4 expression or activity in a subject is monitored over time prior to administration of a compound provided herein, in order to determine whether the subject has a natural or baseline cycle of DUX4 expression or activity. In the event such cycle is detected, the subject or patient may be monitored over time after administration of the compound at timepoints that approximate the same point in the cycle, such as the beginning of the cycle, the peak of the cycle, the nadir of the cycle, or the end of the cycle.

In certain particular embodiments, more than one compound of the current disclosure may be administered at a time to a subject. In some embodiments, two compounds of the current disclosure in combination make act synergistically or additively, and either compound may be used in a lesser amount than if administered alone.

Any of the compounds or agents provided herein may be administered to a subject in combination with a cell therapy. The effects of the combination may be additive, in some cases, the effects of the combination are synergistic. The compounds may be administered before, during or after the administration of the cell therapy. In some cases, the compounds or agents are administered separately from the cell therapy. In some cases, the cell therapy is mixed with one or more of the compounds. In some examples, the cell therapy may involve introducing skeletal muscle cells into a subject and a compound provided herein is also administered into the subject in order to repress DUX4 expression in vivo in skeletal muscle cells.

EXAMPLES

Drug Screening

Example 1—Workflow

Figure 6:
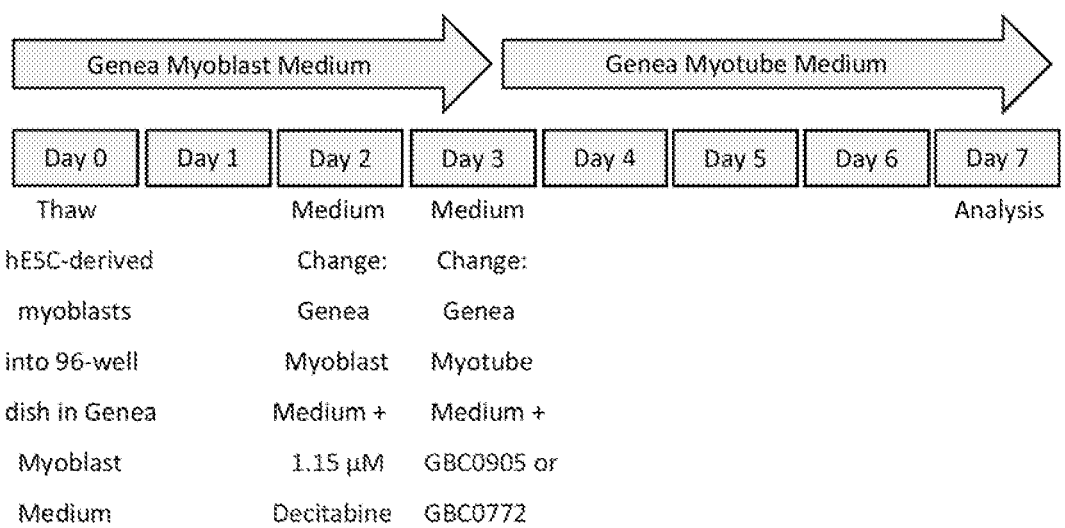
FIG. 6 provides the workflow for hESC-SkM assays.

FIG. 6 provides an example of a screening and culturing workflow for hESC-SkM assays. At Day 0, hESC-derived myoblasts are thawed into a 96-well plate in myoblast medium (Genea BioCells). On Day 2, the medium is replaced with new myoblast medium containing 1.15 µM Decitabine. On Day 3, the medium is changed again, this time the new medium is Myotube Medium (Genea BioCells) containing GBC0905 or GBC0772. On Day 7, the myotubes are analyzed. For example, the myotubes may be analyzed for MHC expression or DUX4 expression.

Example 2—FSHD hESC-SkM Primary Screen

Assay:

Immunocytochemistry—DUX4, Myosin Heavy Chain, Nuclei 100 nM GBC0905 (Rebastinib) treatment of FSHD hESC-SkM results in decreased DUX4 expression with no significant off-target toxicity as evidenced by myonuclear count or Myosin. Heavy Chain area while a positive control GBC0772 (MLN4924) inhibits myogenesis and leads to a non-specific decrease in DUX4 and Myosin Heavy Chain expression.

Methods:

Genea049 FSHD-affected human Embryonic Stem Cells (hESCs) were differentiated using Genea's myogenic differentiation protocol (Caron et 2015) to the myoblast stage and cryopreserved. Frozen myoblasts were resuscitated and 4500 cells were plated into each well of a 96-well collagen I coated tissue culture plate in myoblast medium. After two days of cell growth medium was changed to 100 µL per well myoblast medium containing 1.15 µM Decitabine. After 1 day of additional growth medium was changed to 100 µL per well myotube medium containing 100 nM GBC0772 (MLN4924) or GBC0905 (Rebastinib) or DMSO vehicle. Cells were allowed to differentiate to myotubes for four additional days then were fixed and analyzed for quantification of DUX4 expression, Myosin Heavy Chain expression, and nuclei number. Triplicate wells of each condition were averaged.

Figure 7:
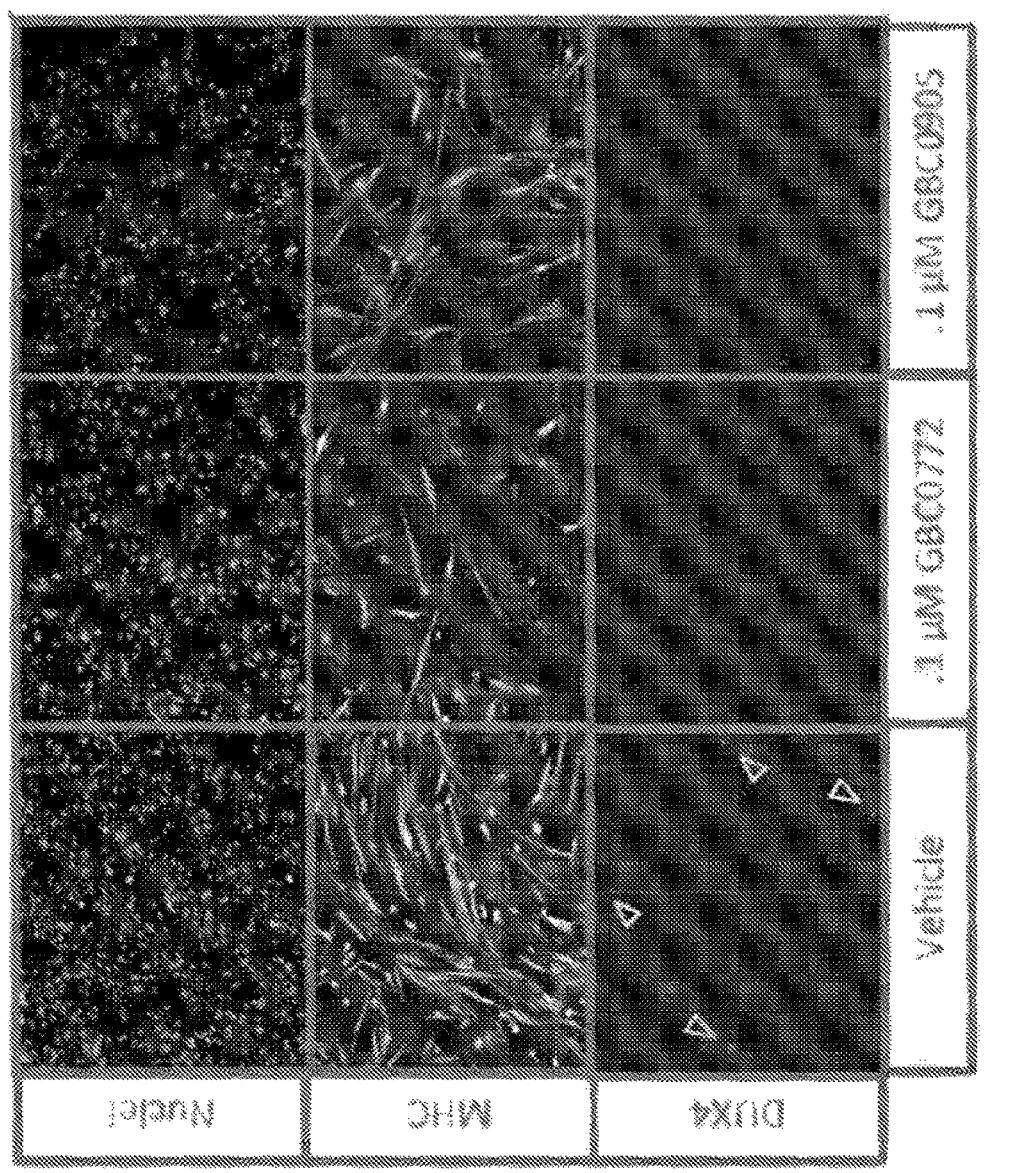
FIG. 7 FSHD hESC-SkM Primary Screen for GBC0905 (Rebastinib, DCC-2036). 100 nM GBC0905 treatment of FSHD hESC-SkM results in decreased DUX4 expression with no significant off-target toxicity as evidenced by myonuclear count or Myosin Heavy Chain area while a positive control GBC0772 (MLN4924) inhibits myogenesis and leads to a non-specific decrease in DUX4 and Myosin Heavy Chain expression.
Figure 7:
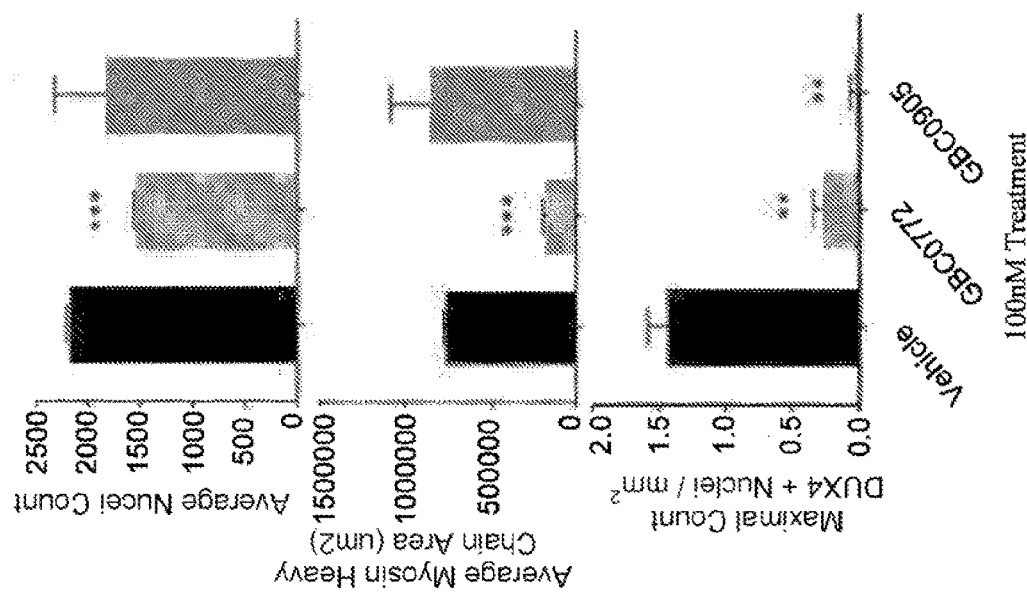

Results:

As illustrated in FIG. 7, treatment of Genea049 hFSC-SkM during myotube formation with either 100 nM GBC0772 (MLN4924) GBC0905 (Rebastinib) results in decreased DUX4 expression after four days of culture. While GBC0772 treatment also results in decreased Myosin Heavy Chain expression and nuclei count characteristic of myogenic inhibition/toxicity, these effects are not seen in cells treated with GBC0905 (Rebastinib). These results indicate a specific DUX4-suppressive, pro-therapeutic effect of GBC0905 (Rebastinib) treatment.

Example 3—FSHD hESC-SkM Dose Curve

Assay:

Immunocytochemistry—DUX4, Myosin Heavy Chain, Nuclei GBC0905 treatment of FSHD hESC-SkM results in decreased DUX4 expression in a dose-dependent manner. In contrast, treatment with myogenesis inhibitor GBC0772 decreases DUX4 and Myosin Heavy Chain Area equipotently, showing non-specific effect.

Methods:

Genea049 FSHD-affected human Embryonic Stem Cells (hESCs) were differentiated using Genea's myogenic differentiation protocol (Caron et al., 2015) to the myoblast stage and cryopreserved. Frozen myoblasts were resuscitated and 4500 cells were plated into each well of a 96-well collagen I coated tissue culture plate in myoblast medium. After two days of cell growth medium was changed to 100 µL per well myoblast medium containing 1.15 µM Decitabine. After 1 day of additional growth medium was changed to 100 µL per well myotube medium containing GBC0772 (MLN4924) or GBC0905 (Rebastinib) at concentrations ranging from 10 nM-3 µM or equivolume DMSO vehicle. Cells were allowed to differentiate to myotubes for four additional days then were fixed and analyzed for quantification of DUX4 expression, Myosin Heavy Chain expression, and nuclei number by high-content imaging. Triplicate wells of each condition were averaged.

Figure 8B:
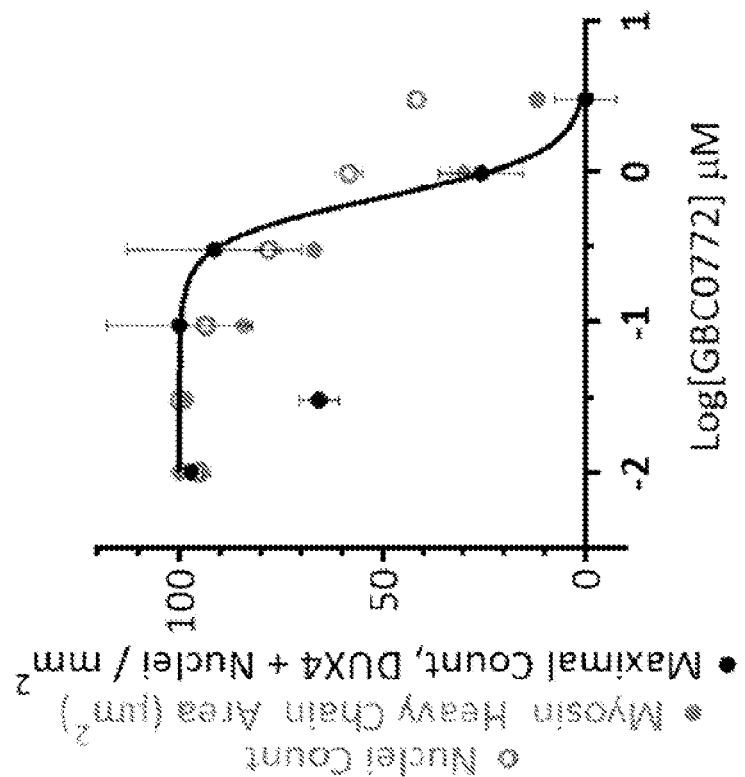
FIG. 8A and FIG. 8B FSHD hESC-SkM Dose Curve: GBC0905 (Rebastinib. DCC-2036) treatment of FSHD hESC-SkM results in decreased DUX4 expression in a dose-dependent manner. In contrast, treatment with myogenesis inhibitor GBC0772 (MLN4924) decreases DUX4 and Myosin Heavy Chain Area equipotently, showing non-specific effect.
Figure 8A:
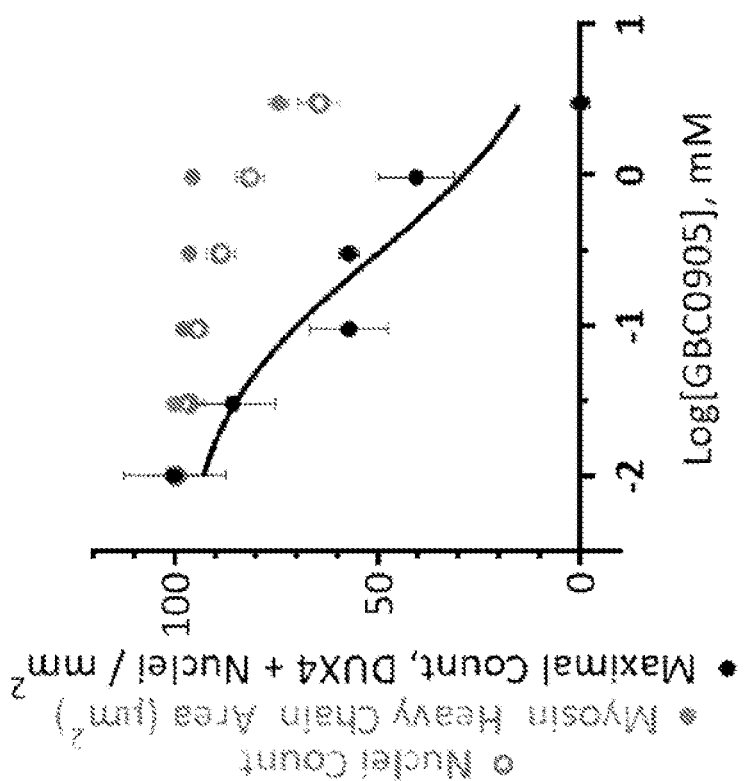

Results:

As shown in FIG. 8, treatment of Genea049 hESC-SkM during myotube formation at six concentration points for both GBC0772 (MLN4924) or GBC0905 (Rebastinib) results in dose-dependent decreased DUX4 expression after four days of culture. GBC0772 (MLN4924) treatment also results in decreased Myosin Heavy Chain expression and nuclei count characteristic of myogenic inhibition/toxicity at all concentrations where DUX4 decrease is apparent. In contrast, effects on Myosin Heavy Chain are not seen in cells treated with GBC0905 (Rebastinib) at concentrations lower than 3 µM. These results indicate a specific DUX4-suppressive, therapeutic effect of GBC0905 (Rebastinib) treatment with an estimated IC50 value of approximately 100 nM.

Figure 9:
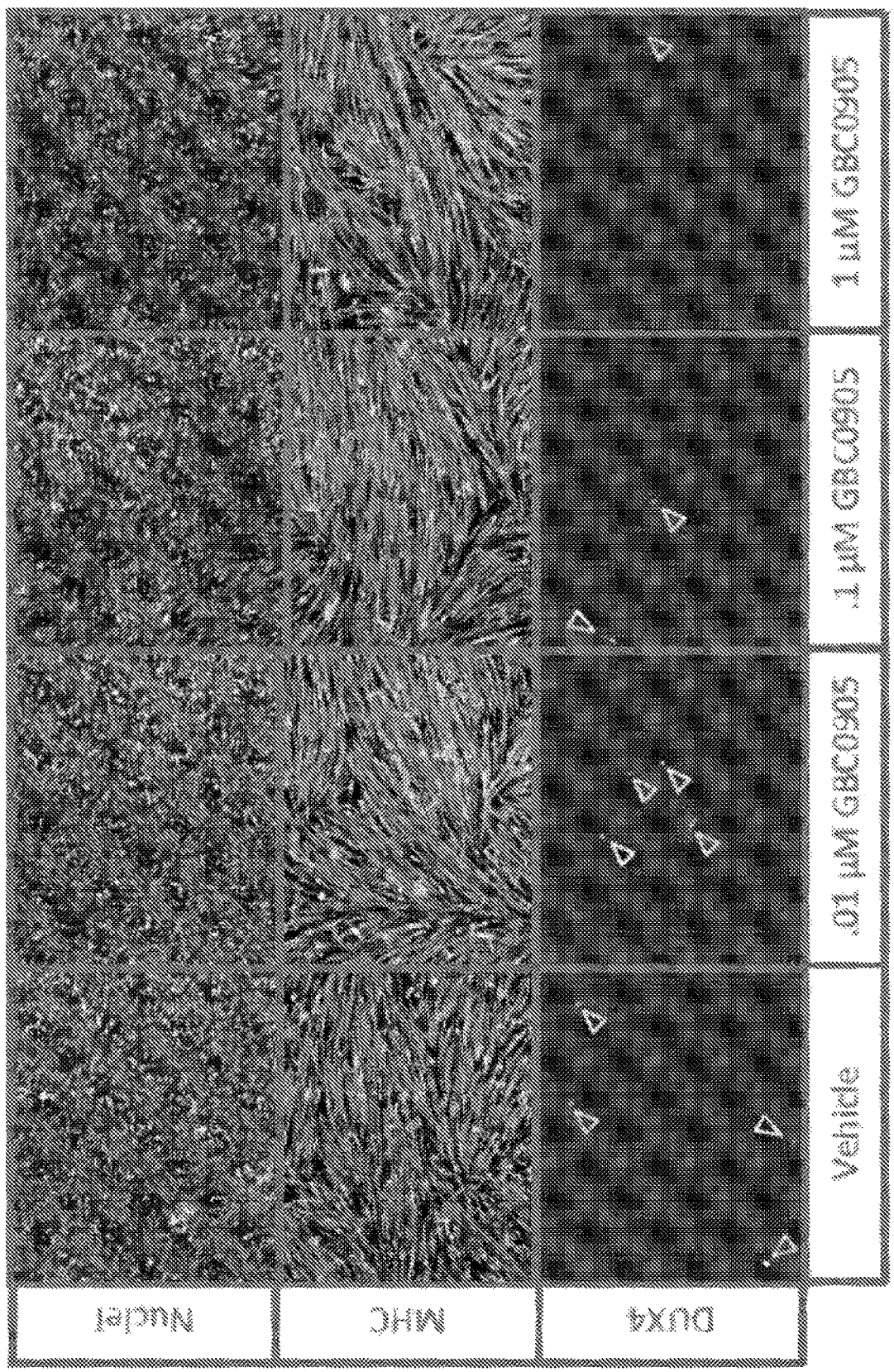
FIG. 9 provides representative images from the dose response experiment of GBC0905 (Rebastinib, DCC-2036)

FIG. 9 provides representative images from the dose response experiment of example 3.

Example 4—Primary Patient Biopsy-Derived Muscle

Figure 10:
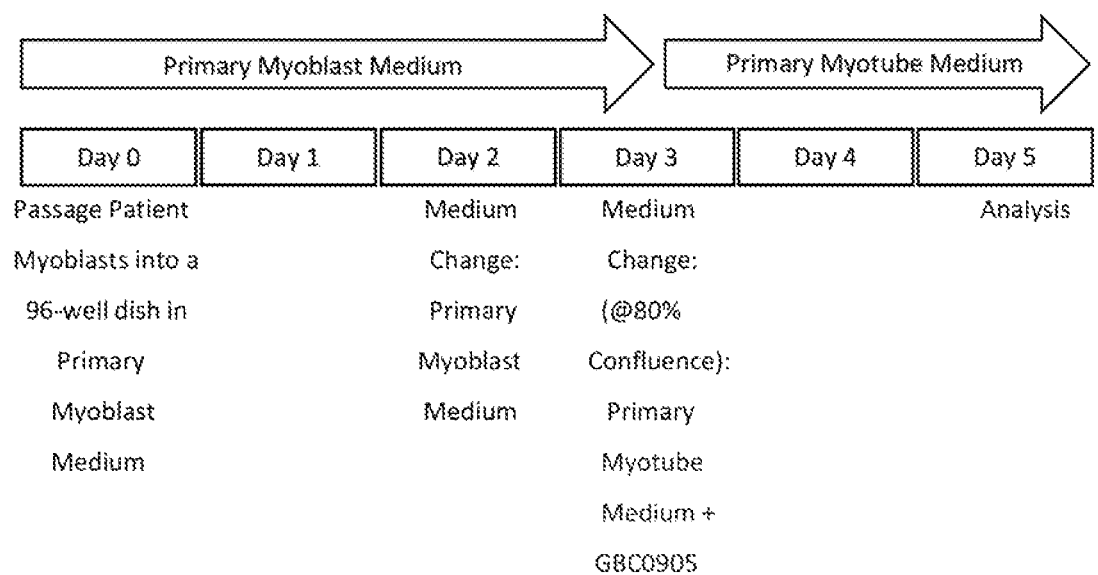
FIG. 10 provides the workflow for assays with primary patient biopsy-derived muscle.
Figure 11B:
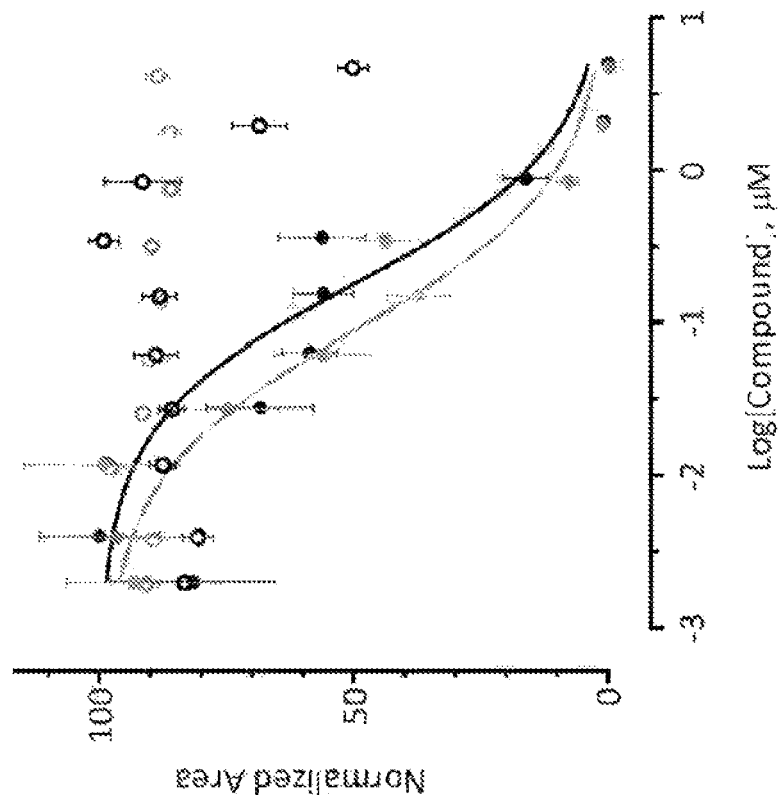
FIG. 11A, FIG. 11B, FIG. 11C, FIG. 11D FSHD Primary Patient Biopsy Myotube Dose Curve: GBC0905 (Rebastinib, DCC-2036) treatment of FSHD primary patient biopsy muscle cultures reduces clinically relevant DUX4 and H3.X/Y stress marker expression in a dose-dependent manner without yielding a toxic or myogenic inhibitory effect.
Figure 11A:
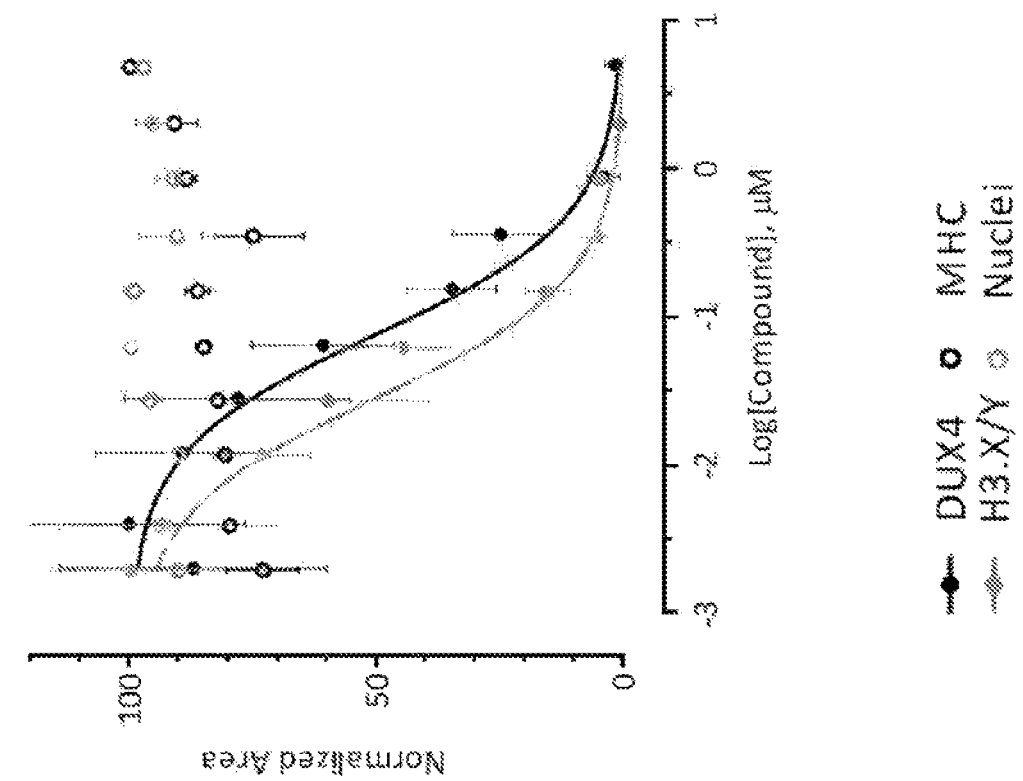
Figure 11D:
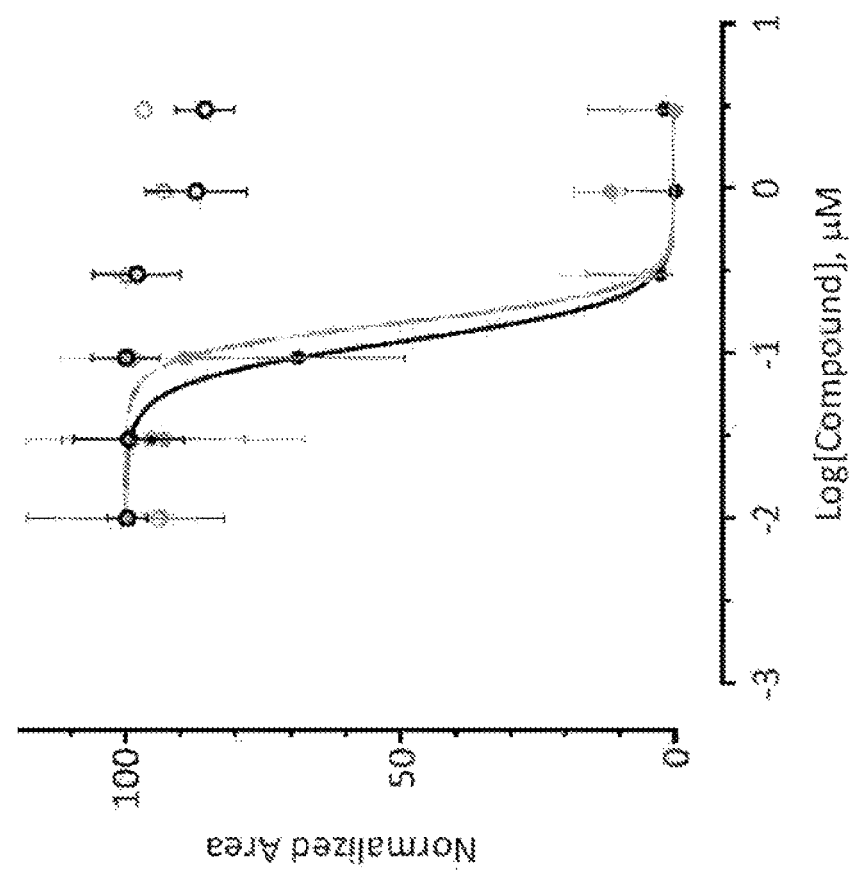
Figure 11C:
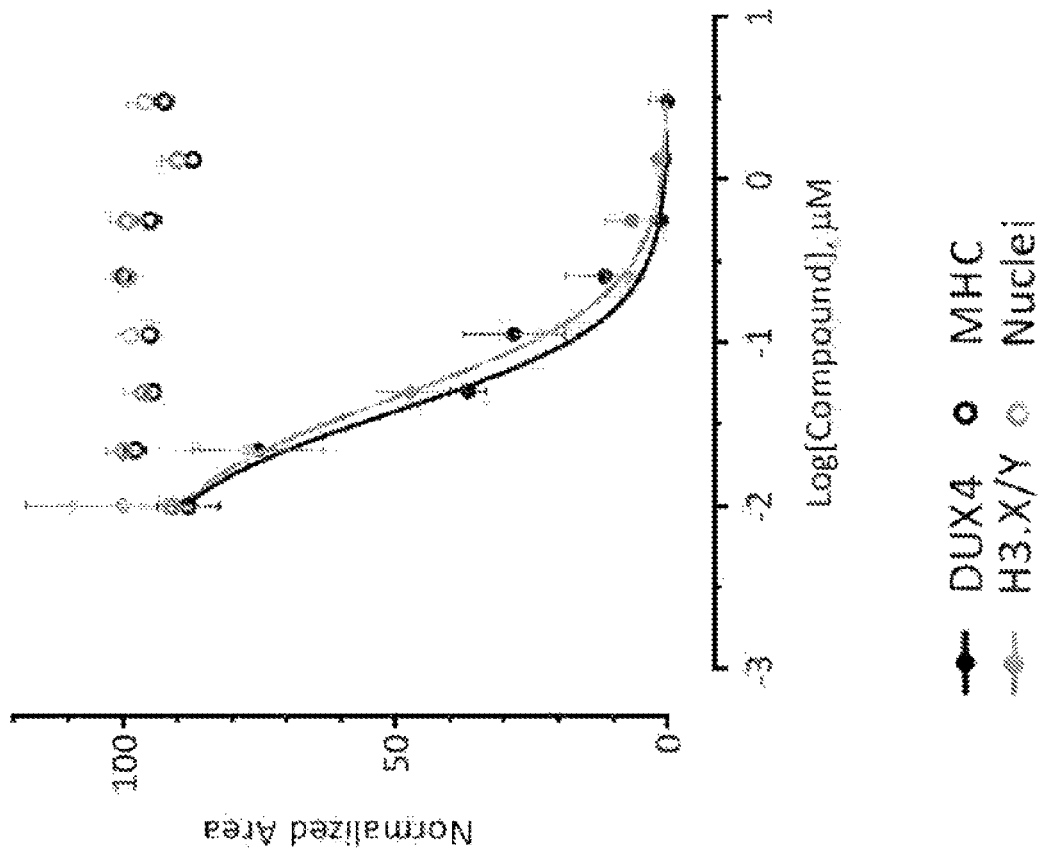

FIG. 10 provides the workflow for assays performed with patient biopsy-derived muscle. On Day 0, patient myoblasts are passaged in a 96-well dish in primary myoblast medium (Genea BioCells). On Day 2, the medium is changed to primary myoblast medium. On Day 3, the medium is changed to primary myotube medium containing GBC0905 On Day 5, the myotubes are analyzed.

Example 5—FSHD Primary Patient Biopsy Myotube Dose Response

2° Assay: Immunocytochemistry—DUX4, H3.X/Y (Cell Stress), Myosin heavy Chain, Nuclei: GBC0905 (Rebastinib) treatment of FSHD primary patient biopsy muscle cultures reduces clinically relevant DUX4 and H3.X/Y stress marker expression in a dose-dependent manner without yielding a toxic or myogenic inhibitory effect.

Methods:

17MB026 primary FSHD-affected patient myoblasts (obtained from the University of Rochester FSHD Biorepository) were thawed and cultured as described in Rickard et al., 2015 in primary myoblast medium. Cells (6000 per well) were seeded to a collagen-I coated 96-well plate in 100 µl primary myoblast medium. Medium was changed every other day until cells reached 80% confluence followed by a switch to 100 µL per well primary myotube medium. GBC0905 (Rebastinib, 2 nM-5 µM dose range) or DMSO vehicle was delivered to each well. Cells were fixed and analyzed after 2.5 days of myotube formation by immunocytochemistry and high-content imaging for DUX4, H3.X/Y, Myosin Heavy Chain expression and nuclei number. Five or six replicate wells were averaged per condition, Results:

Treatment of FSHD primary patient myotubes with a 10-point dose curve of GBC0905 (Rebastinib) results in a dose-dependent decrease of DUX4 expression and a similar alleviation of cell stress mediated by H3.X/Y without reducing Myosin Heavy Chain or nuclei count. These data indicate a DUX4-suppressive effect of GBC0905 (Rebastinib) with an IC50 value of approximately 100 nM.

FIGS. 11a-11d provide the dose response curves from individual experiments performed in patient biopsy-derived muscle.

Figure 12:
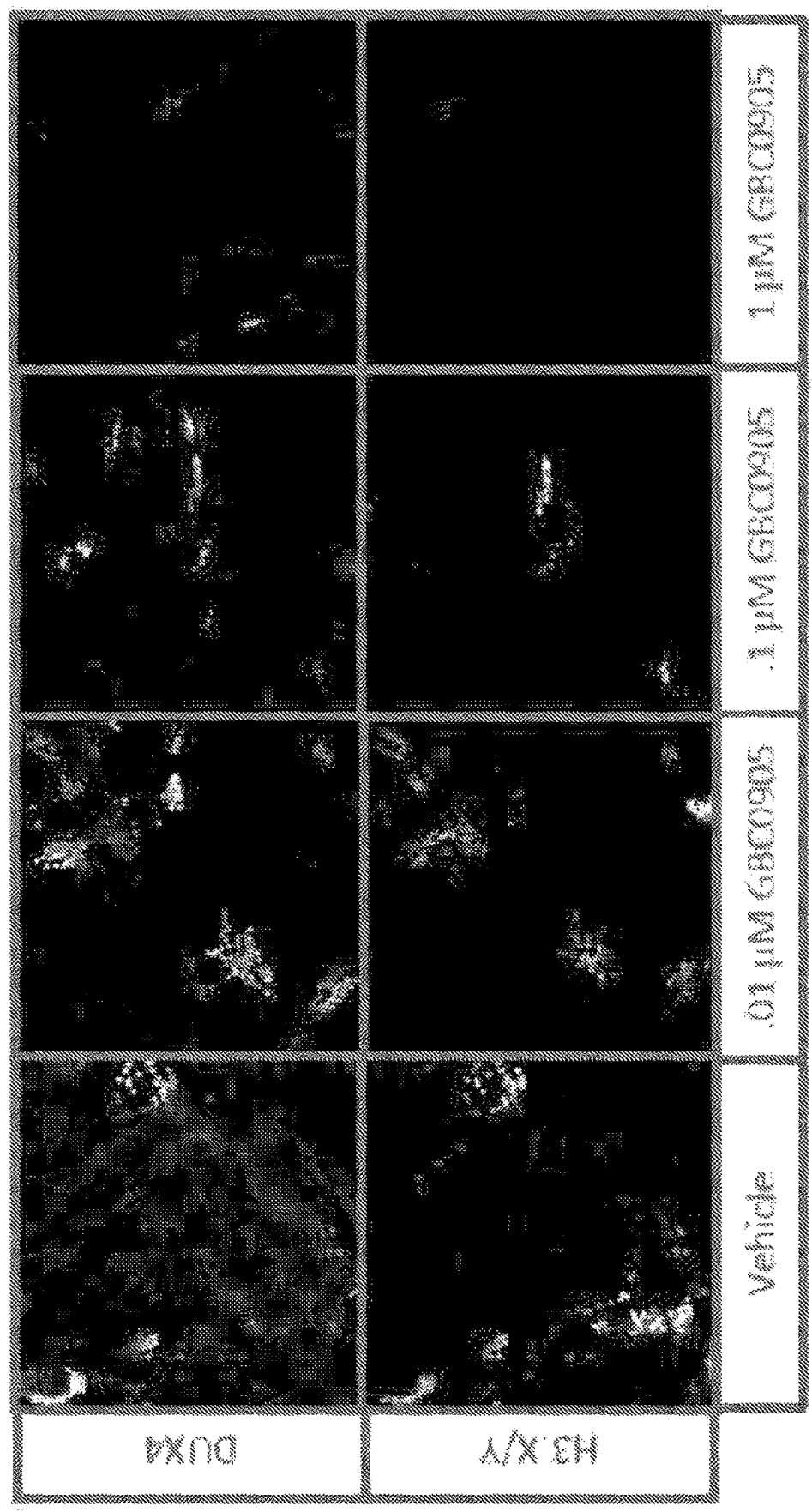
FIG. 12 and FIG. 13 Representative images from the dose response studies of GBC0905 (Rebastinib, DCC-2036) in FSHD primary patient biopsy myotubes.
Figure 13:
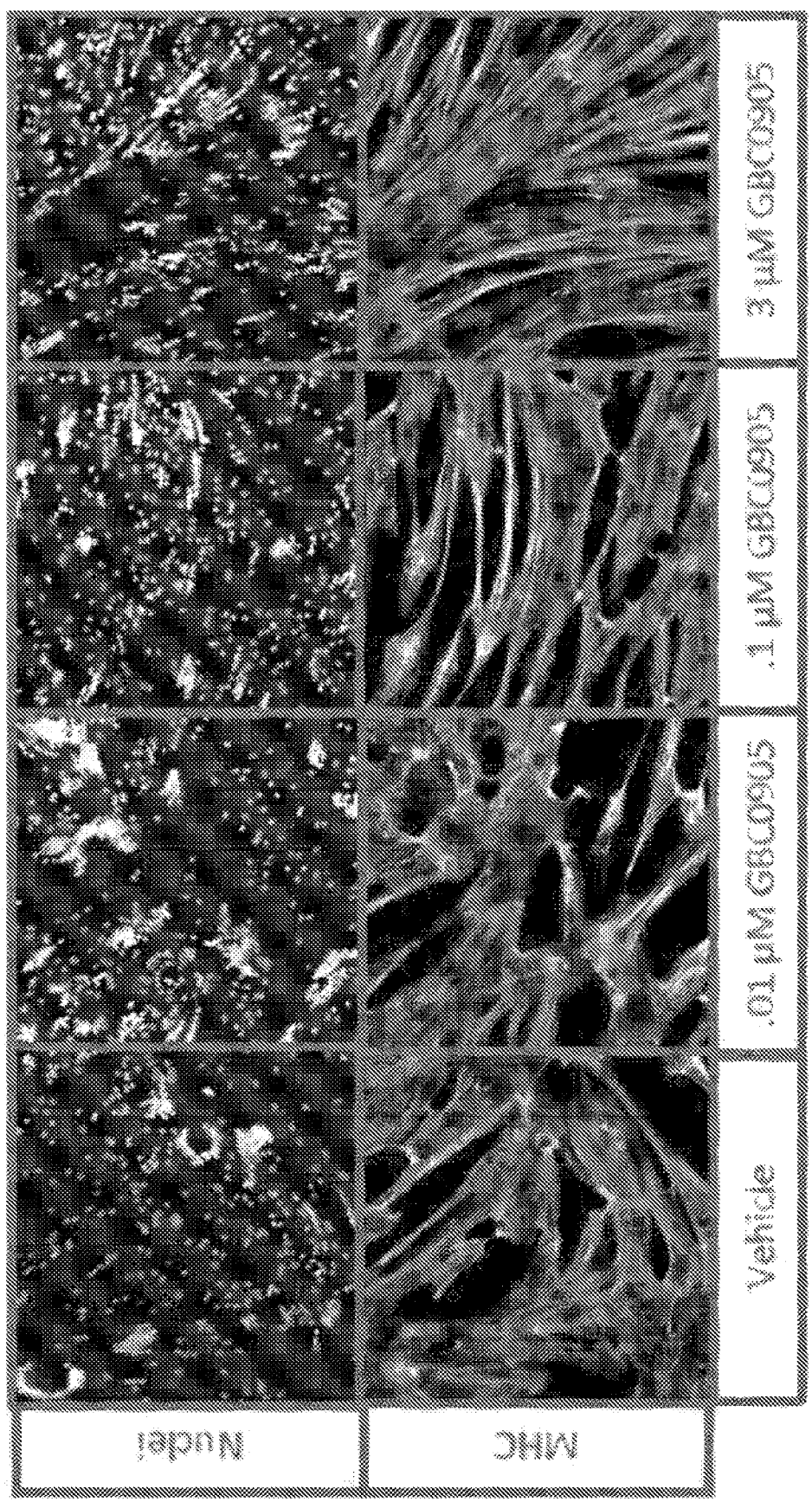

FIGS. 12 and 13 provide representative images from the dose response studies of GBC0905 (Rebastinib) in FSHD primary patient biopsy myotubes Example 6—MID Primary Patient Biopsy Myotube Dose Curve: Inhibition of Caspases 3/7 Mediated Apoptosis 2° Assay: Live Cell Imaging of Caspase 3/7 Cleavage Dye Fluorescence Through Myotube Formation: GBC0905 (Rebastinib) rescues FSHD patient-derived myotubes from DUX4-induced death by Caspase 3/7-mediated apoptosis.

Methods:

17MB026 primary FSHD-affected patient myoblasts (obtained from the University of Rochester FSHD Biorepository) were thawed and cultured as described in Rickard et al., 2015 in primary myoblast medium. Cells (4000 per well) were seeded to a collagen-I coated 96-well plate in 100 µL primary myoblast medium. Medium was changed every other day until cells reached 80% continence followed by a switch to 100 µL per well primary myotube medium containing 1:5000 diluted Caspase 3/7 Green. Apoptosis Assay Reagent (Essen Bioscience). GBC0905 (Rebastinib, 10 nM-3 µM range of concentrations) of or DMSO vehicle was delivered to each well. Cells were imaged in the phase and green channels every six hours for four days to quantify green intensity×area per image. Triplicate wells of each condition were averaged.

Figure 14B:
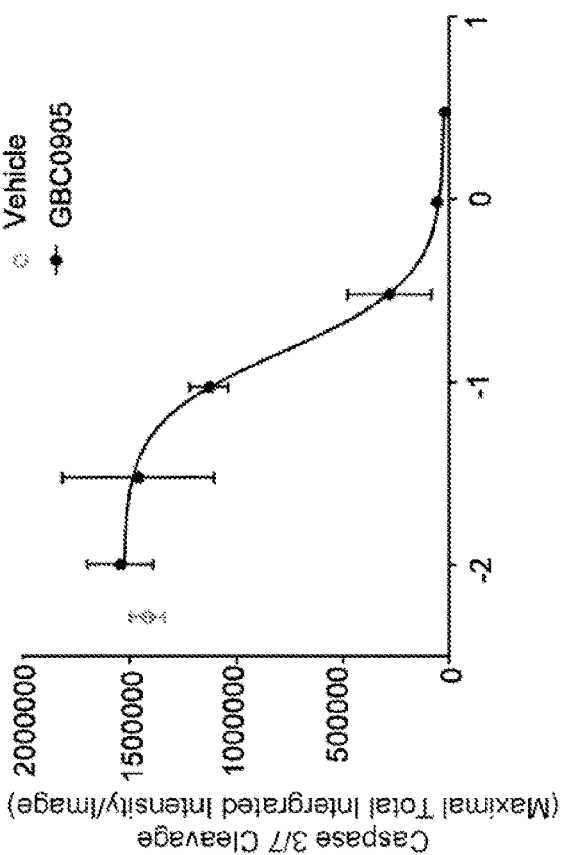
FIGS. 14A and 14B FSHD Primary Patient Biopsy Myotube Dose Curve: Inhibition of Caspases 3/7 mediated apoptosis. GBC0905 rescues FSHD patient-derived myotubes from DUX4-induced death by Caspase 3/7-mediated apoptosis.
Figure 14A:
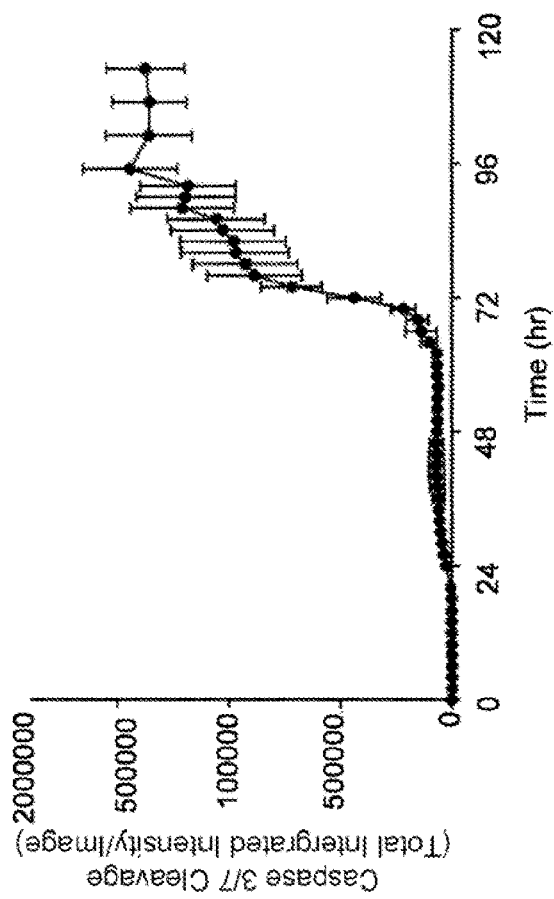

Results:

As shown in FIGS. 14(a) and 14(b), treatment of FSHD primary patient myotubes with six distinct concentrations of GBC0905 (Rebastinib) results in a dose-dependent decrease in Caspase 3/7 activation to levels found in unaffected primary myotube cultures, indicating an apoptosis rescue effect of OBC0905 (Rebastinib) treatment.

Example 7—FSHD Primary Patient Biopsy Myotube Dose Curve-GBC0905 (Rebastinib) Rescues DUX4-mediated Cell Death in a Dose Response Manner 2° Assay: Live Cell imaging of % Cell. Confluence Through Myotube Formation GBC0905 (Rebastinib) rescues FSHD patient-derived myotubes from DUX4-induced cell death, Methods:

17MB026 primary FSHD-affected patient myoblasts (obtained from the University of Rochester FSHD Biorepository) were thawed and cultured as described in Rickard et al., 2015 in primary myoblast medium. Cells (4000 per well) were seeded to a collagen-I coated 96-well plate in 100 µL primary myoblast medium. Medium was changed every other day until cells reached 80% confluence followed by a switch to 100 µL per well primary myotube medium. GBC0905 (Rebastinib, 1.0 nM-3 µM concentration range) or DMSO vehicle was delivered to each well. Cells were imaged in the phase contrast channel every six hours for four days and cell confluence in each image was quantified, Triplicate wells of each condition were averaged.

Figure 15B:
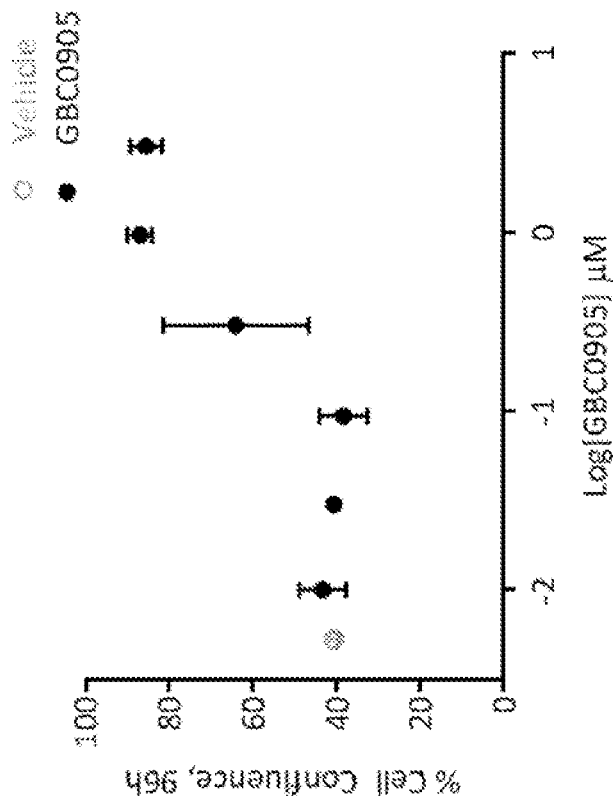
FIGS. 15A and 15B FSHD Primary Patient Biopsy Myotube Dose Curve-GBC0905 (Rebastinib, DCC-2036) rescues DUX4-mediated cell death in a dose response manner.
Figure 15A:
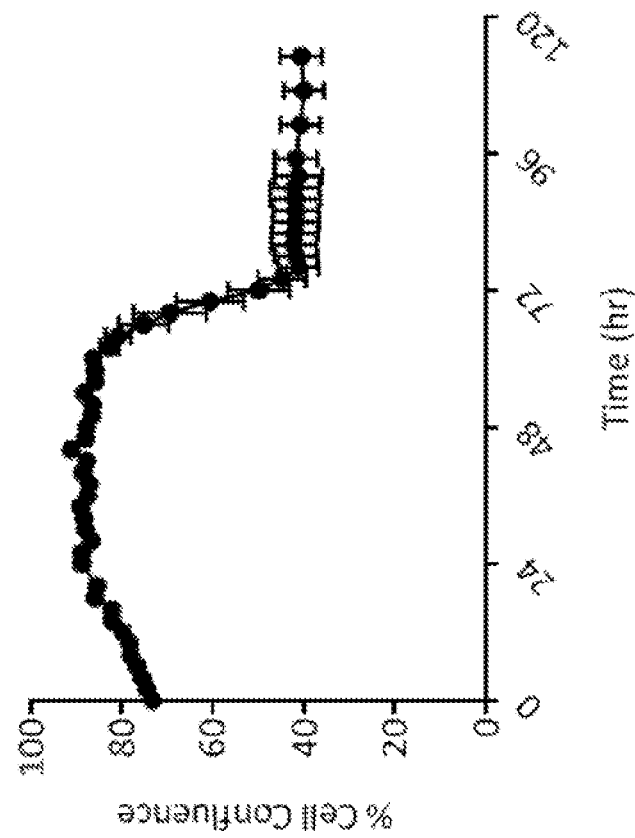

Results:

As shown in FIGS. 15(a) and 15(b), treatment of FSHD primary patient myotubes with six distinct concentrations of GBC0905 (Rebastinib) results in a dose-dependent rescue of FSHD cell death as measured by retained % cell confluence through our days of myotube formation.

Figure 16:
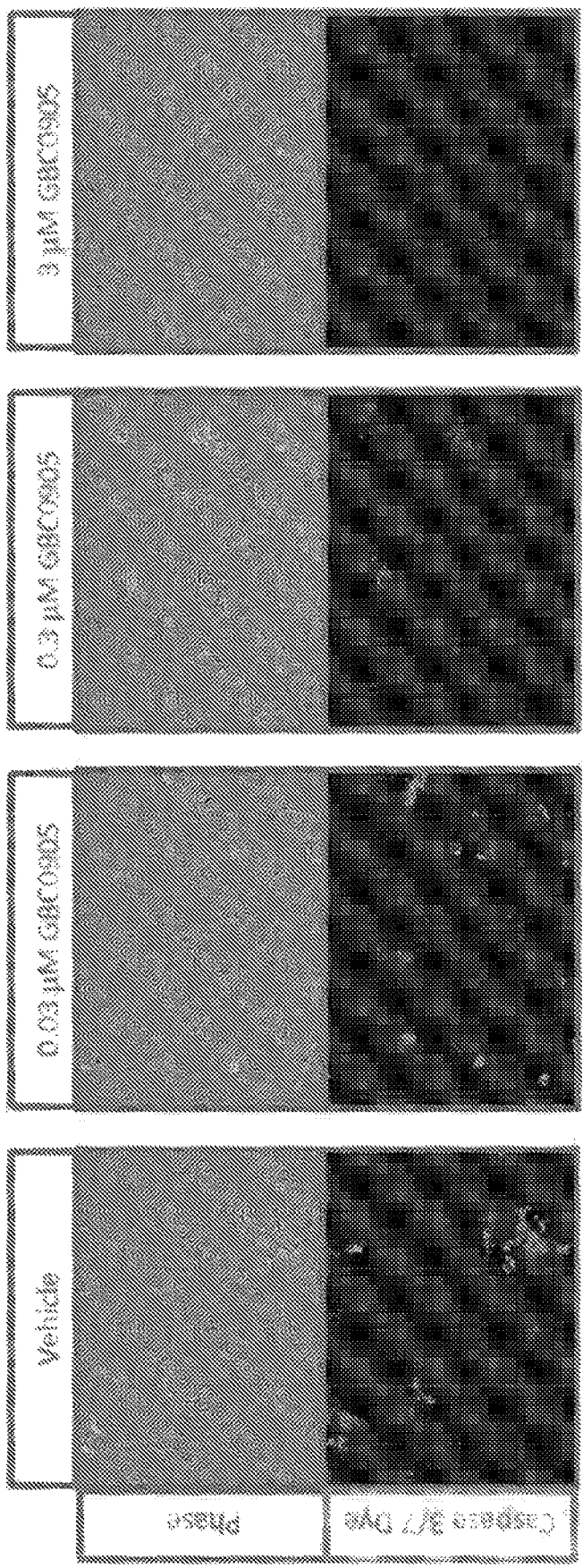
FIG. 16 provides representative images for GBC0905 (Rebastinib, DCC-2036)-mediated protection of FSHD affected primary patient biopsy myotubes at 3 concentration points.

FIG. 16 provides representative images for GBC0905 (Rebastinib)-mediated protection of FSHD affected primary patient biopsy myotubes at 3 concentration paints.

Example 8—FSHD Primary Patient Biopsy Myotube Dose Curve—DL X4 Target Gene and Myogenic Gene Expression 2° Assay: Nanostring Panel Transcript Analysis: GBC0905 (Rebastinib) treatment induces a concentration-dependent reduction of a suite of reported DUX4 target genes with no negative effect on myogenic gene expression.

Methods:

17MB026 primary FSHD-affected patient myoblasts (obtained from the University of Rochester FSHD Biorepository) were thawed and cultured as described in Rickard et al., 2015 in primary myoblast medium. Cells (4000 per well) were seeded to a collagen-I coated 96-well plate in 100 µL primary myoblast medium. Medium was changed every other day until cells reached 80% confluence followed by a switch to 100 µL per well primary myotube medium. GBC0905 (Rebastinib, 30 nM-3 µM concentration range) or DMSO vehicle was delivered to each well. Cells were lysed after 3 days of myotube formation using 10 µL of iScript Buffer (Biorad) per well. The resulting lysates were frozen at −30° C. After thaw, 5 µL of each lysate was combined with a custom-designed Nanostring transcript probe and capture codeset. Probes were hybridized to lysates and run cartridge was loaded and run per standard protocol. Normalization and background subtraction were performed using the nSolver 3.0 software using standard conditions DUX4 target gene and myotube marker gene expression values were normalized to a standard set of housekeeping genes. Duplicate wells of each condition were averaged.

Figure 17A:
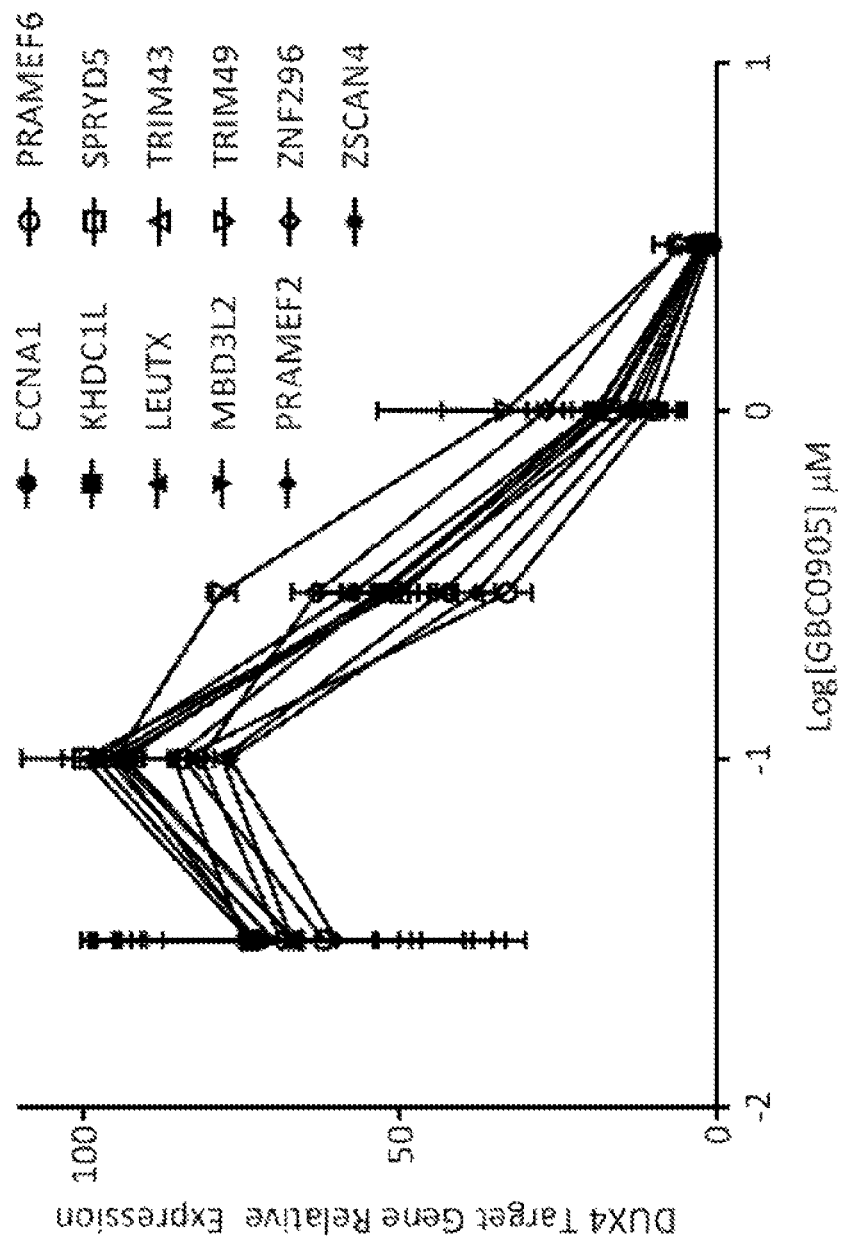
FIGS. 17A and 17B FSHD Primary Patient Biopsy Myotube Dose Curve—DUX4 Target Gene and Myogenic Gene Expression. GBC0905 (Rebastinib, DCC-2036) treatment induces a concentration-dependent reduction of a suite of reported DUX4 target genes with no negative effect on myogenic gene expression.
Figure 17B:
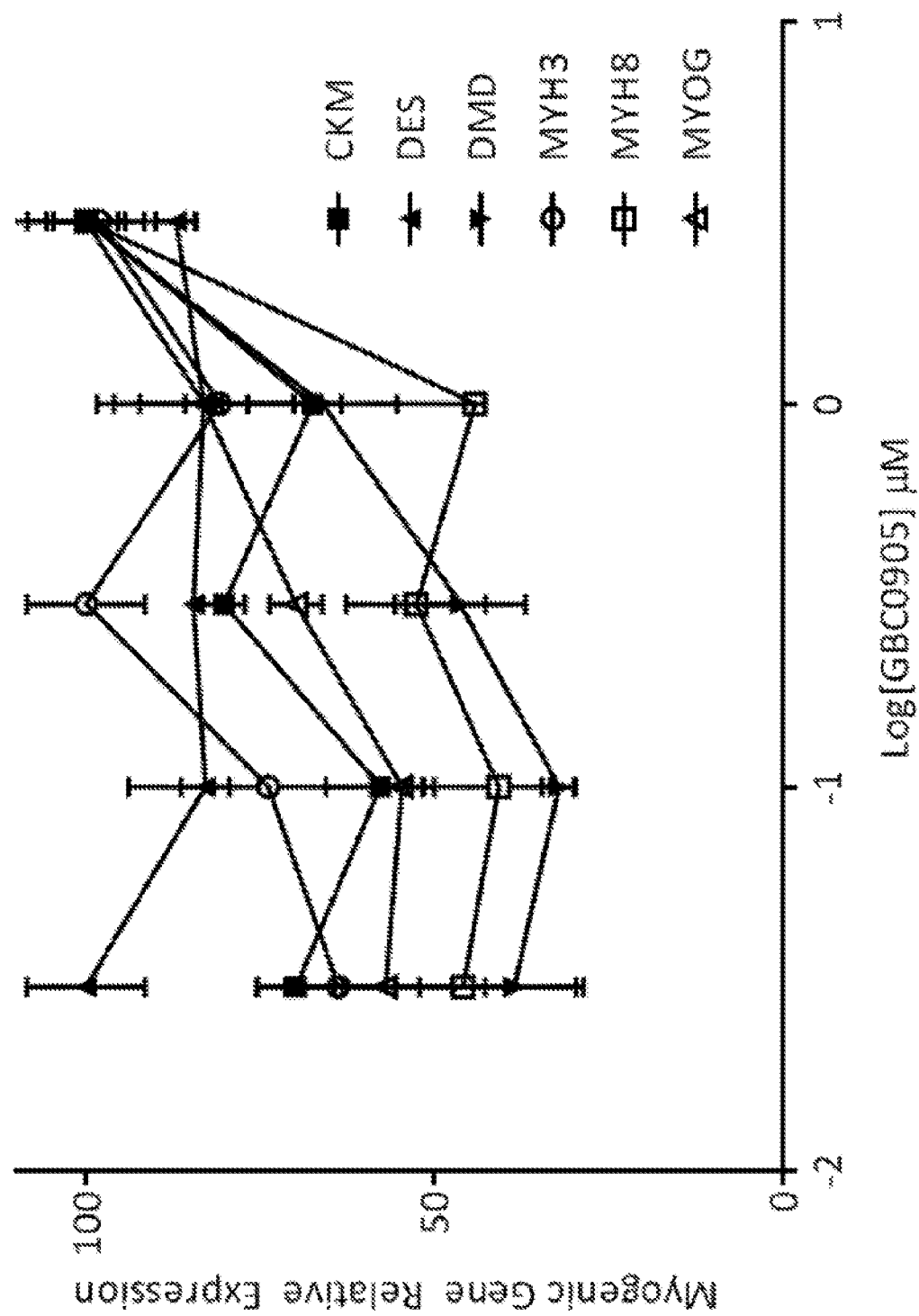

Results:

As shown in FIGS. 17(a) and 17(b), treatment of FSHD primary patient myotubes with a six-point dose curve of GBC0905 results in a dose-dependent decrease of 11 DUX4-activated genes not normally expressed in muscle (17(a)) and does not decrease expression of queried characteristic myotube genes (17(b)). This data suggests that GBC0905 (Rebastinib) specifically rescues the measured gene expression effect of DUX4 activation in FSHD muscle cells without affecting skeletal muscle health.

According to the methods provided herein, small molecules that are known or suspected to target networks and pathways related to FSHD may be used to treat the disease. The small molecules may have known or suspected targets that are involved in Src, Lck, Fyn, Lyn., Syk, FAK, TrkA TrkB, TrkC, Tie1, Tie2, VEGFR1, VEGER2, Flt4, EGFR1FGFR2, FGFR3, FGFR4, c-Met Ron, ErbB1, ErbB2, ErbB4, EphB2EphB4, PDGFRa, PDGFRb, DNA- PK (or PRKDC), a compound of Table 1, FIGS. 1-5, or a compound of any one of Formulas (I)-(VII).

Example 9—Pharmacokinetic Study and Tissue Distribution Study

In this acute pharmacokinetic study, mice were administered a single dose of GBC0905 (rebastinib) at 10 mg/kg or 50 mg/kg by either intraperitoneal or intramuscular injection formulated in Miglyol 810N: Phosal 50 PG: Polysorbate 80 (Tween 80) at 45:50:5 (V:V). Intraperitoneal injection, which provides the drug via absorption into the mesenteric blood supply and is thus subject to hepatic first-pass metabolism, was used to approximate oral dosings total of 96 mice were utilized: 3 naive CD-1 male mice and 3 naïve CD-1 female mice were dosed per route of administration per 2 doses plus 3 naive CD-1 male mice and 3 naïve CD-1 female mice were per route of administration per dose for tissue collection. Following administration, blood, brain, and muscle samples were collected as follows; Two blood samples were collected from each mouse at 2 distinct timepoints over 24 bout post-dose to include 0.25, 0.5, 1, 2, 4, 8, and 24 hours. Blood samples were centrifuged to obtain plasma samples. For each time point, duplicate aliquots of plasma were transferred into an appropriately labeled sample tube containing a volume of buffer. The diluted plasma samples were stored at −20° C. for the first 24 hours and then transferred to −80° C. 24 hours of processing. Terminal brain and muscle samples were collected at 1 hour and 24 hours after administration. Tissue samples were temporarily put on dry ice and then stored at −20° C. for the first 24 hours and then transferred to −80° C. 24 hours of collection Plasma, brain and muscle samples were analyzed for test substance quantification using a method based on protein precipitation followed by HPLC-MS/MS analysis within optimized bioanalytical method.

All mice survived to scheduled sacrifice and no adverse clinical signs occurred during this study, Mean peak plasma concentrations occurred within a median time to maximum concentration ($T_{max}$) of 2 hours using intraperitoneal injection or 2-4 hours with an intramuscular injection. Exposure, including mean maximum concentration ($C_{max}$), area under the curve from 0-24 hours ($AUC_{last}$), and area under the curve to infinity ($AUC_\infty$) increased with dose (Table 2) but in less than a dose-proportional manner. Selected Plasma PK parameters are presented in Table 2.

Figure 30:
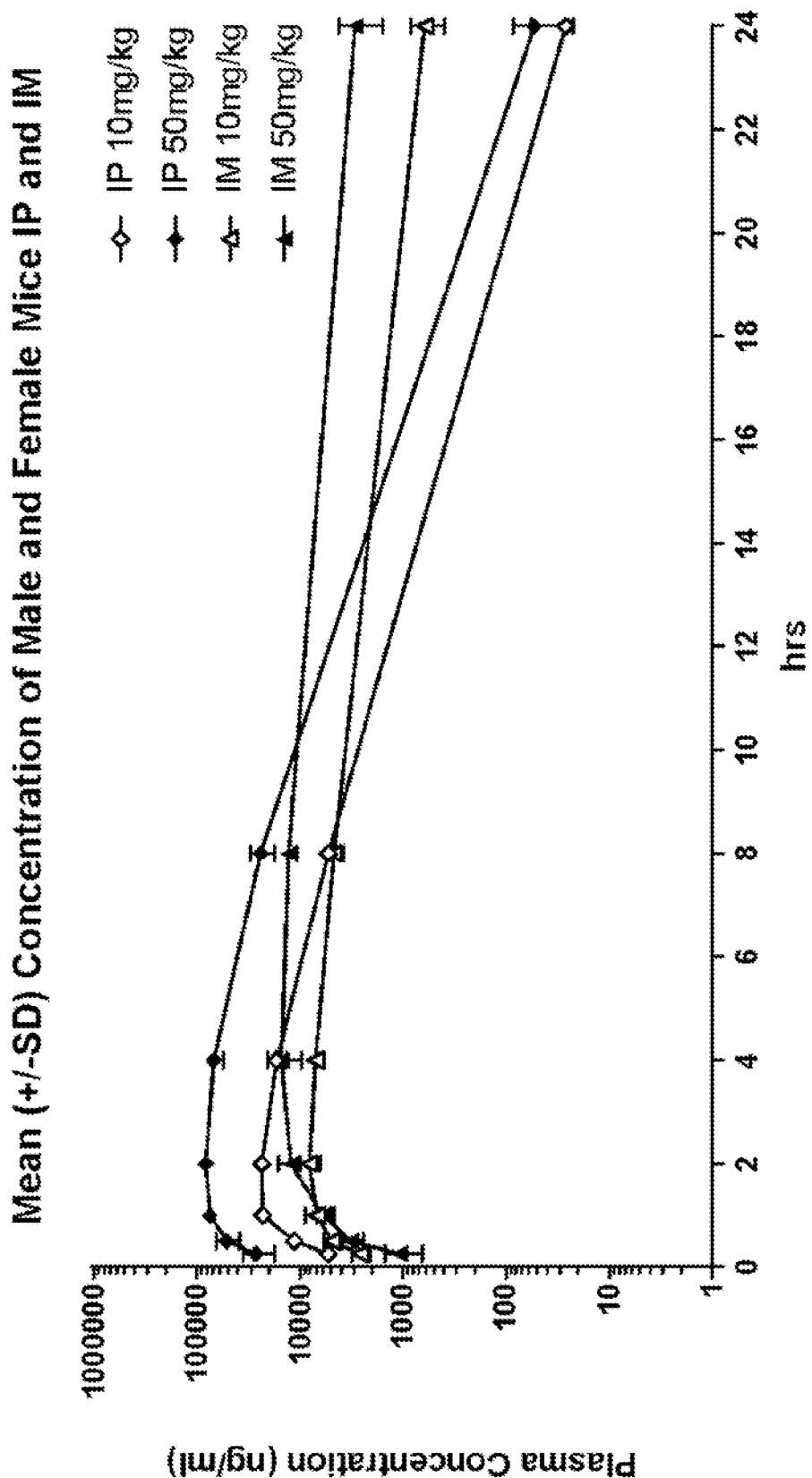
FIG. 30 provides mean plasma rebistinib concentration-time profile following a single administration of rebastinib by either intraperitoneal (IP) or intramuscular injection (IM).

FIG. 30 provides mean plasma rebastinib concentration-time profile following a single administration of rebastinib by either intraperitoneal (IP) or intramuscular injection (IM). Blood samples were obtained from the saphenous vein at the indicated time following administration of rebastinib (IP injection of 10 mg/kg, IP injection of 50 mg/kg, IM injection of 10 mg/kg, or IM injection of 50 mg/kg). Plasma concentrations of rebastinib were determined by LC-MS/MS.

TABLE 2

| Dose Route | Dose Level (mg/kg) | $t_{1/2}$ (hr) | $t_{max}$ (hr) | $C_{max}$ (ng/mL) | $AUC_{last}$ (hr*ng/mL) | $AUC_\infty$ (hr*ng/mL) | $MRT_\infty$ (hr) |
|---|---|---|---|---|---|---|---|
| IP | 10 | 2.12 | 2 | 23683 | 162488 | 162568 | 4.46 |
|  | 50 | 1.90 | 2 | 81633 | 651387 | 651534 | 4.73 |
| IM | 10 | 5.59 | 2 | 8203 | 93540 | 98469 | 7.83 |
|  | 50 | 8.10 | 4 | 15103 | 222518 | 256486 | 11.8 |

Plasma PK parameters. $t_{1/2}$: half-life; $t_{max}$: time to maximum concentration; $C_{max}$: maximum concentration; $AUC_{last}$: area under the curve from 0 to 24 hours; $AUC_\infty$: area under the curve to infinity; $MRT_\infty$: mean residence time to infinity; N = 6

Terminal brain and muscle samples were collected at 1 hour and 24 hours after intraperitoneal or intramuscular dose. Uninjected muscle exposure was significantly higher (up to 1336 ng/g by intraperitoneal administration or 157 ng/g by intramuscular administration) than brain exposure (up to 441 ng/g by intraperitoneal administration or 351 ng/g by intramuscular administration). Exposure of the injected muscle (gastrocnemius) after intramuscular dosing remained high after 24 hours (1441667 ng/g), however brain and contralateral muscle exposure remained low in comparison.

Figure 31A:
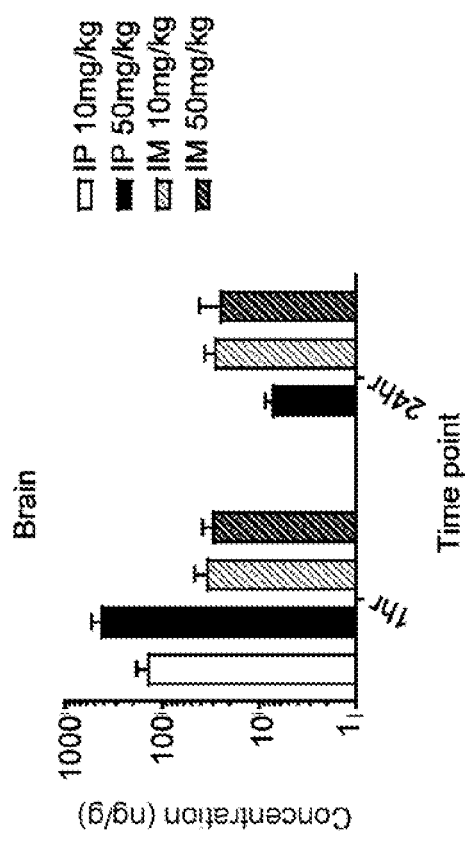
FIGS. 31A and 31B provides mean brain and muscle rebastinib concentration-time profile following a single administration of rebastinib by either intraperitoneal (IP) or intramuscular injection (IM).
Figure 31B:
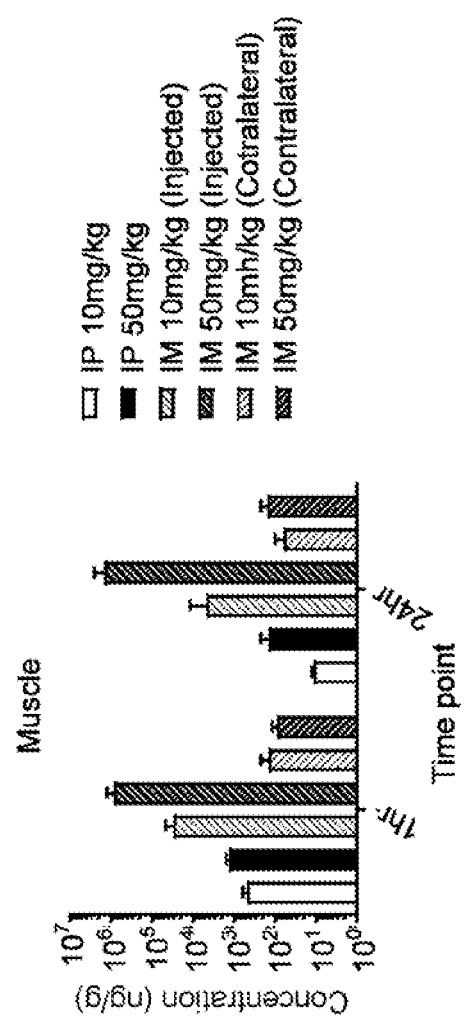

FIGS. 31A and 31B provide mean brain and muscle rebastinib concentration-time profile following a single administration of rebastinib by either intraperitoneal (IP) or intramuscular injection (IM). FIG. 31A Brain was collected at the indicated time following administration of rebastinib (IP injection of 10 mg/kg, IP injection of 50 mg/kg, IM injection of 10 mg/kg, or IM injection of 50 mg/kg). Brain concentrations of rebastinib were determined by LC-MS/MS. Brain concentration of rebastinib 24 hours after IM injection at 10 mg/kg was below the Lower Limit of Quantification (LLOQ). FIG. 31B. Gastrocnemius muscle was collected at the indicated time following administration of rebastinib (IP injection of 10 mg/kg, IP injection of 50 mg/kg, IM injection of 10 mg/kg, or IM injection of 50 mg/kg). For IM injected animals, both the injected gastrocnemius muscle and the contralateral (uninjected gastrocnemius)) muscle were collected. Muscle concentrations of rebastinib were determined by LC-MS/MS. Concentrations are shown as mean with SD, N=6

Example 10—Mechanism of Action Study

GBC0905 does not modify the methylation levels of D4Z4 array in FSHD-affected myotubes. Facioscapulohumeral muscular dystrophy (FSHD) is linked to hypomethylation of the D4Z4 macrosatellite repeat array in the subtelomere region of chromosome 4 at 4q35 and the associated epigenetic derepression of DUX4. (Himeda, C. et al. (2015); Antioxid Redox Signal 22(16): 1463-1482.). To examine the mechanism of action of GBC0905 in inhibiting DUX4 expression, we started by testing whether GBC0905 affects the methylation levels of the D4Z4 array. Human embryonic stem cell (hESC)-derived healthy (Genea015) or FSHD-affected (Genea049) myoblasts were cultured and differentiated into myotubes. Their DNA methylation levels at the 4qA and D4Z4 regions on chromosome 4 were assessed through bisulfite sequencing analysis. (Jones, T. I., et al. (2015) Clin Epigenetics 7:37). Correlating with the disease phenotype, the DNA methylation levels of the FSHD-affected myotubes at 4qA or D4Z4 regions were significantly lower than that of the healthy myotubes (FIGS. 32A and 32B—DNA methylation levels in hESC-derived myotubes at the 4qA and D4Z4 regions on chromosome 4 correlate with FHSD disease). No statistically significant effect of GBC090S treatment was observed in the DNA methylation levels at 4qA or D4Z4 regions of FHSD-affected myotubes at any of the tested concentrations (FIGS.

33A and 33B). Thus, GBC0905 does not silence DUX4 expression through increasing the methylation levels of D4Z4 array.

Healthy (Genea015) or FSHD-affected (Genea049) MSC-derived myoblasts were cultured in Myoblast Media (Genea Biocells) while performing media changes every other day. When cells reached confluence, the medium was switched to Myottibe Medium (Genea Biocells) without any further media changes. On myotube day 3, cells were trypsinized and cell pellets were prepared for bisulfite sequencing analysis. Genomic DNA was isolated from cell pellets using QIAamp DNA Blood Mini Kit (Qiagen) and bisultite converted using the EpiTect Kit (Qiagen). The 4qA and D4Z4 regions were amplified and cloned into the pCR2.1 TOPO vector. The 4qA or D4Z4 containing plasmids were transformed into TOP10 chemically competent E. coli and selected for kanamycin resistance. Sequencing of kanamycin resistant colonies was completed by Sequegen and methylation analysis was performed using Bisulfite Sequencing DNA Methylation Analysis (BISMA) online software.

Figure 32B:
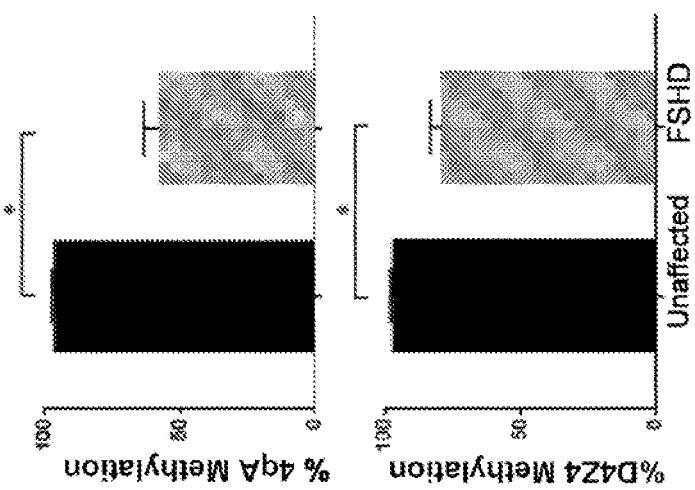
FIGS. 32A and 32B illustrates DNA methylation levels in hESC-derived myotubes at the 4qA and D4Z4 regions on chromosome L correlate with FHSD disease.
Figure 32A:
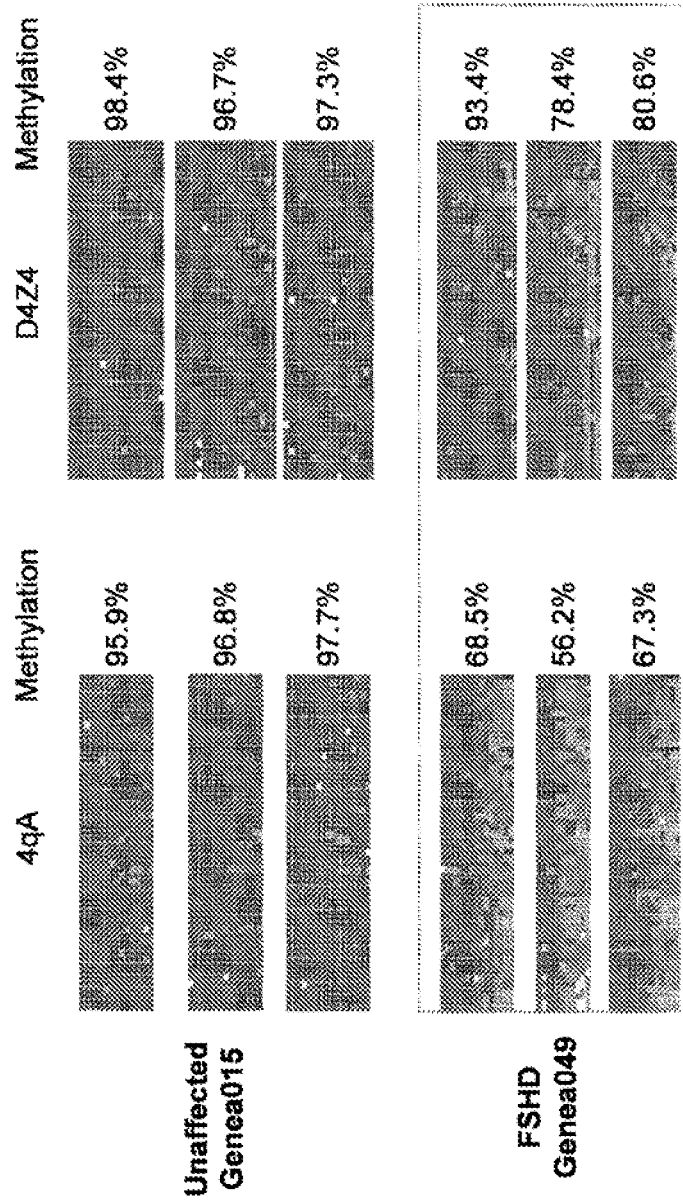

FIG. 32A shows bisulfite sequencing analysis of the 4qA and D4Z4 regions of myotubes derived from unaffected (Genea015, top row) and FSHD-affected (Genea049, bottom row) subjects. 4qA bisulfite sequencing assay analyzed 56 CpGs in the distal D4Z4 repeat on 4qA-containing chromosomes and D4Z4 assay analyzed 59 CpGs upstream of the DUX4 open reading frame. Each independent chromosome assayed is represented by a row with each CpG represented by a box (dark grey boxes indicating methylation, light grey boxes indicating lack of methylation, and empty boxes indicating lack of a CpG detected at that site). FIG. 32B shows quantification of the DNA methylation levels at 4qA or D4Z4 regions in myotubes derived from hESCs of healthy unaffected and FSHD-affected subjects. *$P \leq 0.05$, student's t-test.

Figure 33A:
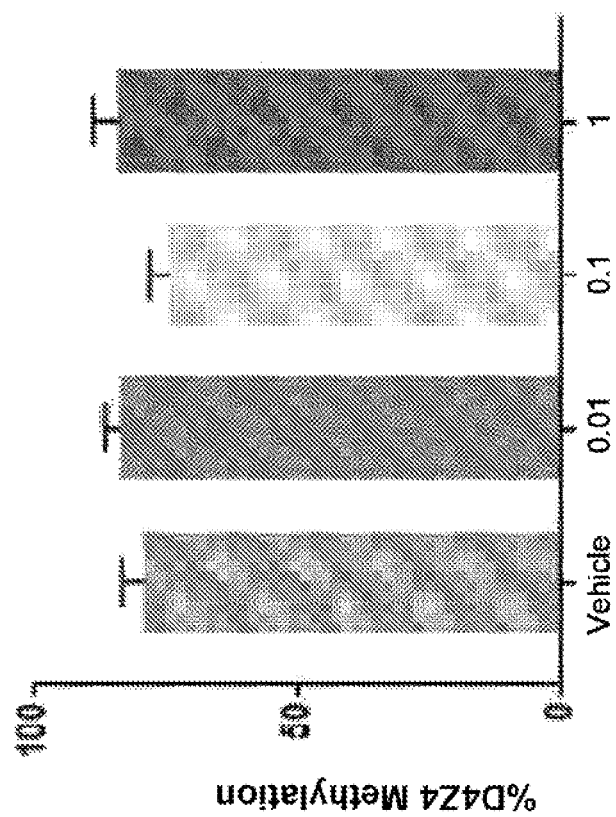
FIGS. 33A and FIG. 33B illustrates GBC0905 does not modify DNA methylation levels in FHSD-affected myotubes at the 4qA or D4Z4 regions of chromosome 4.
Figure 33B:
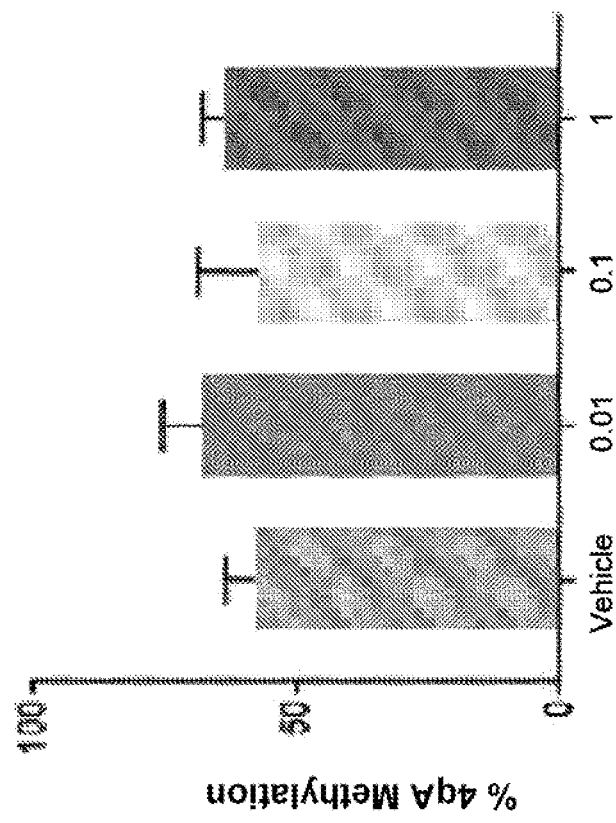

FIGS. 33A and 33B show GBC0905 does not modify DNA methylation levels in FHSD-affected myotubes at the 4qA or D4Z4 regions of chromosome 4.

FSHD-affected. (Genea049) embryonic stem cell-derived myoblasts were cultured in Myoblast Media (Genea Biocells) while performing media changes every other day. When cells reached confluence, the medium was switched to Myotube Medium (Genea. Biocells) without any further media changes. During myotube formation, cells were treated with DMSO vehicle or 3 concentrations (10 nM, 100 nM or 1 µM) of GBC0905. On myotube day 3, myotubes were trypsinized and cell pellets were prepared for bisulfite sequencing analysis. Refer to the FIG. 1 legend for additional details.

Quantification of bisulfite sequencing results of the DNA methylation levels at 4qA (FIG. 33A) or (FIG. 33B) D4Z4 regions of FSHD-affected myotubes treated with DMSO or GBC0905 at different concentrations.

Knockdown of GBC0905 target kinases leads to DUX4 repression in FSHD-affected myotubes.

Figure 34A:
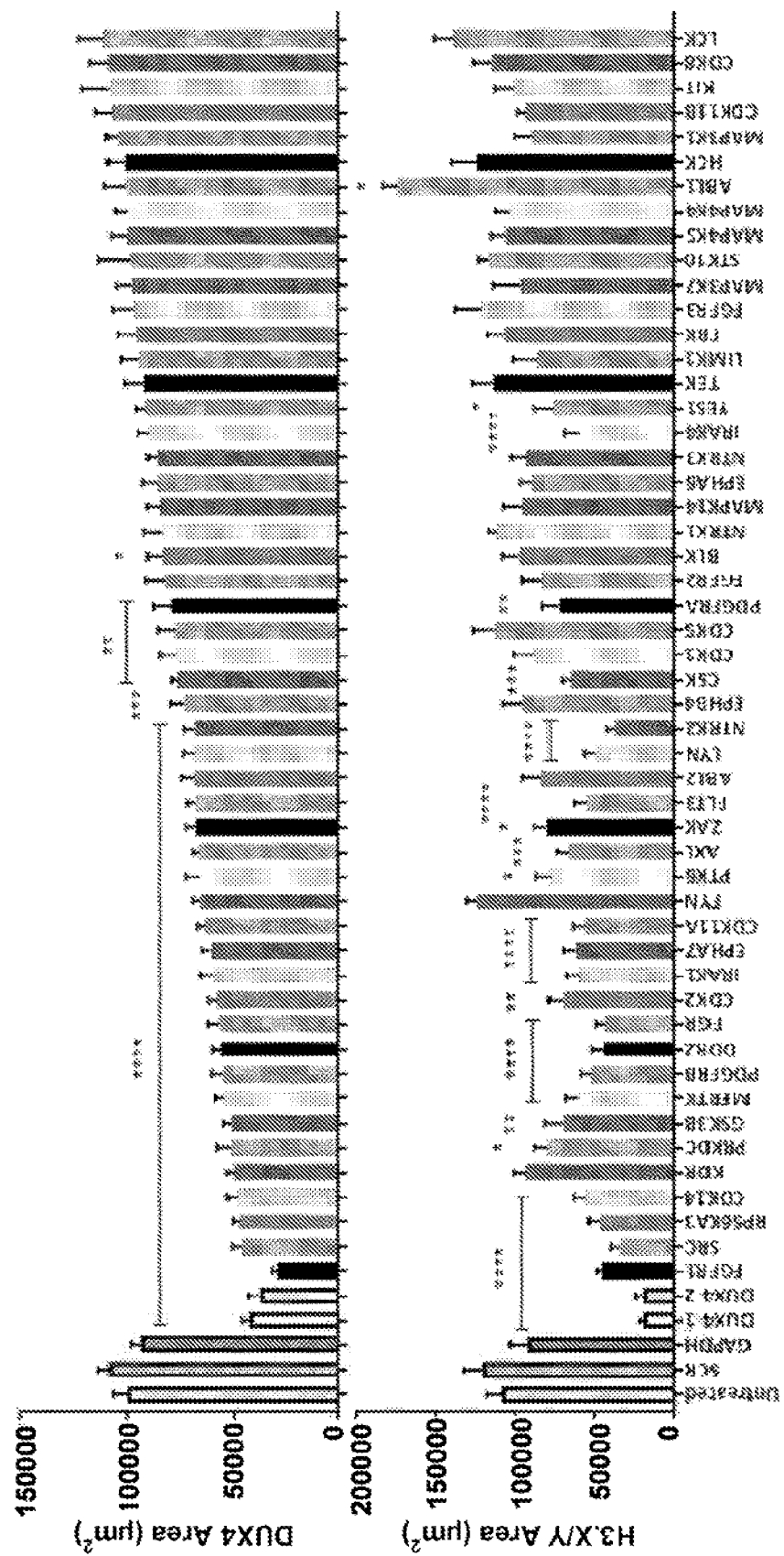
FIGS. 34A and FIG. 34B illustrate knockdown of GBC0905 target kinases such as PRKDC and SRC inhibits DUX4 and H3.X/Y expression without cell toxicity or myogenic inhibition effects in FSHD-affected myotubes.
Figure 34B:
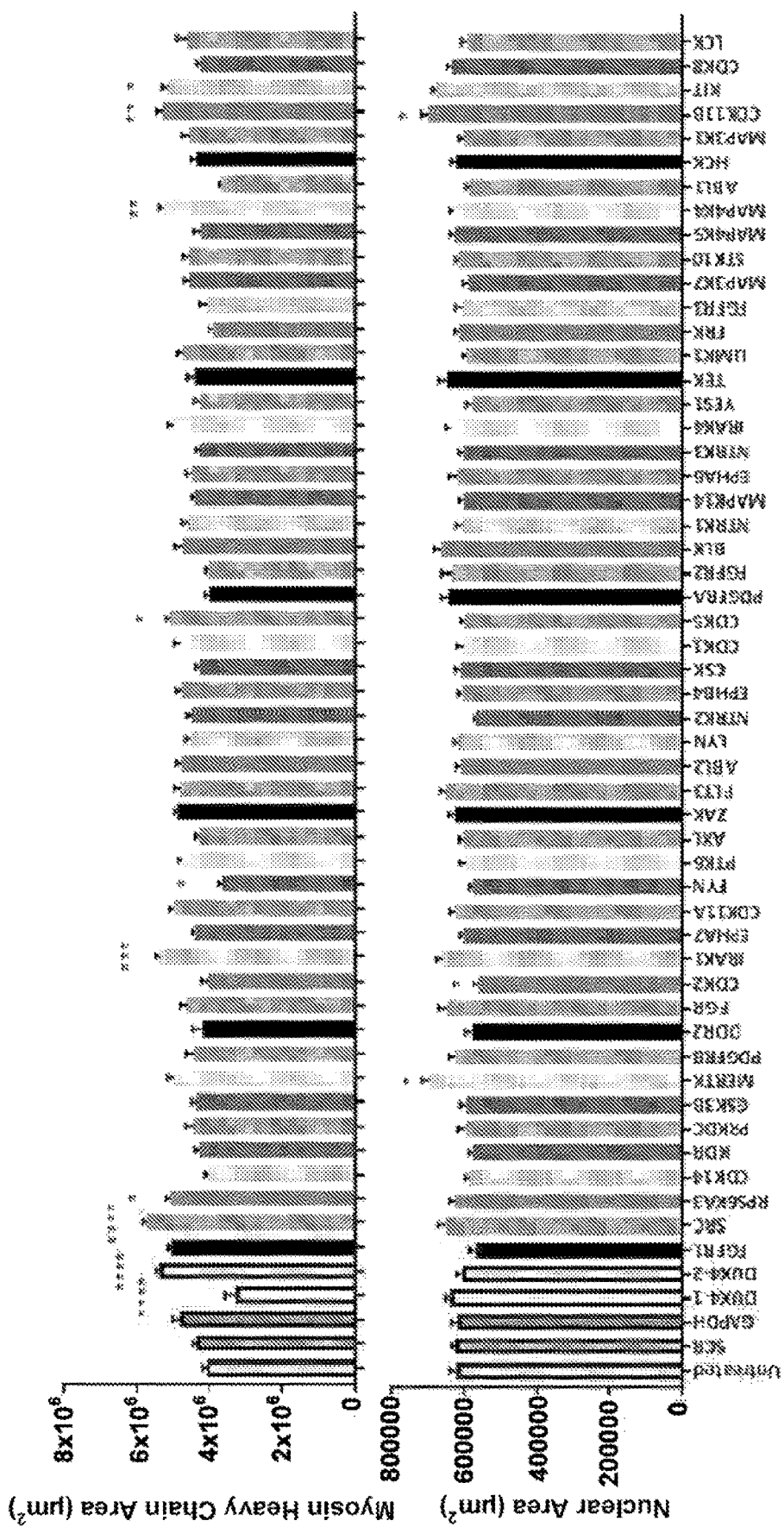
Figure 35A:
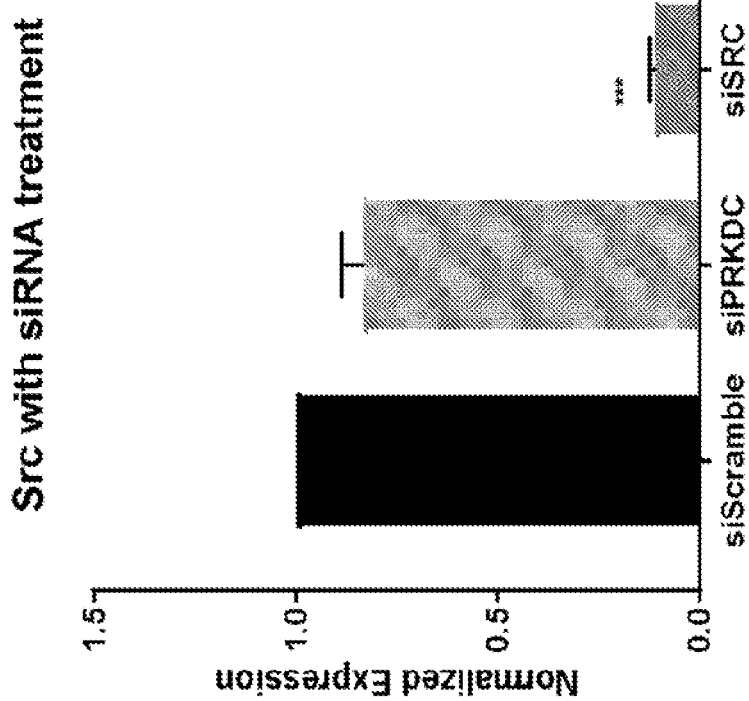
FIGS. 35A and FIG. 35B illustrate RT-PCR results verify the specificity of siPRKDC and siSRC.
Figure 35B:
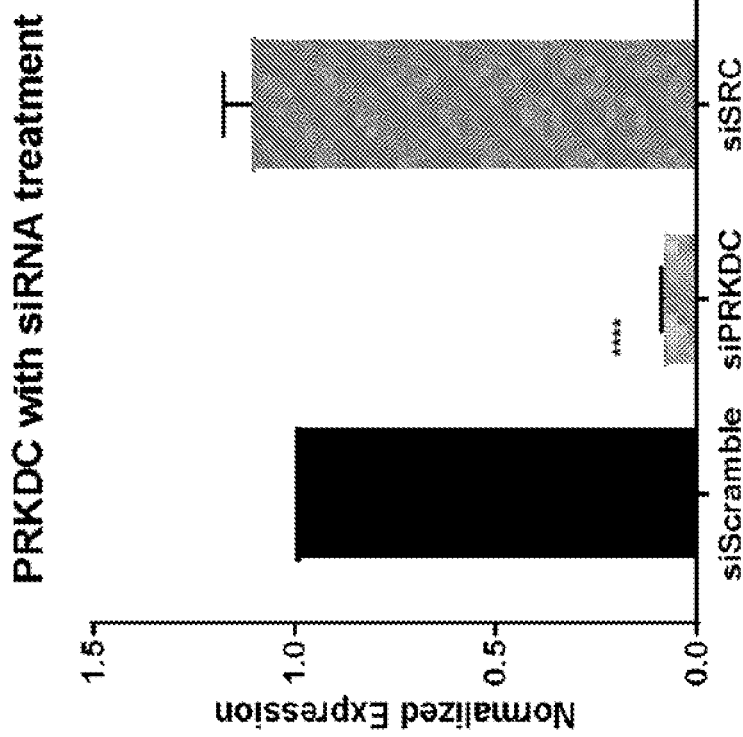

Previously GBC0905 was reported to possibly be an inhibitor of multiple kinases, such as SRC family kinases, ABLs, and TIE2. (Chan, W. W., et al. (2011) Cancer Cell 19(4): 556-568; and Harney, A. S., et al. (2017). Mol Cancer Ther 16(11): 2486-2501) A list of 51 potential GBC0905 targets was generated. A library of siRNAs against each of these GBC0905 targets were delivered to patient biopsy-derived primary myoblasts to identify the potential targets through which GBC0905 inhibits DUX4 in FSHD-affected myotubes. Examination of DUX4 expression levels at myotube stage revealed that knockdown of multiple previously reported GBC0905 targets, including SRC and PRKDC, significantly reduced the expression of DUX4 and also H3.X/Y, primate-specific histones and a cell stress marker (FIG. 34A). In addition, knockdown of SRC or PRKDC did net lead to cell toxicity or negatively affect myotube formation (FIG. 34B). RT-PCR analysis of PRKDC and SRC mRNA levels 2.5 days post-transfection verified the significant and specific knockdown of PRKDC and SRC in primary myotubes transfected siPRKDC or siSRC (FIG. 35).

Patient biopsy-derived primary myoblasts were derived from the quadricep biopsies of FSHD patients and were obtained from the University of Rochester FSHD Bioreposi-tory. Cells were seeded to a collagen-I coated plate in primary myoblast medium. Medium was changed every other day until cells reached 80% confluence followed by a switch to primary myotube medium. Control siRNA (scramble (SCR), siGAPDH, siDUX4, siDUX4-2) or siR-NAs against GBC0905 targets were transfected with Dhar-maFECT 1 at a final concentration of 25 nM. After 2.5 days of myotube formation, the cells were fixed and analyzed by immunocytochemistry and high-content imaging for DUX4, H3.X/Y, Myosin Heavy Chain and nuclei.

FIG. 34 shows quantification results of the expression levels of DUX4 (FIG. 34A) and H3.X/Y or myosin heavy chain and nuclear areas (FIG. 34B) in patient biopsy-derived primary myotubes 2.5 days after siRNA transfection *$P \leq 0.05$,  $P \leq 0.01$, *$P \leq 0.001$, ****$P \leq 0.0001$, one-way ANOVA compared to scramble siRNA (SCR)-treated group.

Patient biopsy-derived primary myoblasts were seeded to a collagen-I coated plate in primary myoblast medium. Medium was changed every other day until cells reached 80% confluence followed by a switch to primary myotube medium. Control siRNA (scramble) or siRNAs against PRKDC and SRC were transfected with DharmaFECT 1 at a final concentration of 25 nM. After 2.5 days of myotube formation, the cells were lysed with buffer RLT followed by RNA isolation with RNeasy Plus Mini Kit (Qiagen) 500 ng of RNA was used for cDNA synthesis with Superscript III first-strand synthesis system for RT-PCR (Invitrogen) and both random hexamers and oligo(dT)$_{20}$ primers. RT-PCR was performed using TaqMan™ Fast Advanced Master Mix (Applied Biosystems). Reactions were analyzed upon a QuantStudio 3 Real-Time PCR machine using the following cycle conditions: 50° C. for 2 minutes, 95° C. for 2 minutes, followed by 40 cycles at 95° C. for 15 seconds, 60° C. for 1 minute. Results were normalized against GAPDH expression.

Figure 36:
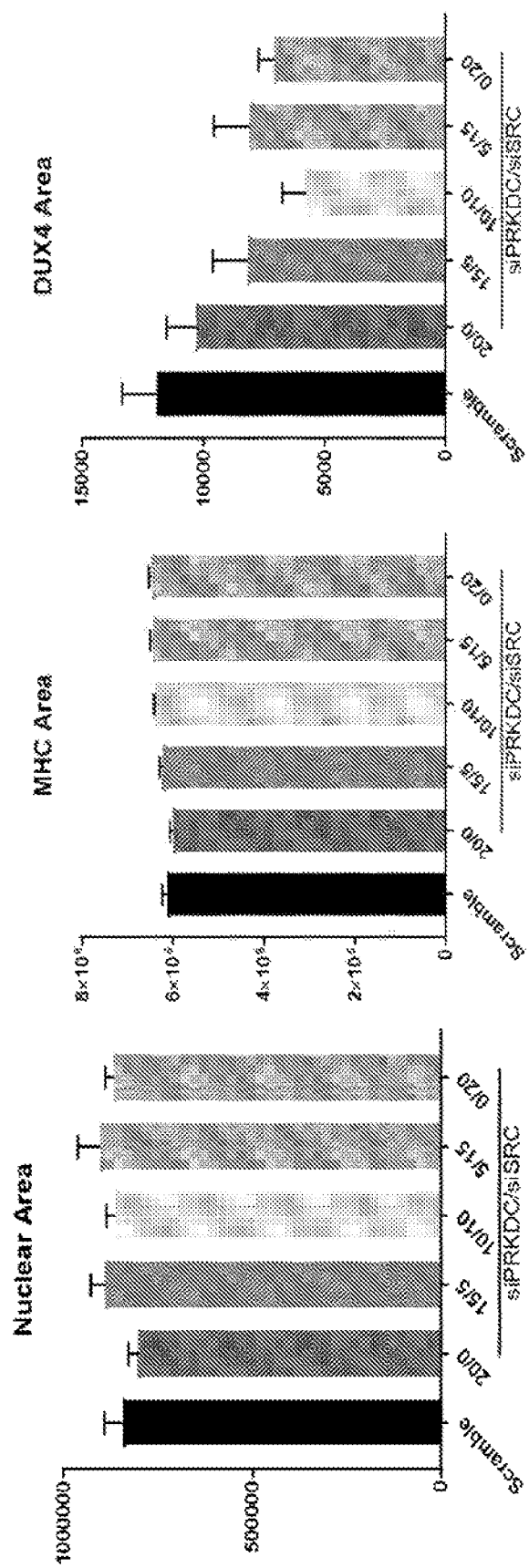
FIG. 36 illustrates combined knockdown of GBC0905 target kinases PRKDC and SRC appears to inhibit DUX4 expression synergistically without cell toxicity or myogenic inhibition effects in FSHD-affected myotubes.

Normalized expression levels of PRKDC (FIG. 35A) and SRC (FIG. 35B) in patient-derived primary myotubes transfected with scramble siRNAs, siPRKDC or siSRC. * $P \leq 0.001$, **$P \leq 0.0001$, one-way ANOVA compared to scramble siRNA-treated group. Combined knockdown of GBC0905 target kinases PRKDC and SRC appears to inhibit DUX4 expression synergistically without cell toxicity or myogenic inhibition effects in FSHD-affected myotubes (FIG. 36).

GBC0905 Decreases the Activity Levels of PRKDC and SRC in FSHD-Affected Myocytes.

Figure 37A:
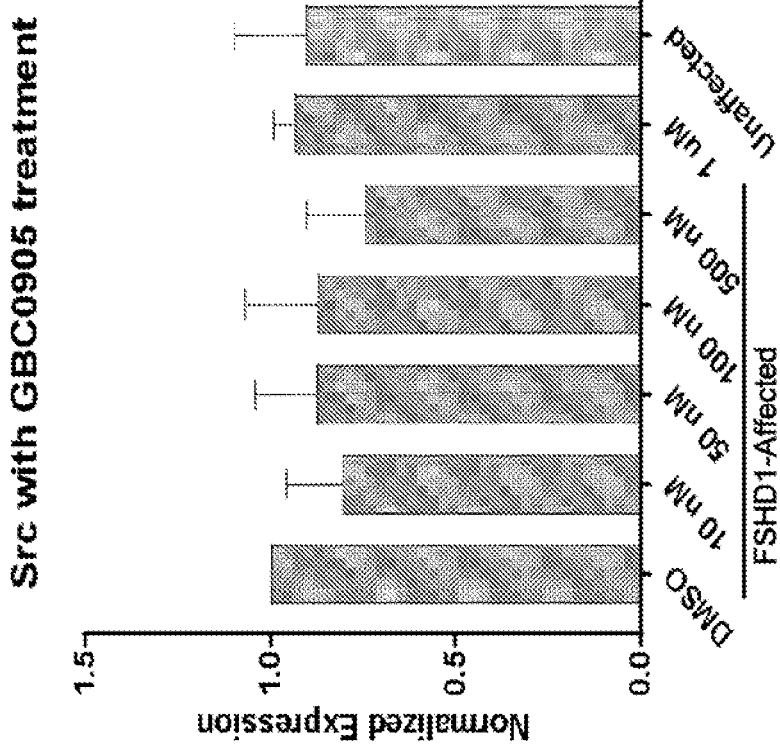
FIG. 37A and FIG. 37B illustrate GBC0905 treatment does not affect the mRNA levels of PRKDC and SRC in patient biopsy-derived primary myotubes.
Figure 37B:
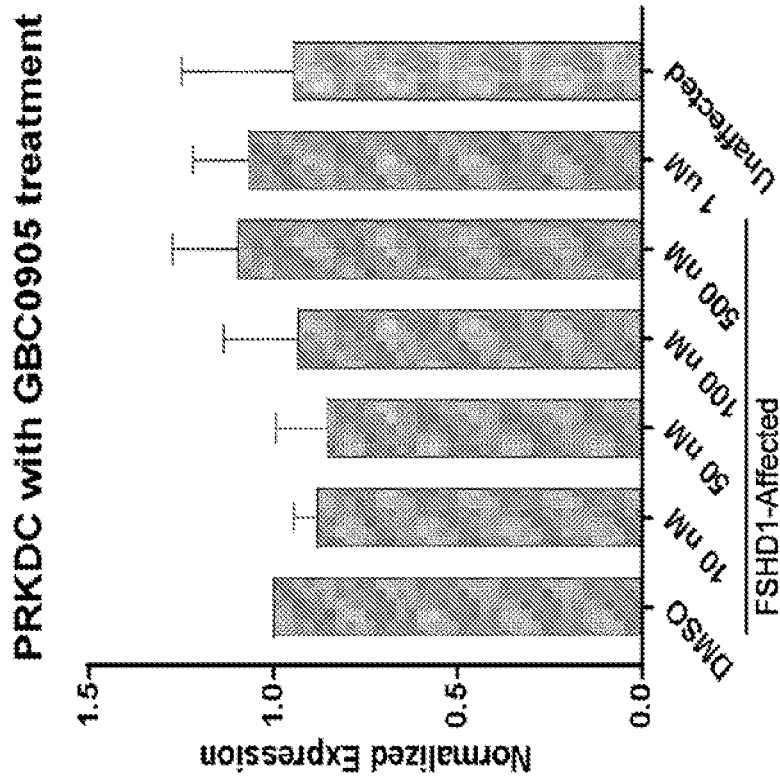
Figure 38A:
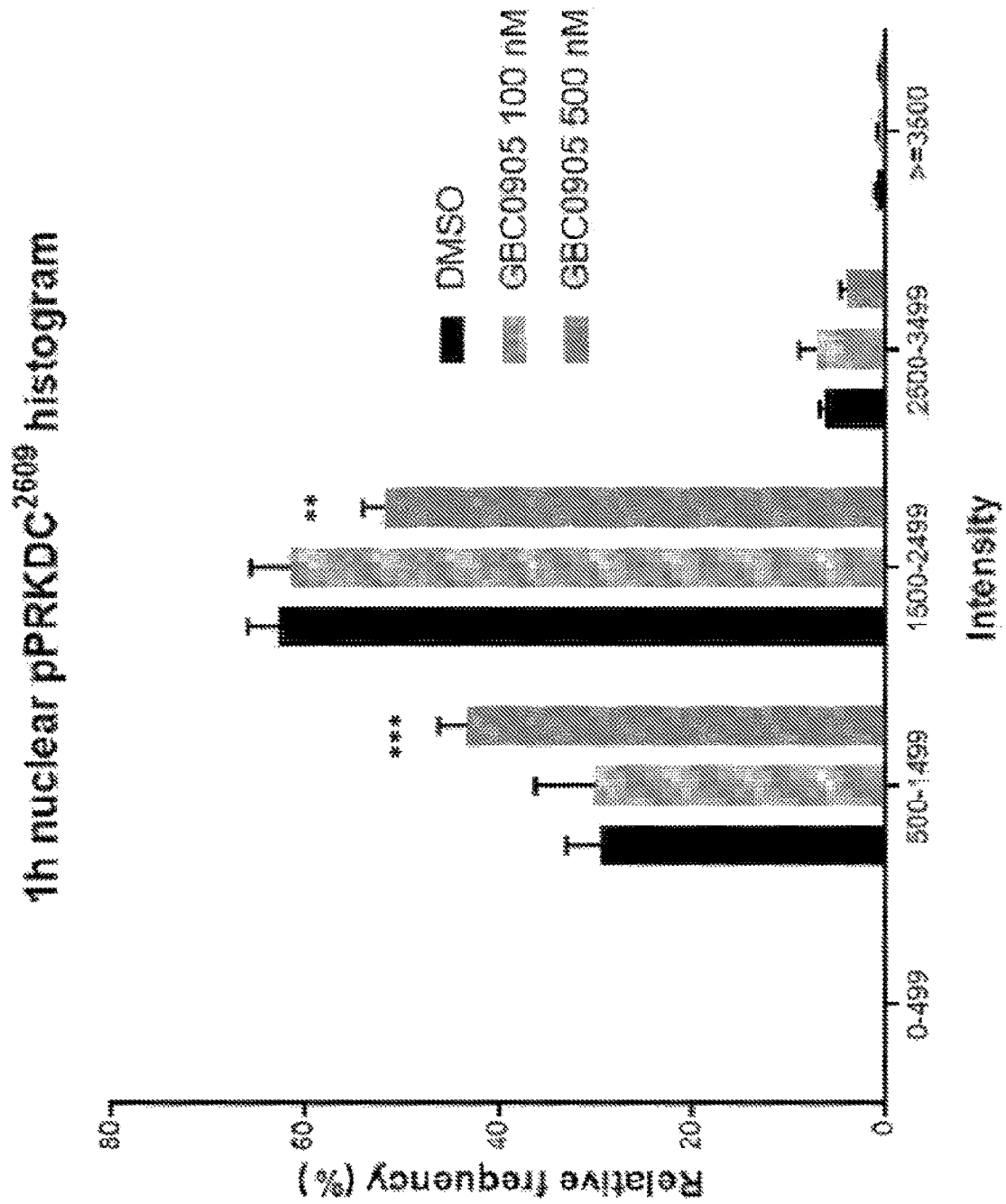
FIG. 38A and FIG. 38B illustrate GBC0905 inhibits PRKDC and SRC activities in patient biopsy-derived primary myocytes.
Figure 38B:
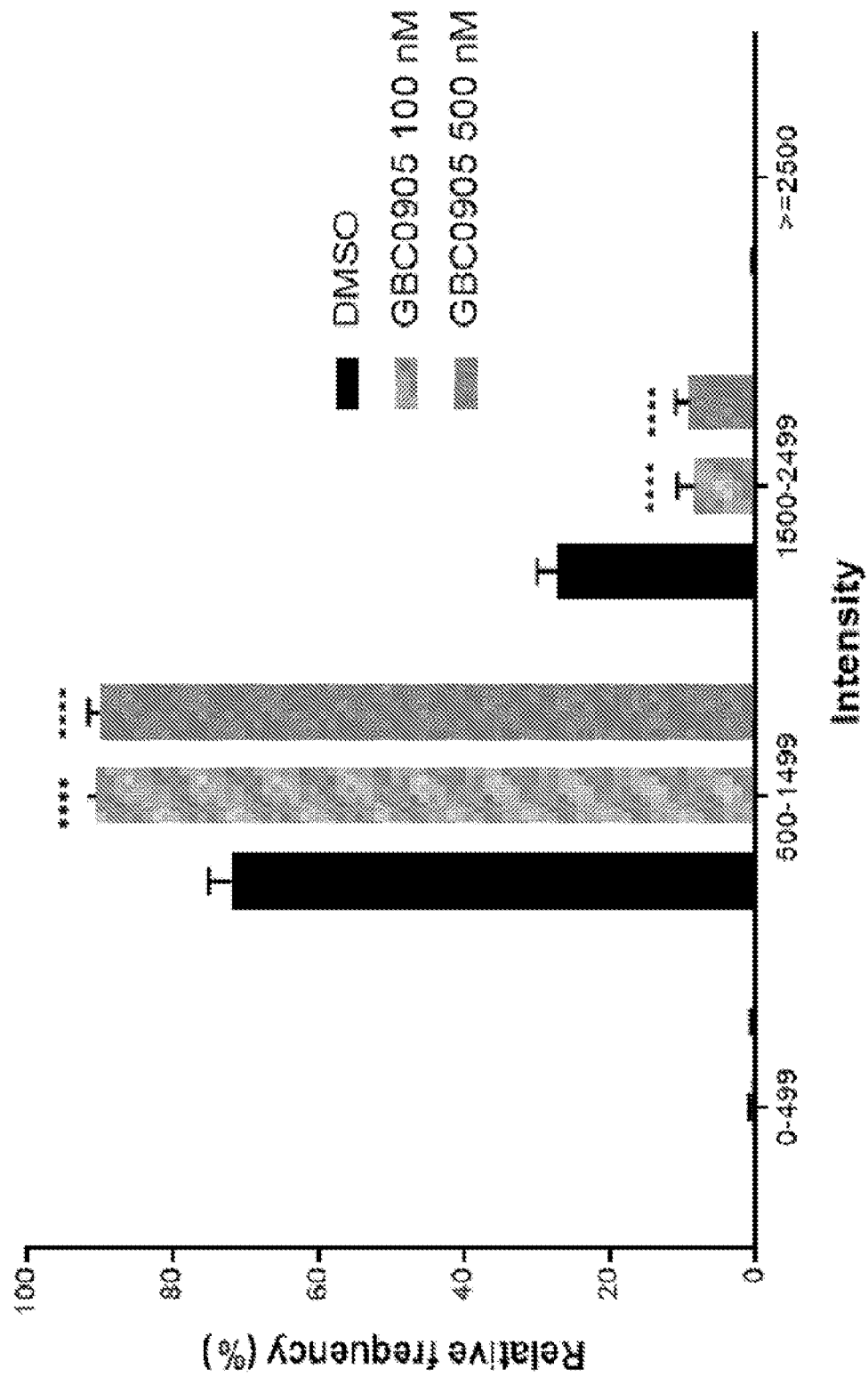

PRKDC and SRC mRNA levels and kinase activity levels were examined to verily the previously described inhibitory effects of GBC0905 on PRKDC and SRC. First, to understand whether GBC0905 inhibits PRKDC or SRC at the transcription level, RT-PCR was performed on vehicle or GBC0905 treated patient biopsy-derived primary myotubes. No significant difference was observed in the expression levels of PRKDC or SRC between vehicle and GBC0905 treated myotubes (FIG. 37A and FIG. 37B). The kinase activity levels of PRKDC and SRC were then assessed through immunofluorescence stain of phosphorylated PRKDC[2609] and phosphorylated SRC[416] in vehicle or GBC0905 treated primary cells. The intensity distribution of nuclear phosphorylated PRKDC[2609] and SRC[416] demonstrated that GBC0905 led to a significant shift towards lower intensity levels, indicating that GBC0905 inhibits PRKDC and SRC activities in FSHD-affected myocytes (FIG. 38A and FIG. 38B). Together with the evidence that knockdown of PRKDC and SRC led to reduced levels of DUX4 expression, we hypothesize that GBC0905 repress DUX4 expression in FSHD-affected myotubes via inhibiting PRKDC and SRC activities.

Patient biopsy-derived primary myoblasts were seeded to a collagen-I coated plate in primary myoblast medium. Medium was changed every other day until cells reached 80% confluence followed by a switch to primary myotube medium. Cells were treated with vehicle control DMSO or GBC0905 at 10 nm, 50 nM, lot) nM, 500 nM or 1 µM. After 2.5 days of myotube formation, the cells were lysed with buffer RLT followed by RNA isolation with RNeasy Plus Mini Kit (Qiagen). 500 ng of RNA was used for cDNA synthesis with SuperScript III first-strand synthesis system for RT-PCR (Invitrogen) and both random hexamers and oligo(dT)$_{20}$ primers. RT-PCR was performed using TaqMan™ Fast Advanced Master Mix (Applied Biosystems). Reactions were analyzed upon a QuantStudio 3 Real-Time PCR machine using the following cycle conditions: 50° C. for 2 minutes, 95° C. for 2 minutes, followed by 40 cycles at 95° C. for 15 seconds, 60° C. for 1 minute, Results were normalized against GAPDH expression.

Normalized expression levels of PRKDC (FIG. 37A) and SRC (FIG. 37B) in patient-derived primary myotubes treated with DMSO or GBC0905 at different concentrations.

Patient biopsy-derived primary myoblasts were seeded to a collagen-I coated plate in primary myoblast medium. Medium was changed every other day until cells reached 80% confluence followed by a switch to primary myotube medium. Cells were treated with vehicle control DMSO or GBC0905 at 100 nM or 500 nM, After 1 hour of compound treatment, the cells were fixed and analyzed by immunocytochemistry and high-content imaging for active. PRKDC (phosphorylated PRKDC[2609]), active SRC (phosphorylated SRC[416]), and nuclei.

Histograms of intensity distribution of nuclear phosphorylated PRKDC[2609] (FIG. 38A) and nuclear phosphorylated SRC[416] (FIG. 38B) in patient biopsy-derived primary myocytes treated with vehicle or 100/500 nM of GBC0905 for 1 hour.

The invention claimed is:

1. A method for modulating DUX4 activity in a subject in need thereof comprising administering to the subject in need thereof a composition comprising a compound, or a pharmaceutically acceptable salt thereof, having the structure of Formula (III):

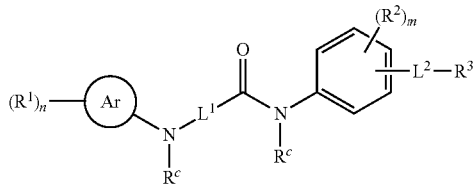

Formula (III)

wherein:
Ar is phenyl or 5- or 6-membered heteroaryl;
each $R^1$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, unsubstituted or substituted heteroaryl, unsubstituted or substituted —$C_1$-$C_6$-alkylene-cycloalkyl, unsubstituted or substituted —$C_1$-$C_6$-alkylene-heterocycloalkyl, unsubstituted or substituted —$C_1$-$C_6$-alkylene-aryl, or unsubstituted or substituted —$C_1$-$C_6$-alkylene-heteroaryl;
n is 0-5;
$L^1$ is absent or *—(CR$^a$R$^b$)—C(=O)—, wherein * denotes attachment point to the carbonyl carbon;
$R^a$ and $R^b$ are independently selected from hydrogen, $C_1$-$C_6$ alkyl, or $C_1$-$C_6$ haloalkyl;
or $R^a$ and $R^b$ are taken together with the carbon to which they are attached to form a 3-, 4-, 5-, or 6-membered cycloalkyl or a 3-, 4-, 5-, or 6-membered heterocycloalkyl;
each $R^2$ is independently hydrogen, halogen, —CN, —OH, —OR$^{20}$, —NR$^{21}$R$^{21}$, —C(=O)R$^{20}$, —OC(=O)R$^{20}$, —C(=O)OR$^{21}$, —C(=O)NR$^{21}$R$^{21}$, —NR$^{21}$C(=O)R$^{20}$, $C_1$-$C_6$ alkyl, or $C_1$-$C_6$ haloalkyl;
or two $R^2$ on adjacent atoms are taken together with the atoms to which they are attached to form an unsubstituted or substituted cycloalkyl, unsubstituted or substituted heterocycloalkyl, unsubstituted or substituted aryl, or unsubstituted or substituted heteroaryl;
m is 0-4;
$L^2$ is absent, —O—, —O—($C_1$-$C_4$ alkylene)-, or —NR$^c$—C(=O)—;
each $R^c$ is independently selected from hydrogen, $C_1$-$C_6$ alkyl, or $C_1$-$C_6$ haloalkyl;
$R^3$ is unsubstituted or substituted cycloalkyl, unsubstituted or substituted heterocycloalkyl, unsubstituted or substituted aryl, or unsubstituted or substituted heteroaryl; wherein when $R^3$ is substituted, it is substituted by 1-3 $R^4$;
each $R^4$ is independently hydrogen, halogen, —CN, —OH, —OR$^{20}$, —SH, —SR$^{20}$, —NO$_2$, —NR$^{21}$R$^{21}$, —S(=O)$_2$R$^{20}$, —NR$^{21}$S(=O)$_2$R$^{20}$, —S(=O)R$^{20}$, —S(=O)$_2$NR$^{21}$R$^{21}$, —C(=O)R$^{20}$, —OC(=O)R$^{20}$, —C(=O)OR$^{21}$, —OC(=O)OR$^{21}$, —C(=O)NR$^{21}$R$^{21}$, —OC(=O)NR$^{21}$R$^{21}$, —NR$^{21}$C(=O)NR$^{21}$R$^{21}$, —NR$^{21}$C(=O)R$^{20}$, —NR$^{21}$C(=O)OR$^{21}$, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;
each $R^{20}$ is independently selected from unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted cycloalkyl, unsubstituted or substituted heterocycloalkyl, unsubstituted or substituted aryl, or unsubstituted or substituted heteroaryl;

each $R^{21}$ is independently selected from hydrogen, unsubstituted or substituted $C_1$-$C_6$ alkyl, unsubstituted or substituted $C_1$-$C_6$ alkenyl, unsubstituted or substituted $C_1$-$C_6$ alkynyl, unsubstituted or substituted cycloalkyl, unsubstituted or substituted heterocycloalkyl, unsubstituted or substituted aryl, or unsubstituted or substituted heteroaryl;

or two $R^{21}$ on the same N atom are taken together with the N atom to which they are attached to form an unsubstituted or substituted N-containing heterocycle;

wherein when any $R^1$, $R^2$, $R^4$, $R^{20}$, or $R^{21}$ is substituted, substituents on the $R^1$, $R^2$, $R^4$, $R^{20}$, or $R^{21}$ are independently selected at each occurrence from halogen, —CN, —NO$_2$, —OR$^{22}$, —CO$_2$R$^{22}$, —C(=O)R$^{23}$, —C(=O)N$^{22}$R$^{22}$, —NR$^{22}$R$^{22}$, —NR$^{22}$C(=O)R$^{23}$, —NR$^{22}$C(=O)OR$^{22}$, —SR$^{22}$, —S(=O)R$^{23}$, —SO$_2$R$^{23}$, —SO$_2$NR$^{22}$R$^{22}$, $C_1$-$C_6$ alkyl, $C_1$-$C_6$ haloalkyl, monocyclic cycloalkyl, monocyclic heterocycloalkyl, phenyl, benzyl, 5-membered heteroaryl, and 6-membered heteroaryl; or two substituents on the same carbon atom are taken together to form a C=O or C=S;

each $R^{22}$ is independently selected from hydrogen, $C_1$-$C_6$ alkyl, $C_3$-$C_6$ cycloalkyl, phenyl, benzyl, 5-membered heteroaryl, and 6-membered heteroaryl;

or two $R^{22}$ groups are taken together with the N atom to which they are attached to form a N-containing heterocycle; and each $R^{23}$ is independently selected from $C_1$-$C_6$ alkyl, $C_3$-$C_6$ cycloalkyl, phenyl, benzyl, 5-membered heteroaryl, and 6-membered heteroaryl.

2. The method of claim 1, wherein the modulating DUX4 activity comprises reducing expression of DUX4.

3. The method of claim 1, wherein DUX4 expression is monitored by monitoring DUX4 mRNA expression, DUX4 protein expression, or both DUX4 mRNA expression and DUX4 protein expression.

4. The method of claim 1, wherein the DUX4 target gene is one or more genes selected from the group consisting of CCNA1, KHDC1L, LEUTX, M8D3L2, PRAMEF2, PRAMEF6, SPRYD5, TRIM43, TRIM49, ZNF296, and ZSCAN4.

5. The method of claim 1, wherein the compound comprises rebastinib, 4-(4-(3-(3-(tert-butyl)-1-(quinolin-6-yl)-1H-pyrazol-5-yl)ureido)-2-methylphenoxy)-N-methylpicolinamide, or 4-(4-(3-(3-(tert-butyl)-1-(1H-indazol-5-yl)-1H-pyrazol-5-yl)ureido)-3-fluorophenoxy)-N-methylpicolinamide.

* * * * *